US008716242B2

(12) United States Patent
Barthélémy et al.

(10) Patent No.: US 8,716,242 B2
(45) Date of Patent: May 6, 2014

(54) β-HAIRPIN PEPTIDOMIMETICS

(75) Inventors: Sophie Barthélémy, Folgensbourg (FR); Christian Bisang, Basel (CH); Frank Otto Gombert, Basel (CH); Alexander Lederer, Basel (CH); Daniel Obrecht, Bättwil (CH); Barbara Romagnoli, Binningen (CH); Jürg Zumbrunn, Wittinsburg (CH); Tobias Remus, Basel (CH); Guillaume Lemercier, Village-Neuf (FR)

(73) Assignee: Polyphor AG, Allschwil (CH)

( * ) Notice: Subject to any disclaimer, the term of this patent is extended or adjusted under 35 U.S.C. 154(b) by 0 days.

(21) Appl. No.: 13/513,550

(22) PCT Filed: Dec. 4, 2009

(86) PCT No.: PCT/EP2009/066462
§ 371 (c)(1),
(2), (4) Date: Jul. 27, 2012

(87) PCT Pub. No.: WO2011/066869
PCT Pub. Date: Jun. 9, 2011

(65) Prior Publication Data
US 2012/0283196 A1    Nov. 8, 2012

(51) Int. Cl.
*A61K 38/12* (2006.01)
*C07K 7/08* (2006.01)
(52) U.S. Cl.
CPC .......................... *C07K 7/08* (2013.01)
USPC ........................................................ 514/21.1
(58) Field of Classification Search
CPC ........................................................ C07K 7/08
USPC ........................................................ 514/21.1
See application file for complete search history.

(56) References Cited

FOREIGN PATENT DOCUMENTS

| WO | WO 2006/117011 A1 | 11/2006 |
| WO | WO 2006117011 A1 * | 11/2006 |
| WO | WO 2008/104090 A1 | 9/2008 |

OTHER PUBLICATIONS

International Search Report for PCT/EP2009/066462 dated Jul. 26, 2010.

* cited by examiner

*Primary Examiner* — Marcela M Cordero Garcia
*Assistant Examiner* — Kaipeen Yang
(74) *Attorney, Agent, or Firm* — Birch, Stewart, Kolasch & Birch, LLP

(57) ABSTRACT

β-Hairpin peptidomimetics of the general formula Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-), and pharmaceutically acceptable salts thereof, with Xaa 1-Xaa 16 being amino acid residues of certain types which are defined in the description and the claims, have CXCR4 antagonizing properties and prolonged half-lives in vivo and can be used for preventing HIV infections in healthy individuals or for slowing and halting viral progression in infected patients; or where cancer is mediated or resulting from CXCR4 receptor activity; or where immunological diseases are mediated or resulting from CXCR4 receptor activity; or for treating immunosuppression; or during apheresis collections of peripheral blood stem cells and/or as agents to induce mobilization of stem cells to regulate tissue repair. These peptidomimetics can be manufactured by a process which is based on a mixed solid- and solution phase synthetic strategy.

20 Claims, No Drawings

β-HAIRPIN PEPTIDOMIMETICS

The present invention provides β-hairpin peptidomimetics having CXCR4 antagonizing activity and prolonged half-lives in vivo.

The β-hairpin peptidomimetics of the invention are Cyclo (-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$-), and pharmaceutically acceptable salts thereof, with $Xaa^1$ to $Xaa^{16}$ being as described herein below.

In addition, the present invention provides an efficient synthetic process by which these compounds can, if desired, be made in parallel library-format. These β-hairpin peptidomimetics show a significantly enhanced ratio between CXCR4 antagonizing activity on the one hand, and reduced hemolysis of red blood cells and reduced or no cytotoxicity on the other, and most importantly, prolonged plasma half-lives in vivo which can improve efficacy and bioavailability significantly.

Many medically significant biological processes are mediated by signal transduction that involves chemokines and their receptors in general and stromal derived factor 1 (SDF-1/CXCL12) and its receptor CXCR4 in particular.

CXCR4 and its ligand SDF-1 are involved in trafficking of B-cells, hematopoietic stem cells (HSC) and hematopoietic progenitor cells (HPC). For instance, CXCR4 is expressed on CD34+ cells and has been implicated in the process of CD34+ cell migration and homing (S. M. Watt, S. P. Forde, *Vox sanguinis* 2008, 94, 18-32). It has also been shown that the CXCR4 receptor plays an important role in the release of stem and progenitor cells from the bone marrow to the peripheral blood (L. M. Pelus, S. Fukuda, *Leukemia* 2008, 22, 466-473). This activity of CXCR4 could be very important for efficient apheresis collections of peripheral blood stem cells. Autologous peripheral blood cells provide a rapid and sustained hematopoietic recovery following auto-transplantation after the administration of high-dose chemotherapy or radiotherapy in patients with haematological malignancies and solid tumors (W. C. Liles et al., *Blood* 2003, 102, 2728-2730).

Recently, it has been demonstrated that SDF-1 is locally up-regulated in animal models of injury including focal ischemic stroke, global cerebral ischemia, myocardial infarction and hind limb ischemia as well as being involved in recovery after peripheral ischemia or following injury to the liver, kidney or lung (A. E. Ting, R. W. Mays, M. R. Frey, W. Van't H of, S. Medicetty, R. Deans, *Critical Reviews in Oncology/Hematology* 2008, 65, 81-93 and literature cited herein; F. Lin, K. Cordes, L. Li, L. Hood, W. G. Couser, S. J. Shankland et al., *J. Am. Soc. Nephrol.* 2003, 14, 1188-1199; C. C. Dos Santos, *Intensive Care Med.* 2008, 34, 619-630). These results suggest that SDF-1 may be a chemoattractant for CXCR4-positive stem cells for tissue and organ repair/regeneration (M. Z. Ratajczak, M. Kucia, R. Reca, M. Majka, A. Janowska-Wieczorek, J. Ratajczak, *Leukemia* 2004, 18, 29-40). Therefore, modulating the SDF-1/CXCR4 axis by CXCR4 inhibitors should result in a significant therapeutic benefit by using released stem cells to regulate tissue repair.

More recently, it has been shown that disrupting the CXCR4/SDF-1 axis by CXCR4 inhibitors plays a crucial role in differential mobilization of progenitor cells like HPCs, endothelial (EPCs) and stromal progenitor cells (SPCs) from the bone marrow (S. C. Pitchford, R. C. Furze, C. P. Jones, A. M. Wegner, S. M. Rankin, *Cell Stem Cell* 2009, 4, 62). In addition, bone marrow-derived CXCR4+ Very Small Embryonic-Like Stem Cells (VSELs) were mobilized in patients with acute myocardial infarction indicating a hypothetical reparatory mechanism (W. Wojakowski, M. Tendra, M. Kucia, E. Zuba-Surma, E. Paczkowska, J. Ciosek, M. Halasa, M. Król, M. Kazmierski, P. Buszman, A. Ochala, J. Ratajczak, B. Machalinski, M. Z. Ratajczak, *J. Am. Coll. Cardiol.* 2009, 53, 1). These findings may be exploited to provide efficacious stem cell therapy for tissue regeneration.

Mesenchymal stem cells (MSC) are nonhematopoietic progenitor cells having the capability of differentiating into tissues such as bone and cartilage (D. J. Prockop, *Science* 1997, 276, 71). As a small proportion of MSCs strongly expresses functionally active CXCR4, modulation of the CXCR4/SDF-1 axis may mediate specific migration and homing of these cells (R. F. Wynn, C. A. Hart, C. Corradi-Perini, L. O'Neill, C. A. Evans, J. E. Wraith, L. J. Fairbaim, I. Bellantuono, *Blood* 2004, 104, 2643).

There is increasing evidence suggesting that chemokines in general and the SDF-1/CXCR4 interaction in particular play a pivotal role in angiogenesis. Chemokines induce angiogenesis directly by binding their cognate receptors on endothelial cells or indirectly by promoting inflammatory cell infiltrates, which deliver other angiogenic stimuli. A number of proinflammatory chemokines including interleukin (IL-8), growth-regulated oncogene, stromal cell-derived factor 1 (SDF-1), monocyte chemotactic protein 1 (MCP-1), eotaxin 1, and 1-309 have been shown to act as direct inducers of angiogenesis (X. Chen, J. A. Beutler, T. G. McCloud, A. Loehfelm, L. Yang, H. F. Dong, O. Y. Chertov, R. Salcedo, J. J. Oppenheim, O. M. Howard. *Clin. Cancer Res.* 2003, 9(8), 3115-3123; R. Salcedo, J. J. Oppenheim, *Microcirculation* 2003, (3-4), 359-370).

Recently obtained results show that the CXCR4 receptor is involved in the chemotactic activity of cancer cells, such as breast cancer metastasis or in metastasis of ovarian cancer (A. Muller, B. Homey, H. Soto, N. Ge, D. Catron, M. E. Buchanan, T. Mc Clanahan, E. Murphey, W. Yuan, S. N. Wagner, J. L. Barrera, A. Mohar, E. Verastegui, A. Zlotnik, *Nature* 2001, 50, 410; J. M. Hall, K. S. Korach, *Molecular Endocrinology* 2003, 17, 792-803), Non-Hodgin's Lymphoma (F. Bertolini, C. Dell'Agnola, P. Manusco, C. Rabascio, A. Burlini, S. Monestiroli, A. Gobbi, G. Pruneri, G. Martinelli, *Cancer Research* 2002, 62, 3106-3112), or lung cancer (T. Kijima, G. Maulik, P. C. Ma, E. V. Tibaldi, R. E. Turner, B. Rollins, M. Sattler, B. E. Johnson, R. Salgia, *Cancer Research* 2002, 62, 6304-6311), melanoma, prostate cancer, kidney cancer, neuroblastomia, pancreatic cancer, multiple myeloma, chronic lymphocytic leukemia, hepatocellular carcinoma, colorectal carcinoma, endometrial cancer, germ cell tumor (H. Tamamura et al., *FEBS Letters* 2003, 550, 79-83, cited ref.; Z. Wang, Q. Ma, Q. Liu, H. Yu, L. Zhao, S. Shen, J. Yao, British *Journal of Cancer* 2008, 99, 1695; B. Sung, S. Jhurani, K. S. Ahn, Y. Mastuo, T. Yi, S. Guha, M. Liu, B. Aggarwal, *Cancer Res.* 2008, 68, 8938; H. Liu, Z. Pan, A. Li, S. Fu, Y. Lei, H. Sun, M. Wu, W. Zhou, *Cellular and Molecular Immunology*, 2008, 5, 373; C. Rubie, O. Kollmar, V. O. Frick, M. Wagner, B. Brittner, S. Graber, M. K. Schilling, *Scandinavian Journal of Immunology* 2008, 68, 635; S. Gelmini, M. Mangoni, F. Castiglioe, C. Beltrami, A. Pieralli, K. L. Andersson, M. Fambrini, G. 1. Taddie, M. Serio, C. Orlando, *Clin. Exp. Metastasis* 2009, 26, 261; D. C. Gilbert, I. Chandler, A. McIntyre, N. C. Goddard, R. Gabe, R. A. Huddart, J. Shipley, *J. Pathol.* 2009, 217, 94). Blocking the chemotactic activity with a CXCR4 inhibitor should stop the migration of cancer cells and thus metastasis.

CXCR4 has also been implicated in the growth and proliferation of solid tumors and leukemia/lymphoma. It was shown that activation of the CXCR4 receptor was critical for the growth of both malignant neuronal and glial tumors. Moreover, systemic administration of the CXCR4 antagonist AMD3100 inhibits growth of intracranial glioblastoma and medulloblastoma xenografts by increasing apoptosis and decreasing the proliferation of tumor cells (J. B. Rubin, A. L Kung, R. S Klein, J. A. Chan, Y. Sun, K. Schmidt, M. W. Kieran, A. D. Luster, R. A. Segal, *Proc Natl Acad Sci USA*. 2003, 100(23), 13513-13518; S. Barbero, R. Bonavia, A. Bajetto, C. Porcile, P. Pirani, J. L. Ravetti, G. L. Zona, R. Spaziante, T. Florio, G. Schettini, *Cancer Res.* 2003, 63(8), 1969-1974; T. Kijima, G. Maulik, P. C. Ma, E. V. Tibaldi, R. E. Turner, B. Rollins, M. Sattler, B. E. Johnson, R. Salgia. *Cancer Res.* 2002, 62(21), 6304-6311). CXCR4 inhibitors also showed promising in vitro and in vivo efficacies in breast cancer, small cell lung cancer, pancreatic cancer, gastric cancer, colorectal cancer, malignant melanoma, ovarian cancer, rhabdomyo-sarcoma, prostate cancer as well as chronic lymphocytic leukemia, acute myelogenous leukemia, acute lymphoblastic leukemia, multiple myeloma and Non-Hodgkin's lymphoma (J. A. Burger, A. Peled, *Leukemia* 2009, 23, 43-52 and literature cited herein).

It is well established that chemokines are involved in a number of inflammatory pathologies and some of them show a pivotal role in the modulation of osteoclast development. Immunostaining for SDF-1 (CXCL12) on synovial and bone tissue biopsies from both rheumatoid arthritis (RA) and osteoarthritis (OA) samples have revealed strong increases in the expression levels of chemokines under inflammatory conditions (F. Grassi, S. Cristino, S. Toneguzzi, A. Piacentini, A. Facchini, G. Lisignoli, *J. Cell Physiol.* 2004; 199(2), 244-251). It seems likely that the CXCR4 receptor plays an important role in inflammatory diseases such as rheumatoid arthritis, asthma, multiple sclerosis, Alzheimer's disease, Parkinson's disease, atherosclerosis, or eye diseases such as diabetic retinopathy and age related macular degeneration (K. R. Shadidi et al., Scandinavian *Journal of Immunology* 2003, 57, 192-198; J. A. Gonzalo, *J. Immunol.* 2000, 165, 499-508; S. Hatse et al., *FEBS Letters* 2002, 527, 255-262 and cited references, A. T. Weeraratna, A. Kalehua, I. DeLeon, D. Bertak, G. Maher, M. S. Wade, A. Lustig, K. G. Becker, W. Wood, D. G. Walker, T. G. Beach, D. D. Taub, *Exp. Cell Res.* 2007, 313, 450; M. Shimoji, F. Pagan, E. B. Healton, I. Mocchetti, *Neurotox. Res.* 2009, 16, 318; A. Zernecke, E. Shagdarsuren, C. Weber, *Arterioscler. Thromb. Vasc. Biol.* 2008, 28, 1897; R. Lima e Silva, J. Shen, S. F. Hackett, S. Kachi, H. Akiyama et al., *FASEB* 2007, 21, 3219). The mediation of recruitment of immune cells to sites of inflammation should be stopped by a CXCR4 inhibitor.

To date the available therapies for the treatment of HIV infections have been leading to a remarkable improvement in symptoms and recovery from disease in infected people. Although the highly active anti-retroviral therapy (HAART) which involves a combination of reverse transcriptase/protease-inhibitor has dramatically improved the clinical treatment of individuals with AIDS or HIV infection, there have still remained several serious problems including multi drug resistance, significant adverse effects and high costs. Particularly desired are anti-HIV agents that block the HIV infection at an early stage of the infection, such as the viral entry. It has recently been recognized that for efficient entry into target cells, human immunodeficiency viruses require the chemokine receptors CCR5 and CXCR4 as well as the primary receptor CD4 (N. Levy, *Engl. J. Med.* 1996, 335, 1528-1530). Accordingly, an agent which could block the CXCR4 chemokine receptors should prevent infections in healthy individuals and slow or halt viral progression in infected patients (J. Cohen, *Science* 1997, 275, 1261-1264).

Among the different types of CXCR4 inhibitors (M. Schwarz, T. N. C. Wells, A. E. I. Proudfoot, *Receptors and Channels* 2001, 7, 417-428; Y. Lavrovsky, Y. A. Ivanenkov, K. V. Balakin, D. A. Medvedewa, P. V. Ivachtchenko, *Mini Rev. Med. Chem.* 2008, 11, 1075-1087), one emerging class is based on naturally occurring cationic peptide analogues derived from Polyphemusin II which have an antiparallel (β-sheet structure, and a β-hairpin that is maintained by two disulfide bridges (H. Nakashima, M. Masuda, T. Murakami, Y. Koyanagi, A. Matsumoto, N. Fujii, N. Yamamoto, *Antimicrobial Agents and Chemoth.* 1992, 36, 1249-1255; H. Tamamura, M. Kuroda, M. Masuda, A. Otaka, S. Funakoshi, H. Nakashima, N. Yamamoto, M. Waki, A. Matsumotu, J. M. Lancelin, D. Kohda, S. Tate, F. Inagaki, N. Fujii, *Biochim. Biophys. Acta* 1993, 209, 1163; WO 95/10534 A1).

Synthesis of structural analogs and structural studies by nuclear magnetic resonance (NMR) spectroscopy have shown that the cationic peptides adopt well defined β-hairpin conformations, due to the constraining effect of one or two disulfide bridges (H. Tamamura, M. Sugioka, Y. Odagaki, A. Omagari, Y. Kahn, S. Oishi, H. Nakashima, N. Yamamoto, S. C. Peiper, N. Hamanaka, A. Otaka, N. Fujii, *Bioorg. Med. Chem. Lett.* 2001, 359-362). These results show that the β-hairpin structure plays an important role in CXCR4 antagonizing activity.

Additional structural studies have indicated that the antagonizing activity can also be influenced by modulating amphiphilic structure and the pharmacophore (H. Tamamura, A. Omagari, K. Hiramatsu, K. Gotoh, T. Kanamoto, Y. Xu, E. Kodama, M. Matsuoka, T. Hattori, N. Yamamoto, H. Nakashima, A. Otaka, N. Fujii, *Bioorg. Med. Chem. Lett.* 2001, 11, 1897-1902; H. Tamamura, A. Omagari, K. Hiramatsu, S. Oishi, H. Habashita, T. Kanamoto, K. Gotoh, N. Yamamoto, H. Nakashima, A. Otaka N. Fujii, *Bioorg. Med. Chem.* 2002, 10, 1417-1426; H. Tamamura, K. Hiramatsu, K. Miyamoto, A. Omagari, S. Oishi, H. Nakashima, N. Yamamoto, Y. Kuroda, T. Nakagawa, A. Otaki, N. Fujii, *Bioorg. Med. Chem. Letters* 2002, 12, 923-928).

The compounds Cyclo (-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$-) of the invention are cyclic β-hairpin peptidomimetics exhibiting high CXCR4 antagonizing activity, being useful for efficient apheresis collections of mobilized peripheral blood stem cells and/or using these mobilized cells to regulate tissue repair, and having anti-cancer activity, anti-inflammatory activity and anti-HIV activity.

The cyclic β-hairpin conformation is induced by the D-amino acid residue $Xaa^7$ and the D-amino acid or N-substituted glycine residue $Xaa^{15}$. Further stabilization of the hairpin conformation is achieved by the amino acid residues at positions 4 and 11, which, taken together, form bridges like e.g. a disulfide bridge or a lactam bridge. In addition, incorporation of amino acid residues having lipophilic moieties attached into cyclic β-hairpin peptidomimetics has been realized, a new approach which has not previously been evaluated for development of β-hairpin peptidomimetics with CXCR4 antagonizing activity.

Modifications, such as incorporation of amino acid residues bearing lipophilic moieties to cyclic β-hairpin peptidomimetics result in compounds showing highly protracted plasma profiles in vitro and prolonged half-lives in vivo. Surprisingly, the insertion of these relatively bulky amino acid residues is well accepted at even several positions of the rather small cyclic β-hairpin peptidomimetics effecting molecules which retain their CXCR4 antagonizing activity. Following this approach, compounds are obtained which can show significantly improved efficacy and bioavailability and therefore provide a longer duration of action in vivo.

β-hairpin mimetic peptides have been described in the literature (D. Obrecht, M. Altorfer, J. A. Robinson, *Adv. Med.*

*Chem.* 1999, 4, 1-68; J. A. Robinson, *Syn. Lett.* 2000, 4, 429-441), and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). However, the additional incorporation of amino acid residues bearing lipophilic moieties to β-hairpin mimetics by applying and altering these methods has not previously been evaluated for development of CXCR4 antagonizing peptides. The methods described here allow the synthesis and screening of large hairpin mimetic libraries, which in turn considerably facilitates structure-activity studies, and hence the discovery of new molecules with highly potent CXCR4 antagonizing activity or anti-cancer activity or anti-inflammatory activity or anti-HIV activity and low hemolytic activity to human red blood cells.

β-Hairpin peptidomimetics obtained by the approach described here can be used in apheresis collections of peripheral blood stem cells and/or as agents to induce mobilization of stem cells to regulate tissue repair or are useful as anti-cancer agents, as inhibitors of tumor growth or as apoptosis inducing agents, as anti-metastasis agents, as anti-inflammatory agents and as anti-HIV agents.

The β-hairpin peptidomimetics of the present invention are compounds of the general formula Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-),
wherein
Xaa$^1$ is Gly, NMeGly, Leu, Val, Ser, Asp, Glu or an amino acid residue of type D as defined herein below,
Xaa$^2$ is His, Tyr, Arg, Lys or an amino acid residue of type O as defined herein below,
Xaa$^3$ is Ala, Cha, Tyr, Thr, Cit, Gln or an amino acid residue of type O as defined herein below,
Xaa$^4$ and Xaa$^{11}$ are amino acid residues, taken together, forming a group of type H as defined herein below,
Xaa$^5$ is Ser, Arg, Dab, Dap or the D-isomer of an amino acid residue of type F as defined herein below,
Xaa$^6$ is Ala or Gly,
Xaa$^7$ is -A-CO— as defined herein below or the D-isomer of an amino acid residue of type D as defined herein below,
Xaa$^8$ is Dab, Arg, Tyr, His, Thr or an amino acid residue of type O as defined herein below,
Xaa$^9$ is Arg or an amino acid residue of type O as defined herein below,
Xaa$^{10}$ is an amino acid residue of type D as described herein below or an amino acid residue of type O as described herein below,
Xaa$^{12}$ is Ala, Leu, Lys, Ser, Thr or an amino acid residue of type D as defined herein below,
Xaa$^{13}$ is Gln, Thr, Cit or an amino acid residue of type O as defined herein below,
Xaa$^{14}$ is Lys, Orn, Arg, Ala, Gln, Glu or an amino acid residue of type O as defined herein below,
Xaa$^{15}$ is -A-CO— as defined herein below or the D-isomer of an amino acid residue of type C, or of type D, or of type E, or of type F, as defined herein below or a N-substituted glycine residue of type I as defined herein below, and
Xaa$^{16}$ is —B—CO— as defined herein below;
with the proviso that
Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) contains at least one amino acid residue of type O as defined herein below not exceeding four amino acid residues of type O as defined herein below, and/or
Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) contains -A-CO— having a residue designated as "lipophilic moiety" as defined herein below;

—B—CO— is Gly, NMeGly or the residue of an L-α-amino acid with B being a residue of formula —NR$^{20}$CH(R$^{71}$)—, or —NR$^{20}$CH(R$^{72}$)—, or —NR$^{20}$CH(R$^{73}$)—, or —NR$^{20}$CH(R$^{74}$)—, or —NR$^{20}$CH(R$^{84}$)—, or the enantiomer of one of the groups A1 to A69 and A105 as defined hereinafter;

A of -A-CO— is a group of one of the formulae

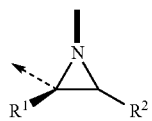

A1

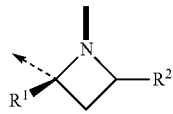

A2

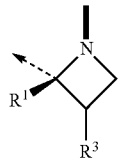

A3

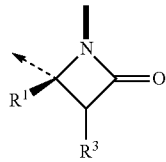

A4

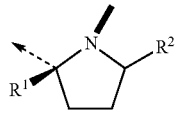

A5

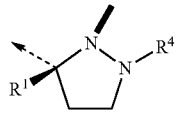

A6

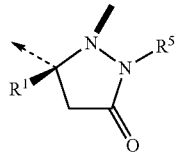

A7

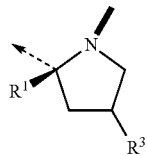

A8

-continued
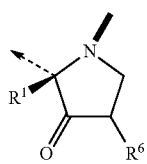 A9
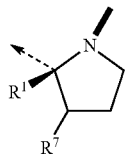 A10
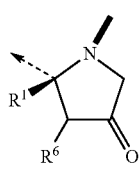 A11
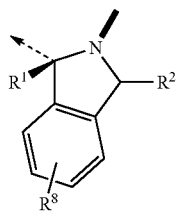 A12
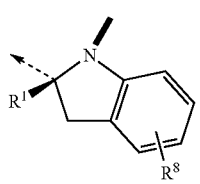 A13
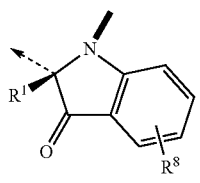 A14
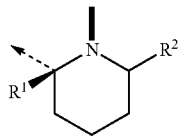 A15
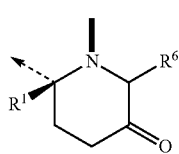 A16
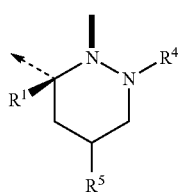 A17
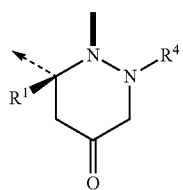 A18
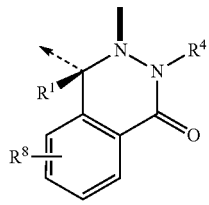 A19
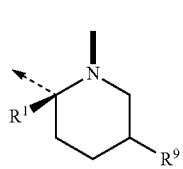 A20
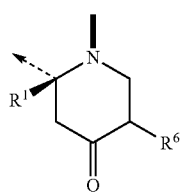 A21
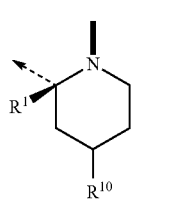 A22
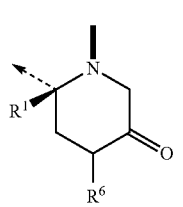 A23
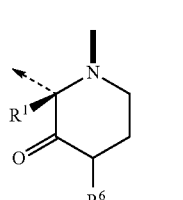 A24
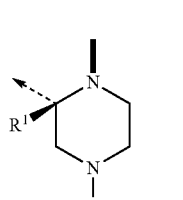 A25

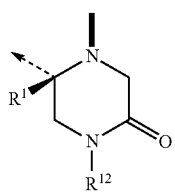
A26
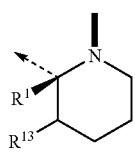
A27
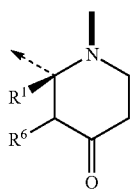
A28
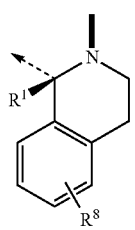
A29
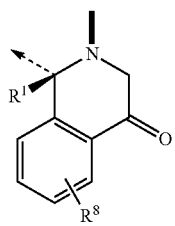
A30
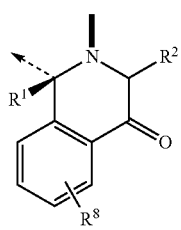
A31
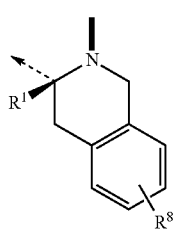
A32
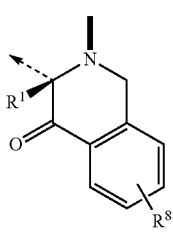
A33
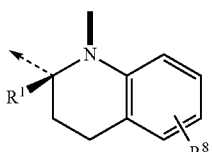
A34
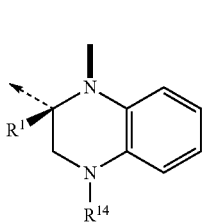
A35
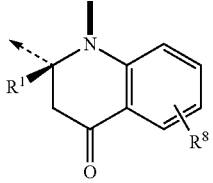
A36
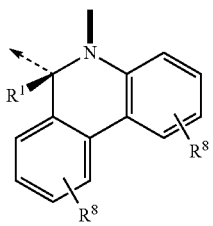
A37
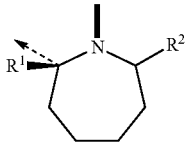
A38
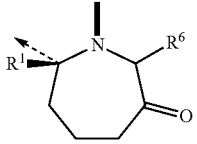
A39
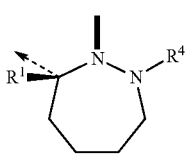
A40

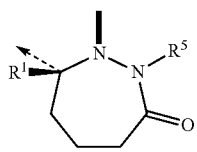 A41
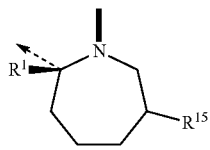 A42
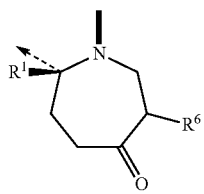 A43
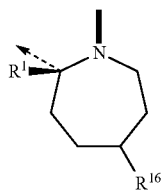 A44
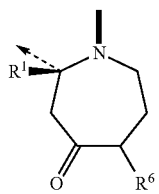 A45
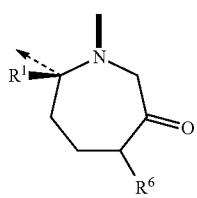 A46
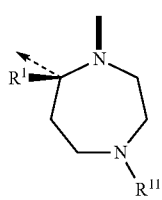 A47
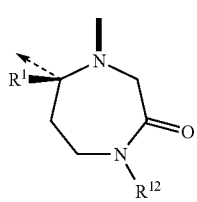 A48
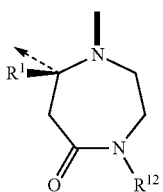 A49
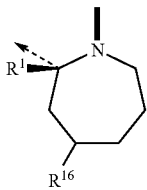 A50
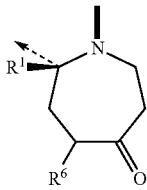 A51
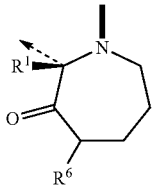 A52
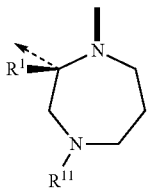 A53
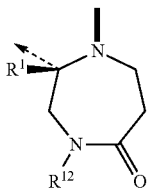 A54
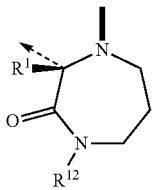 A55
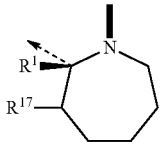 A56

-continued
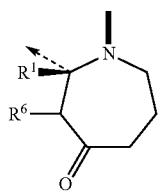
A57
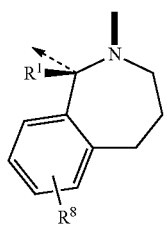
A58
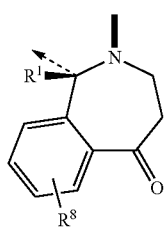
A59
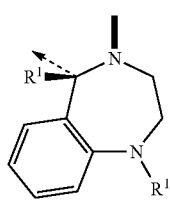
A60
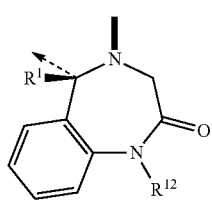
A61
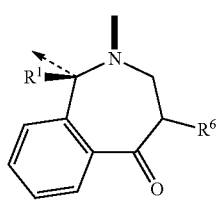
A62
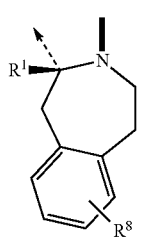
A63
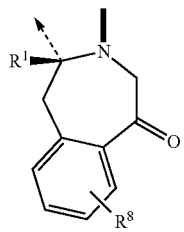
A64
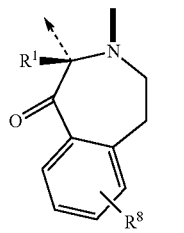
A65
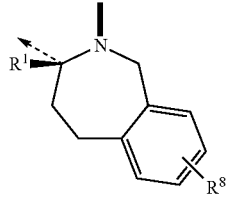
A66
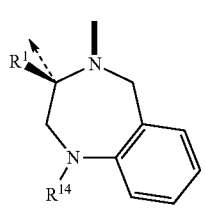
A67
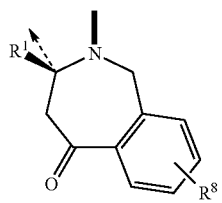
A68
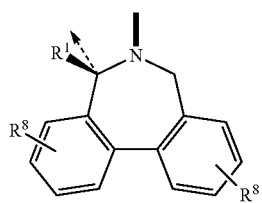
A69
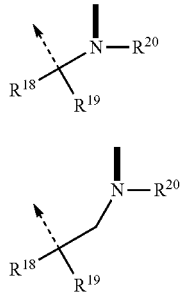
A70
A71

-continued
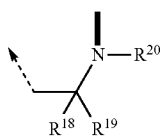
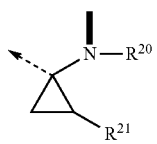
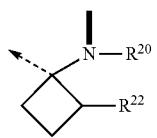
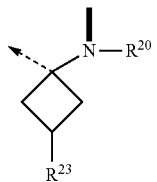
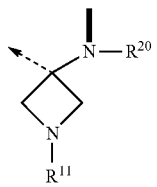
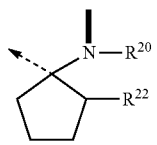
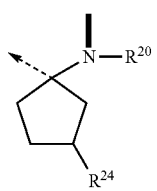
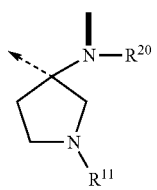
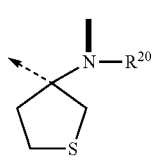
-continued
A72
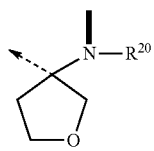
A73
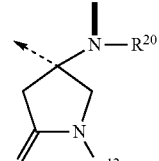
A74
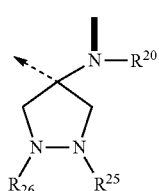
A75
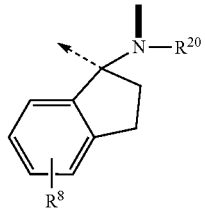
A76
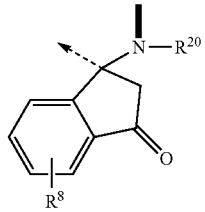
A77
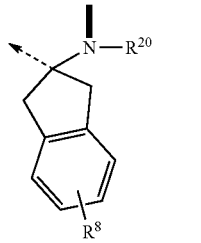
A78
A79
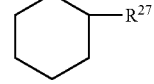
A80
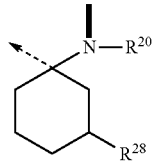
A81
A82
A83
A84
A85
A86
A87
A88

-continued
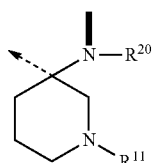 A89
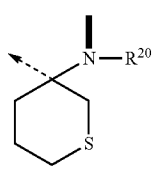 A90
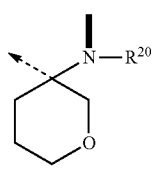 A91
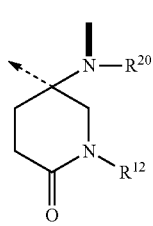 A92
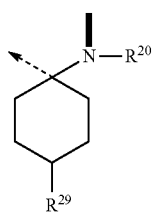 A93
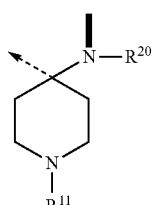 A94
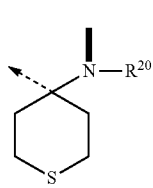 A95
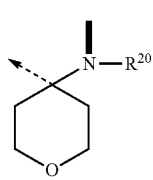 A96
-continued
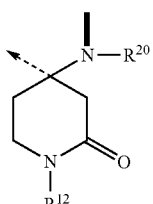 A97
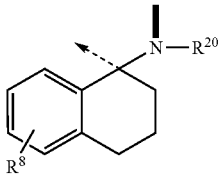 A98
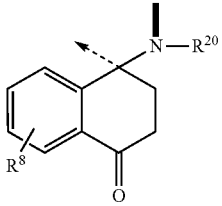 A99
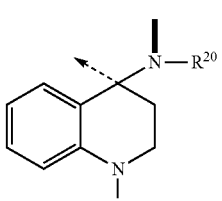 A100
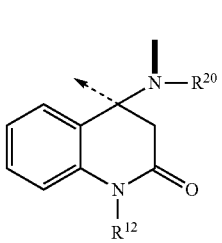 A101
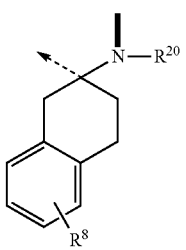 A102
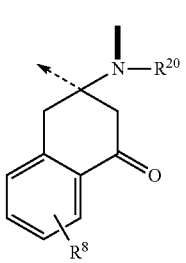 A103

-continued

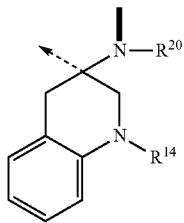
A104

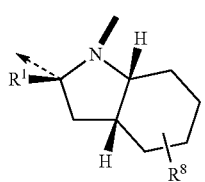
A105

R$^1$ is H; lower alkyl; aryl-lower alkyl; lower alkyl-aryl
R$^2$ is H; lower alkyl; lower alkenyl; —(CH$_2$)$_p$(CHR$^{61}$)$_s$OR$^{55}$;
—(CH$_2$)$_p$(CHR$^{61}$)$_s$SR$^{56}$;
—(CH$_2$)$_p$(CHR$^{61}$)$_s$NR$^{33}$R$^{34}$; —(CH$_2$)$_p$(CHR$^{61}$)$_s$OCONR$^{33}$R$^{75}$;
—(CH$_2$)$_p$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_s$PO(OR$^{60}$)$_2$;
—(CH$_2$)$_o$(CHR$^{61}$)$_s$SO$_2$R$^{62}$; —(CH$_2$)$_o$(CHR$^{61}$)$_s$R$^{77}$;
R$^{89}$; —(CH$_2$)$_p$(CHR$^{61}$)$_s$OR$^{89}$;
—(CH$_2$)$_p$(CHR$^{61}$)$_s$SR$^{89}$;
—(CH$_2$)$_p$(CHR$^{61}$)$_s$NR$^{89}$R$^{34}$; —(CH$_2$)$_p$(CHR$^{61}$)$_s$OCONR$^{89}$R$^{75}$;
—(CH$_2$)$_p$(CHR$^{61}$)$_s$NR$^{20}$CONR$^{89}$R$^{82}$; —(CH$_2$)$_o$(CHR$^{61}$)$_s$COOR$^{89}$;
—(CH$_2$)$_o$(CHR$^{61}$)$_s$CONR$^{29}$R$^{59}$; —(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$R$^{91}$;
R$^3$ is lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_o$(CHR$^{61}$)$_s$OR$^{89}$;
—(CH$_2$)$_o$(CHR$^{61}$)$_s$SR$^{89}$;
—(CH$_2$)$_o$(CHR$^{61}$)$_s$NR$^{89}$R$^{34}$; —(CH$_2$)$_o$(CHR$^{61}$)$_s$OCONR$^{29}$R$^{75}$;
—(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$; —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$C$_6$H$_4$R$^8$;
R$^4$ is H; lower alkyl; lower alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_p$(CHR$^{61}$)$_s$COOR$^{59}$; —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$;
R$^{89}$; —(CH$_2$)$_m$(CHR$^{61}$)$_s$OR$^{89}$; —(CH$_2$)$_m$(CHR$^{61}$)$_s$SR$^{89}$;
—(CH$_2$)$_m$(CHR$^{61}$)$_s$NR$^{89}$R$^{34}$;
—(CH$_2$)$_m$(CHR$^{61}$)$_s$OCONR$^{29}$R$^{75}$; —(CH$_2$)$_m$(CHR$^{61}$)$_s$NR$^{20}$CONR$^{89}$R$^{82}$;
—(CH$_2$)$_p$(CHR$^{61}$)$_s$COOR$^{89}$; —(CH$_2$)$_p$(CHR$^{61}$)$_s$CONR$^{89}$R$^{59}$;
—(CH$_2$)$_p$(CHR$^{61}$)$_s$PO(OR$^{60}$)(OR$^{89}$);
—(CH$_2$)$_p$(CHR$^{61}$)$_s$SO$_2$R$^{89}$; or —(CH$_2$)$_o$(CHR$^{61}$)$_s$C$_6$H$_4$R$^8$;
R$^5$ is H; lower alkyl; lower alkenyl;
—(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_m$(CHR$^{61}$)$_s$OR$^{89}$;
—(CH$_2$)$_m$(CHR$^{61}$)$_s$SR$^{89}$;
—(CH$_2$)$_m$(CHR$^{61}$)$_s$NR$^{89}$R$^{34}$; —(CH$_2$)$_m$(CHR$^{61}$)$_s$OCONR$^{89}$R$^{75}$;
—(CH$_2$)$_m$(CHR$^{61}$)$_s$NR$^{20}$CONR$^{89}$R$^{82}$; —(CH$_2$)$_o$(CHR$^{61}$)$_s$COOR$^{89}$;
—(CH$_2$)$_o$(CHR$^{61}$)$_s$CONR$^{89}$R$^{59}$; —(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$C$_6$H$_4$R$^8$;
R$^6$ is H; lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_o$(CHR$^{61}$)$_s$OR$^{89}$;
—(CH$_2$)$_o$(CHR$^{61}$)$_s$SR$^{89}$; —(CH$_2$)$_o$(CHR$^{61}$)$_s$NR$^{89}$R$^{34}$;
—(CH$_2$)$_o$(CHR$^{61}$)$_s$OCONR$^{89}$R$^{75}$; —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$; —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$C$_6$H$_4$R$^8$;
R$^7$ is lower alkyl; lower alkenyl; —(CH$_2$)$_q$(CHR$^{61}$)$_s$OR$^{55}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$;
—(CH$_2$)$_r$(CHR$^{61}$)$_s$COOR$^{57}$; —(CH$_2$)$_r$(CHR$^{61}$)$_s$CONR$^{58}$R$^{59}$;
—(CH$_2$)$_r$(CHR$^{61}$)$_s$PO(OR$^{60}$)$_2$;
—(CH$_2$)$_r$(CHR$^{61}$)$_s$SO$_2$R$^{62}$;
R$^{89}$; —(CH$_2$)$_q$(CHR$^{61}$)$_s$OR$^{89}$; —(CH$_2$)$_q$(CHR$^{61}$)$_s$NR$^{89}$R$^{34}$;
—(CH$_2$)$_q$(CHR$^{61}$)$_s$OCONR$^{89}$R$^{75}$; —(CH$_2$)$_q$(CHR$^{61}$)$_s$NR$^{20}$CONR$^{89}$R$^{82}$;
—(CH$_2$)$_r$(CHR$^{61}$)$_s$COOR$^{89}$; —(CH$_2$)$_r$(CHR$^{61}$)$_s$CONR$^{89}$R$^{59}$;
—(CH$_2$)$_r$(CHR$^{61}$)$_s$PO(OR$^{60}$)(OR$^{89}$);
—(CH$_2$)$_r$(CHR$^{61}$)$_s$SO$_2$R$^{89}$; or —(CH$_2$)$_r$(CHR$^{61}$)$_s$C$_6$H$_4$R$^8$;
R$^8$ is H; Cl; F; CF$_3$; NO$_2$; lower alkyl; lower alkenyl; ary lower alkyl-aryl; aryl-lower alkyl; —(CH$_2$)$_o$(CHR$^{61}$)$_s$R$^{77}$
—(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)NR$^{33}$R$^{34}$;

—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; —(CH$_2$)$_o$(CHR$^{61}$)$_s$COR$^{64}$;
R$^{89}$; —(CH$_2$)$_o$(CHR$^{61}$)$_s$R$^{89}$;
—(CH$_2$)$_o$(CHR$^{61}$)$_s$OR$^{89}$; —(CH$_2$)$_o$(CHR$^{61}$)$_s$SR$^{89}$;
—(CH$_2$)$_o$(CHR$^{61}$)NR$^{89}$R$^{34}$;
—(CH$_2$)$_o$(CHR$^{61}$)$_s$OCONR$^{89}$R$^{75}$; —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$; —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$;

R$^9$ is lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_o$(CHR$^{61}$)$_s$OR$^{89}$; —(CH$_2$)$_o$(CHR$^{61}$)$_s$SR$^{89}$;
—(CH$_2$)$_o$(CHR$^{61}$)$_s$NR$^{89}$R$^{34}$;
—(CH$_2$)$_o$(CHR$^{61}$)$_s$OCONR$^{89}$R$^{75}$; —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$; —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$)$_2$;
—(CH$_2$)$_o$(CHR$^{61}$)$_s$SO$_2$R$^{89}$; or —(CH$_2$)$_o$(CHR$^{61}$)$_s$C$_6$H$_4$R$^8$;

R$^{10}$ is lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_o$(CHR$^{61}$)$_s$OR$^{89}$; —(CH$_2$)$_o$(CHR$^{61}$)$_s$SR$^{89}$;
—(CH$_2$)$_o$(CHR$^{61}$)$_s$NR$^{89}$R$^{34}$;
—(CH$_2$)$_o$(CHR$^{61}$)$_s$OCONR$^{89}$R$^{75}$; —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$; —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$C$_6$H$_4$R$^8$;

R$^{11}$ is H; lower alkyl; lower alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_m$(CHR$^{61}$)$_s$OR$^{89}$; —(CH$_2$)$_m$(CHR$^{61}$)$_s$NR$^{89}$R$^{34}$;
—(CH$_2$)$_m$(CHR$^{61}$)$_s$OCONR$^{89}$R$^{75}$; —(CH$_2$)$_m$(CHR$^{61}$)$_s$NR$^{20}$CONR$^{89}$R$^{82}$;
—(CH$_2$)$_o$(CHR$^{61}$)$_s$COOR$^{89}$; —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$C$_6$H$_4$R$^8$;

R$^{12}$ is H; lower alkyl; lower alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_r$(CHR$^{61}$)$_s$COOR$^{57}$;
—(CH$_2$)$_r$(CHR$^{61}$)$_s$CONR$^{58}$R$^{59}$; —(CH$_2$)$_r$(CHR$^{61}$)$_s$PO(OR$^{60}$)$_2$;
—(CH$_2$)$_r$(CHR$^{61}$)$_s$SO$_2$R$^{62}$;
R$^{89}$; —(CH$_2$)$_m$(CHR$^{61}$)$_s$OR$^{89}$;
—(CH$_2$)$_m$(CHR$^{61}$)$_s$SR$^{89}$;
—(CH$_2$)$_m$(CHR$^{61}$)$_s$NR$^{89}$R$^{34}$; —(CH$_2$)$_m$(CHR$^{61}$)$_s$OCONR$^{89}$R$^{75}$;
—(CH$_2$)$_m$(CHR$^{61}$)$_s$NR$^{20}$CONR$^{89}$R$^{82}$; —(CH$_2$)$_r$(CHR$^{61}$)$_s$COOR$^{89}$;
—(CH$_2$)$_r$(CHR$^{61}$)$_s$CONR$^{89}$R$^{59}$; —(CH$_2$)$_r$(CHR$^{61}$)$_s$PO(OR$^{60}$)(OR$^{89}$);
—(CH$_2$)$_r$(CHR$^{61}$)$_s$SO$_2$R$^{89}$; or —(CH$_2$)$_r$(CHR$^{61}$)$_s$C$_6$H$_4$R$^8$;

R$^{13}$ is lower alkyl; lower alkenyl; —(CH$_2$)$_q$(CHR$^{61}$)$_s$OR$^{55}$;
—(CH$_2$)$_q$(CHR$^{61}$)$_s$SR$^{56}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$;
—(CH$_2$)$_q$(CHR$^{61}$)$_s$COOR$^{57}$; —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SO$_2$R$^{62}$;
R$^{89}$; —(CH$_2$)$_q$(CHR$^{61}$)$_s$OR$^{89}$; —(CH$_2$)$_q$(CHR$^{61}$)$_s$SR$^{89}$;
—(CH$_2$)$_q$(CHR$^{61}$)$_s$NR$^{89}$R$^{34}$;
—(CH$_2$)$_q$(CHR$^{61}$)$_s$OCONR$^{89}$R$^{75}$; —(CH$_2$)$_q$(CHR$^{61}$)$_s$NR$^{20}$CONR$^{89}$R$^{82}$;
—(CH$_2$)$_q$(CHR$^{61}$)$_s$COOR$^{89}$; —(CH$_2$)$_q$(CHR$^{61}$)$_s$CONR$^{89}$R$^{59}$;
—(CH$_2$)$_q$(CHR$^{61}$)$_s$PO(OR$^{60}$)(OR$^{89}$);
—(CH$_2$)$_q$(CHR$^{61}$)$_s$SO$_2$R$^{89}$; or —(CH$_2$)$_q$(CHR$^{61}$)$_s$C$_6$H$_4$R$^8$;

R$^{14}$ is H; lower alkyl; lower alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_q$(CHR$^{61}$)$_s$COOR$^{57}$; —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SOR$^{62}$;
R$^{89}$; —(CH$_2$)$_m$(CHR$^{61}$)$_s$OR$^{89}$;
—(CH$_2$)$_m$(CHR$^{61}$)$_s$NR$^{89}$R$^{34}$;
—(CH$_2$)$_m$(CHR$^{61}$)$_s$OCONR$^{89}$R$^{75}$; —(CH$_2$)$_m$(CHR$^{61}$)$_s$NR$^{20}$CONR$^{89}$R$^{82}$;
—(CH$_2$)$_q$(CHR$^{61}$)$_s$COOR$^{89}$; —(CH$_2$)$_q$(CHR$^{61}$)$_s$CONR$^{89}$R$^{59}$;
—(CH$_2$)$_q$(CHR$^{61}$)$_s$PO(OR$^{60}$)(OR$^{89}$);
—(CH$_2$)$_q$(CHR$^{61}$)$_s$SOR$^{89}$; or —(CH$_2$)$_q$(CHR$^{61}$)$_s$C$_6$H$_4$R$^8$;

R$^{15}$ is lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$; —(CH$_2$)$_o$(CHR$^{61}$)$_s$OR$^{89}$; —(CH$_2$)$_o$(CHR$^{61}$)$_s$SR$^{89}$;

—$(CH_2)_o(CHR^{61})_sNR^{89}R^{34}$;
—$(CH_2)_o(CHR^{61})_sOCONR^{89}R^{75}$; —$(CH_2)_o(CHR^{61})_s$ NR$^{20}$CONR$^{89}$R$^{82}$;
—$(CH_2)_o(CHR^{61})_sCOOR^{89}$; —$(CH_2)_o(CHR^{61})_s$ CONR$^{89}$R$^{59}$;
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_s$ C$_6$H$_4$R$^8$;

R$^{16}$ is lower alkyl; lower alkenyl; —$(CH_2)_o(CHR^{61})_sOR^{55}$;
—$(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_s$ NR$^{20}$CONR$^{33}$R$^{82}$;
—$(CH_2)_o(CHR^{61})_sCOOR^{57}$; —$(CH_2)_o(CHR^{61})_s$ CONR$^{58}$R$^{59}$;
—$(CH_2)_o(CHR^{61})_sPO(OR^{60})_2$;
—$(CH_2)_o(CHR^{61})_sSO_2R^{62}$;
R$^{89}$; —$(CH_2)_o(CHR^{61})_sOR^{89}$; —$(CH_2)_o(CHR^{61})_sSR^{89}$;
—$(CH_2)_o(CHR^{61})_sNR^{89}R^{34}$;
—$(CH_2)_o(CHR^{61})_sOCONR^{89}R^{75}$; —$(CH_2)_o(CHR^{61})_s$ NR$^{20}$CONR$^{89}$R$^{82}$;
—$(CH_2)_o(CHR^{61})_sCOOR^{89}$; —$(CH_2)_o(CHR^{61})_s$ CONR$^{89}$R$^{59}$;
—$(CH_2)_o(CHR^{61})_sPO(OR^{80})(OR^{89})$;
—$(CH_2)_o(CHR^{61})_sSO_2R^{89}$; or —$(CH_2)_o(CHR^{61})_s$ C$_6$H$_4$R$^8$;

R$^{17}$ is lower alkyl; lower alkenyl; —$(CH_2)_q(CHR^{61})_sOR^{55}$;
—$(CH_2)_q(CHR^{61})_sSR^{56}$;
—$(CH_2)_q(CHR^{61})_sNR^{33}R^{34}$;
—$(CH_2)_q(CHR^{61})_sOCONR^{33}R^{75}$; —$(CH_2)_q(CHR^{61})_s$ NR$^{20}$CONR$^{33}$R$^{82}$;
—$(CH_2)_q(CHR^{61})_sCOOR^{57}$; —$(CH_2)_q(CHR^{61})_s$ CONR$^{58}$R$^{59}$;
—$(CH_2)_q(CHR^{61})_sPO(OR^{60})_2$;
—$(CH_2)_q(CHR^{61})_sSO_2R^{62}$;
R$^{89}$; —$(CH_2)_q(CHR^{61})_sOR^{89}$; —$(CH_2)_q(CHR^{61})_sSR^{89}$;
—$(CH_2)_q(CHR^{61})_sNR^{89}R^{34}$;
—$(CH_2)_q(CHR^{61})_sOCONR^{89}R^{75}$; —$(CH_2)_q(CHR^{61})_s$ NR$^{20}$CONR$^{89}$R$^{82}$;
—$(CH_2)_q(CHR^{61})_sCOOR^{89}$; —$(CH_2)_q(CHR^{61})_s$ CONR$^{89}$R$^{59}$;
—$(CH_2)_q(CHR^{61})_sPO(OR^{80})(OR^{89})$;
—$(CH_2)_q(CHR^{61})_sSO_2R^{89}$; or —$(CH_2)_q(CHR^{61})_s$ C$_6$H$_4$R$^8$;

R$^{18}$ is lower alkyl; lower alkenyl; —$(CH_2)_p(CHR^{61})_sOR^{55}$;
—$(CH_2)_p(CHR^{61})_sSR^{56}$;
—$(CH_2)_p(CHR^{61})_sNR^{33}R^{34}$;
—$(CH_2)_p(CHR^{61})_sOCONR^{33}R^{75}$; —$(CH_2)_p(CHR^{61})_s$ NR$^{20}$CONR$^{33}$R$^{82}$;
—$(CH_2)_p(CHR^{61})_sCOOR^{57}$; —$(CH_2)_p(CHR^{61})_s$ CONR$^{58}$R$^{59}$;
—$(CH_2)_p(CHR^{61})_sPO(OR^{60})_2$;
—$(CH_2)_p(CHR^{61})_sSO_2R^{62}$;
R$^{89}$; —$(CH_2)_p(CHR^{61})_sOR^{89}$; —$(CH_2)_p(CHR^{61})_sSR^{89}$;
—$(CH_2)_p(CHR^{61})_sNR^{89}R^{34}$;
—$(CH_2)_p(CHR^{61})_sOCONR^{89}R^{75}$; —$(CH_2)_p(CHR^{61})_s$ NR$^{20}$CONR$^{89}$R$^{82}$;
—$(CH_2)_p(CHR^{61})_sCOOR^{89}$; —$(CH_2)_p(CHR^{61})_s$ CONR$^{89}$R$^{59}$;
—$(CH_2)_p(CHR^{61})_sPO(OR^{80})(OR^{89})$;
—$(CH_2)_p(CHR^{61})_sSO_2R^{89}$; or —$(CH_2)_o(CHR^{61})_s$ C$_6$H$_4$R$^8$;

R$^{19}$ is lower alkyl; lower alkenyl; —$(CH_2)_p(CHR^{61})_sOR^{55}$;
—$(CH_2)_p(CHR^{61})_sSR^{58}$;
—$(CH_2)_p(CHR^{61})_sNR^{33}R^{34}$;
—$(CH_2)_p(CHR^{61})_sOCONR^{33}R^{75}$; —$(CH_2)_p(CHR^{61})_s$ NR$^{20}$CONR$^{33}$R$^{82}$;
—$(CH_2)_p(CHR^{61})_sCOOR^{57}$; —$(CH_2)_p(CHR^{61})_s$ CONR$^{58}$R$^{59}$;
—$(CH_2)_p(CHR^{61})_sPO(OR^{60})_2$;
—$(CH_2)_p(CHR^{61})_sSO_2R^{62}$;
R$^{89}$; —$(CH_2)_p(CHR^{61})_sOR^{89}$; —$(CH_2)_p(CHR^{61})_sSR^{89}$;
—$(CH_2)_p(CHR^{61})_sNR^{89}R^{34}$;
—$(CH_2)_p(CHR^{61})_sOCONR^{89}R^{75}$; —$(CH_2)_p(CHR^{61})_s$ NR$^{20}$CONR$^{89}$R$^{82}$;
—$(CH_2)_p(CHR^{61})_sCOOR^{89}$; —$(CH_2)_p(CHR^{61})_s$ CONR$^{89}$R$^{59}$;
—$(CH_2)_p(CHR^{61})_sPO(OR^{60})(OR^{89})$;
—$(CH_2)_p(CHR^{61})_sSO_2R^{89}$; or —$(CH_2)_o(CHR^{61})_s$ C$_6$H$_4$R$^8$; or R$^{18}$ and R$^{19}$ taken together can form: —$(CH_2)_{2-6}$—;
—$(CH_2)_2O(CH_2)_2$—; —$(CH_2)_2S(CH_2)_2$—; —$(CH_2)_2$ NR$^{57}$(CH$_2$)$_2$—;
—$(CH_2)_2NR^{89}(CH_2)_2$—;

R$^{20}$ is H; alkyl; alkenyl; or R$^{89}$;

R$^{21}$ is H; lower alkyl; lower alkenyl; —$(CH_2)_o(CHR^{61})_sOR^{55}$;
—$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s$ NR$^{20}$CONR$^{33}$R$^{82}$;
—$(CH_2)_o(CHR^{61})_sCOOR^{57}$; —$(CH_2)_o(CHR^{61})_s$ CONR$^{58}$R$^{59}$;
—$(CH_2)_o(CHR^{61})_sPO(OR^{60})_2$;
—$(CH_2)_o(CHR^{61})_sSO_2R^{82}$;
R$^{89}$; —$(CH_2)_o(CHR^{61})_sOR^{89}$;
—$(CH_2)_o(CHR^{61})_sSR^{89}$; —$(CH_2)_o(CHR^{61})_sNR^{89}R^{34}$;
—$(CH_2)_o(CHR^{61})_sOCONR^{89}R^{75}$; —$(CH_2)_o(CHR^{61})_s$ NR$^{20}$CONR$^{89}$R$^{82}$;
—$(CH_2)_o(CHR^{61})_sCOOR^{89}$; —$(CH_2)_o(CHR^{61})_s$ CONR$^{89}$R$^{59}$;
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_s$ C$_6$H$_4$R$^8$;

R$^{22}$ is H lower alkyl; lower alkenyl; —$(CH_2)_o(CHR^{61})_sOR^{55}$;
—$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s$ NR$^{20}$CONR$^{33}$R$^{82}$;
—$(CH_2)_o(CHR^{61})_sCOOR^{57}$; —$(CH_2)_o(CHR^{61})_s$ CONR$^{58}$R$^{59}$;
—$(CH_2)_o(CHR^{61})_sPO(OR^{60})_2$;
—$(CH_2)_o(CHR^{61})_sSO_2R^{82}$;
R$^{89}$; —$(CH_2)_o(CHR^{61})_sOR^{89}$;
—$(CH_2)_o(CHR^{61})_sSR^{89}$; —$(CH_2)_o(CHR^{61})_sNR^{89}R^{34}$;
—$(CH_2)_o(CHR^{61})_sOCONR^{89}R^{75}$; —$(CH_2)_o(CHR^{61})_s$ NR$^{20}$CONR$^{89}$R$^{82}$;
—$(CH_2)_o(CHR^{61})_sCOOR^{89}$; —$(CH_2)_o(CHR^{61})_s$ CONR$^{89}$R$^{59}$;
—$(CH_2)_o(CHR^{61})_sPO(OR^{80})(OR^{89})$;
—$(CH_2)_o(CHR^{61})_sSO_2R^{89}$; or —$(CH_2)_o(CHR^{61})_s$ C$_6$H$_4$R$^8$;

R$^{23}$ is lower alkyl; lower alkenyl; —$(CH_2)_o(CHR^{61})_sOR^{55}$;
—$(CH_2)_o(CHR^{61})_sSR^{58}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_s$ NR$^{20}$CONR$^{33}$R$^{82}$;
—$(CH_2)_o(CHR^{61})_sCOOR^{57}$; —$(CH_2)_o(CHR^{61})_s$ CONR$^{58}$R$^{59}$;
—$(CH_2)_o(CHR^{61})_sPO(OR^{60})_2$;
—$(CH_2)_o(CHR^{61})_sSO_2R^{62}$;
R$^{89}$; —$(CH_2)_o(CHR^{61})_sOR^{89}$; —$(CH_2)_o(CHR^{61})_sSR^{89}$;
—$(CH_2)_o(CHR^{61})_sNR^{89}R^{34}$;
—$(CH_2)_o(CHR^{61})_sOCONR^{89}R^{75}$; —$(CH_2)_o(CHR^{61})_s$ NR$^{20}$CONR$^{89}$R$^{82}$;

—$(CH_2)_o(CHR^{61})_sCOOR^{89}$; —$(CH_2)_o(CHR^{61})_s$
CONR$^{89}$R$^{59}$;
—$(CH_2)_o(CHR^{61})_sPO(OR^{80})(OR^{89})$;
—$(CH_2)_o(CHR^{61})_sSO_2R^{89}$; or —$(CH_2)_o(CHR^{61})_s$
C$_6$H$_4$R$^8$;

R$^{24}$ is lower alkyl; lower alkenyl; —$(CH_2)_o(CHR^{61})_sOR^{55}$;
 —$(CH_2)_o(CHR^{61})_sSR^{58}$;
 —$(CH_2)_o(CHR^{61})_sNR^{33}R^{34}$;
 —$(CH_2)_o(CHR^{61})_sOCONR^{33}R^{75}$; —$(CH_2)_o(CHR^{61})_s$
 NR$^{20}$CONR$^{33}$R$^{82}$;
 —$(CH_2)_o(CHR^{61})_sCOOR^{57}$; —$(CH_2)_o(CHR^{61})_s$
 CONR$^{58}$R$^{59}$;
 —$(CH_2)_o(CHR^{61})_sPO(OR^{60})_2$;
 —$(CH_2)_o(CHR^{61})_sSO_2R^{82}$;
 R$^{89}$; —$(CH_2)_o(CHR^{61})_sOR^{89}$;
 —$(CH_2)_o(CHR^{61})_sSR^{89}$;
 —$(CH_2)_o(CHR^{61})_sNR^{89}R^{34}$;
 —$(CH_2)_o(CHR^{61})_sOCONR^{89}R^{75}$; —$(CH_2)_o(CHR^{61})_s$
 NR$^{20}$CONR$^{89}$R$^{82}$;
 —$(CH_2)_o(CHR^{61})_sCOOR^{89}$; —$(CH_2)_o(CHR^{61})_s$
 CONR$^{89}$R$^{59}$;
 —$(CH_2)_o(CHR^{61})_sPO(OR^{80})(OR^{89})$;
 —$(CH_2)_o(CHR^{61})_sSO_2R^{89}$; or —$(CH_2)_o(CHR^{61})_s$
 C$_6$H$_4$R$^8$;

R$^{25}$ is H; lower alkyl; lower alkenyl; —$(CH_2)_m(CHR^{61})_sR^{55}$;
 —$(CH_2)_m(CHR^{61})_sSR^{58}$;
 —$(CH_2)_m(CHR^{61})_sNR^{33}R^{34}$; —$(CH_2)_m(CHR^{61})_s$
 OCONR$^{33}$R$^{75}$;
 —$(CH_2)_m(CHR^{61})_sNR^{20}CONR^{33}R^{82}$; —$(CH_2)_o$
 $(CHR^{61})_s$ COOR$^{57}$;
 —$(CH_2)_o(CHR^{61})_sCONR^{58}R^{59}$; —$(CH_2)_o(CHR^{61})_sPO$
 (OR$^{60}$)$_2$;
 —$(CH_2)_o(CHR^{61})_sSO_2R^{62}$;
 R$^{89}$; —$(CH_2)_m(CHR^{61})_sOR^{89}$;
 —$(CH_2)_m(CHR^{61})_sSR^{89}$;
 —$(CH_2)_m(CHR^{61})_sNR^{89}R^{34}$; —$(CH_2)_m(CHR^{61})_s$
 OCONR$^{89}$R$^{75}$;
 —$(CH_2)_m(CHR^{61})_sNR^{20}CONR^{89}R^{82}$; —$(CH_2)_o$
 $(CHR^{61})_s$ COOR$^{89}$;
 —$(CH_2)_o(CHR^{61})_sCONR^{89}R^{59}$; —$(CH_2)_o(CHR^{61})_sPO$
 (OR$^{60}$)(OR$^{89}$);
 —$(CH_2)_o(CHR^{61})_sSO_2R^{89}$; or —$(CH_2)_o(CHR^{61})_s$
 C$_6$H$_4$R$^8$;

R$^{26}$ is H; lower alkyl; lower alkenyl; —$(CH_2)_m(CHR^{61})_s$
 OR$^{55}$;
 —$(CH_2)_m(CHR^{61})_sSR^{56}$;
 —$(CH_2)_m(CHR^{61})_sNR^{33}R^{34}$; —$(CH_2)_m(CHR^{61})_s$
 OCONR$^{33}$R$^{75}$;
 —$(CH_2)_m(CHR^{61})_sNR^{20}CONR^{33}R^{82}$; —$(CH_2)_o$
 $(CHR^{61})_s$ COOR$^{57}$;
 —$(CH_2)_o(CHR^{61})_sCONR^{58}R^{59}$; —$(CH_2)_o(CHR^{61})_sPO$
 (OR$^{60}$)$_2$;
 —$(CH_2)_o(CHR^{61})_sSO_2R^{62}$;
 R$^{89}$; —$(CH_2)_m(CHR^{61})_sOR^{89}$;
 —$(CH_2)_m(CHR^{61})_sSR^{89}$;
 —$(CH_2)_m(CHR^{61})_sNR^{89}R^{34}$; —$(CH_2)_m(CHR^{61})_s$
 OCONR$^{89}$R$^{75}$;
 —$(CH_2)_m(CHR^{61})_sNR^{20}CONR^{89}R^{82}$; —$(CH_2)_o$
 $(CHR^{61})_s$ COOR$^{89}$;
 —$(CH_2)_o(CHR^{61})_sCONR^{89}R^{59}$; —$(CH_2)_o(CHR^{61})_sPO$
 (OR$^{60}$)(OR$^{89}$);
 —$(CH_2)_o(CHR^{61})_sSO_2R^{89}$; —$(CH_2)_o(CHR^{61})_sC_6H_4R^8$;
 or
R$^{25}$ and R$^{26}$ taken together can form: —$(CH_2)_{2\text{-}6}$—;
 —$(CH_2)_r$ O$(CH_2)_r$;

—$(CH_2)_rS(CH_2)_r$—; —$(CH_2)_rNR^{57}(CH_2)_m$—; or
 —$(CH_2)_rNR^{89}(CH_2)_r$—;

R$^{27}$ is H; lower alkyl; lower alkenyl; —$(CH_2)_o(CHR^{61})_s$
 OR$^{55}$;
 —$(CH_2)_o(CHR^{61})_sSR^{56}$; —$(CH_2)_o(CHR^{61})_sNR^{33}R^{34}$;
 —$(CH_2)_o(CHR^{61})_sCOOR^{57}$; —$(CH_2)_o(CHR^{61})_s$
 ONR$^{58}$R$^{59}$;
 —$(CH_2)_o(CHR^{61})_sOCONR^{33}R^{75}$;
 —$(CH_2)_o(CHR^{61})_sNR^{20}CONR^{33}R^{82}$; —$(CH_2)_o(CHR^{61})_s$
 PO(OR$^{60}$)$_2$;
 —$(CH_2)_o(CHR^{61})_sSO_2R^{62}$;
 R$^{89}$; —$(CH_2)_o(CHR^{61})_sOR^{89}$;
 —$(CH_2)_o(CHR^{61})_sSR^{89}$; —$(CH_2)_o(CHR^{61})_sNR^{89}R^{34}$;
 —$(CH_2)_o(CHR^{61})_sCOOR^{89}$; —$(CH_2)_o(CHR^{61})_s$
 CONR$^{89}$R$^{59}$;
 —$(CH_2)_o(CHR^{61})_sOCONR^{89}R^{75}$;
 —$(CH_2)_o(CHR^{61})_sNR^{20}CONR^{89}R^{82}$; —$(CH_2)_o(CHR^{61})_s$
 PO(OR$^{60}$)(OR$^{89}$);
 —$(CH_2)_o(CHR^{61})_sSO_2R^{89}$; or —$(CH_2)_o(CHR^{61})_s$
 C$_6$H$_4$R$^8$;

R$^{28}$ is lower alkyl; lower alkenyl; —$(CH_2)_o(CHR^{61})_s$—
 OR$^{55}$;
 —$(CH_2)_o(CHR^{61})_sSR^{56}$;
 —$(CH_2)_o(CHR^{61})_sNR^{33}R^{34}$;
 —$(CH_2)_o(CHR^{61})_sOCONR^{33}R^{75}$; —$(CH_2)_o(CHR^{61})_s$
 NR$^{20}$CONR$^{33}$R$^{82}$;
 —$(CH_2)_o(CHR^{61})_sCOOR^{57}$; —$(CH_2)_o(CHR^{61})_s$
 CONR$^{58}$R$^{59}$;
 —$(CH_2)_o(CHR^{61})_sPO(OR^{60})_2$;
 —$(CH_2)_o(CHR^{61})_sSO_2R^{62}$;
 R$^{89}$; —$(CH_2)_o(CHR^{61})_s$—OR$^{89}$;
 —$(CH_2)_o(CHR^{61})_sSR^{89}$;
 —$(CH_2)_o(CHR^{61})_sNR^{89}R^{34}$;
 —$(CH_2)_o(CHR^{61})_sOCONR^{89}R^{75}$; —$(CH_2)_o(CHR^{61})_s$
 NR$^{20}$CONR$^{89}$R$^{82}$;
 —$(CH_2)_o(CHR^{61})_sCOOR^{89}$; —$(CH_2)_o(CHR^{61})_s$
 CONR$^{89}$R$^{59}$;
 —$(CH_2)_o(CHR^{61})_sPO(OR^{60})(OR^{89})$;
 —$(CH_2)_o(CHR^{61})_sSO_2R^{89}$; or —$(CH_2)_o(CHR^{61})_s$
 C$_6$H$_4$R$^8$;

R$^{29}$ is lower alkyl; lower alkenyl; —$(CH_2)_o(CHR^{61})_sOR^{55}$;
 —$(CH_2)_o(CHR^{61})_sSR^{56}$;
 —$(CH_2)_o(CHR^{61})_sNR^{33}R^{34}$;
 —$(CH_2)_o(CHR^{61})_sOCONR^{33}R^{75}$; —$(CH_2)_o(CHR^{61})_s$
 NR$^{20}$CONR$^{33}$R$^{82}$;
 —$(CH_2)_o(CHR^{61})_sCOOR^{57}$; —$(CH_2)_o(CHR^{61})_s$
 CONR$^{58}$R$^{59}$;
 —$(CH_2)_o(CHR^{61})_sPO(OR^{60})_2$;
 —$(CH_2)_o(CHR^{61})_sSO_2R^{62}$;
 R$^{89}$; —$(CH_2)_o(CHR^{61})_sOR^{89}$; —$(CH_2)_o(CHR^{61})_sSR^{896}$;
 —$(CH_2)_o(CHR^{61})_sNR^{89}R^{34}$;
 —$(CH_2)_o(CHR^{61})_sOCONR^{89}R^{75}$; —$(CH_2)_o(CHR^{61})_s$
 NR$^{20}$CONR$^{89}$R$^{82}$;
 —$(CH_2)_o(CHR^{61})_sCOOR^{89}$; —$(CH_2)_o(CHR^{61})_s$
 CONR$^{89}$R$^{59}$;
 —$(CH_2)_o(CHR^{61})_sPO(OR^{60})(OR^{89})$;
 —$(CH_2)_o(CHR^{61})_sSO_2R^{89}$; or —$(CH_2)_o(CHR^{61})_s$
 C$_6$H$_4$R$^8$ R$^{33}$ is H; lower alkyl; lower alkenyl; —$(CH_2)_m(CHR^{61})_s$
 OR$^{55}$;
 —$(CH_2)_m(CHR^{61})_sNR^{34}R^{63}$;
 —$(CH_2)_m(CHR^{61})_sOCONR^{75}R^{82}$; —$(CH_2)_m(CHR^{61})_s$
 NR$^{20}$CONR$^{78}$R$^{82}$;
 —$(CH_2)_m(CHR^{61})_sCOR^{64}$; —$(CH_2)_o(CHR^{61})_s$—
 CONR$^{58}$R$^{59}$, —$(CH_2)_o(CHR^{61})_sPO(OR^{60})_2$;
 —$(CH_2)_o(CHR^{61})_sSO_2R^{62}$;
 R$^{89}$; —$(CH_2)_m(CHR^{61})_sOR^{89}$;

—$(CH_2)_m(CHR^{61})_sNR^{34}R^{89}$;
—$(CH_2)_m(CHR^{61})_sOCONR^{89}R^{75}$; —$(CH_2)_m(CHR^{61})_s$ NR$^{20}$CONR$^{89}$R$^{82}$;
—$(CH_2)_o(CHR^{61})_sCOR^{89}$; —$(CH_2)_o(CHR^{61})_s$— CONR$^{89}$R$^{59}$,
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_s$ C$_6$H$_4$R$^8$;

$R^{34}$ is H; lower alkyl; aryl, lower alkyl-aryl; aryl-lower alkyl; or $R^{33}$ and $R^{34}$ taken together can form: —$(CH_2)_{2-6}$—;
—$(CH_2)_2$—O—$(CH_2)_2$—; —$(CH_2)_2S(CH_2)_2$—;
—$(CH_2)_2$ NR$^{57}$(CH$_2$)$_2$—; or —$(CH_2)_2NR^{89}(CH_2)_2$—;

$R^{50}$ is H; lower alkyl; lower alkyl-aryl; or aryl-lower alkyl;

$R^{55}$ is H; lower alkyl; lower alkenyl; lower alkyl-aryl; aryl-lower alkyl;
—$(CH_2)_m(CHR^{61})_sOR^{57}$;
—$(CH_2)_m(CHR^{61})_sNR^{34}R^{83}$; —$(CH_2)_m(CHR^{61})_s$ OCONR$^{75}$R$^{82}$;
—$(CH_2)_m(CHR^{61})_sNR^{20}CONR^{78}R^{82}$; —$(CH_2)_o$ (CHR$^{61}$)$_s$—COR$^{64}$;
—$(CH_2)_o(CHR^{61})COOR^{57}$; or
—$(CH_2)_o(CHR^{61})_sCONR^{58}R^{59}$;

$R^{56}$ is H; lower alkyl; lower alkenyl; lower alkyl-aryl; aryl-lower alkyl;
—$(CH_2)_m(CHR^{61})_sOR^{57}$;
—$(CH_2)_m(CHR^{61})_sNR^{34}R^{83}$; —$(CH_2)_m(CHR^{61})_s$ OCONR$^{75}$R$^{82}$;
—$(CH_2)_m(CHR^{61})_sNR^{20}CONR^{78}R^{82}$; —$(CH_2)_o$ (CHR$^{61}$)$_s$—COR$^{64}$; or
—$(CH_2)_o(CHR^{61})_sCONR^{58}R^{59}$;

$R^{57}$ is H; lower alkyl; lower alkenyl; lower alkyl-aryl; lower alkyl-heteroaryl; aryl-lower alkyl; or heteroaryl-lower alkyl;

$R^{58}$ is H; lower alkyl; lower alkenyl; lower alkyl-aryl; lower alkyl-heteroaryl; aryl; aryl-lower alkyl; heteroaryl; or heteroaryl-lower alkyl;

$R^{59}$ is H; lower alkyl; lower alkenyl; lower alkyl-aryl; lower alkyl-heteroaryl; aryl; aryl-lower alkyl; heteroaryl; or heteroaryl-lower alkyl; or $R^{58}$ and $R^{59}$ taken together can form: —$(CH_2)_{2-6}$—;
—$(CH_2)_2O(CH_2)_2$—;
—$(CH_2)_2S(CH_2)_2$—; or
—$(CH_2)_2NR^{57}(CH_2)_2$—;

$R^{60}$ is H; t lower alkyl; lower alkenyl; lower alkyl-aryl; aryl-lower alkyl; aryl;

$R^{61}$ is alkyl; alkenyl; lower alkyl-aryl; lower alkyl-heteroaryl; aryl; aryl-lower alkyl; heteroaryl; heteroaryl-lower alkyl;
—$(CH_2)_pOR^{55}$; —$(CH_2)_pNR^{33}R^{34}$; —$(CH_2)_p$ OCONR$^{75}$R$^{82}$;
—$(CH_2)_pNR^{20}CONR^{78}R^{82}$; —$(CH_2)_oCOOR^{57}$; or
—$(CH_2)_oPO(OR^{60})_2$;

$R^{62}$ is lower alkyl; lower alkenyl; lower alkyl-aryl; lower alkyl-heteroaryl; aryl, aryl-lower alkyl; heteroaryl; or heteroaryl-lower alkyl;

$R^{63}$ is H; lower alkyl; lower alkenyl; lower alkyl-aryl; lower alkyl-heteroaryl; aryl, aryl-lower alkyl; heteroaryl; heteroaryl-lower alkyl;
—COR$^{64}$; —COOR$^{57}$; —CONR$^{58}$R$^{59}$; —SO$_2$R$^{62}$; or —PO(OR$^{60}$)$_2$; or $R^{34}$ and $R^{63}$ taken together can form: —$(CH_2)_{2-6}$—;
—$(CH_2)_2O(CH_2)_2$—;
—$(CH_2)_2S(CH_2)_2$—; or —$(CH_2)_2NR^{57}(CH_2)_2$—;

$R^{64}$ is H; lower alkyl; lower alkenyl; lower alkyl-aryl; lower alkyl-heteroaryl; aryl, aryl-lower alkyl; heteroaryl; heteroaryl-lower alkyl;
—$(CH_2)_p(CHR^{61})_sOR^{65}$; —$(CH_2)_p(CHR^{61})_sSR^{66}$;
—$(CH_2)_p(CHR^{61})_sNR^{34}R^{63}$;
—$(CH_2)_p(CHR^{61})_sOCONR^{75}R^{82}$; or —$(CH_2)_p(CHR^{61})_s$ NR$^{20}$CONR$^{78}$R$^{82}$;

$R^{65}$ is H; lower alkyl; lower alkenyl; lower alkyl-aryl; lower alkyl-heteroaryl; aryl, aryl-lower alkyl; heteroaryl; heteroaryl-lower alkyl;
—COR$^{57}$; —COOR$^{57}$; or —CONR$^{58}$R$^{59}$;

$R^{66}$ is H; lower alkyl; lower alkenyl; lower alkyl-aryl; lower alkyl-heteroaryl; aryl, aryl-lower alkyl; heteroaryl; heteroaryl-lower alkyl; or —CONR$^{58}$R$^{59}$;

$R^{67}$ is H; Cl; Br; F; NO$_2$; —NR$^{34}$COR$^{57}$; —CF$_3$; CN; —OCF$_3$; —OCHF$_2$;
—OR$^{57}$; —SR$^{62}$; lower alkyl; or lower alkenyl;

$R^{68}$ is H; Cl; Br; F; NO$_2$; —NR$^{34}$COR$^{57}$; —CF$_3$; CN; —OCF$_3$; —OCHF$_2$;
—OR$^{57}$; —SR$^{62}$; lower alkyl; or lower alkenyl;

$R^{69}$ is H; Cl; Br; F; NO$_2$; —NR$^{34}$COR$^{57}$; —CF$_3$; CN; —OCF$_3$; —OCHF$_2$;
—OR$^{57}$; —SR$^{62}$; lower alkyl; or lower alkenyl;

$R^{70}$ is H; Cl; Br; F; NO$_2$; —NR$^{34}$COR$^{57}$; —CF$_3$; CN; —OCF$_3$; —OCHF$_2$;
—OR$^{57}$; —SR$^{62}$; lower alkyl; or lower alkenyl;

$R^{74}$ is lower alkyl; lower alkenyl; —$(CH_2)_p(CHR^{61})_sOR^{75}$;
—$(CH_2)_p(CHR^{61})_sSR^{75}$;
—$(CH_2)_p(CHR^{61})_sNR^{33}R^{34}$; —$(CH_2)_p(CHR^{61})_s$ OCONR$^{33}$R$^{75}$;
—$(CH_2)_p(CHR^{61})_sNR^{20}CONR^{33}R^{82}$;
—$(CH_2)_o(CHR^{61})_sCOOR^{75}$; —$(CH_2)_pCONR^{58}R^{59}$;
—$(CH_2)_pPO(OR^{62})_2$;
—$(CH_2)_pSO_2R^{62}$; or
—$(CH_2)_o$—C$_6$R$^{67}$R$^{68}$R$^{69}$R$^{70}$R$^{76}$;

$R^{72}$ is alkyl; alkenyl; —$(CH_2)_p(CHR^{61})_sOR^{85}$; or
—$(CH_2)_p(CHR^{61})_sSR^{85}$;

$R^{73}$ is —$(CH_2)_oR^{77}$; —$(CH_2)_rO(CH_2)_oR^{77}$; —$(CH_2)_rS$ (CH$_2$)$_o$ R$^{77}$; or
—$(CH_2)_rNR^{20}(CH_2)_oR^{77}$;

$R^{74}$ is —$(CH_2)_pNR^{78}R^{79}$; —$(CH_2)_pNR^{77}R^{80}$; —$(CH_2)_pC$ (=NR$^{80}$)NR$^{78}$R$^{79}$;
—$(CH_2)_pC(=NOR^{50})NR^{78}R^{79}$;
—$(CH_2)_pC(=NNR^{78}R^{79})NR^{78}R^{79}$; —$(CH_2)_pNR^{80}$ (=NR$^{80}$)NR$^{78}$R$^{79}$;
—$(CH_2)_pN=C(NR^{78}R^{80})NR^{79}R^{80}$; —$(CH_2)_p$ C$_6$H$_4$NR$^{78}$R$^{79}$;
—$(CH_2)_pC_6H_4NR^{77}R^{80}$;
—$(CH_2)_pC_6H_4C(=NR$ NR$^{78}$R$^{79}$; —$(CH_2)_pC_6H_4C$ (=NOR$^{50}$NR$^{78}$R$^{79}$;
—$(CH_2)_pC_6H_4C(=NNR^{78}R^{79})NR^{78}R^{79}$; —$(CH_2)_p$ C$_6$H$_4$NR$^{80}$C(=NR$^{80}$)NR$^{78}$R$^{79}$;
—$(CH_2)_pC_6H_4N=C(NR^{78}R^{80})NR^{79}R^{80}$; —$(CH_2)_rO$ (CH$_2$)$_m$NR$^{78}$R$^{79}$;
—$(CH_2)_rO(CH_2)_mNR^{77}R^{80}$;
—$(CH_2)_rO(CH_2)_pC(=NR^{80})NR^{78}R^{79}$; —$(CH_2)_rO$ (CH$_2$)$_p$ C(=NOR$^{50}$)NR$^{78}$R$^{79}$;
—$(CH_2)_rO(CH_2)_pC(=NNR^{78}R^{79})NR^{78}R^{79}$;
—$(CH_2)_rO(CH_2)_mNR^{80}C(=NR^{80})NR^{78}R^{79}$;
—$(CH_2)_rO(CH_2)_mN=C(NR^{78}R^{80})NR^{79}R^{80}$;
—$(CH_2)_rO(CH_2)_pC_6H_4NR^{78}R^{79}$;
—$(CH_2)_rO(CH_2)_pC_6H_4C(=NR^{80})NR^{78}R^{79}$;
—$(CH_2)_rO(CH_2)_pC_6H_4C(=NOR^{50})NR^{78}R^{79}$;
—$(CH_2)_rO(CH_2)_pC_6H_4C(=NNR^{78}R^{79})NR^{78}R^{79}$;

—(CH$_2$)$_r$O(CH$_2$)$_p$C$_6$H$_4$NR$^{80}$C(=NR$^{80}$)NR$^{78}$R$^{79}$;
—(CH$_2$)$_r$S(CH$_2$)$_m$NR$^{78}$R$^{79}$;
—(CH$_2$)$_r$S(CH$_2$)$_m$NR$^{77}$R$^{80}$; —(CH$_2$)$_r$S(CH$_2$)$_p$C(=NR$^{80}$)NR$^{78}$R$^{79}$;
—(CH$_2$)$_r$S(CH$_2$)$_p$C(=NOR$^{50}$)NR$^{78}$R$^{79}$;
—(CH$_2$)$_r$S(CH$_2$)$_p$C(=NNR$^{78}$R$^{79}$)NR$^{78}$R$^{79}$;
—(CH$_2$)$_r$S(CH$_2$)$_m$NR$^{80}$C(=NR$^{80}$)NR$^{78}$R$^{79}$;
—(CH$_2$)$_r$S(CH$_2$)$_m$N=C(NR$^{78}$R$^{80}$)NR$^{79}$R$^{80}$;
—(CH$_2$)$_r$S(CH$_2$)$_p$C$_6$H$_4$CNR$^{78}$R$^{79}$; —(CH$_2$)$_r$S(CH$_2$)$_p$C$_6$H$_4$C(=NR$^{80}$)NR$^{78}$R$^{79}$;
—(CH$_2$)$_r$S(CH$_2$)$_p$C$_6$H$_4$C(=NOR$^{50}$)NR$^{78}$R$^{79}$;
—(CH$_2$)$_r$S(CH$_2$)$_p$C$_6$H$_4$C(=NNR$^{78}$R$^{79}$)NR$^{78}$R$^{79}$;
—(CH$_2$)$_r$S(CH$_2$)$_p$C$_6$H$_4$NR$^{80}$C(=NR$^{80}$)NR$^{78}$R$^{79}$;
—(CH$_2$)$_p$NR$^{80}$COR$^{64}$;
—(CH$_2$)$_p$NR$^{80}$COR$^{77}$;
—(CH$_2$)$_p$NR$^{80}$CONR$^{78}$R$^{79}$; or —(CH$_2$)$_p$C$_6$H$_4$NR$^{80}$CONR$^{78}$R$^{79}$;

R$^{75}$ is lower alkyl; lower alkenyl; or aryl-lower alkyl; or

R$^{33}$ and R$^{75}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; or R$^{75}$ and R$^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{76}$ is H; lower alkyl; lower alkenyl; lower alkyl-aryl; aryl-lower alkyl; —(CH$_2$)$_o$OR$^{72}$; —(CH$_2$)$_p$SR$^{72}$; —(CH$_2$)$_o$NR$^{33}$R$^{34}$; —(CH$_2$)$_o$OCONR$^{33}$R$^{75}$; —(CH$_2$)$_o$NR$^{20}$CONR$^{33}$R$^{81}$; —(CH$_2$)$_o$COOR$^{75}$; —(CH$_2$)$_p$CONR$^{58}$R$^{59}$; —(CH$_2$)$_p$PO(OR$^{60}$)$_2$; —(CH$_2$)$_p$SO$_2$R$^{62}$; or —(CH$_2$)$_o$COR$^{64}$;

R$^{77}$ is —C$_6$R$^{67}$R$^{68}$R$^{69}$R$^{70}$R$^{76}$ with the proviso that at least two of R$^{67}$, R$^{68}$, R$^{69}$ and R$^{70}$ are H; or a heteroaryl group of one of the formulae

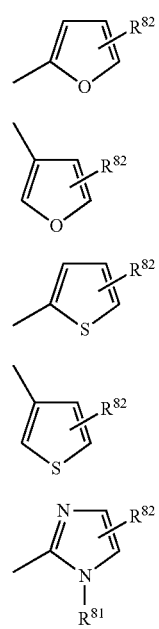

H1

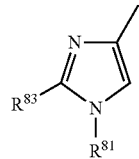 H6

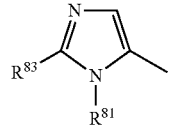 H7

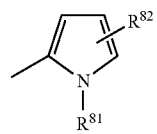 H8

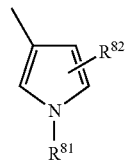 H9

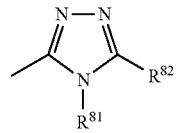 H10

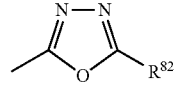 H11

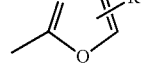 H12

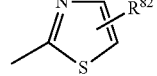 H13

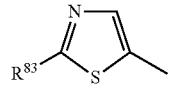 H14

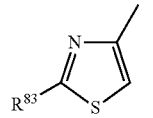 H15

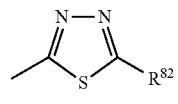 H16

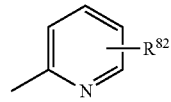 H17

| | |
|---|---|
| H18 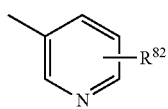 | H30 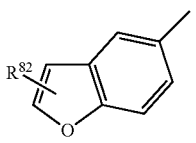 |
| H19 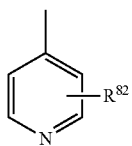 | H31 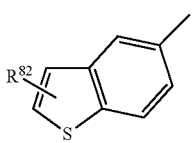 |
| H20 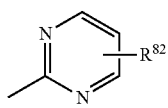 | H32 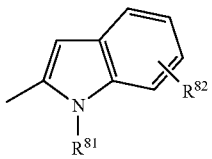 |
| H21 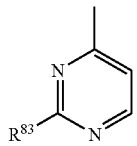 | H33 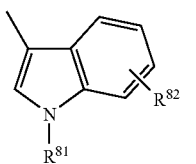 |
| H22 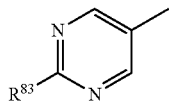 | H34 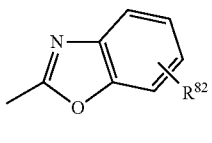 |
| H23 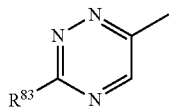 | H35 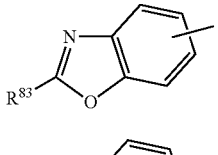 |
| H24 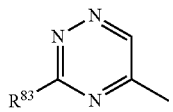 | H36 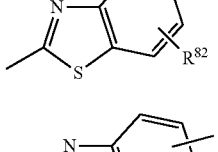 |
| H25 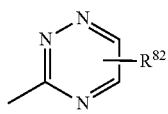 | H37 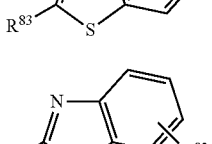 |
| H26 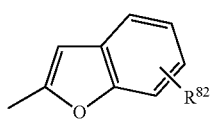 | H38 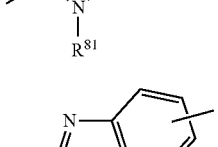 |
| H27 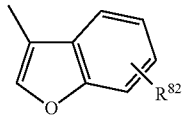 | H39 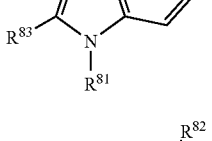 |
| H28 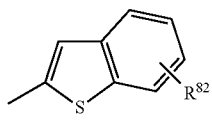 | H40 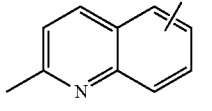 |
| H29 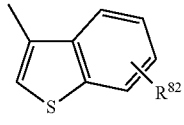 | |

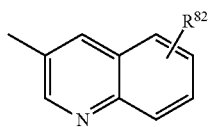
H41

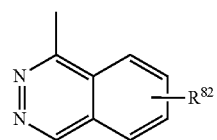
H51

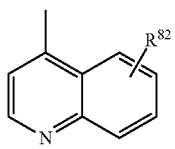
H42

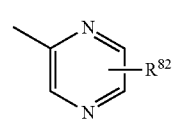
H52

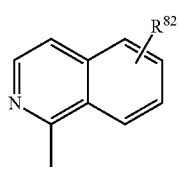
H43

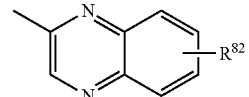
H53

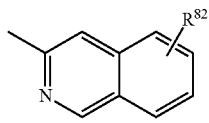
H44

H54

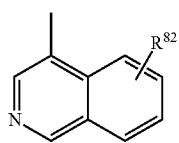
H45

H55

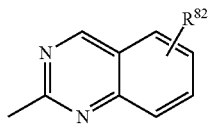
H46

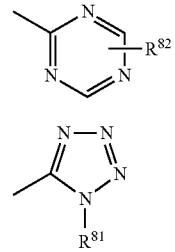

$R^{78}$ is H; lower alkyl; lower alkyl-aryl; aryl; or
  aryl-lower alkyl; or
$R^{78}$ and $R^{82}$ taken together can form: $-(CH_2)_{2-6}-$;
  $-(CH_2)_2O(CH_2)_2-$;
  $-(CH_2)_2S(CH_2)_2-$; or $-(CH_2)_2NR^{57}(CH_2)_2-$;
$R^{79}$ is H; lower alkyl; lower alkyl-aryl; aryl; or
  aryl-lower alkyl; or
$R^{78}$ and $R^{79}$, taken together, can be $-(CH_2)_{2-7}-$;
  $-(CH_2)_2O(CH_2)_2-$;
  or $-(CH_2)_2NR^{57}(CH_2)_2-$;
$R^{80}$ is H; or lower alkyl;
$R^{81}$ is H; lower alkyl; lower alkyl-aryl; aryl-lower alkyl; or
$R^{33}$ and $R^{81}$ taken together can form: $-(CH_2)_{2-6}-$;
  $-(CH_2)_2O(CH_2)_2-$;
  $-(CH_2)_2S(CH_2)_2-$; or $-(CH_2)_2NR^{57}(CH_2)_2-$;
$R^{82}$ is H; $-CF_3$; $-OCF_3$; $-OCHF_2$; lower alkyl;
  lower alkyl-aryl; lower alkyl-heteroaryl; aryl;
  aryl-lower alkyl; heteroaryl; heteroaryl-lower alkyl;
$R^{83}$ is H; lower alkyl; aryl; or $-NR^{78}R^{79}$;
$R^{84}$ is $-(CH_2)_p(CHR^{61})_sOH$; $-(CH_2)pCOOR^{80}$; $-(CH_2)_p(CHR^{61})_sSH$;
  $-(CH_2)_pCONR^{78}R^{79}$; $-(CH_2)_pNR^{80}CONR^{78}R^{79}$;
  $-(CH_2)_pC_6H_4CONR^{78}R^{79}$;
  or $-(CH_2)_pC_6H_4NR^{80}CONR^{78}R^{79}$;
$R^{85}$ is lower alkyl; or lower alkenyl;
$R^{86}$ is $R^{74}$; $-(CH_2)_oR^{77}$; $-(CH_2)_o-CHR^{33}R^{75}$; $R^{84}$;
  $-[(CH_2)_u-X']_t-(CH_2)_vNR^{78}R^{79}$;
  $-[(CH_2)_u-X']_t-(CH_2)_v-C(=NR^{80})NR^{78}R^{79}$;
  $-[(CH_2)_u-X']_t-(CH_2)_vOR^{78}$; $-[(CH_2)_u-X']_t-(CH_2)_v-CONR^{78}R^{79}$;
  $-[(CH_2)_u-X']_t-(CH_2)_v-NR^{80}CONR^{78}R^{79}$;
  $-[(CH_2)_u-X']_t-(CH_2)_vSR^{78}$
  where X' is $-O-$, $-NR^{20}-$, $-S-$; or $-OCOO-$, u is
  1-3, t is 1-6, and v is 1-3;
$R^{87}$ is fatty alkyl; fatty alkyl-$OR^{65}$; fatty alkyl-$SR^{66}$;
  fatty alkyl-$NR^{78}R^{92}$; fatty alkyl-$OCONR^{75}R^{92}$;

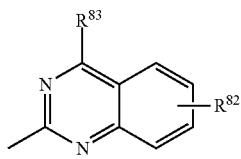
H47

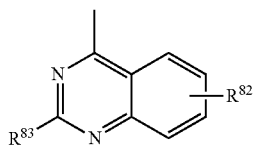
H48

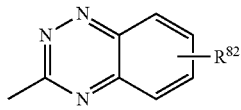
H49

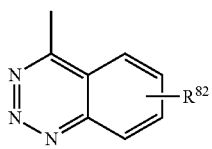
H50 fatty alkyl-NR$^{34}$CONR$^{78}$R$^{92}$;
fatty alkyl-COOR$^{80}$; fatty alkyl-CONR$^{75}$R$^{92}$;
fatty alkenyl; fatty alkenyl-OR$^{65}$; fatty alkenyl-SR$^{66}$;
fatty alkenyl-NR$^{78}$R$^{92}$; fatty alkenyl-OCONR$^{75}$R$^{92}$;
fatty alkenyl-NR$^{34}$CONR$^{78}$R$^{92}$;
fatty alkenyl-COOR$^{80}$; fatty alkenyl-CONR$^{75}$R$^{92}$;
fatty alkyl-aryl; fatty alkyl-aryl-OR$^{65}$;
fatty alkyl-aryl-SR$^{66}$;
fatty alkyl-aryl-NR$^{78}$R$^{92}$; fatty alkyl-aryl-OCONR$^{75}$R$^{92}$;
fatty alkyl-aryl-NR$^{34}$CONR$^{78}$R$^{92}$;
fatty alkyl-aryl-COOR$^{80}$; fatty alkyl-aryl-CONR$^{75}$R$^{92}$;
fatty alkyl-heteroaryl; fatty alkyl-heteroaryl-OR$^{65}$;
fatty alkyl-heteroaryl-SR$^{66}$;
fatty alkyl-heteroaryl-NR$^{78}$R$^{82}$;
fatty alkyl-heteroaryl-OCONR$^{75}$R$^{92}$;
fatty alkyl-heteroaryl-NR$^{34}$CONR$^{78}$R$^{92}$;
fatty alkyl-heteroaryl-COOR$^{80}$;
fatty alkyl-heteroaryl-CONR$^{75}$R$^{92}$;
fatty alkenyl-aryl; fatty alkenyl-aryl-OR$^{65}$;
fatty alkenyl-aryl-SR$^{66}$;
fatty alkenyl-aryl-NR$^{78}$R$^{82}$;
fatty alkenyl-aryl-OCONR$^{75}$R$^{92}$;
fatty alkenyl-aryl-NR$^{34}$CONR$^{78}$R$^{92}$;
fatty alkenyl-aryl-COOR$^{80}$;
fatty alkenyl-aryl-CONR$^{75}$R$^{92}$;
fatty alkenyl-heteroaryl;
fatty alkenyl-heteroaryl-OR$^{65}$;
fatty alkenyl-heteroaryl-SR$^{66}$;
fatty alkenyl-heteroaryl-NR$^{78}$R$^{82}$;
fatty alkenyl-heteroaryl-OCONR$^{75}$R$^{92}$;
fatty alkenyl-heteroaryl-NR$^{34}$CONR$^{78}$R$^{92}$;
fatty alkenyl-heteroaryl-COOR$^{80}$;
fatty alkenyl-heteroaryl-CONR$^{75}$R$^{92}$;
aryl-fatty alkyl; aryl-fatty alkyl-OR$^{65}$;
aryl-fatty alkyl-SR$^{66}$;
aryl-fatty alkyl-NR$^{78}$R$^{82}$; aryl-fatty alkyl-OCONR$^{75}$R$^{92}$;
aryl-fatty alkyl-NR$^{34}$CONR$^{78}$R$^{92}$;
aryl-fatty alkyl-COOR$^{80}$;
aryl-fatty alkyl-CONR$^{75}$R$^{92}$;
aryl-fatty alkenyl; aryl-fatty alkenyl-OR$^{65}$;
aryl-fatty alkyenl-SR$^{66}$;
aryl-fatty alkenyl-NR$^{78}$R$^{82}$;
aryl-fatty alkenyl-OCONR$^{75}$R$^{92}$;
aryl-fatty alkenyl-NR$^{34}$CONR$^{78}$R$^{92}$;
aryl-fatty alkenyl-COOR$^{80}$;
aryl-fatty alkenyl-CONR$^{75}$R$^{92}$;
heteroaryl-fatty alkyl; heteroaryl-fatty alkyl-OR$^{65}$;
heteroaryl-fatty alkyl-SR$^{66}$;
heteroaryl-fatty alkyl-NR$^{78}$R$^{82}$;
heteroaryl-fatty alkyl-OCONR$^{75}$R$^{92}$;
heteroaryl-fatty alkyl-NR$^{34}$CONR$^{78}$R$^{92}$;
heteroaryl-fatty alkyl-COOR$^{80}$;
heteroaryl-fatty alkyl-CONR$^{75}$R$^{92}$;
heteroaryl-fatty alkenyl;
heteroaryl-fatty alkenyl-OR$^{65}$;
heteroaryl-fatty alkenyl-SR$^{66}$;
heteroaryl-fatty alkenyl-NR$^{78}$R$^{82}$;
heteroaryl-fatty alkenyl-OCONR$^{75}$R$^{92}$;
heteroaryl-fatty alkenyl-NR$^{34}$CONR$^{78}$R$^{92}$;
heteroaryl-fatty alkenyl-COOR$^{80}$;
heteroaryl-fatty alkenyl-CONR$^{75}$R$^{92}$;
adamantyl;
—(CH$_2$)$_p$(CHR$^{61}$)$_s$OR$^{89}$; —(CH$_2$)$_p$(CHR$^{61}$)$_s$SR$^{89}$;
—(CH$_2$)$_o$R$^{91}$; —(CH$_2$)$_r$O(CH$_2$)$_o$R$^{91}$; —(CH$_2$)$_r$S(CH$_2$)$_o$R$^{91}$
—(CH$_2$)$_r$NR$^{20}$(CH$_2$)$_o$R$^{91}$;

—(CH$_2$)$_p$NR$^{88}$R$^{79}$; —(CH$_2$)$_p$NR$^{77}$R$^{88}$; —(CH$_2$)$_p$C(=NR$^{80}$)NR$^{88}$R$^{79}$;
—(CH$_2$)$_p$C(=NOR$^{50}$)NR$^{88}$R$^{79}$;
—(CH$_2$)$_p$C(=NNR$^{78}$R$^{79}$)NR$^{78}$R$^{79}$; —(CH$_2$)$_p$NR$^{80}$C(=NR$^{80}$)NR$^{88}$R$^{79}$;
—(CH$_2$)$_p$N=C(NR$^{88}$R$^{80}$)NR$^{79}$R$^{80}$; —(CH$_2$)$_p$N=C(NR$^{78}$R$^{80}$)NR$^{79}$R$^{88}$;
—(CH$_2$)$_p$C$_6$H$_4$NR$^{88}$R$^{79}$; —(CH$_2$)$_p$C$_6$H$_4$NR$^{77}$R$^{88}$;
—(CH$_2$)$_p$C$_6$H$_4$C(=NR NR$^{88}$R$^{79}$; —(CH$_2$)$_p$C$_6$H$_4$C(=NOR$^{50}$)NR$^{88}$R$^{79}$;
—(CH$_2$)$_p$C$_6$H$_4$C(=NNR$^{78}$R$^{79}$)NR$^{78}$R$^{79}$; —(CH$_2$)$_p$C$_6$H$_4$NR$^{80}$C(=NR$^{80}$)NR$^{78}$R$^{79}$;
—(CH$_2$)$_p$C$_6$H$_4$N=C(NR$^{88}$R$^{80}$)NR$^{79}$R$^{80}$; —(CH$_2$)$_p$C$_6$H$_4$N=C(NR$^{78}$R$^{80}$)NR$^{79}$R$^{88}$;
—(CH$_2$)$_r$O(CH$_2$)$_m$NR$^{88}$R$^{79}$; —(CH$_2$)$_r$O(CH$_2$)$_m$NR$^{77}$R$^{88}$;
—(CH$_2$)$_r$O(CH$_2$)$_p$C(=NR$^{88}$)NR$^{78}$R$^{79}$; —(CH$_2$)$_r$O(CH$_2$)$_p$C(=NR$^{80}$)NR$^{88}$R$^{79}$;
—(CH$_2$)$_r$O(CH$_2$)$_p$C(=NOR$^{50}$)NR$^{88}$R$^{79}$;
—(CH$_2$)$_r$O(CH$_2$)$_p$C(=NNR$^{88}$R$^{79}$)NR$^{78}$R$^{79}$;
—(CH$_2$)$_r$O(CH$_2$)$_p$C(=NNR$^{78}$R$^{79}$)NR$^{88}$R$^{79}$;
—(CH$_2$)$_r$O(CH$_2$)$_m$NR$^{88}$C(=NR$^{80}$)NR$^{78}$R$^{79}$;
—(CH$_2$)$_r$O(CH$_2$)$_m$NR$^{80}$C(=NR$^{80}$)NR$^{88}$R$^{79}$;
—(CH$_2$)$_r$O(CH$_2$)$_m$N=C(NR$^{88}$R$^{80}$)NR$^{79}$R$^{80}$;
—(CH$_2$)$_r$O(CH$_2$)$_m$N=C(NR$^{78}$R$^{80}$)NR$^{79}$R$^{88}$; —(CH$_2$)$_r$O(CH$_2$)$_p$C$_6$H$_4$CNR$^{88}$R$^{79}$;
—(CH$_2$)$_r$O(CH$_2$)$_p$C$_6$H$_4$C(=NR$^{80}$)NR$^{88}$R$^{79}$;
—(CH$_2$)$_r$O(CH$_2$)$_p$C$_6$H$_4$C(=NOR$^{50}$)NR$^{88}$R$^{79}$;
—(CH$_2$)$_r$O(CH$_2$)$_p$C$_6$H$_4$C(=NNR$^{88}$R$^{79}$)NR$^{78}$R$^{79}$;
—(CH$_2$)$_r$O(CH$_2$)$_p$C$_6$H$_4$C(=NNR$^{78}$R$^{79}$)NR$^{88}$R$^{79}$;
—(CH$_2$)$_r$O(CH$_2$)$_p$C$_6$H$_4$NR$^{88}$C(=NR$^{80}$)NR$^{78}$R$^{79}$;
—(CH$_2$)$_r$O(CH$_2$)$_p$C$_6$H$_4$NR$^{80}$C(=NR$^{80}$)NR$^{88}$R$^{79}$;
—(CH$_2$)$_r$S(CH$_2$)$_m$NR$^{88}$R$^{79}$;
—(CH$_2$)$_r$S(CH$_2$)$_m$NR$^{77}$R$^{88}$; —(CH$_2$)$_r$S(CH$_2$)$_p$C(=NR$^{80}$)NR$^{88}$R$^{79}$;
—(CH$_2$)$_r$S(CH$_2$)$_p$C(=NOR$^{50}$)NR$^{88}$R$^{79}$;
—(CH$_2$)$_r$S(CH$_2$)$_p$C(=NNR$^{88}$R$^{79}$)NR$^{78}$R$^{79}$;
—(CH$_2$)$_r$S(CH$_2$)$_p$C(=NNR$^{78}$R$^{79}$)NR$^{88}$R$^{79}$;
—(CH$_2$)$_r$S(CH$_2$)$_m$NR$^{88}$C(=NR$^{80}$)NR$^{78}$R$^{79}$;
—(CH$_2$)$_r$S(CH$_2$)$_m$NR$^{80}$C(=NR$^{80}$)NR$^{88}$R$^{79}$;
—(CH$_2$)$_r$S(CH$_2$)$_m$N=C(NR$^{88}$R$^{80}$)NR$^{79}$R$^{80}$;
—(CH$_2$)$_r$S(CH$_2$)$_m$N=C(NR$^{78}$R$^{80}$)NR$^{79}$R$^{88}$;
—(CH$_2$)$_r$S(CH$_2$)$_p$C$_6$H$_4$CNR$^{88}$R$^{79}$; —(CH$_2$)$_r$S(CH$_2$)$_p$C$_6$H$_4$C(=NR$^{80}$)NR$^{88}$R$^{79}$;
—(CH$_2$)$_r$S(CH$_2$)$_p$C$_6$H$_4$C(=NOR$^{50}$)NR$^{88}$R$^{79}$;
—(CH$_2$)$_r$S(CH$_2$)$_p$C$_6$H$_4$C(=NNR$^{88}$R$^{79}$)NR$^{78}$R$^{79}$;
—(CH$_2$)$_r$S(CH$_2$)$_p$C$_6$H$_4$C(=NNR$^{78}$R$^{79}$)NR$^{88}$R$^{79}$;
—(CH$_2$)$_r$S(CH$_2$)$_p$C$_6$H$_4$NR$^{88}$C(=NR$^{80}$)NR$^{78}$R$^{79}$;
—(CH$_2$)$_r$S(CH$_2$)$_p$C$_6$H$_4$NR$^{80}$C(=NR$^{80}$)NR$^{88}$R$^{79}$;
—(CH$_2$)$_p$COOR$^{89}$; —(CH$_2$)$_p$CONR$^{89}$R$^{79}$; —(CH$_2$)$_p$NR$^{80}$CONR$^{89}$R$^{79}$;
—(CH$_2$)$_p$C$_6$H$_4$CONR$^{89}$R$^{79}$; or —(CH$_2$)$_p$C$_6$H$_4$NR$^{80}$CONR$^{89}$R$^{79}$;

R$^{88}$ is —COR$^{89}$; —COOR$^{89}$; —CONR$^{34}$R$^{89}$;
—CO(CH$_2$)$_p$(CHCOOR$^{34}$)$_s$NR$^{34}$COR$^{89}$;
—CO(CH$_2$)$_p$(CHCOOR$^{34}$)$_s$NR$^{34}$COOR$^{89}$;
—CO(CH$_2$)$_p$(CHCONR$^{34}$)$_s$NR$^{34}$CONR$^{34}$R$^{89}$;
—COCHR$^{90}$NR$^{34}$COR$^{89}$;
—COCHR$^{90}$NR$^{34}$COOR$^{89}$;
—COCHR$^{90}$NR$^{34}$CONR$^{34}$R$^{89}$;
—CO(CH$_2$)$_p$(CHCONR$^{34}$)$_s$NR$^{34}$-choloyl;
—CO(CH$_2$)$_p$(CHCONR$^{34}$)$_s$NR$^{34}$-chenodeoxycholoyl;
—CO(CH$_2$)$_p$(CHCONR$^{34}$)$_s$NR$^{34}$-deoxycholoyl;
—SO$_2$(CH$_2$)$_p$(CHCONR$^{34}$)$_s$NR$^{34}$choloyl;
—[CO(CH$_2$)$_v$—[X'—(CH$_2$)$_u$]$_t$—NR$^{34}$]$_t$—R$^{88}$ where X' is —O—,
—NR$^{20}$—, —S—; or —OCOO—, t is 1-6, t' is 1-6, u is 1-3, and v is 1-3 with the proviso that R$^{88}$ in —[CO(CH$_2$)$_v$—[X'—(CH$_2$)$_u$]$_t$—NR$^{34}$]$_{t'}$—R$^{88}$ is not —[CO(CH$_2$)$_v$—[X'—(CH$_2$)$_u$]$_t$—NR$^{34}$]$_{t'}$—R$^{88}$;

R$^{89}$ is fatty alkyl; fatty alkyl-OR$^{65}$; fatty alkyl-SR$^{66}$;
  fatty alkyl-NR$^{78}$R$^{82}$; fatty alkyl-OCONR$^{75}$R$^{82}$;
  fatty alkyl-NR$^{34}$CONR$^{78}$R$^{82}$;
  fatty alkyl-COOR$^{80}$; fatty alkyl-CONR$^{75}$R$^{82}$;
  fatty alkenyl; fatty alkenyl-OR$^{65}$; fatty alkenyl-SR$^{66}$;
  fatty alkenyl-NR$^{78}$R$^{82}$; fatty alkenyl-OCONR$^{75}$R$^{82}$;
  fatty alkenyl-NR$^{34}$CONR$^{78}$R$^{82}$;
  fatty alkenyl-COOR$^{80}$; fatty alkenyl-CONR$^{75}$R$^{82}$;
  fatty alkyl-aryl; fatty alkyl-aryl-OR$^{65}$;
  fatty alkyl-aryl-SR$^{66}$;
  fatty alkyl-aryl-NR$^{78}$R$^{82}$; fatty alkyl-aryl-OCONR$^{75}$R$^{82}$;
  fatty alkyl-aryl-NR$^{34}$CONR$^{78}$R$^{82}$;
  fatty alkyl-aryl-COOR$^{80}$; fatty alkyl-aryl-CONR$^{75}$R$^{82}$;
  fatty alkyl-heteroaryl; fatty alkyl-heteroaryl-OR$^{65}$;
  fatty alkyl-heteroaryl-SR$^{66}$;
  fatty alkyl-heteroaryl-NR$^{78}$R$^{82}$;
  fatty alkyl-heteroaryl-OCONR$^{75}$R$^{92}$;
  fatty alkyl-heteroaryl-NR$^{34}$CONR$^{78}$R$^{92}$;
  fatty alkyl-heteroaryl-COOR$^{80}$;
  fatty alkyl-heteroaryl-CONR$^{75}$R$^{92}$;
  fatty alkenyl-aryl; fatty alkenyl-aryl-OR$^{65}$;
  fatty alkenyl-aryl-SR$^{66}$;
  fatty alkenyl-aryl-NR$^{78}$R$^{82}$;
  fatty alkenyl-aryl-OCONR$^{75}$R$^{92}$;
  fatty alkenyl-aryl-NR$^{34}$CONR$^{78}$R$^{92}$;
  fatty alkenyl-aryl-COOR$^{80}$;
  fatty alkenyl-aryl-CONR$^{75}$R$^{92}$;
  fatty alkenyl-heteroaryl;
  fatty alkenyl-heteroaryl-OR$^{65}$;
  fatty alkenyl-heteroaryl-SR$^{66}$;
  fatty alkenyl-heteroaryl-NR$^{78}$R$^{82}$;
  fatty alkenyl-heteroaryl-OCONR$^{75}$R$^{92}$;
  fatty alkenyl-heteroaryl-NR$^{34}$CONR$^{78}$R$^{92}$;
  fatty alkenyl-heteroaryl-COOR$^{80}$;
  fatty alkenyl-heteroaryl-CONR$^{75}$R$^{92}$;
  aryl-fatty alkyl; aryl-fatty alkyl-OR$^{65}$;
  aryl-fatty alkyl-SR$^{66}$;
  aryl-fatty alkyl-NR$^{78}$R$^{92}$; aryl-fatty alkyl-OCONR$^{75}$R$^{92}$;
  aryl-fatty alkyl-NR$^{34}$CONR$^{78}$R$^{92}$;
  aryl-fatty alkyl-COOR$^{80}$;
  aryl-fatty alkyl-CONR$^{75}$R$^{92}$;
  aryl-fatty alkenyl; aryl-fatty alkenyl-OR$^{65}$;
  aryl-fatty alkyenl-SR$^{66}$;
  aryl-fatty alkenyl-NR$^{78}$R$^{82}$;
  aryl-fatty alkenyl-OCONR$^{75}$R$^{92}$;
  aryl-fatty alkenyl-NR$^{34}$CONR$^{78}$R$^{92}$;
  aryl-fatty alkenyl-COOR$^{80}$;
  aryl-fatty alkenyl-CONR$^{75}$R$^{92}$;
  heteroaryl-fatty alkyl; heteroaryl-fatty alkyl-OR$^{65}$;
  heteroaryl-fatty alkyl-SR$^{66}$;
  heteroaryl-fatty alkyl-NR$^{78}$R$^{82}$;
  heteroaryl-fatty alkyl-OCONR$^{75}$R$^{92}$;
  heteroaryl-fatty alkyl-NR$^{34}$CONR$^{78}$R$^{92}$;
  heteroaryl-fatty alkyl-COOR$^{80}$;
  heteroaryl-fatty alkyl-CONR$^{75}$R$^{92}$;
  heteroaryl-fatty alkenyl;
  heteroaryl-fatty alkenyl-OR$^{65}$;
  heteroaryl-fatty alkenyl-SR$^{66}$;
  heteroaryl-fatty alkenyl-NR$^{78}$R$^{82}$;
  heteroaryl-fatty alkenyl-OCONR$^{75}$R$^{92}$;
  heteroaryl-fatty alkenyl-NR$^{34}$CONR$^{78}$R$^{92}$;
  heteroaryl-fatty alkenyl-COOR$^{80}$;
  heteroaryl-fatty alkenyl-CONR$^{75}$R$^{92}$;
  adamantyl;
  —C$_6$R$^{67}$R$^{68}$R$^{69}$R$^{70}$R$^{89}$; with the proviso that at least two of R$^{67}$, R$^{68}$, R$^{69}$ and R$^{70}$ are H, and with the further proviso that R$^{89}$ in —C$_6$R$^{67}$R$^{68}$R$^{69}$R$^{70}$R$^{89}$ is not —C$_6$R$^{67}$R$^{68}$R$^{69}$R$^{70}$R$^{89}$;

R$^{90}$ is —(CH$_2$)$_p$COOR$^{34}$; —(CH$_2$)$_p$CONR$^{34}$;
R$^{91}$ is —C$_6$R$^{67}$R$^{68}$R$^{69}$R$^{70}$R$^{89}$; —C$_6$R$^{67}$R$^{68}$R$^{69}$R$^{70}$OR$^{89}$; or —C$_6$R$^{67}$R$^{68}$R$^{69}$R$^{70}$NR$^{34}$R$^{89}$; with the proviso that at least two of R$^{67}$, R$^{68}$, R$^{69}$ and R$^{70}$ are H, and with the further that R$^{89}$ in —C$_6$R$^{67}$R$^{68}$R$^{69}$R$^{70}$R$^{89}$, —C$_6$R$^{67}$R$^{68}$R$^{69}$R$^{70}$OR$^{89}$ or —C$_6$R$^{67}$R$^{68}$R$^{69}$R$^{70}$NR$^{34}$R$^{89}$ is not C$_6$R$^{67}$R$^{68}$R$^{69}$R$^{70}$R$^{89}$, —C$_6$R$^{67}$R$^{68}$R$^{69}$R$^{70}$OR$^{89}$ or —C$_6$R$^{67}$R$^{68}$R$^{69}$R$^{70}$NR$^{34}$R$^{89}$;

m is 2-4; o is 0-4; p is 1-4; q is 0-2; r is 1 or 2; s is 0 or 1;

the amino acid residue of type C is a residue of formula —NR$^{20}$CH(R$^{72}$)CO— but not octylglycine;

the amino acid residue of type D is a residue of formula —NR$^{20}$CH(R$^{73}$)CO—;

the amino acid residue of type E is a residue of the formula —NR$^{20}$CH(R$^{74}$)CO—;

the amino acid residue of type F is a residue of the formula —NR$^{20}$CH(R$^{84}$)CO—;

the amino acid residue of type His a residue of the one of the formulae —NR$^{20}$—CH(CO—)-alkylene-CH(CO—)—NR$^{20}$—; —NR$^{20}$—CH(CO—)-alkenylene-CH(CO—)—NR$^{20}$—; —NR$^{20}$—CH(CO—)-alkynylene-CH(CO—)—NR$^{20}$—; —NR$^{20}$—CH(CO—)—(CH$_2$)$_p$SS(CH$_2$)$_p$—CH(CO—)—NR$^{20}$—; —NR$^{20}$—CH(CO—)—(—(CH$_2$)$_p$NR$^{20}$CO(CH$_2$)$_p$—CH(CO—)—NR$^{20}$—; and —NR$^{20}$—CH(CO—)—(—(CH$_2$)$_p$NR$^{20}$CONR$^{20}$(CH$_2$)$_p$—CH(CO—)—NR$^{20}$—;

the N-substituted glycine residue of type I is a residue of formula —NR$^{86}$CH$_2$CO—;

the amino acid residue of type O is a residue of formula —NR$^{20}$CH(R$^{87}$)CO— but not octylglycine;

the term "lipophilic moiety" designates a substituent or a part of a substituent comprising a hydrocarbon radical designated as "fatty alkyl" or a hydrocarbon radical designated as "fatty alkenyl" or a radical comprising a cyclopentanophenanthrene skeleton or an adamantyl radical, and the term "fatty" designates a radical having 7 up to 40 carbon atoms;

and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid which in the desired end-product corresponds to Xaa$^n$, wherein n is 16, 13, 8, 7, 5 or 2, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product corresponds to Xaa$^{n-1}$, any functional group which may be present in said N-protected amino acid derivative being likewise appropriately protected;

(d) removing the N-protecting group from the product obtained in step (c);

(e) effecting steps substantially corresponding to steps (c) and (d) using appropriately N-protected derivatives of amino acids which in the desired end-product are in positions n−2 to 1, any functional group(s) which may be present in said N-protected amino acid derivatives being likewise appropriately protected;

(f) if n is not 16, further effecting steps substantially corresponding to steps (c) and (d) using appropriately N-protected derivatives of amino acids which in the desired end-product are in positions 16 to n+1, any functional group(s) which may be present in said N-protected amino acid derivatives being likewise appropriately protected;

(g) if desired, selectively deprotecting one or several protected functional group(s) present in the molecule and appropriately substituting the reactive group(s) thus liberated by attaching one or several lipophilic moieties.

(h) if desired, forming an interstrand linkage between side-chains of appropriate amino acid residues at P4 and P11; or alternatively, forming the aforesaid linkage subsequent to step (m), as described herein below;

(i) detaching the product thus obtained from the solid support;

(j) cyclizing the product cleaved from the solid support;

(k) removing any protecting groups present on functional groups of any members of the chain of amino acid residues and, if desired, any protecting group(s) which may in addition be present in the molecule; and (l) if desired, attaching one or several lipophilic moieties; and (m) if required, removing any protecting groups present on functional groups of any members of the chain of amino acid residues and, if desired, any protecting group(s) which may in addition be present in the molecule; and (n) if desired, converting the product thus obtained into a pharmaceutically acceptable salt or converting a pharmaceutically acceptable, or unacceptable, salt thus obtained into the corresponding free compound or into a different, pharmaceutically acceptable, salt.

As used in this description, the term "lipophilic moiety" designates a substituent or a part of a substituent comprising a hydrocarbon radical designated as "fatty alkyl" or a hydrocarbon radical designated as "fatty alkenyl" or a radical comprising a cyclopentanophenanthrene skeleton or an adamantyl radical. Substituents like $R^{88}$ or $R^{89}$ are examples of such a lipophilic moiety. The term "fatty alkyl", taken alone or in combinations, designates saturated, straight-chain or branched hydrocarbon radicals having 7 up to 40, preferably 7 up to 28, carbon atoms. Similarly, the term "fatty alkenyl", taken alone or in combinations, designates straight chain or branched hydrocarbon radicals having 7 up to 40, preferably 7 up to 28, carbon atoms and containing at least one or, depending on the chain length, up to 14, preferably up to 8, olefinic double bonds. The term "alkyl", taken alone or in combinations, designates saturated, straight-chain or branched hydrocarbon radicals having up to 24, preferably up to 12, carbon atoms. Similarly, the term "alkenyl", taken alone or in combinations, designates straight chain or branched hydrocarbon radicals having up to 24, preferably up to 12, carbon atoms and containing at least one or, depending on the chain length, up to four olefinic double bonds. The term "alkylene" designates a divalent "alkyl", e.g. —$CH_2$—$CH_2$—$CH_2$—$CH_2$—, having 4 to 24, preferably 4 to 12, carbon atoms. Similarly, the term "alkenylene" designates a divalent "alkenyl", e.g. —$CH_2$—$CH$=$CH$—$CH_2$—, having 4 to 24, preferably 4 to 12, carbon atoms and containing at least one or, depending on the chain length, up to four olefinic double bonds. Likewise, the term "alkynylene" designates a divalent straight chain or branched hydrocarbon radical, having 4 to 24, preferably 4 to 12, carbon atoms and containing at least one or, depending on the chain length, up to four carbon-carbon triple bonds. The term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, sec.-butyl, isobutyl, tert.-butyl, and the like. Similarly, the term "lower cycloalkyl" designates saturated cyclic hydrocarbon radicals having up to 6 carbon atoms, such as cyclopentyl, cyclohexyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

In a particular embodiment, the fatty alkyl and alkenyl moieties have at least 9 carbon atoms.

The β-hairpin conformation of Cyclo (-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$-) is highly relevant for the CXCR4 antagonizing activity of the β-hairpin mimetics of the present invention. The β-hairpin stabilizing conformational properties induced by the D-amino acid residue $Xaa^7$ and the D-amino acid or N-substituted glycine residue $Xaa^{15}$ play a key role not only for the selective antagonizing activity but also for the synthesis process defined hereinabove, as incorporation of aforesaid residues $Xaa^7$ and $Xaa^{15}$ near the beginning or near the middle of the linear protected peptide precursors enhances cyclization yields significantly.

Building blocks A1-A69 and A105 of the structural element -A-CO— belong to a class of amino acids wherein the N-terminus is a secondary amine forming part of a ring. Among the genetically encoded amino acids only proline falls into this class. The configuration of building block A1 through A69 and A105 is (D), and they can be combined with a building block —B—CO— of (L)-configuration. Thus, for example, $^D$Pro-$^L$Pro constitutes the prototype of such a combination.

It will be appreciated that building blocks -A1-CO— to -A69-CO— and A105-CO— in which A has (D)-configuration, are carrying a group $R^1$ at the β-position to the N-terminus. The preferred values for $R^1$ are H and lower alkyl with the most preferred values for $R^1$ being H and methyl. It will be recognized by those skilled in the art, that A1-A69 and A105 are shown in (D)-configuration which, for $R^1$ being H and methyl, corresponds to the (R)-configuration. Depending on the priority of other values for $R^1$ according to the Cahn, Ingold and Prelog rules, this configuration may also have to be expressed as (S).

In addition to $R^1$ building blocks -A1-CO— to -A69-CO— and A105-CO— can carry an additional substituent designated as $R^2$ to $R^{17}$. This additional substituent can be H, and if it is other than H, it is preferably a small to medium-sized aliphatic or aromatic group. Examples of preferred values for $R^1$ to $R^{17}$ are:

$R^1$ is hydrogen or lower alkyl;

$R^2$ is H; lower alkyl; lower alkenyl;
—$(CH_2)_p OR^{55}$ (where $R^{55}$: lower alkyl; or lower alkenyl);
—$(CH_2)_p SR^{56}$ (where $R^{56}$: lower alkyl; or lower alkenyl);
—$(CH_2)_p NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
—$(CH_2)_p OCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—); —$(CH_2)_2 O(CH_2)_2$—;

—$(CH_2)_2S(CH_2)_2$—; or —$(CH_2)_2NR^{57}(CH_2)_2$— (where $R^{57}$: H; or lower alkyl);

—$(CH_2)_pNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: H; lower alkyl; or lower alkenyl);

—$(CH_2)_oSO_2R^{62}$ (where $R^{62}$: lower alkyl; or lower alkenyl);

—$(CH_2)_qC_6H_4R^8$ (where $R^8$: H; F; Cl; $CF_3$; lower alkyl; lower alkenyl; or lower alkoxy); or —$(CH_2)_qCHN_4R^8$.

$R^3$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^4$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^5$ is lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: alkyl; alkenyl; aryl; aryl-lower alkyl; or heteroaryl-lower alkyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^6$ is H; lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy).

$R^7$ is lower alkyl; lower alkenyl;
- —$(CH_2)_qOR^{55}$ (where $R^{55}$: lower alkyl; or lower alkenyl);
- —$(CH_2)_qSR^{56}$ (where $R^{56}$: lower alkyl; or lower alkenyl);
- —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_qN(R^{20})COR^{84}$ (where $R^{20}$: H; or lower alkyl; $R^{64}$: lower alkyl; or lower alkenyl);
- —$(CH_2)_rCOOR^{57}$ (where $R^{57}$: lower alkyl; or lower alkenyl);
- —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_rPO(OR^{80})_2$ (where $R^{80}$: lower alkyl; or lower alkenyl);
- —$(CH_2)_rSO_2R^{82}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy).

$R^8$ is H; F; Cl; $CF_3$; lower alkyl; lower alkenyl;
- —$(CH_2)_oOR^{55}$ (where $R^{55}$: lower alkyl; or lower alkenyl);
- —$(CH_2)_oSR^{58}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$; —$(CH_2)_2S(CH_2)_2$; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy).

$R^9$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{10}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{11}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{84}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{12}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{84}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_mCOOR^{57}$ (where $R^{57}$: lower alkyl; or lower alkenyl);

—$(CH_2)_mCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_rPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{13}$ is lower alkyl; lower alkenyl;

—$(CH_2)_qOR^{55}$ (where $R^{55}$: lower alkyl; or lower alkenyl);

—$(CH_2)_qSR^{56}$ (where $R^{56}$: lower alkyl; or lower alkenyl);

—$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

- —$(CH_2)_q NR^{20}CONR^{33}R^{21}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_q N(R^{20})COR^{64}$ (where $R^{20}$: H; or lower alkyl; $R^{64}$: lower alkyl; or lower alkenyl);
- —$(CH_2)_r COO^{57}$ (where $R^{57}$: lower alkyl; or lower alkenyl);
- —$(CH_2)_q CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2 O (CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_r PO(OR^{60})_2$ (where $R^{60}$: lower alkyl; or lower alkenyl);
- —$(CH_2)_r SO_2 R^{62}$ (where $R^{62}$: lower alkyl; or lower alkenyl); or
- —$(CH_2)_q C_6 H_4 R^8$ (where $R^8$: H; F; Cl; $CF_3$; lower alkyl; lower alkenyl; or lower alkoxy).

$R^{14}$ is H; lower alkyl; lower alkenyl;
- —$(CH_2)_m OR^{55}$ (where $R^{55}$: lower alkyl; or lower alkenyl);
- —$(CH_2)_m SR^{56}$ (where $R^{56}$: lower alkyl; or lower alkenyl);
- —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_m OCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_m NR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_m N(R^{20})COR^{64}$ (where $R^{20}$: H; lower alkyl; $R^{64}$: lower alkyl; or lower alkenyl);
- —$(CH_2)_o COOR^{57}$ (where $R^{57}$: lower alkyl; or lower alkenyl);
- —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2 O (CH_2)_2$—; —$(CH_2)_2 S(CH_2)_2$—; or —$(CH_2)_2 NR^{57} (CH_2)_2$— (where $R^{57}$: H; or lower alkyl);
- —$(CH_2)_o PO(OR^{60})_2$ (where $R^{60}$: lower alkyl; or lower alkenyl);
- —$(CH_2)_o SO_2 R^{62}$ (where $R^{62}$: lower alkyl; or lower alkenyl);
- —$(CH_2)_q C_6 H_4 R^8$ (where $R^8$: H; F; Cl; $CF_3$; lower alkyl; lower alkenyl; or lower alkoxy).

$R^{15}$ is lower alkyl; lower alkenyl;
- —$(CH_2)_o OR^{55}$ (where $R^{55}$: lower alkyl; or lower alkenyl);
- —$(CH_2)_o SR^{56}$ (where $R^{56}$: lower alkyl; or lower alkenyl);
- —$(CH_2)_o NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_o OCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_o NR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2 O(CH_2)_2$; —$(CH_2)_2 S(CH_2)_2$—; or —$(CH_2)_2 NR^{57}(CH_2)_2$— (where $R^{57}$: H; or lower alkyl);
- —$(CH_2)_o N(R^{20})COR^{64}$ (where $R^{20}$: H; or lower alkyl; $R^{64}$: lower alkyl; or lower alkenyl); particularly favoured being —$NR^{20}CO$-lower alkyl (where $R^{20}$: H; or lower alkyl);
- —$(CH_2)_o COOR^{57}$ (where $R^{57}$: lower alkyl; or lower alkenyl);
- —$(CH_2)_o CONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2 O (CH_2)_2$—; —$(CH_2)_2 S(CH_2)_2$—; or —$(CH_2)_2 NR^{57} (CH_2)_2$— (where $R^{57}$: H; or lower alkyl);
- —$(CH_2)_o PO(OR^{60})_2$ (where $R^{60}$: lower alkyl; or lower alkenyl);
- —$(CH_2)_o SO_2 R^{62}$ (where $R^{62}$: lower alkyl; or lower alkenyl); or
- —$(CH_2)_q C_6 H_4 R^8$ (where $R^8$: H; F; Cl; $CF_3$; lower alkyl; lower alkenyl; or lower alkoxy).

$R^{16}$ is lower alkyl; lower alkenyl;
- —$(CH_2)_o OR^{55}$ (where $R^{55}$: lower alkyl; or lower alkenyl);
- —$(CH_2)_o SR^{56}$ (where $R^{56}$: lower alkyl; or lower alkenyl);
- —$(CH_2)_o NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_o OCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl);
- —$(CH_2)_o NR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2 O(CH_2)_2$; —$(CH_2)_2 S(CH_2)_2$—; or —$(CH_2)_2 NR^{57}(CH_2)_2$— (where $R^{57}$: H; or lower alkyl);
- —$(CH_2)_o N(R^{20})COR^{64}$ (where $R^{20}$: H; or lower alkyl; $R^{64}$: lower alkyl; or lower alkenyl);
- —$(CH_2)_o COOR^{57}$ (where $R^{57}$: lower alkyl; or lower alkenyl);
- —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2 O (CH_2)_2$—; —$(CH_2)_2 S(CH_2)_2$—; or —$(CH_2)_2 NR^{57} (CH_2)_2$— (where $R^{57}$: H; or lower alkyl);
- —$(CH_2)_o PO(OR^{60})_2$ (where $R^{60}$: lower alkyl; or lower alkenyl);
- —$(CH_2)_o SO_2 R^{62}$ (where $R^{62}$: lower alkyl; or lower alkenyl); or
- —$(CH_2)_q C_6 H_4 R^8$ (where $R^8$: H; F; Cl; $CF_3$; lower alkyl; lower alkenyl; or lower alkoxy).

$R^{17}$ is lower alkyl; lower alkenyl;
- —$(CH_2)_q OR^{55}$ (where $R^{55}$: lower alkyl; or lower alkenyl);

—(CH$_2$)$_q$SR$^{56}$ (where R$^{56}$: lower alkyl; or lower alkenyl);

—(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$NR$^{20}$CONR$^{33}$R$^{81}$ (where R$^{20}$: H; or lower alkyl; R$^{33}$: H; lower alkyl; or lower alkenyl; R: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$N(R$^{20}$)COR$^{64}$ (where R$^{20}$: H; or lower alkyl; R$^{64}$: lower alkyl; or lower alkenyl);

—(CH$_2$)$_r$COOR$^{57}$ (where R$^{57}$: lower alkyl; or lower alkenyl);

—(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_r$PO(OR$^{60}$)$_2$ (where R$^{60}$: lower alkyl; or lower alkenyl);

—(CH$_2$)$_r$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 and A105 the following are preferred: A5, A8, A22, A25, A38, A42, A47, A50 and A105. Most preferred are building blocks of type A8', A8" and A8'":

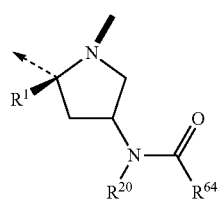

A8'

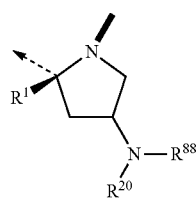

A8"

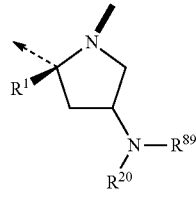

A8'"

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers* 1968, 6, 1425-1434; W. Kabsch, C. Sander, Biopolymers 1983, 22, 2577). Such building blocks are ideally suited for the stabilization of β-hairpin conformations in peptide loops (D. Obrecht, M. Altorfer, J. A. Robinson, "Novel Peptide Mimetic Building Blocks and Straties for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— being an α-amino acid with L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Preferred values for R$^{20}$ in A70 to A104 are H or lower alkyl with methyl being most preferred. Preferred values for R$^{18}$, R$^{19}$ and R$^{21}$-R$^{29}$ in building blocks A70 to A104 are the following:

R$^{18}$ is lower alkyl.

R$^{19}$ is lower alkyl; lower alkenyl;

—(CH$_2$)$_p$OR$^{55}$ (where R$^{55}$: lower alkyl; or lower alkenyl);

—(CH$_2$)$_p$SR$^{56}$ (where R$^{56}$: lower alkyl; or lower alkenyl);

—(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_p$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_p$NR$^{20}$CONR$^{33}$R$^{81}$ (where R$^{20}$: H; or lower alkyl; R$^{33}$: H; lower alkyl; or lower alkenyl; H; or lower alkyl; or R$^{33}$ and R$^{84}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$— (where R$^{57}$: H; or lower alkyl);

—(CH$_2$)$_p$N(R$^{20}$)COR$^{64}$ (where R$^{20}$: H; or lower alkyl; R$^{64}$: lower alkyl; or lower alkenyl);

—(CH$_2$)$_p$COOR$^{57}$ (where R$^{57}$: lower alkyl; or lower alkenyl);

—$(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_pPO(OR^{60})_2$ (where $R^{60}$: lower alkyl; or lower alkenyl);

—$(CH_2)_pSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{21}$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{80}$ taken together form: —$(CH_2)_{2-6}$—; —$(CH_2)_2O(CH_2)_2$; —$(CH_2)_2S(CH_2)_2$; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{22}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; CF; lower alkyl; lower alkenyl; or lower alkoxy).

$R^{23}$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl); particularly favoured are $NR^{20}CO$-lower alkyl (where $R^{20}$: H; or lower alkyl); —$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{24}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{80}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl); particularly favoured are $NR^{20}CO$-lower alkyl (where $R^{20}$: H; or lower alkyl); —$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{25}$ is H; lower alkyl; lower alkenyl;

—$(CH_2)_mOR^{55}$ (where $R^{55}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{26}$ is H; lower alkyl; lower alkenyl;

—$(CH_2)_mOR^{55}$ (where $R^{55}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy); or, alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl).

$R^{27}$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{28}$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy).

$R^{29}$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl); particularly favored are $NR^{20}CO$-lower-alkyl (where $R^{20}$: H; or lower alkyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy).

Among the building blocks A70 to A104 the following are preferred: A74 with $R^{22}$ being H, A75, A76, A77 with $R^{22}$ being H, A78 and A79.

The building block —B—CO— designates an L-amino acid residue. Preferred values for B are: —$NR^{20}CH(R^{71})$—, enantiomers of groups A5 with $R^2$ being H, A8, A22, A25, A38 with $R^2$ being H, A42, A47, and A50. Most preferred building blocks —B—CO— are Ala L-Alanine
Arg L-Arginine
Asn L-Asparagine
Asp L-Aspartic acid
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Phe L-Phenylalanine
Pro L-Proline
Ser L-Serine
Thr L-Threonine
Trp L-Tryptophan
Tyr L-Tyrosine
Val L-Valine
Cit L-Citrulline
Orn L-Ornithine
tBuA L-t-Butylalanine
Sar Sarcosine
t-BuG L-tert.-Butylglycine
4AmPhe L-para-Aminophenylalanine
3AmPhe L-meta-Aminophenylalanine
2AmPhe L-ortho-Aminophenylalanine
Phe (mC(NH$_2$)=NH) L-meta-Amidinophenylalanine
Phe (pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
Phg L-Phenylglycine
Cha L-Cyclohexylalanine
C$_4$al L-3-Cyclobutylalanine
C$_5$al L-3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic L-1,2,3,4-Tetrahydroisoquinoline-3-carboxylic acid
Thi L-β-2-Thienylalanine
Tza L-2-Thiazolylalanine
Mso L-Methionine sulfoxide
AcLys L-N-Acetyllysine Dpr L-2,3-Diaminopropionic acid
Dab L-2,4-Diaminobutyric acid
Dbu (2S,3S)-2,3-Diaminobutyric acid
Abu γ-Aminobutyric acid (GABA)
Aha ε-Aminohexanoic acid
Aib α-Aminoisobutyric acid
Y(Bzl) L-O-Benzyltyrosine
Bip L-Biphenylalanine
S(Bzl) L-O-Benzylserine
T(Bzl) L-O-Benzylthreonine
hCha L-Homo-cyclohexylalanine
hCys L-Homo-cysteine
hSer L-Homo-serine
hArg L-Homo-arginine
hPhe L-Homo-phenylalanine
Bpa L-4-Benzoylphenylalanine
Pip L-Pipecolic acid
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methvaline
MeLeu L-N-Methylleucine
4Hyp1 (4S)-L-Hydroxyproline
4Hyp2 (4R)-L-Hydroxyproline
4 Mp1 (4S)-L-Mercaptoproline
4 Mp2 (4R)-L-Mercaptoproline
Oic (3aS,7aS)-L-1-Octahydro-1H-indole-2-carboxylic acid In addition, the most preferred values for B also include groups of type A8"" of (L)-configuration:

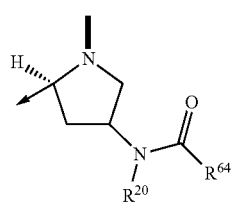

wherein $R^{20}$ is H or lower alkyl and $R^{64}$ is alkyl; alkenyl; —[(CH$_2$), —X]$_t$—CH$_3$ (where X is —O—; —NR$^{20}$—, or —S—; u=1-3, and t=1-6), aryl; aryl-lower alkyl; or heteroaryl-lower alkyl; especially those wherein $R^{64}$ is n-hexyl (A8"-21); n-heptyl (A8"-22); 4-(phenyl)benzyl (A8"-23); diphenylmethyl (A8"-24); 3-amino-propyl (A8"-25); 5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexyl-methyl (A8"-33); n-butyl (A8"-34); phenyl (A8"-35); benzyl (A8"-36); (3-indolyl)methyl (A8"-37); 2-(3-indolyl)ethyl (A8"-38); (4-phenyl)-phenyl (A8"-39); n-nonyl (A8"-40); CH$_3$—OCH$_2$CH$_2$—OCH$_2$— (A8"-41) and CH$_3$—(OCH$_2$CH$_2$)$_2$—OCH$_2$— (A8'-42).

Besides the structural element —B—CO— the β-hairpin peptidomimetics of the present invention can comprise the structural element -A-CO— and amino acid residues belonging to one of the following groups:
Group C —NR$^{20}$CH(R$^{72}$)CO—; "hydrophobic: small to medium-sized"
Group D —NR$^{20}$CH(R$^{73}$)CO—; "hydrophobic: large aromatic or heteroaromatic"
Group E —NR$^{20}$CH(R$^{74}$)CO—; "polar-cationic" and "urea-derived"
Group F —NR$^{20}$CH(R$^{94}$)CO—; "polar-non-charged or anionic"
Group H —NR$^{20}$—CH(CO—)—(CH$_2$)$_{4-7}$—CH(CO—)—NR$^{20}$—; —NR$^{20}$—CH(CO—)—(CH$_2$)$_p$SS(CH$_2$)$_p$—CH(CO—)—NR$^{20}$—; —NR$^{20}$—CH(CO—)—(CH$_2$)$_p$NR$^{20}$CO(CH$_2$)$_p$—CH(CO—)—NR$^{20}$—; —NR$^{20}$—CH(CO—)—(CH$_2$)$_p$NR$^{20}$CONR$^{20}$(CH$_2$)$_p$—CH(CO—)—NR$^{20}$—; "interstrand linkage"
Group I —NR$^{86}$CH$_2$CO—; "N-substituted glycines"
Group O —NR$^{20}$CHR$^{87}$CO—; "amino acid residue bearing a lipophilic moiety"

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized hydrophobic amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl—or aryl phosphonates—and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl—or aryl phosphonates—and phosphates or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxylic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tertiary amides, carboxylic acids and carboxylates, alkyl—or aryl phosphonates—and phosphates or tertiary amines. Genetically encoded polar-non-charged amino acids include asparagine, cysteine, glutamine, serine and threonine, but also aspartic acid and glutamic acid.

Group H comprises side chains of preferably (L)-amino acids at opposite positions of the β-strand region that can form an interstrand linkage. Various methods are known to form interstrand linkages including those described by: J. P. Tam et al., *Synthesis* 1979, 955-957; Stewart et al., *Solid Phase Peptide Synthesis,* 2d Ed., Pierce Chemical Company, Rockford, III, 1984; Ahmed et al. *J. Biol. Chem.* 1975, 250, 8477-8482; and Pennington et al., *Peptides*, pages 164-166, Giralt and Andreu, Eds., ESCOM Leiden, The Netherlands, 1990; C. E. Schafineister et al., *J. Am. Chem. Soc.* 2000, 122, 5891. The most widely known linkage is the disulfide bridge formed by cysteines and homo-cysteines positioned at opposite positions of the β-strand. Preferrably, for the scope of the present invention, disulfide linkages can be prepared using acetamidomethyl (Acm)-protective groups for cysteine. Another well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

Group I comprises glycine having the amino group substituted by chains containing polar-cationic, hydrophobic, aromatic, heteroaromatic, polar-non-charged or anionic residues according to the general definition for substituent $R^{86}$. Polar-cationic refers to a basic side chain which is protonated at physiological pH. A hydrophobic residue refers to an amino acid side chain that is uncharged at physiological pH and that is repelled by aqueous solution. Aromatic refers to a hydrophobic side chain containing at least one ring having a conjugated π-electron system (aromatic group). Heteroaromatic refers to a hydrophobic side chain containing at least one ring having a conjugated π-system incorporating at least one heteroatom. A polar-non-charged or anionic residue refers to a hydrophilic side chain that is uncharged and, respectively anionic at physiological pH (carboxylic acids being included), but that is not repelled by aqueous solutions.

Group O comprises amino acids containing side chains according to the general definition for substituent $R^{87}$. This substituent comprises polar-cationic, hydrophobic, aromatic, heteroaromatic, or polar-non-charged residues, additionally conjugated with one of the substituents $R^{88}$, $R^{89}$ or $R^{91}$ according to the general definition for $R^{88}$, $R^{89}$ and $R^{91}$, being or containing a lipophilic moiety according to the general definition for lipophilic moiety causing protracted plasma profiles in vitro and in vivo of β-hairpin peptidomimetics. Polar-cationic refers to a basic side chain which is protonated at physiological pH. A hydrophobic residue refers to an amino acid side chain that is uncharged at physiological pH and that is repelled by aqueous solution. Aromatic refers to a hydrophobic side chain containing at least one ring having a conjugated π-electron system (aromatic group). Heteroaromatic refers to a hydrophobic side chain containing at least one ring having a conjugated π-system incorporating at least one heteroatom. A polar-non-charged residue refers to a hydrophilic side chain that is uncharged at physiological pH, but that is not repelled by aqueous solutions.

As mentioned earlier, $Xaa^4$ and $Xaa^{11}$ of Cyclo (-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$-) are amino acid residues which, taken together, form an interstrand linkage. Such an interstrand linkage is known to stabilize the β-hairpin conformations and thus constitute an important structural element for the design of β-hairpin mimetics.

Most preferred amino acid residues in Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$-), are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| $^D$Ala | D-Alanine | $^D$A |
| Arg | L-Arginine | R |
| $^D$Arg | D-Arginine | $^D$R |
| Asn | L-Asparagine | N |
| $^D$Asn | D-Asparagine | $^D$N |
| Asp | L-Aspartic acid | D |
| $^D$Asp | D-Aspartic acid | $^D$D |
| Cys | L-Cysteine | C |
| $^D$Cys | D-Cysteine | $^D$C |
| Glu | L-Glutamic acid | E |
| $^D$Glu | D-Glutamic acid | $^D$E |
| Gln | L-Glutamine | Q |
| $^D$Gln | D-Glutamine | $^D$Q |
| Gly | Glycine | G |
| His | L-Histidine | H |
| $^D$His | D-Histidine | $^D$H |
| Ile | L-Isoleucine | I |
| $^D$Ile | D-Isoleucine | $^D$I |
| Leu | L-Leucine | L |
| $^D$Leu | D-Leucine | $^D$L |
| Lys | L-Lysine | K |
| $^D$Lys | D-Lysine | $^D$K |
| Met | L-Methionine | M |
| $^D$Met | D-Methionine | $^D$M |
| Phe | L-Phenylalanine | F |
| $^D$Phe | D-Phenylalanine | $^D$F |
| Pro | L-Proline | P |
| $^D$Pro | D-Proline | $^D$P |
| Ser | L-Serine | S |
| $^D$Ser | D-Serine | $^D$S |
| Thr | L-Threonine | T |
| $^D$Thr | D-Threonine | $^D$T |
| Trp | L-Tryptophan | W |
| $^D$Trp | D-Tryptophan | $^D$W |
| Tyr | L-Tyrosine | Y |
| $^D$Tyr | D-Tyrosine | $^D$Y |
| Val | L-Valine | V |
| $^D$Val | D-Valine | $^D$V |

Other α-amino acids which, or the residues of which, are suitable for the purposes of the present invention include:
Cit L-Citrulline
$^D$Cit D-Citrulline
Orn L-Ornithine
$^D$Orn D-Ornithine
tBuA L-t-Butylalanine
$^D$tBuA D-t-Butylalanine Sar Sarcosine
Pen L-Penicillamine
<sup>D</sup>Pen D-Penicillamine
tBuG L-tert.-Butylglycine
<sup>D</sup>tBuG D-tert.-Butylglycine
4AmPhe L-para-Aminophenylalanine
<sup>D</sup>4AmPhe D-para-Aminophenylalanine
3AmPhe L-meta-Aminophenylalanine
<sup>D</sup>3AmPhe D-meta-Aminophenylalanine
2AmPhe L-ortho-Aminophenylalanine
<sup>D</sup>2AmPhe D-ortho-Aminophenylalanine
Phe(mC(NH$_2$)=NH) L-meta-Amidinophenylalanine
<sup>D</sup>Phe (mC(NH$_2$)=NH) D-meta-Amidinophenylalanine
Phe (pC(NH$_2$)=NH) L-para-Amidinophenylalanine
<sup>D</sup>Phe (pC(NH$_2$)=NH) D-para-Amidinophenylalanine
Phe(mNHC(NH$_2$)=NH) L-meta-Guanidinophenylalanine
<sup>D</sup>Phe(mNHC(NH$_2$)=NH) D-meta-Guanidinophenylalanine
Phe(pNHC(NH$_2$)=NH) L-para-Guanidinophenylalanine
<sup>D</sup>Phe(pNHC(NH$_2$)=NH) D-para-Guanidinophenylalanine
2Pal (2S)-2-Amino-3-(pyridine-2'-yl)-propionic acid
<sup>D</sup>2Pal (2R)-2-Amino-3-(pyridine-2'-yl)-propionic acid
4Pal (2S)-2-Amino-3-(pyridine-4'-yl)-propionic acid
<sup>D</sup>4Pal (2R)-2-Amino-3-(pyridine-4'-yl)-propionic acid
Phg L-Phenylglycine
<sup>D</sup>Phg D-Phenylglycine
Cha L-Cyclohexylalanine
<sup>D</sup>Cha D-Cyclohexylalanine
C$_4$al L-3-Cyclobutylalanine
<sup>D</sup>C$_4$al D-3-Cyclobutylalanine
C$_5$al L-3-Cyclopentylalanine
<sup>D</sup>C$_5$al D-3-Cyclopentylalanine
Nle L-Norleucine
<sup>D</sup>Nle D-Norleucine
2-Nal L-2-Naphthylalanine
<sup>D</sup>2Nal D-2-Naphthylalanine
1-Nal L-1-Naphthylalanine
<sup>D</sup>1Nal D-1-Naphthylalanine
4Cl Phe L-4-Chlorophenylalanine
<sup>D</sup>4Cl Phe D-4-Chlorophenylalanine
3Cl Phe L-3-Chlorophenylalanine
<sup>D</sup>3Cl Phe D-3-Chlorophenylalanine
2Cl Phe L-2-Chlorophenylalanine
<sup>D</sup>2Cl Phe D-2-Chlorophenylalanine
3,4Cl$_2$Phe L-3,4-Dichlorophenylalanine
<sup>D</sup>3,4Cl$_2$Phe D-3,4-Dichlorophenylalanine
4FPhe L-4-Fluorophenylalanine
<sup>D</sup>4FPhe D-4-Fluorophenylalanine
3FPhe L-3-Fluorophenylalanine
<sup>D</sup>3FPhe D-3-Fluorophenylalanine
2FPhe L-2-Fluorophenylalanine
<sup>D</sup>2FPhe D-2-Fluorophenylalanine
Thi L-β-2-Thienylalanine
<sup>D</sup>Thi D-β-2-Thienylalanine
Tza L-2-Thiazolylalanine
<sup>D</sup>Tza D-2-Thiazolylalanine
Mso L-Methionine sulfoxide
<sup>D</sup>Mso D-Methionine sulfoxide
AcLys N-Acetyllysine
<sup>D</sup>AcLys N-Acetyl-D-lysine
Dpr 2,3-Diaminopropionic acid
<sup>D</sup>Dpr D-2,3-Diaminopropionic acid
Dab 2,4-Diaminobutyric acid
<sup>D</sup>Dab(2R)-2,4-Diamino-butyric acid
Dbu (2S)-2,3-Diamino-butyric acid
<sup>D</sup>Dbu (2R) 2,3-Diamino-butyric acid
Abu γ-Aminobutyric acid (GABA)
Aha ε-Aminohexanoic acid
Aib α-Aminoisobutyric acid
Cyp 1-Aminocyclopentane carboxylic acid
Y(Bzl) L-O-Benzyltyrosine
<sup>D</sup>Y(Bzl) D-O-Benzyltyrosine
H(Bzl) (3S)-2-Amino-3-(1'-benzylimidazole-4'-yl)-propionic acid
<sup>D</sup>H(Bzl) (3R)-2-Amino-3-(1'-benzylimidazole-4'-yl)-propionic acid
Bip L-(4-phenyl)phenylalanine
<sup>D</sup>Bip D-(4-phenyl)phenylalanine
S(Bzl) L-O-Benzylserine
<sup>D</sup>S(Bzl) D-O-Benzylserine
T(Bzl) L-O-Benzylthreonine
<sup>D</sup>T(Bzl) D-O-Benzylthreonine
alloT (2S,3S)-2-Amino-3-hydroxy-butyric acid
<sup>D</sup>alloT (2R,3S)-2-Amino-3-hydroxy-butyric acid
Leu3OH (2S,3R)-2-Amino-3-hydroxy-4-methyl-pentanoic acid
<sup>D</sup>Leu3OH (2R,3R)-2-Amino-3-hydroxy-4-methyl-pentanoic acid
hAla L-Homo-alanine
<sup>D</sup>hAla D-Homo-alanine
hArg L-Homo-arginine
<sup>D</sup>hArg D-Homo-arginine
hCys L-Homo-cysteine
<sup>D</sup>hCys D-Homo-cysteine
hGlu L-Homo-glutamic acid
<sup>D</sup>hGlu D-glutamic acid
hGln L-Homo-glutamine
<sup>D</sup>hGln D-Homo-glutamine
hHis L-Homo-histidine
<sup>D</sup>hHis D-Homo-histidine
hIle L-Homo-isoleucine
<sup>D</sup>hIle D-Homo-isoleucine
hLeu L-Homo-leucine
<sup>D</sup>hLeu D-Homo-leucine
hNle L-Homo-norleucine
<sup>D</sup>hNle D-Homo-norleucine
hLys L-Homo-lysine
<sup>D</sup>hLys D-Homo-lysine
hMet L-Homo-Methionine
<sup>D</sup>hMet D-Homo-Methionine
hPhe L-Homo-phenylalanine
<sup>D</sup>hPhe D-Homo-phenylalanine
hSer L-Homo-serine
<sup>D</sup>hSer D-Homo-serine
hThr L-Homo-threonine
<sup>D</sup>hThr D-Homo-threonine
hTrp L-Homo-tryptophan
<sup>D</sup>hTrp D-Homo-tryptophan
hTyr L-Homo-tyrosine
<sup>D</sup>hTyr D-Homo-tyrosine
hVal L-Homo-valine
<sup>D</sup>hVal D-Homo-valine
hCha L-Homo-cyclohexylalanine
<sup>D</sup>hCha D-Homo-cyclohexylalanine
Bpa L-4-Benzoylphenylalanine
<sup>D</sup>Bpa D-4-Benzoylphenylalanin
Tic (3S)-1,2,3,4-Tetrahydroisoquinoline-3-carboxylic acid
<sup>D</sup>Tic (3R)-1,2,3,4-Tetrahydroisoquinoline-3-carboxylic acid
Tiq (1S)-1,2,3,4-Tetrahydroisoquinoline-1-carboxylic acid
<sup>D</sup>Tiq (1R)-1,2,3,4-Tetrahydroisoquinoline-1-carboxylic acid
Oic (2S,3aS,7aS)-1-Octahydro-1H-indole-2-carboxylic acid
<sup>D</sup>Oic (2R,3aS,7aS)-1-Octahydro-1H-indole-2-carboxylic acid
4AmPyrrl (2S,4S)-4-Amino-pyrrolidine-2-carboxylic acid
<sup>D</sup>4AmPyrrl (2R,4S)-4-Amino-pyrrolidine-2-carboxylic acid 4AmPyrr2 (2S,4R)-4-Amino-pyrrolidine-2-carboxylic acid
$^D$4AmPyrr2 (2R,4R)-4-Amino-pyrrolidine-2-carboxylic acid
4PhePyrr1 (2S,4R)-4-Phenyl-pyrrolidine-2-carboxylic acid
$^D$4PhePyrr1 (2R,4R)-4-Phenyl-pyrrolidine-2-carboxylic acid
4PhePyrr2 (2S,4S)-4-Phenyl-pyrrolidine-2-carboxylic acid
$^D$4PhePyrr2 (2R,4S)-4-Phenyl-pyrrolidine-2-carboxylic acid
5PhePyrr1 (2S,5R)-5-Phenyl-pyrrolidine-2-carboxylic acid
$^D$5PhePyrr1 (2R,5R)-5-Phenyl-pyrrolidine-2-carboxylic acid
5PhePyrr2 (2S,5S)-5-Phenyl-pyrrolidine-2-carboxylic acid
$^D$5PhePyrr2 (2R,5S)-5-Phenyl-pyrrolidine-2-carboxylic acid
4Hyp1 (4S)-L-Hydroxyproline
$^D$4Hyp1 (4S)-D-Hydroxyproline
4Hyp2 (4R)-L-Hydroxyproline
$^D$4Hyp2 (4R)-D-Hydroxyproline
4 Mp1 (4S)-L-Mercaptoproline
$^D$4 Mp1 (4S)-D-Mercaptoproline
4 Mp2 (4R)-L-Mercaptoproline
$^D$4 Mp2 (4R)-D-Mercaptoproline
Pip L-Pipecolic acid
$^D$Pip D-Pipecolic acid
(AEt)G N-(2-Aminoethyl)glycine
(APr)G N-(3-Amino-n-propyl)glycine
(ABu)G N-(4-Amino-n-butyl)glycine
(APe)G N-(5-Amino-n-pentyl)glycine
(GuEt)G N-(2-Guanidinoethyl)glycine
(GuPr)G N-(3-Guanidino-n-propyl)glycine
(GuBu)G N-(4-Guanidino-n-butyl)glycine
(GuPe)G N-(5-Guanidino-n-pentyl)glycine
(PEG$_3$-NH$_2$)G N—[H$_2$N—(CH$_2$)$_3$—(OCH$_2$—CH$_2$)$_2$—O(CH$_2$)$_3$]glycine
(Me)G N-Methylglycine
(Et)G N-Ethylglycine
(Bu)G N-Butylglycine
(Pe)G N-Pentylglycine
(Ip)G N-Isopropylglycine
(2MePr)G N-(2-Methylpropyl)glycine
(3MeBu)G N-(3-Methylbutyl)glycine
(1MePr)G (1S)—N-(1-Methylpropyl)glycine
(2MeBu)G (2S)—N-(2-Methylbutyl)glycine
(MthEt)G N-(Methylthioethyl)glycine
(MthPr)G N-(Methylthiopropyl)glycine
(Ben)G N-(Benzyl)glycine
(PhEt)G N-(2-Phenylethyl)glycine
(HphMe)G N-([4'-hydroxyphenyl]methyl)glycine
(HphEt)G N-(2-[4'-hydroxyphenyl]ethyl)glycine
(ImMe)G N-(Imidazol-5-yl-methyl)glycine
(ImEt)G N-(2-(Imidazol-5'-yl)ethyl)glycine
(InMe)G N-(Indol-2-yl-methyl)glycine
(InEt)G N-(2-(Indol-2'-yl)ethyl)glycine
(CboMe)G N-(Carboxymethyl)glycine
(CboEt)G N-(2-Carboxyethyl)glycine
(CboPr)G N-(3-Carboxypropyl)glycine
(CbaMe)G N-(Carbamoylmethyl)glycine
(CbaEt)G N-(2-Carbamoylethyl)glycine
(CbaPr)G N-(3-Carbamoylpropyl)glycine
(HyEt)G N-(2-Hydroxyethyl)glycine
(HyPr)G (2R)—N-(2-Hydroxypropyl)glycine
(Mcet)G N-(2-Mercaptoethyl)glycine
NMeGly N-Methylglycine
NMeAla L-N-Methylalanine
NMe$^D$Ala D-N-Methylalanine
NMeVal L-N-Methylvaline
NMe$^D$Val D-N-Methylvaline
NMeIle L-N-Methylisoleucine
NMe$^D$Ile D-N-Methylisoleucine
NMeLeu L-N-Methylleucine
NMe$^D$Leu D-N-Methylleucine
NMeNle L-N-Methylnorleucine
NMe$^D$Nle D-N-Methylnorleucine
NMeMet L-N-Methylmethionine
NMe$^D$Met D-N-Methylmethionine
NMeTyr L-N-Methyltyrosine
NMe$^D$Tyr D-N-Methyltyrosine
NMeHis L-N-Methylhistidine
NMe$^D$His D-N-Methylhistidine
NMePhe L-N-Methylphenylalanine
NMe$^D$Phe D-N-Methylphenylalanine
NMeTrp L-N-Methyltryptophane
NMe$^D$Trp D-N-Methyltryptophane
NMeSer L-N-Methylserine
NMe$^D$Ser D-N-Methylserine
NMeAsp L-N-Methylaspartic acid
NMe$^D$Asp D-N-Methylaspartic acid
NMeGlu L-N-Methylglutamic acid
NMe$^D$Glu D-N-Methylglutamic acid
NMeLys L-N-Methyllysine
NMe$^D$Lys D-N-Methyllysine
NMeArg L-N-Methylarginine
NMe$^D$Arg D-N-Methylarginine
NMeDab L-N-Methyl-2,4-diamino butyric acid
NMe$^D$Dab D-N-Methyl-2,4-diamino butyric acid
NMeCys L-N-Methylcysteine
NMe$^D$Cys D-N-Methylcysteine
NMeAsn L-N-Methylasparagine
NMe$^D$Asn D-N-Methylasparagine
NMeGln L-N-Methylglutamine
NMe$^D$Gln D-N-Methylglutamine
NMeThr L-N-Methylthreonine
NMe$^D$Thr D-N-Methylthreonine
Tyr(Oo) Tyr(O-octyl)
$^D$Tyr(Oo) D-Tyr(O-octyl)
Tyr(Od) Tyr(O-decyl)
$^D$Tyr(Od) D-Tyr(O-decyl)
Tyr(Odd) Tyr(O-dodecyl)
$^D$Tyr(Odd) D-Tyr(O-dodecyl)
Tyr(Otd) Tyr(O-tetradecyl)
$^D$Tyr(Otd) D-Tyr(O-tetradecyl)
Tyr(Ohd) Tyr(O-hexadecyl)
$^D$Tyr(Ohd) D-Tyr(O-hexadecyl)
2Amdd-OH 2-Aminododecanoic acid
$^D$2Amdd-OH D-2-Aminododecanoic acid
2Amtd-OH 2-Aminotetradecanoic acid
$^D$2Amtd-OH D-2-Aminotetradecanoic acid
2Amhd-OH 2-Aminohexadecanoic acid
$^D$2Amhd-OH D-2-Aminohexadecanoic acid
Dab(N$^\gamma$o) Dab(N$^\gamma$-octanoyl)
$^D$Dab(N$^\gamma$o) D-Dab(N$^\gamma$-octanoyl)
Dab(N$^\gamma$2bo) Dab(N$^\gamma$2-butyloctanoyl)
$^D$Dab(N$^\gamma$2bo) D-Dab(N$^\gamma$2-butyloctanoyl)
Dab(N$^\gamma$d) Dab(N$^\gamma$-decanoyl)
$^D$Dab(N$^\gamma$d) D-Dab(N$^\gamma$-decanoyl)
Dab(N$^\gamma$dd) Dab(N$^\gamma$-dodecanoyl)
$^D$Dab(N$^\gamma$dd) D-Dab(N$^\gamma$-dodecanoyl)
Dab(N$^\gamma$td) Dab(N$^\gamma$-tetradecanoyl)
$^D$Dab(N$^\gamma$td) D-Dab(N$^\gamma$-tetradecanoyl)
Dab(N$^\gamma$hd) Dab(N$^\gamma$-hexadecanoyl)
$^D$Dab(N$^\gamma$hd) D-Dab(N$^\gamma$-hexadecanoyl)
Lys(N$^\epsilon$o) Lys(N$^\epsilon$-octanoyl)
$^D$Lys(N$^\epsilon$o) D-Lys(N$^\epsilon$-octanoyl)
Lys(N$^\epsilon$2bo) Lys(N$^\epsilon$2-butyloctanoyl)

$^D$Lys(N$^ε$2bo) D-Lys(N$^ε$-2-butyloctanoyl)
Lys(N$^ε$d) Lys(N$^ε$-decanoyl)
$^D$Lys(N$^ε$d) D-Lys(N$^ε$-decanoyl)
Lys(N$^ε$dd) Lys(N$^ε$-dodecanoyl)
$^D$Lys(N$^ε$dd) D-Lys(N$^ε$-dodecanoyl)
Lys(N$^ε$td) Lys(N$^ε$-tetradecanoyl)
$^D$Lys(N$^ε$td) D-Lys(N$^ε$-tetradecanoyl)
Lys(N$^γ$hd) Lys(N$^γ$-hexadecanoyl)
$^D$Lys(N$^γ$hd) D-Lys(N$^ε$-hexadecanoyl)
Lys((N$^ε$od) Lys(N$^ε$-octadecanoyl)
$^D$Lys((N$^ε$od) D-Lys(N$^ε$-octadecanoyl)
Dab(N$^γ$8amo) Dab(N$^γ$-8-aminooctanoyl)
$^D$Dab(N$^γ$8amo) D-Dab(N$^γ$-8-aminooctanoyl)
Dab(N$^γ$10amd) Dab(N$^γ$-10-aminodecanoyl)
$^D$Dab(N$^γ$10amd) D-Dab(N$^γ$-10-aminodecanoyl)
Dab(N$^γ$12amdd) Dab(N$^γ$-12-aminododecanoyl)
$^D$Dab(N$^γ$12amdd) D-Dab(N$^γ$-12-aminododecanoyl)
Dab(N$^γ$14amtd) Dab(N$^γ$-14-aminotetradecanoyl)
$^D$Dab(N$^γ$14amtd) D-Dab(N$^γ$-14-aminotetradecanoyl)
Dab(N$^γ$16amhd) Dab(N$^γ$-16-aminohexadecanoyl)
$^D$Dab(N$^γ$16amhd) D-Dab(N$^γ$-16-aminohexadecanoyl)
Lys(N$^ε$8amo) Lys(N$^ε$-8-aminooctanoyl)
$^D$Lys(N$^ε$8amo) D-Lys(N$^ε$-8-aminooctanoyl)
Lys(N$^ε$10amd) Lys(N$^γ$-10-aminodecanoyl)
$^D$Lys(N$^ε$10amd) D-Lys(N$^ε$-10-aminodecanoyl)
Lys(N$^ε$12amdd) Lys(N$^ε$-12-aminododecanoyl)
$^D$Lys(N$^ε$12amdd) D-Lys(N$^ε$-12-aminododecanoyl)
Lys(N$^ε$14amtd) Lys(N$^ε$-14-aminotetradecanoyl)
$^D$Lys(N$^ε$14amtd) D-Lys(N$^ε$-14-aminotetradecanoyl)
Lys(N$^ε$16amhd) Lys(N$^ε$-16-aminohexadecanoyl)
$^D$Lys(N$^ε$16amhd) D-Lys(N$^ε$-16-aminohexadecanoyl)
Dab(N$^γ$8OHo) Dab(N$^γ$-8-hydroxyoctanoyl)
$^D$Dab(N$^γ$8OHo) D-Dab(N$^γ$-8-hydroxyoctanoyl)
Dab(N$^γ$10OHd) Dab(N$^γ$-10-hydroxydecanoyl)
$^D$Dab(N$^γ$10OHd) D-Dab(N$^γ$-10-hydroxydecanoyl)
Dab(N$^γ$12OHdd) Dab(N$^γ$-12-hydroxydodecanoyl)
$^D$Dab(N$^γ$12OHdd) D-Dab(N$^γ$-12-hydroxydodecanoyl)
Dab(N$^γ$14OHtd) Dab(N$^γ$-14-hydroxytetradecanoyl)
$^D$Dab(N$^γ$14OHtd) D-Dab(N$^γ$-14-hydroxytetradecanoyl)
Dab(N$^γ$16OHhd) Dab(N$^γ$-16-hydroxyhexadecanoyl)
$^D$Dab(N$^γ$16OHhd) D-Dab(N$^γ$-16-hydroxyhexadecanoyl)
Lys(N$^ε$8OHo) Lys(N$^ε$-8-hydroxyoctanoyl)
$^D$Lys(N$^ε$8OHo) D-Lys(N$^ε$-8-hydroxyoctanoyl)
Lys(N$^ε$10OHd) Lys(N$^ε$-10-hydroxydecanoyl)
$^D$Lys(N$^ε$10OHd) D-Lys(N$^ε$-10-hydroxydecanoyl)
Lys(N$^ε$12OHdd) Lys(N$^ε$-12-hydroxydodecanoyl)
$^D$Lys(N$^ε$12OHdd) D-Lys(N$^ε$-12-hydroxydodecanoyl)
Lys(N$^ε$14OHtd) Lys(N$^ε$-14-hydroxytetradecanoyl)
$^D$Lys(N$^ε$14OHtd) D-Lys(N$^ε$-14-hydroxytetradecanoyl)
Lys(N$^ε$16OHhd) Lys(N$^ε$-16-hydroxyhexadecanoyl)
$^D$Lys(N$^γ$16OHhd) D-Lys(N$^ε$-16-hydroxyhexadecanoyl)
Dab(N$^γ$4ooxbe) Dab(N$^γ$-4-octyloxybenzoyl)
$^D$Dab(N$^γ$4ooxbe) D-Dab(N$^γ$-4-octyloxybenzoyl)
Dab(N$^γ$4doxbe) Dab(N$^γ$-4-decyloxybenzoyl)
$^D$Dab(N$^γ$4doxbe) D-Dab(N$^γ$-4-decyloxybenzoyl)
Dab(N$^γ$4ddoxbe) Dab(N$^γ$-4-dodecyloxybenzoyl)
$^D$Dab(N$^γ$4ddoxe) D-Dab(N$^γ$-4-dodecyloxybenzoyl)
Dab(N$^γ$4tdoxbe) Dab(N$^γ$-4-tetradecyloxybenzoyl)
$^D$Dab(N$^γ$4tdoxe) D-Dab(N$^γ$-4-tetradecyloxybenzoyl)
Dab(N$^γ$4hdoxbe) Dab(N$^γ$-4-hexadecyloxybenzoyl)
$^D$Dab(N$^γ$4hdoxe) D-Dab(N$^γ$-4-hexadecyloxybenzoyl)
Lys(N$^ε$4ooxbe) Lys(N$^ε$-4-octyloxybenzoyl)
$^D$Lys(N$^ε$4ooxbe) D-Lys(N$^ε$-4-octyloxybenzoyl)
Lys(N$^ε$4doxbe) Lys(N$^ε$-4-decyloxybenzoyl)
$^D$Lys(N$^ε$4doxbe) D-Lys(N$^ε$-4-decyloxybenzoyl)
Lys(N$^ε$4ddoxbe) Lys(N$^ε$-4-dodecyloxybenzoyl)
$^D$Lys(N$^ε$4ddoxe) D-Lys(N$^ε$-4-dodecyloxybenzoyl)
Lys(N$^ε$4tdoxbe) Lys(N$^ε$-4-tetradecyloxybenzoyl)
$^D$Lys(N$^ε$4tdoxe) D-Lys(N$^ε$-4-tetradecyloxybenzoyl)
Lys(N$^ε$4hdoxbe) Lys(N$^ε$-4-hexadecyloxybenzoyl)
$^D$Lys(N$^ε$4hdoxe) D-Lys(N$^ε$-4-hexadecyloxybenzoyl)
Dab(N$^γ$glcho) Dab(N$^γ$-glycocholoyl)
$^D$Dab(N$^γ$glcho) D-Dab(N$^γ$-glycocholoyl)
Lys(N$^ε$glcho) Lys(N$^ε$-glycocholoyl)
$^D$Lys(N$^ε$glcho) D-Lys(N$^ε$-glycocholoyl)
Dab(N$^γ$ado) Dab(N$^γ$-adamantoyl)
$^D$Dab(N$^γ$ado) D-Dab(N$^γ$-adamantoyl)
Lys(N$^ε$ado) Lys(N$^ε$-adamantoyl)
$^D$Lys(N$^ε$ado) D-Lys(N$^ε$-adamantoyl)
Dab(N$^γ$γgluN$^α$o) Dab(N$^γ$-(γ-glutamyl(N$^α$-octanoyl)))
$^D$Dab(N$^γ$γgluN$^α$o) D-Dab(N$^γ$-(γ-glutamyl(N$^α$-octanoyl)))
Dab(N$^γ$γgluN$^α$2bo) Dab(N$^γ$-(γ-glutamyl(N$^α$-2-butyloctanoyl)))
$^D$Dab(N$^γ$γgluN$^α$2bo) D-Dab(N$^γ$-(γ-glutamyl(N$^α$-2-butyloctanoyl)))
Dab(N$^γ$γgluN$^α$d) Dab(N$^γ$-(γ-glutamyl(N$^α$-decanoyl)))
$^D$Dab(N$^γ$γgluN$^α$d) D-Dab(N$^γ$-(γ-glutamyl(N$^α$-decanoyl)))
Dab(N$^γ$γgluN$^α$dd) Dab(N$^γ$-(γ-glutamyl(N$^α$-dodecanoyl)))
$^D$Dab(N$^γ$γgluN$^α$dd) D-Dab(N$^γ$-(γ-glutamyl(N$^α$-dodecanoyl)))
Dab(N$^γ$γgluN$^α$td) Dab(N$^γ$-(γ-glutamyl(N$^α$-tetradecanoyl)))
$^D$Dab(N$^γ$γgluN$^α$td) D-Dab(N$^γ$-(γ-glutamyl(N$^α$-tetradecanoyl)))
Dab(N$^γ$γgluN$^α$hd) Dab(N$^γ$-(γ-glutamyl(N$^α$-hexadecanoyl)))
$^D$Dab(N$^γ$γgluN$^α$hd) D-Dab(N$^γ$-(γ-glutamyl(N$^α$-hexadecanoyl)))
Lys(N$^ε$γgluN$^α$o) Lys(N$^ε$-(γ-glutamyl(N$^α$-octanoyl)))
$^D$Lys(N$^ε$γgluN$^α$o) D-Lys(N$^ε$-(γ-glutamyl(N$^α$-octanoyl)))
Lys(N$^ε$γgluN$^α$2bo) Lys(N$^ε$-(γ-glutamyl(N$^α$-2-butyloctanoyl)))
$^D$Lys(N$^ε$γgluN$^α$2bo) D-Lys(N$^ε$-(γ-glutamyl(N$^α$-2-butyloctanoyl)))
Lys(N$^ε$γgluN$^α$d) Lys(N$^ε$-(γ-glutamyl(N$^α$-decanoyl)))
$^D$Lys(N$^ε$γgluN$^α$d) D-Lys(N$^ε$-(γ-glutamyl(N$^α$-decanoyl)))
Lys(N$^ε$γgluN$^α$dd) Lys(N$^ε$-(γ-glutamyl(N$^α$-dodecanoyl)))
$^D$Lys(N$^ε$γgluN$^α$dd) D-Lys(N$^ε$-(γ-glutamyl(N$^α$-dodecanoyl)))
Lys(N$^ε$γgluN$^α$td) Lys(N$^ε$-(γ-glutamyl(N$^α$-tetradecanoyl)))
$^D$Lys(N$^ε$γgluN$^α$td) D-Lys(N$^ε$-(γ-glutamyl(N$^α$-tetradecanoyl)))
Lys(N$^ε$γgluN$^α$hd) Lys(N$^ε$-(γ-glutamyl(N$^α$-hexadecanoyl)))
$^D$Lys(N$^ε$γgluN$^α$hd) D-Lys(N$^ε$-(γ-glutamyl(N$^α$-hexadecanoyl)))
Arg(N$^ω$ooxca) Arg(N$^ω$-octyloxycarbonyl)
$^D$Arg(N$^ω$ooxca) D-Arg(N$^ω$-octyloxycarbonyl)
Arg(N$^ω$doxca) Arg(N$^ω$-decyloxycarbonyl)
$^D$Arg(N$^ω$doxca) D-Arg(N$^ω$-decyloxycarbonyl)
Arg(N$^ω$ddoxca) Arg(N$^ω$-dodecyloxycarbonyl)
$^D$Arg($^ω$ddoxca) D-Arg(N$^ω$-dodecyloxycarbonyl)
Arg(N$^ω$tdoxca) Arg(N$^ω$-tetradecyloxycarbonyl)
$^D$Arg(N$^ω$tdoxca) D-Arg(N$^ω$-tetradecyloxycarbonyl)
Arg(N$^ω$hdoxca) Arg(N$^ω$-hexadecyloxycarbonyl)
$^D$Arg(N$^ω$hdoxca) D-Arg(N$^ω$-hexadecyloxycarbonyl)
Gln(N$^ω$ad) Gln(N$^ω$-adamantyl)
$^D$Gln(N$^ω$ad) D-Gln(N$^ω$-adamantyl)
Ser(Oo) Ser(O-octyl)
$^D$Ser(Oo) D-Ser(O-octyl)
Ser(Od) Ser(O-decyl)
$^D$Ser(Od) D-Ser(O-decyl)
Ser(Odd) Ser(O-dodecyl)
$^D$Ser(Odd) D-Ser(O-dodecyl)
Ser(Otd) Ser(O-tetradecyl)
$^D$Ser(Otd) D-Ser(O-tetradecyl)
Ser(Ohd) Ser(O-hexadecyl)

ᴰSer(Ohd) D-Ser(O-hexadecyl)
4AmPyrr1(o) (2S,4S)-4-Octanoylamino-pyrrolidine-2-carboxylic acid
ᴰ4AmPyrr1(o) (2R,4S)-4-Octanoylamino-pyrrolidine-2-carboxylic acid
4AmPyrr1(d) (2S,4S)-4-Decanoylamino-pyrrolidine-2-carboxylic acid
ᴰ4AmPyrr1(d) (2R,4S)-4-Decanoylamino-pyrrolidine-2-carboxylic acid
4AmPyrr1(dd) (2S,4S)-4-Dodecanoylamino-pyrrolidine-2-carboxylic acid
ᴰ4AmPyrr1(dd) (2R,4S)-4-Dodecanoylamino-pyrrolidine-2-carboxylic acid
4AmPyrr1(td) (2S,4S)-4-Tetradecanoylamino-pyrrolidine-2-carboxylic acid
ᴰ4AmPyrr1(td) (2R,4S)-4-Tetradecanoylamino-pyrrolidine-2-carboxylic acid
4AmPyrr1(hd) (2S,4S)-4-Hexadecanoylamino-pyrrolidine-2-carboxylic acid
ᴰ4AmPyrr1(hd) (2R,4S)-4-Hexadecanoylamino-pyrrolidine-2-carboxylic acid
4AmPyrr2(o) (2S,4R)-4-Octanoylamino-pyrrolidine-2-carboxylic acid
ᴰ4AmPyrr2(o) (2R,4R)-4-Octanoylamino-pyrrolidine-2-carboxylic acid
4AmPyrr2(d) (2S,4R)-4-Decanoylamino-pyrrolidine-2-carboxylic acid
ᴰ4AmPyrr2(d) (2R,4R)-4-Decanoylamino-pyrrolidine-2-carboxylic acid
4AmPyrr2(dd) (2S,4R)-4-Dodecanoylamino-pyrrolidine-2-carboxylic acid
ᴰ4AmPyrr2(dd) (2R,4R)-4-Dodecanoylamino-pyrrolidine-2-carboxylic acid
4AmPyrr2(td) (2S,4R)-4-Tetradecanoylamino-pyrrolidine-2-carboxylic acid
ᴰ4AmPyrr2(td) (2R,4R)-4-Tetradecanoylamino-pyrrolidine-2-carboxylic acid
4AmPyrr2(hd) (2S,4R)-4-Hexadecanoylamino-pyrrolidine-2-carboxylic acid
ᴰ4AmPyrr2(hd) (2R,4R)-4-Hexadecanoylamino-pyrrolidine-2-carboxylic acid
Particularly preferred residues for group C are:
Ala L-Alanine
ᴰAla D-Alanine
Ile L-Isoleucine
ᴰIle D-Isoleucine
Leu L-Leucine
ᴰLeu D-Leucine
Met L-Methionine
ᴰMet D-Methionine
Val L-Valine
ᴰVal D-Valine
tBuA L-t-Butylalanine
ᴰtBuA D-t-Butylalanine
tBuG L-tert.-Butylglycine
ᴰtBuG D-tert.-Butylglycine
Cha L-Cyclohexylalanine
ᴰCha D-Cyclohexylalanine
C₄al L-3-Cyclobutylalanine
ᴰC₄al D-3-Cyclobutylalanine
C₅al L-3-Cyclopentylalanine
ᴰC₅al D-3-Cyclopentylalanine
Nle L-Norleucine
ᴰNle D-Norleucine
hAla L-Homo-alanine
ᴰhAla D-Homo-alanine
hIle L-Homo-isoleucine
ᴰhIle D-Homo-isoleucine
hLeu L-Homo-leucine
ᴰhLeu D-Homo-leucine
hMet L-Homo-Methionine
ᴰhMet D-Homo-Methionine
hVal L-Homo-valine
ᴰhVal D-Homo-valine
hCha L-Homo-cyclohexylalanine
ᴰhCha D-Homo-cyclohexylalanine
NMeAla L-N-Methylalanine
NMeᴰAla D-N-Methylalanine
NMeVal L-N-Methylvaline
NMeᴰVal D-N-Methylvaline
NMeIle L-N-Methylisoleucine
NMeᴰIle D-N-Methylisoleucine
NMeLeu L-N-Methylleucine
NMeᴰLeu D-N-Methylleucine
NMeNle L-N-Methylnorleucine
NMeᴰNle D-N-Methylnorleucine
NMeNle L-N-Methylnorleucine
NMeᴰNle D-N-Methylnorleucine
NMeMet L-N-Methylmethionine
NMeᴰMet D-N-Methylmethionine
Particularly preferred residues for group D are:
His L-Histidine
ᴰHis D-Histidine
Phe L-Phenylalanine
ᴰPhe D-Phenylalanine
Trp L-Tryptophan
ᴰTrp D-Tryptophan
Tyr L-Tyrosine
ᴰTyr D-Tyrosine
2Pal (2S)-2-Amino-3-(pyridine-2'-yl)-propionic acid
ᴰ2Pal (2R)-2-Amino-3-(pyridine-2'-yl)-propionic acid
4Pal (2S)-2-Amino-3-(pyridine-4'-yl)-propionic acid
ᴰ4Pal (2R)-2-Amino-3-(pyridine-4'-yl)-propionic acid
Phg L-Phenylglycine
ᴰPhg D-Phenylglycine
2Nal L-2-Naphthylalanine
ᴰ2Nal D-2-Naphthylalanine
1-Nal L-1-Naphthylalanine
ᴰ1Nal D-1-Naphthylalanine
4Cl Phe L-4-Chlorophenylalanine
ᴰ4Cl Phe D-4-Chlorophenylalanine
3Cl Phe L-3-Chlorophenylalanine
ᴰ3Cl Phe D-3-Chlorophenylalanine
2Cl Phe L-2-Chlorophenylalanine
ᴰ2Cl Phe D-2-Chlorophenylalanine
3,4Cl₂Phe L-3,4-Dichlorophenylalanine
ᴰ3,4Cl₂Phe D-3,4-Dichlorophenylalanine
4FPhe L-4-Fluorophenylalanine
ᴰ4FPhe D-4-Fluorophenylalanine
3FPhe L-3-Fluorophenylalanine
ᴰ3FPhe D-3-Fluorophenylalanine
2FPhe L-2-Fluorophenylalanine
ᴰ2FPhe D-2-Fluorophenylalanine
Thi L-β-2-Thienylalanine
ᴰThi D-β-2-Thienylalanine
Tza L-2-Thiazolylalanine
ᴰTza D-2-Thiazolylalanine
Y(Bzl) L-O-Benzyltyrosine
ᴰY(Bzl) D-O-Benzyltyrosine
H(Bzl) (3S)-2-Amino-3-(1'-benzylimidazole-4'-yl)-propionic acid
ᴰH(Bzl) (3R)-2-Amino-3-(1'-benzylimidazole-4'-yl)-propionic acid
Bip L-(4-phenyl)phenylalanine $^D$Bip D-(4-phenyl)phenylalanine
S(Bzl) L-O-Benzylserine
$^D$S(Bzl) D-O-Benzylserine
T(Bzl) L-O-Benzylthreonine
$^D$T(Bzl) D-O-Benzylthreonine
hPhe L-Homo-phenylalanine
$^D$hPhe D-Homo-phenylalanine
hTrp L-Homo-tryptophan
$^D$hTrp D-Homo-tryptophan
hTyr L-Homo-tyrosine
$^D$hTyr D-Homo-tyrosine
hHis L-Homo-histidine
$^D$hHis D-Homo-histidine
Bpa L-4-Benzoylphenylalanine
$^D$Bpa D-4-Benzoylphenylalanine
NMePhe L-N-Methylphenylalanine
NMe$^D$Phe D-N-Methylphenylalanine
NMeTyr L-N-Methyltyrosine
NMe$^D$Tyr D-N-Methyltyrosine
NMeHis L-N-Methylhistidine
NMe$^c$His D-N-Methylhistidine
NMeTrp L-N-Methyltryptophane
NMe$^D$Trp D-N-Methyltryptophane
  Particularly preferred residues for group E are
Arg L-Arginine
$^D$Arg D-Arginine
Lys L-Lysine
$^D$Lys D-Lysine
Orn L-Ornithine
$^D$Orn D-Ornithine
Dpr L-2,3-Diaminopropionic acid
$^D$Dpr D-2,3-Diaminopropionic acid
Dab L-2,4-Diaminobutyric acid
$^D$Dab(2R)-2,4-Diaminobutyric acid
Dbu (2S,3S)-2,3-Diaminobutyric acid
$^D$Dbu (2R)-2,3-Diamino-butyric acid
Cit L-Citrulline
$^D$Cit D-Citrulline
4AmPhe L-para-Aminophenylalanine
$^D$4AmPhe D-para-Aminophenylalanine
3AmPhe L-meta-Aminophenylalanine
$^D$3AmPne D-meta-Aminophenylalanine
2AmPhe L-ortho-Aminophenylalanine
$^D$2AmPhe D-ortho-Aminophenylalanine
Phe (mC(NH$_2$)=NH) L-meta-Amidinophenylalanine
$^D$Phe (mC(NH$_2$)=NH) D-meta-Amidinophenylalanine
Phe (pC(NH$_2$)=NH) L-para-Amidinophenylalanine
$^D$Phe (pC(NH$_2$)=NH) D-para-Amidinophenylalanine
Phe(mNHC(NH$_2$)=NH) L-meta-Guanidinophenylalanine
$^D$Phe (mNHC(NH$_2$)=NH) D-meta-Guanidinophenylalanine
Phe(pNHC(NH$_2$)=NH) L-para-Guanidinophenylalanine
$^D$Phe(pNHC(NH$_2$)=NH) D-para-Guanidinophenylalanine
hArg L-Homo-arginine
$^D$hArg D-Homo-arginine
hLys L-Homo-lysine
$^D$hLys D-Homo-lysine
NMeLys L-N-Methyllysine
NMe$^D$Lys D-N-Methyllysine
NMeArg L-N-Methylarginine
NMe$^D$Arg D-N-Methylarginine
NMeDab L-N-Methyl-2,4-diamino butyric acid
NMe$^D$Dab D-N-Methyl-2,4-diamino butyric acid
  Particularly preferred residues for group F are
Asn L-Asparagine
$^D$Asn D-Asparagine
Asp L-Aspartic acid
$^D$Asp D-Aspartic acid
Cys L-Cysteine
$^D$Cys D-Cysteine
Gln L-Glutamine
$^D$Gln D-Glutamine
Glu L-Glutamic acid
$^D$Glu D-Glutamic acid
Ser L-Serine
$^D$Ser D-Serine
Thr L-Threonine
$^D$Thr D-Threonine
Pen L-Penicillamine
$^D$Pen D-Penicillamine
AcLys L-N$^r$-Acetyllysine
$^D$AcLys N-Acetyl-D-lysine
alloT (2S,3S)-2-Amino-3-hydroxy-butyric acid
$^D$alloT (2R,3S)-2-Amino-3-hydroxy-butyric acid
Leu3OH (2S,3R)-2-Amino-3-hydroxy-4-methyl-pentanoic acid
$^D$Leu3OH (2R,3R)-2-Amino-3-hydroxy-4-methyl-pentanoic acid
hCys L-Homo-cysteine
$^D$hCys D-Homo-cysteine
hSer L-Homo-serine
$^D$hSer D-Homo-serine
hGlu L-Homo-glutamic acid
$^D$hGlu D-glutamic acid
hGln L-Homo-glutamine
$^D$hGln D-Homo-glutamine
hThr L-Homo-threonine
$^D$hThr D-Homo-threonine
NMeSer L-N-Methylserine
NMe$^D$Ser D-N-Methylserine
NMeAsp L-N-Methylaspartic acid
NMe$^D$Asp D-N-Methylaspartic acid
NMeGlu L-N-Methylglutamic acid
NMe$^D$Glu D-N-Methylglutamic acid
NMeCys L-N-Methylcysteine
NMe$^D$Cys D-N-Methylcysteine
NMeAsn L-N-Methylasparagine
NMe$^D$Asn D-N-Methylasparagine
NMeGln L-N-Methylglutamine
NMe$^D$Gln D-N-Methylglutamine
NMeThr L-N-Methylthreonine
NMe$^D$Thr D-N-Methylthreonine
  Particularly preferred residues for group I are
(AEt)G N-(2-Aminoethyl)glycine
(APr)G N-(3-Amino-n-propyl)glycine
(ABu)G N-(4-Amino-n-butyl)glycine
(APe)G N-(5-Amino-n-pentyl)glycine
(GuEt)G N-(2-Guanidinoethyl)glycine
(GuPr)G N-(3-Guanidino-n-propyl)glycine
(GuBu)G N-(4-Guanidino-n-butyl)glycine
(GuPe)G N-(5-Guanidino-n-pentyl)glycine
(PEG$_3$-NH$_2$)G N—[H$_2$N—(CH$_2$)$_3$—(OCH$_2$—CH$_2$)$_2$—O(CH$_2$)$_3$]glycine
(Me)G N-Methylglycine
(Et)G N-Ethylglycine
(Bu)G N-Butylglycine
(Pe)G N-Pentylglycine
(Ip)G N-Isopropylglycine
(2MePr)G N-(2-Methylpropyl)glycine
(3MeBu)G N-(3-Methylbutyl)glycine
(1MePr)G (1S)—N-(1-Methylpropyl)glycine
(2MeBu)G (2S)—N-(2-Methylbutyl)glycine
(MthEt)G N-(Methylthioethyl)glycine
(MthPr)G N-(Methylthiopropyl)glycine (Ben)G N-(Benzyl)glycine
(PhEt)G N-(2-Phenylethyl)glycine
(HphMe)G N-([4'-hydroxyphenyl]methyl)glycine
(HphEt)G N-(2-[4'-hydroxyphenyl]ethyl)glycine
(ImMe)G N-(Imidazol-5-yl-methyl)glycine
(ImEt)G N-(2-(Imidazol-5'-yl)ethyl)glycine
(InMe)G N-(Indol-2-yl-methyl)glycine
(InEt)G N-(2-(Indol-2'-yl)ethyl)glycine
(CboMe)G N—(Carboxymethyl)glycine
(CboEt)G N-(2-Carboxyethyl)glycine
(CboPr)G N-(3-Carboxypropyl)glycine
(CbaMe)G N—(Carbamoylmethyl)glycine
(CbaEt)G N-(2-Carbamoylethyl)glycine
(CbaPr)G N-(3-Carbamoylpropyl)glycine
(HyEt)G N-(2-Hydroxyethyl)glycine
(HyPr)G (2R)—N-(2-Hydroxypropyl)glycine (Mcet)G N-(2-Mercaptoethyl)glycine
  Particularly preferred residues for group O are
Tyr(Oo) Tyr(O-octyl)
$^D$Tyr(Oo) D-Tyr(O-octyl)
Tyr(Od) Tyr(O-decyl)
$^D$Tyr(Od) D-Tyr(O-decyl)
$^D$Tyr(Odd) D-Tyr(O-dodecyl)
Tyr(Otd) Tyr(O-tetradecyl)
$^D$Tyr(Otd) D-Tyr(O-tetradecyl)
Tyr(Ohd) Tyr(O-hexadecyl)
$^D$Tyr(Ohd) D-Tyr(O-hexadecyl)
2Amdd-OH 2-Aminododecanoic acid
$^D$2Amdd-OH D-2-Aminododecanoic acid
2Amtd-OH 2-Aminotetradecanoic acid
$^D$2Amtd-OH D-2-Aminotetradecanoic acid
2Amhd-OH 2-Aminohexadecanoic acid
$^D$2Amhd-OH D-2-Aminohexadecanoic acid
Dab(N$^\gamma$o) Dab(N$^\gamma$-octanoyl)
$^D$Dab(N$^\gamma$o) D-Dab(N$^\gamma$-octanoyl)
Dab(N$^\gamma$2bo) Dab(N$^\gamma$2-butyloctanoyl)
$^D$Dab(N$^\gamma$2bo) D-Dab(N$^\gamma$2-butyloctanoyl)
Dab(N$^\gamma$d) Dab(N$^\gamma$-decanoyl)
$^D$Dab(N$^\gamma$d) D-Dab(N$^\gamma$-decanoyl)
Dab(N$^\gamma$dd) Dab(N$^\gamma$-dodecanoyl)
$^D$Dab(N$^\gamma$dd) D-Dab(N$^\gamma$-dodecanoyl)
Dab(N$^\gamma$td) Dab(N$^\gamma$-tetradecanoyl)
$^D$Dab(N$^\gamma$td) D-Dab(N$^\gamma$-tetradecanoyl)
Dab(N$^\gamma$hd) Dab(N$^\gamma$-hexadecanoyl)
$^D$Dab(N$^\gamma$hd) D-Dab(N$^\gamma$-hexadecanoyl)
Lys(N$^\epsilon$o) Lys(N$^\epsilon$-octanoyl)
$^D$Lys(N$^\epsilon$o) D-Lys(N$^\epsilon$-octanoyl)
Lys(N$^\epsilon$2bo) Lys(N$^\epsilon$2-butyloctanoyl)
$^D$Lys(N$^\epsilon$2bo) D-Lys(N$^\epsilon$2-butyloctanoyl)
Lys(N$^\epsilon$d) Lys(N$^\epsilon$-decanoyl)
$^D$Lys(N$^\epsilon$d) D-Lys(N$^\epsilon$-decanoyl)
Lys(N$^\epsilon$dd) Lys(N$^\epsilon$-dodecanoyl)
$^D$Lys(N$^\epsilon$dd) D-Lys(N$^\epsilon$-dodecanoyl)
Lys(N$^\epsilon$td) Lys(N$^\epsilon$-tetradecanoyl)
$^D$Lys(N$^\epsilon$td) D-Lys(N$^\epsilon$-tetradecanoyl)
Lys(N$^\epsilon$hd) Lys(N$^\epsilon$-hexadecanoyl)
$^D$Lys(N$^\epsilon$hd) D-Lys(N$^\epsilon$-hexadecanoyl)
Lys((N$^\epsilon$od) Lys(N$^\epsilon$-octadecanoyl)
$^D$Lys((N$^\epsilon$od) D-Lys(N$^\epsilon$-octadecanoyl)
Dab(N$^\gamma$8amo) Dab(N$^\gamma$-8-aminooctanoyl)
$^D$Dab(N$^\gamma$8amo) D-Dab(N$^\gamma$-8-aminooctanoyl)
Dab(N$^\gamma$10amd) Dab(N$^\gamma$-10-aminodecanoyl)
$^D$Dab(N$^\gamma$10amd) D-Dab(N$^\gamma$-10-aminodecanoyl)
Dab(N$^\gamma$12amdd) Dab(N$^\gamma$-12-aminododecanoyl)
$^D$Dab(N$^\gamma$12amdd) D-Dab(N$^\gamma$-12-aminododecanoyl)
Dab(N$^\gamma$14amtd) Dab(N$^\gamma$-14-aminotetradecanoyl)
$^D$Dab(N$^\gamma$14amtd) D-Dab(N$^\gamma$-14-aminotetradecanoyl)
Dab(N$^\gamma$16amhd) Dab(N$^\gamma$-16-aminohexadecanoyl)
$^D$Dab(N$^\gamma$16amhd) D-Dab(N$^\gamma$-16-aminohexadecanoyl)
Lys(N$^\epsilon$8amo) Lys(N$^\epsilon$-8-aminooctanoyl)
$^D$Lys(N$^\epsilon$8amo) D-Lys(N$^\epsilon$-8-aminooctanoyl)
Lys(N$^\epsilon$10amd) Lys(N$^\epsilon$-10-aminodecanoyl)
$^D$Lys(N$^\epsilon$10amd) D-Lys(N$^\epsilon$-10-aminodecanoyl)
Lys(N$^\epsilon$12amdd) Lys(N$^\epsilon$-12-aminododecanoyl)
$^D$Lys(N$^\epsilon$12amdd) D-Lys(N$^\epsilon$-12-aminododecanoyl)
Lys(N$^\epsilon$14amtd) Lys(N$^\epsilon$-14-aminotetradecanoyl)
$^D$Lys(N$^\epsilon$14amtd) D-Lys(N$^\epsilon$-14-aminotetradecanoyl)
Lys(N$^\epsilon$16amhd) Lys(N$^\epsilon$-16-aminohexadecanoyl)
$^D$Lys(N$^\epsilon$16amhd) D-Lys(N$^\epsilon$-16-aminohexadecanoyl)
Dab(N$^\gamma$8OHo) Dab(N$^\gamma$-8-hydroxyoctanoyl)
$^D$Dab(N$^\gamma$8OHo) D-Dab(N$^\gamma$-8-hydroxyoctanoyl)
Dab(N$^\gamma$10OHd) Dab(N$^\gamma$-10-hydroxydecanoyl)
$^D$Dab(N$^\gamma$10OHd) D-Dab(N$^\gamma$-10-hydroxydecanoyl)
Dab(N$^\gamma$12OHdd) Dab(N$^\gamma$-12-hydroxydodecanoyl)
$^D$Dab(N$^\gamma$12OHdd) D-Dab(N$^\gamma$-12-hydroxydodecanoyl)
Dab(N$^\gamma$14OHtd) Dab(N$^\gamma$-14-hydroxytetradecanoyl)
$^D$Dab(N$^\gamma$14OHtd) D-Dab(N$^\gamma$-14-hydroxytetradecanoyl)
Dab(N$^\gamma$16OHhd) Dab(N$^\gamma$-16-hydroxyhexadecanoyl)
$^D$Dab(N$^\gamma$16OHhd) D-Dab(N$^\gamma$-16-hydroxyhexadecanoyl)
Lys(N$^\epsilon$8OHo) Lys(N$^\epsilon$-8-hydroxyoctanoyl)
$^D$Lys(N$^\epsilon$8OHo) D-Lys(N$^\epsilon$-8-hydroxyoctanoyl)
Lys(N$^\epsilon$10OHd) Lys(N$^\epsilon$-10-hydroxydecanoyl)
$^D$Lys(N$^\epsilon$10OHd) D-Lys(N$^\epsilon$-10-hydroxydecanoyl)
Lys(N$^\epsilon$12OHdd) Lys(N$^\epsilon$-12-hydroxydodecanoyl)
$^D$Lys(N N$^\epsilon$12OHdd) D-Lys(N$^\epsilon$-12-hydroxydodecanoyl)
Lys(N$^\epsilon$14OHtd) Lys(N$^\epsilon$-14-hydroxytetradecanoyl)
$^D$Lys(N$^\epsilon$14OHtd) D-Lys(N$^\epsilon$-14-hydroxytetradecanoyl)
Lys(N$^\epsilon$16OHhd) Lys(N$^\epsilon$-16-hydroxyhexadecanoyl)
$^D$Lys(N$^\epsilon$16OHhd) D-Lys(N$^\epsilon$-16-hydroxyhexadecanoyl)
Dab(N$^\gamma$4ooxbe) Dab(N$^\gamma$-4-octyloxybenzoyl)
$^D$Dab(N$^\gamma$4ooxbe) D-Dab(N$^\gamma$-4-octyloxybenzoyl)
Dab(N$^\gamma$4doxbe) Dab(N$^\gamma$-4-decyloxybenzoyl)
$^D$Dab(N$^\gamma$4doxbe) D-Dab(N$^\gamma$-4-decyloxybenzoyl)
Dab(N$^\gamma$4ddoxbe) Dab(N$^\gamma$-4-dodecyloxybenzoyl)
$^D$Dab(N$^\gamma$4ddoxe) D-Dab(N$^\gamma$-4-dodecyloxybenzoyl)
Dab(N$^\gamma$4tdoxbe) Dab(N$^\gamma$-4-tetradecyloxybenzoyl)
$^D$Dab(N$^\gamma$4tdoxe) D-Dab(N$^\gamma$-4-tetradecyloxybenzoyl)
Dab(N$^\gamma$4hdoxbe) Dab(N$^\gamma$-4-hexadecyloxybenzoyl)
$^D$Dab(N$^\gamma$4hdoxe) D-Dab(N$^\gamma$-4-hexadecyloxybenzoyl)
Lys(N$^\epsilon$4ooxbe) Lys(N$^\epsilon$-4-octyloxybenzoyl)
$^D$Lys(N$^\epsilon$4ooxbe) D-Lys(N$^\epsilon$-4-octyloxybenzoyl)
Lys(N$^\epsilon$4doxbe) Lys(N$^\epsilon$-4-decyloxybenzoyl)
$^D$Lys(N$^\epsilon$4doxbe) D-Lys(N$^\epsilon$-4-decyloxybenzoyl)
Lys(N$^\epsilon$4ddoxbe) Lys(N$^\epsilon$-4-dodecyloxybenzoyl)
$^D$Lys(N$^\epsilon$4ddoxe) D-Lys(N$^\epsilon$-4-dodecyloxybenzoyl)
Lys(N$^\epsilon$4tdoxbe) Lys(N$^\epsilon$-4-tetradecyloxybenzoyl)
$^D$Lys(N$^\epsilon$4tdoxe) D-Lys(N$^\epsilon$-4-tetradecyloxybenzoyl)
Lys(N$^\epsilon$4hdoxbe) Lys(N$^\epsilon$-4-hexadecyloxybenzoyl)
$^D$Lys(N$^\epsilon$4hdoxe) D-Lys(N$^\epsilon$-4-hexadecyloxybenzoyl)
Dab(N$^\gamma$glcho) Dab(N$^\gamma$-glycocholoyl)
$^D$Dab(N$^\gamma$glcho) D-Dab(N$^\gamma$-glycocholoyl)
Lys(N$^\epsilon$glcho) Lys(N$^\epsilon$-glycocholoyl)
$^D$Lys(N$^\epsilon$glcho) D-Lys(N$^\epsilon$-glycocholoyl)
Dab(N$^\gamma$ado) Dab(N$^\gamma$-adamantoyl)
$^D$Dab(N$^\gamma$ado) D-Dab(N$^\gamma$-adamantoyl)
Lys(N$^\epsilon$ado) Lys(N$^\epsilon$-adamantoyl)
$^D$Lys(N$^\epsilon$ado) D-Lys(N$^\epsilon$-adamantoyl)
Dab(N$^\gamma$γgluN$^\alpha$o) Dab(N$^\gamma$-(γ-glutamyl(N$^\epsilon$-octanoyl)))
$^D$Dab(N$^\gamma$γgluN$^\alpha$o) D-Dab(N$^\gamma$-(γ-glutamyl(N$^\epsilon$-octanoyl)))
Dab(N$^\gamma$γgluN$^\alpha$2bo) Dab (N$^\gamma$-(γ-glutamyl(N$^\alpha$-2-butyloctanoyl)))
$^D$Dab(N$^\gamma$γgluN$^\alpha$2bo) D-Dab(N$^\gamma$-(γ-glutamyl(N$^\alpha$-2-butyloctanoyl)))
Dab(N$^\gamma$γgluN$^\alpha$d) Dab(N$^\gamma$-(γ-glutamyl(N$^\alpha$-decanoyl)))

$^D$Dab(N$^\gamma$gluN$^\alpha$d) D-Dab(N$^\gamma$-(γ-glutamyl(N$^\alpha$-decanoyl)))
Dab(N$^\gamma$gluN$^\alpha$dd) Dab(N$^\gamma$-(γ-glutamyl(N$^\alpha$-dodecanoyl)))
$^D$Dab(N$^\gamma$gluN$^\alpha$dd) D-Dab(N$^\gamma$-(γ-glutamyl(N$^\alpha$-dodecanoyl)))
Dab(N$^\gamma$gluN$^\alpha$td) Dab(N$^\gamma$-(γ-glutamyl(N$^\alpha$-tetradecanoyl)))
$^D$Dab(N$^\gamma$gluN$^\alpha$td) D-Dab(N$^\gamma$-(γ-glutamyl(N$^\alpha$-tetradecanoyl)))
Dab(N$^\gamma$gluN$^\alpha$hd) Dab(N$^\gamma$-(γ-glutamyl(N$^\alpha$-hexadecanoyl)))
$^D$Dab(N$^\gamma$gluN$^\alpha$hd) D-Dab(N$^\gamma$-(γ-glutamyl(N$^\alpha$-hexadecanoyl)))
Lys(N$^\epsilon$gluN$^\alpha$o) Lys(N$^\epsilon$-(γ-glutamyl(N$^\alpha$-octanoyl)))
$^D$Lys(N$^\epsilon$gluN$^\alpha$o) D-Lys(N$^\epsilon$-(γ-glutamyl(N$^\alpha$-octanoyl)))
Lys(N$^\epsilon$gluN$^\alpha$2bo) Lys(N$^\epsilon$-(γ-glutamyl(N$^\alpha$-2-butyloctanoyl)))
$^D$Lys(N$^\epsilon$gluN$^\alpha$2bo) D-Lys(N$^\epsilon$-(γ-glutamyl(N$^\alpha$-2-butyloctanoyl)))
Lys(N$^\epsilon$gluN$^\alpha$d) Lys(N$^\epsilon$-(γ-glutamyl(N$^\alpha$-decanoyl)))
$^D$Lys(N$^\epsilon$gluN$^\alpha$d) D-Lys(N$^\epsilon$-(γ-glutamyl(N$^\alpha$-decanoyl)))
Lys(N$^\epsilon$gluN$^\alpha$dd) Lys(N$^\epsilon$-(γ-glutamyl(N$^\alpha$-dodecanoyl)))
$^D$Lys(N$^\epsilon$gluN$^\alpha$dd) D-Lys(N$^\epsilon$-(γ-glutamyl(N$^\alpha$-dodecanoyl)))
Lys(N$^\epsilon$gluN$^\alpha$td) Lys(N$^\epsilon$-(γ-glutamyl(N$^\alpha$-tetradecanoyl)))
$^D$Lys(N$^\epsilon$gluN$^\alpha$td) D-Lys(N$^\epsilon$-(γ-glutamyl(N$^\alpha$-tetradecanoyl)))
Lys(N$^\epsilon$gluN$^\alpha$hd) Lys(N$^\epsilon$-(γ-glutamyl(N$^\alpha$-hexadecanoyl)))
$^D$Lys(N$^\epsilon$gluN$^\alpha$hd) D-Lys(N$^\epsilon$-(γ-glutamyl(N$^\alpha$-hexadecanoyl)))
Arg(N$^\omega$ooxca) Arg(N$^\omega$-octyloxycarbonyl)
$^D$Arg(N$^\omega$ooxca) D-Arg(N$^\omega$-octyloxycarbonyl)
Arg(N$^\omega$doxca) Arg(N$^\omega$-decyloxycarbonyl)
$^D$Arg(N$^\omega$doxca) D-Arg(N$^\omega$-decyloxycarbonyl)
Arg(N$^\omega$ddoxca) Arg(N$^\omega$-dodecyloxycarbonyl)
$^D$Arg(N$^\omega$ddoxca) D-Arg(N$^\omega$-dodecyloxycarbonyl)
Arg(N$^\omega$tdoxca) Arg(N$^\omega$-tetradecyloxycarbonyl)
$^D$Arg(N$^\omega$tdoxca) D-Arg(N$^\omega$-tetradecyloxycarbonyl)
Arg(N$^\omega$hdoxca) Arg(N$^\omega$-hexadecyloxycarbonyl)
$^D$Arg(N$^\omega$hdoxca) D-Arg(N$^\omega$-hexadecyloxycarbonyl)
Gln(N$^\omega$ad) Gln (N$^\omega$-adamantyl)
$^D$Gln(N$^\omega$ad) D-Gln (N$^\omega$-adamantyl)
Ser(Oo) Ser(O-octyl)
$^D$Ser(Oo) D-Ser(O-octyl)
Ser(Od) Ser(O-decyl)
$^D$Ser(Od) D-Ser(O-decyl)
Ser(Odd) Ser(O-dodecyl)
$^D$Ser(Odd) D-Ser(O-dodecyl)
Ser(Otd) Ser(O-tetradecyl)
$^D$Ser(Otd) D-Ser(O-tetradecyl)
Ser(Ohd) Ser(O-hexadecyl)
$^D$Ser(Ohd) D-Ser(O-hexadecyl)
4AmPyrr1(o) (2S,4S)-4-Octanoylamino-pyrrolidine-2-carboxylic acid
$^D$4AmPyrr1(o) (2R,4S)-4-Octanoylamino-pyrrolidine-2-carboxylic acid
4AmPyrr1(d) (2S,4S)-4-Decanoylamino-pyrrolidine-2-carboxylic acid
$^D$4AmPyrr1(d) (2R,4S)-4-Decanoylamino-pyrrolidine-2-carboxylic acid
4AmPyrr1(dd) (2S,4S)-4-Dodecanoylamino-pyrrolidine-2-carboxylic acid
$^D$4AmPyrr1(dd) (2R,4S)-4-Dodecanoylamino-pyrrolidine-2-carboxylic acid
4AmPyrr1(td) (2S,4S)-4-Tetradecanoylamino-pyrrolidine-2-carboxylic acid
$^D$4AmPyrr1(td) (2R,4S)-4-Tetradecanoylamino-pyrrolidine-2-carboxylic acid
4AmPyrr1(hd) (2S,4S)-4-Hexadecanoylamino-pyrrolidine-2-carboxylic acid
$^D$4AmPyrr1(hd) (2R,4S)-4-Hexadecanoylamino-pyrrolidine-2-carboxylic acid
4AmPyrr2(o) (2S,4R)-4-Octanoylamino-pyrrolidine-2-carboxylic acid
$^D$4AmPyrr2(o) (2R,4R)-4-Octanoylamino-pyrrolidine-2-carboxylic acid
4AmPyrr2(d) (2S,4R)-4-Decanoylamino-pyrrolidine-2-carboxylic acid
$^D$4AmPyrr2(d) (2R,4R)-4-Decanoylamino-pyrrolidine-2-carboxylic acid
4AmPyrr2(dd) (2S,4R)-4-Dodecanoylamino-pyrrolidine-2-carboxylic acid
$^D$4AmPyrr2(dd) (2R,4R)-4-Dodecanoylamino-pyrrolidine-2-carboxylic acid
4AmPyrr2(td) (2S,4R)-4-Tetradecanoylamino-pyrrolidine-2-carboxylic acid
$^D$4AmPyrr2(td) (2R,4R)-4-Tetradecanoylamino-pyrrolidine-2-carboxylic acid
4AmPyrr2(hd) (2S,4R)-4-Hexadecanoylamino-pyrrolidine-2-carboxylic acid
$^D$4AmPyrr2(hd) (2R,4R)-4-Hexadecanoylamino-pyrrolidine-2-carboxylic acid In a particular embodiment of the invention Xaa$^{15}$ is $^D$Pro, $^D$Cha, NMe$^D$Ile, $^D$Tyr, $^D$His, $^D$His(Bzl), $^D$4Pal, NMe$^P$Tyr, NMe$^D$Lys, (ABu)G, $^D$Ile, NMe$^D$Ala, $^D$Lys, or $^D$Dab; and Xaa$^{18}$ is $^L$Pro or Oic; the aforesaid $^D$Pro moiety and/or the aforesaid $^L$Pro moiety being optionally substituted as shown in formulae A8', A8", A8''' and, respectively, A8'''', as defined above.

The amino acid residues in Cyclo(-Xaa$^2$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) are preferably:
Xaa$^1$: Gly, NMeGly, Leu, Val, Ser, Asp, Glu, His, Tyr or Trp;
Xaa$^2$: His, Tyr, Arg, Lys or of type O;
Xaa$^3$: Ala, Cha, Tyr, Thr, Cit, Gln or of type O;
Xaa$^5$: Ser, Arg, Dab, Dap or the D-Isomer of type F;
Xaa$^6$: Ala, Gly;
Xaa$^7$: of formula -A-CO— or D-isomer of type D;
Xaa$^8$: Tyr, His, Dab, Arg, Thr or of type O;
Xaa$^9$: Arg or of type O;
Xaa$^{10}$: Tyr, Trp, 2Nal or of type O;
Xaa$^{12}$: Ala, Leu, Lys, Ser, Thr, Tyr or Trp;
Xaa$^{13}$: Gln, Thr, Cit or of type O;
Xaa$^{14}$: Ala, Lys, Orn, Arg, Gln, Glu or of type O;
Xaa$^{15}$: of formula -A-CO—, D-isomer of type C, D, E or F, or N-substituted glycine of type I;
Xaa$^{16}$: of formula B—CO—;
Xaa$^4$ and Xaa$^{11}$, taken together, of type H;
with the proviso that
the molecule contains at least one but not more than four amino acid residues of type O and/or -A-CO— having a residue designated as "lipophilic moiety".

Preferably the amino acid residues of type O and/or the amino acid residues of formula -A-CO— are having a substituent R$^{88}$ which is —CO(CH$_2$)$_p$(CHCOOR$^{34}$)$_s$COR$^{89}$, —CO(CH$_2$)$_p$(CHCOOR$^{34}$)$_s$NR$^{34}$COOR$^{89}$ or —CO(CH$_2$)$_p$(CHCONR$^{34}$)$_s$NR$^{34}$CONR$^{34}$R$^{89}$ (R$^{34}$, R$^{89}$, p, and s according to the general definitions of R$^{34}$, R$^{89}$, p, and s).

The amino acid residues in Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) are most preferably:
Xaa$^1$: Tyr;
Xaa$^2$: His, Arg or Dab(N$^\gamma$dd);
Xaa$^3$: Ala, Tyr, Thr, Lys(N$^\epsilon$o) or 2Amtd-OH;
Xaa$^4$: Cys;
Xaa$^5$: Arg or Ser;

Xaa⁶: Ala or Gly;
Xaa⁷: $^D$Pro, $^D$Tyr, or $^D$4AmPyrr1(td);
Xaa⁸: Dab, Arg or Dab(N$^γ$dd);
Xaa⁹: Arg or Arg(N$^ω$ooxca);
Xaa¹⁰: Tyr or Tyr(Odd);
Xaa¹¹: Cys;
Xaa¹²: Tyr
Xaa¹³: Gln, Dab(N$^γ$d), Dab(N$^γ$dd), Lys(N$^ε$o), Lys(N$^ε$d), Lys(N$^ε$dd), Lys(N$^ε$td), Lys(N$^ε$hd), Lys((N$^ε$od), Lys (N$^ε$16OHhd), Lys(N$^ε$4ooxbe), Lys(N$^ε$4ddoxbe), 2Amdd-OH, $^D$2Amdd-OH, Lys(N$^ε$γgluN$^α$old), Lys (N$^ε$γgluN$^α$td), Lys(N$^ε$γgluN$^α$hd), Gln (Wad) or Ser (Od);
Xaa¹⁴: Lys, Gln, Lys(N$^ε$o), Lys(N$^ε$glcho), Lys(N$^ε$ado) or Gln (Wad);
Xaa¹⁵: $^D$Tyr or $^D$Pro;
Xaa¹⁶: Pro;
Xaa⁴ and Xaa¹¹, taken together, can form a disulfide bridge;

In a particularly preferred embodiment of the invention the amino acid residues in Cyclo (-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-Xaa¹⁵-Xaa¹⁶-) are:
Xaa¹: Tyr;
Xaa²: His or Arg;
Xaa³: Ala, Tyr, Thr;
Xaa⁴: Cys;
Xaa⁵: Arg or Ser;
Xaa⁶: Ala or Gly;
Xaa⁷: $^D$Pro, $^D$Tyr;
Xaa⁸: Dab or Arg;
Xaa⁹: Arg;
Xaa¹⁰: Tyr;
Xaa¹¹: Cys;
Xaa¹²: Tyr;
Xaa¹³: Lys(N$^ε$γgluN$^α$dd), Lys(N$^ε$γgluN$^α$td) or Lys(N$^ε$γgluN$^α$hd);
Xaa¹⁴: Lys, or Gln;
Xaa¹⁵: $^D$Tyr or $^D$Pro;
Xaa¹⁶: Pro;
Xaa⁴ and Xaa¹¹, taken together, form a disulfide bridge;

Particularly preferred β-peptidomimetics of the invention include those described in Examples 17, 20, 25, and 26.

The β-hairpin peptidomimetics of this invention can be produced, for example, by following a procedure comprising the synthesis of the linear peptide on resin whereas the lipophilic moiety-bearing amino acid residue(s) will be incorporated as amino acid building block(s) being commercially available or synthesized beforehand; or by following a procedure comprising the synthesis of the linear peptide on resin by applying an orthogonal protecting group strategy whereas, for example, the amino group bearing side chain of at least one amino acid residue is Alloc-protected or the like and thus prone to an individual deprotection and subsequent introduction of a lipophilic moiety on resin; or a procedure comprising the synthesis of a linear peptide on resin by applying an orthogonal protecting group strategy whereas, for example, all amino group bearing side chains of amino acid residues which are not considered to be modified shall be protected by ivDde or the like so that amino group bearing side chains of amino acid residues protected by acid labile protecting groups suitable to the Fmoc-based solid phase peptide synthesis strategy can be derivatized by coupling lipophilic moieties in solution at a very late stage of the synthesis cascade; or following a procedure comprising a suitable combination of the procedures described before.

The processes of the invention can advantageously be carried out as parallel array syntheses to yield libraries of β-hairpin peptidomimetics of the invention. Such parallel syntheses allow one to obtain arrays of numerous (normally 12 to 192, typically 96) compounds as described above in moderate to high yields and defined purities, minimizing the formation of dimeric and polymeric by-products. The proper choice of the functionalized solid-support (i.e. solid support plus linker molecule) and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also D. Obrecht, J.-M. Villalgordo, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, *Tetrahedron Lett.* 1987, 28, 3783-3790). Linkers of this kind form amides of the carboxyl group of the amino acids; examples of resins functionalized by such linker structures include 4-[(((2,4-dimethoxy-phenyl)Fmoc-aminomethyl)phenoxyacetamido)aminomethyl] PS resin, 4-[(((2,4-dimethoxyphenyl)Fmoc-aminomethyl) phenoxyacetamido)aminomethyl]-4-methyl-benzydrylamine PS resin (Rink amide MBHA PS Resin), and 4-[(((2,4-dimethoxy-phenyl)Fmoc-aminomethyl) phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the invention.

A number of reaction vessels (normally 12 to 192, typically 96) equal to the total number of compounds to be synthesized by the parallel method are loaded with 25 to 1000 mg, preferably 60 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)
Cbz benzyloxycarbonyl
Boc tert-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl;
Trt triphenymethyl or trityl
for the carboxyl group (as is present e.g. also in the side-chain of aspartic and glutamic acid) by conversion into esters with the alcohol components
tBu tert-butyl
Bn benzyl
Me methyl
Ph phenyl
Pac phenacyl allyl
Tse trimethylsilylethyl
Tce trichloroethyl;
ivDde (4,4-dimethyl-2,6-dioxocyclohex-1-ylidene)-3-methylbutyl
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl
for the hydroxy group (as is present e.g. in the side-chain of threonine and serine)
tBu tert-butyl
Bn benzyl
Trt trityl
Alloc allyloxycarbonyl and for the mercapto group (as is present e.g. in the side-chain of cysteine)
Acm acetamidomethyl
tBu tert-butyl
Bn benzyl
Trt trityl
Mtr 4-methoxytrityl.

The 9-fluorenylmethoxycarbonyl (Fmoc)-protected amino acid derivatives are preferably used as the building blocks for the construction of the β-hairpin loop mimetics of the invention. For the deprotection, i.e. cleaving off of the Fmoc group, 20% piperidine in DMF or 2% DBU/2% piperidine in DMF can be used.

Lipophilic moieties to be linked to amino acid derivatives to form either an amino acid residue according to type O or a lipophilic moiety-bearing amino acid residue of formula -A-CO— are known in the art. The procedure for introducing a lipophilic moiety can be accomplished by introducing suitable leaving groups as e.g. halogens, or by activating reagents such as those described below depending on the functional groups involved in the linking process. Lipophilic moiety-bearing amino acids like, for example, fatty alkyl substituted tyrosines, can be formed by applying the Mitsunobu reaction. The synthesis of Fmoc-protected 4-hexadecyloxyphenylalanine for example can be accomplished preferably by adding 2.2 eq 1-hexadecanol (0.1 M) dissolved in $CH_2Cl_2$ to tert-butyl-2-((9H-fluoren-9-yl)methoxycarbonyl)-amino-3-(4-hydroxyphenyl)propanoate and 3 eq triphenyl-phosphine under nitrogen. After cooling the reaction mixture to 0° C. 3 eq 1,1'-(azodicarbonyl)dipiperidine (30 mM) in $CH_2Cl_2$ are added dropwise and the mixture is stirred additionally 20 min followed by stirring 1 h at room temperature. After cleaving the tButylester group, preferably by applying TFA in $CH_2Cl_2$ at 0° C., the amino acid building block can be used in the Fmoc-based solid phase peptide synthesis strategy described herein.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxybenzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyluronium tetrafluoroborate (TCTU), or hexafluorophosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-bis(tetramethylene)chlorouronium hexafluorophosphate (PyClU) especially for coupling N-methylated amino acids (J. Coste, E. Frérot, P. Jouin, B. Castro, *Tetrahedron Lett.* 1991, 32, 1967).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s) by one of the two following methods:
1) The reaction vessels are filled with solvent (preferably 5 mL), agitated for 5 to 300 minutes, preferably 15 minutes, and drained to expel the solvent;
2) The reaction vessels are filled with solvent (preferably 5 mL) and drained into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction tubes followed by removal of excess reagents, by-products, and solvents is repeated with each successive transformation until the final resin-bound fully protected linear peptide has been obtained.

Before this fully protected linear peptide is detached from the solid support, it is possible, if desired, to follow the above mentioned orthogonal protecting group strategy for introducing lipophilic moieties on resin by selectively deprotecting one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd(0) and phenylsilane in $CH_2Cl_2$, without affecting the remaining protecting groups, such as Fmoc or acid labile protecting groups suitable to the Fmoc-based solid phase peptide synthesis strategy, present in the molecule. The reactive group thus liberated can then be treated with an agent suitable for introducing the desired substituent e.g. a lipophilic moiety. Thus, for example, an amino group can be acylated by means of an acylating agent corresponding to the acyl substituent to be introduced. Preferably, Alloc will be removed by applying 0.2 eq tetrakis(triphenyl-phosphine)palladium(0) (10 mM) in dry $CH_2Cl_2$ and 10 eq phenylsilane for 15 min at room temperature. After filtration and washing of the resin the deprotection is completed by repeating the procedure with a fresh solution of reagents. The coupling of a fatty acid is started by subsequently adding 3 eq of the desired fatty acid (300 mM) dissolved in DMF/$CH_2Cl_2$, 6 eq of DIPEA and 3 eq of PyBOP® (300 mM) dissolved in DMF to the resin and continued by allowing the reaction mixture to stand for 1 h disrupted only by occasionally stirring. After filtration and washing of the resin the coupling is completed by repeating the procedure with a fresh solution of reagents. Instead of the aforesaid fatty acid suitably protected lipophilic moiety-bearing glutamic acids or the like, as for example 4-tert-butyloxycarbonyl-4-hexadecanoylaminobutyric acid, can be coupled following the same procedure.

The convertion of side chain amino groups into lipophilic moiety-bearing guanidino groups can be accomplished by coupling of suitably protected lipophilic moiety-bearing guanidine derivatives. The coupling of N-Boc-N'-octyloxycarbonyl-N''-trifluoromethanesulfonylguanidine, for example, is carried out by subsequently adding 10 eq DIPEA (530 mM) dissolved in $CH_2Cl_2$ and 3 eq (160 mM) of the aforesaid guanilating agent dissolved in $CH_2Cl_2$ to the resin. The reaction mixture is shaken for 7 h and the procedure is repeated once after filtration and washing of the resin.

Before this fully protected linear peptide is detached from the solid support, an interstrand linkage between $Xaa^4$ and $Xaa^{11}$ of -$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$- can be formed.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of a disulfide bridge preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% $NaHCO_3$ to pH 5-6 for 4 h, or in water after adjusting to pH 8 with ammonium hydroxide solution by stirring for 24 h, or in a solution of NMP and tri-n-butylphosphine (preferably 50 eq.).

Alternatively, the formation of the disulfide bridge between $Xaa^4$ and $Xaa^{11}$ of -$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$- can be carried out subsequent to the work-up method 2), as described herein below, by stirring the crude fully deprotected and cyclized peptide for 24 h in water containing DMSO up to 15% by volume, buffered with 5%

NaHCO$_3$ to pH 5-6, or buffered with ammonium acetate to pH 7-8, or adjusted with ammonium hydroxide to pH 8. Following evaporation to dryness Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-), disulfide bond between Cys$^4$ and Cys$^{11}$ is obtained as end-product.

Detachment of the fully protected linear peptide from the solid support is achieved by exposing the loaded resin with a solution of the reagent used for cleavage (preferably 3 to 5 mL). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 mL of an appropriate solvent to extract (wash out) as much of the detached products as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% H$_2$O, 2.5% TIS or another combination of scavengers for effecting the cleavage of protecting groups. The cleavage reaction time is commonly 30 minutes to 12 hours, preferably about 2.5 hours.

Alternatively, the detachment and complete deprotection of the fully protected peptide from the solid support can be achieved manually in glass vessels.

After full deprotection one of the following methods can be used for further work-up:
1) The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected peptide, Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-), is obtained as final product;
2) The deprotection mixture is concentrated under vacuum. Following precipitation of the fully deprotected peptide in diethylether at preferably 0° C. the solid is washed up to about 10 times, preferably 3 times, dried, and the fully deprotected peptide, Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) is obtained as final product, if a disulfide bond between Xaa$^4$ and Xaa$^{11}$ has been formed on solid support as described herein above.

If the above mentioned orthogonal protecting group strategy for introducing lipophilic moieties in solution has been followed, then all functional groups of side chains of amino acid residues are still protected by non-acid labile protecting groups whereas functional groups of amino acid residues formerly protected by acid labile protecting groups have been liberated at this stage of the synthesis cascade. Thus, it is possible, if desired, to couple a lipophilic moiety. Preferably, ivDde or the like are acid stable protecting groups for amino group bearing side chains which are kept unmodified during the coupling of lipophilic moieties to liberated amino groups. This coupling can be accomplished by applying activated lipophilic moieties like, for example, N-hydroxy succinimide esters of fatty acids, whereof, preferably, 2 eq (8 mM) dissolved in acetonitrile are added to a 4 mM solution of the peptide dissolved in PBS-buffer at pH ~8 and stirred for 3 h at 0° C. A different applicable coupling method follows the activation of the carboxyl group as described above in the course of the amide bond formation necessary for the peptide synthesis. Preferably, the amide bond will be formed by using a mixture of 0.01 M cyclic peptide having a liberated amino group, 0.01 M lipophilic moiety-containing acid, 15 eq DIPEA, 1.1 eq HOBt and 1.1 eq PyBop® in DMF. Following the coupling step a solution of 5% hydrazine in DMF will be used to finally remove the ivDe-protecting groups.

As mentioned earlier, it is thereafter possible, if desired, to convert the fully deprotected product of Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-), thus obtained into a pharmaceutically acceptable salt or to convert a pharmaceutically acceptable, or unacceptable, salt thus obtained into the corresponding free compound of Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-), or a different, into pharmaceutically acceptable, salt. Any of these operations can be carried out by methods well known in the art.

The β-hairpin peptidomimetics of the invention can be used in a wide range of applications in order to prevent HIV infections in healthy individuals and slow or halt viral progression in infected patients, or where cancer is mediated or resulting from the CXCR4 receptor activity, or where immunological diseases are mediated or resulting from CXCR4 receptor activity; or these β-hairpin peptidomimetics can be used to treat immunosuppression, or they can be used during apheresis collections of peripheral blood stem cells and/or as agents to induce mobilization of stem cells to regulate tissue repair.

The β-hairpin peptidomimetics of the invention may be administered per se or may be applied as an appropriate formulation together with carriers, diluents or excipients well known in the art.

When used to treat or prevent HIV infections or cancer such as breast cancer, brain cancer, prostate cancer, hepatocellular carcinoma, colorectal cancer, lung cancer, kidney cancer, neuroblastoma, ovarian cancer, endometrial cancer, germ cell tumor, eye cancer, multiple myeloma, pancreatic cancer, gastric cancer, rhabdomyo-sarcoma, melanoma, chronic lyphomphocytic leukemia, acute myelogenous leukemia, acute lymphoblastic leukemia, multiple myeloma, Non-Hodgkin's lymphoma; metastasis, angiogenesis, and haematopoetic tissues; or inflammatory disorders such as asthma, allergic rhinitis, hypersensitivity lung diseases, hypersensitivity pneumonitis, eosinophilic pneumonias, delayed-type hypersensitivity, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, systemic anaphylaxis or hypersensitivity responses, drug allergies, rheumatoid arthritis, psoriatic arthritis, multiple sclerosis, Alzheimer's disease, Parkinson's disease, atherosclerosis, myasthenia gravis, juvenile onset diabetes, glomerulonephritis, autoimmune throiditis, graft rejection, including allograft rejection or graft-versus-host disease, inflammatory bowel diseases, inflammatory dermatoses; or to treat eye diseases like glaucoma, diabetic retinopathy and age related macular degeneration; or to treat focal ischemic stroke, global cerebral ischemia, myocardial infarction, hind limb ischemia and peripheral ischemia; or to treat injury of the liver, kidney and lung or to treat immunosuppression, including immunosuppression induced by chemotherapy, radiation therapy or graft/transplantation rejection, the β-hairpin peptidomimetics of the invention can be administered singly, as mixtures of several β-hairpin peptidomimetics, in combination with other anti-HIV agents, or antimicrobial agents or anti-cancer agents or anti-inflammatory agents, or in combination with other pharmaceutically active agents. The β-hairpin peptidomimetics of the invention can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.^

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For topical administration to treat or prevent HIV infections a therapeutically effective dose can be determined using, for example, the in vitro assays provided in the examples. The treatment may be applied while the HIV infection is visible, or even when it is not visible. An ordinary skilled expert will be able to determine therapeutically effective amounts to treat topical HIV infections without undue experimentation.

For systemic administration, a therapeutically effective dose can be estimated initially from in vitro assays. For example, a dose can be formulated in animal models to achieve a circulating β-hairpin peptidomimetic concentration range that includes the IC$_{50}$ as determined in the cell culture (i.e. the concentration of a test compound that is lethal to 50% of a cell culture). Such information can be used to more accurately determine useful doses in humans. Initial dosages can also be determined from in vivo data, e.g. animal models, using techniques that are well known in the art. One having ordinary skill in the art could readily optimize administration to humans based on animal data.

Dosage amounts for applications as anti-HIV agents may be adjusted individually to provide plasma levels of the β-hairpin peptidomimetics of the invention which are sufficient to maintain the therapeutic effect.

Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-HIV therapy may be repeated intermittently while infections are detectable or even when they are not detectable. The therapy may be provided alone or in combination with other drugs, such as for example other anti-HIV agents or anti-cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the LD$_{50}$ (the dose lethal to 50% of the population) or the LD$_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The present invention may also include compounds, which are identical to the compounds of the general formula Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-), except that one or more atoms are replaced by an atom having an atomic mass number or mass different from the atomic mass number or mass usually found in nature, e.g. compounds enriched in 2H (D), 3H, 11C, 14C, 127I etc. These isotopic analogs and their pharmaceutical salts and formulations are considered useful agents in the therapy and/or diagnostic, for example, but not limited to, where a fine-tuning of in vivo half-life time could lead to an optimized dosage regimen.

The following Examples illustrate the present invention but are not to be construed as limiting its scope in any way.

EXAMPLES

1. Peptide Synthesis

Coupling of the First Protected Amino Acid Residue to the Resin 1 g (1.4 mMol) 2-chlorotritylchloride resin (1.4 mMol/g; Barlos et al. *Tetrahedron Lett.* 1989, 30, 3943-3946) was filled into a dried flask. The resin was suspended in CH$_2$Cl$_2$ (5 mL) and allowed to swell at room temperature under constant shaking for 30 min. A solution of 0.98 mMol (0.7 eq) of the first suitably protected amino acid residue (see below) in CH$_2$Cl$_2$ (5 mL) mixed with 960 µl (4 eq) of diisopropylethylamine (DIEA) was added. After shaking the reaction mixture for 4 hours at 25° C., the resin was filtered off and washed successively with CH$_2$Cl$_2$ (1×), DMF (1×) and CH$_2$Cl$_2$ (1×). A solution of CH$_2$Cl$_2$/MeOH/DIEA (17/2/1, mL) was added to the resin and the suspension was shaken for 30 min. After filtration the resin was washed in the following order with CH$_2$Cl$_2$ (1×), DMF (1×), CH$_2$Cl$_2$ (1×), MeOH (1×), CH$_2$Cl$_2$ (1×), MeOH (1×), CH$_2$Cl$_2$ (2×), Et$_2$O (2×) and dried under vacuum for 6 hours.

Loading was typically 0.6-0.7 mMol/g.

The following preloaded resins were prepared: Fmoc-Pro-O-chlorotrityl resin, Fmoc-Lys(Alloc)-O-chlorotrityl resin, Fmoc-Dab(Alloc)O-chlorotrityl resin, Fmoc-Dab(Boc)-O—chlorotrityl resin and Fmoc-Ser(tBu)—O-chlorotrityl resin.

The synthesis was carried out employing a Syro-peptide synthesizer (MultiSynTech) using 24-96 reaction vessels. In each vessel 0.04 mMol of the above resin was placed and the resin was swollen in CH$_2$Cl$_2$ and DMF for 15 min, respectively.

The following reaction cycles were programmed and carried out:

| Step | Reagent | Time |
| --- | --- | --- |
| 1 | DMF, wash | 2x1 min |
| 2 | 20% piperidine/DMF | 1x5 min, 1x15 min |
| 3 | DMF, wash | 5x1 min |
| 4a | 5 eq Fmoc amino acid/DMF + 5 eq HCTU/DMF, 10 eq DIEA/DMF | 1x60 min |
| 5 | DMF, wash | 3x1 min |

Step 4a was repeated once.

Unless indicated otherwise, the final coupling of an amino acid was followed by a Fmoc deprotection by applying steps 1-3 of the above described reaction cycle.

Amino Acid Building Block Syntheses

The synthesis of (2S)-2-((9H-fluoren-9-yl)methoxy-carbonyl)amino-3-(4-hexadecyloxyphenyl)propanoic acid has been described in the context of the general procedure.

Syntheses of Precursors of Lipophilic Moiety-Bearing Substituents

The synthesis of (4S)—N-hexadecanoyl-4-amino-4-tert-butyl-oxycarbonyl butyric acid was accomplished by adding dropwise a solution of 1 eq (0.21 M) N-hydroxy succinimid ester of hexadecanoic acid in DMF to a solution of the hydrochloride of H-L-Glu-O-tBu (0.042 M) in DMF containing 1 eq DIPEA at room temperature and stirring the reaction mixture for 36 h. The desired product was obtained following evaporation of the reaction mixture to dryness, dissolving the crude in ethyl acetate, extracting the organic layer 3 times with 5% aqueous citric acid and final evaporation of the organic phase.

The above given protocol was successfully applied to other N-hydroxy succinimid esters of lipophilic moiety-containing acids like dodecanoic acid and tetradecanoic acid.

The synthesis of N-Boc-N'-octyloxycarbonyl-N'''-trifluoromethanesulfonylguanidine was accomplished as follows: 12.5 mMol Boc-protected guanidine were dissolved in a mixture of 10 mL aqueous NaOH (2 eq, 2.5 M) and 15 mL acetone. After cooling down to 0° C. 1.1 eq (6.9 M) octylchloroformate dissolved in acetone were added dropwise. Following warm-up to room temperature the reaction mixture was stirred additionally for 3 h. The crude product was purified by applying column chromatography using $CH_2Cl_2$ as eluent. The introduction of the trifluorosulfonyl-group was performed by adding dropwise triflic anhydride to a mixture of N-Boc-N'-octyloxycarbonylguanidine (0.2 M) and 5 eq DIPEA in $CH_2Cl_2$ at −78° C. under nitrogen. Following slowly warm-up to room temperature the mixture was stirred for 5-6 h. Finally, the crude product was purified by applying column chromatography using $CH_2Cl_2$ as eluent.

Attachment of Lipophilic Moieties
Procedure A
Attachment of Lipophilic Moieties to Selectively Deprotected Linear Peptides on Resin:

To remove alloc-protecting groups from amino functions present in the resin bound peptide the latter (0.04 mMol) was swollen in 5 mL of freshly distilled $CH_2Cl_2$ for at least min followed by adding 0.2 eq tetrakis(triphenyl-phosphine)palladium(0) (10 mM) in dry $CH_2Cl_2$ and 10 eq phenylsilane. After shaking the reaction mixture for 15 min at room temperature, the resin was filtered off and a fresh solution of reagents was added to repeat the procedure. Following subsequent washing of the resin with $CH_2Cl_2$, DMF and $Et_2O$, the resin was swollen again in $CH_2Cl_2$ and the attachment of a lipophilic moiety-bearing acid was accomplished by subsequently adding 3 eq of the desired acid dissolved in 0.5 mL DMF/$CH_2Cl_2$, 6 eq of DIPEA and 3 eq of PyBOP® dissolved in 0.5 mL DMF allowing the reaction mixture to stand for 1 h disrupted only by occasionally stirring. After filtration and washing of the resin three times with mL DMF, the coupling was completed by repeating the procedure with a fresh solution of reagents.

Lipophilic moiety-containing acids used to be coupled by the above described protocol were fatty acids like octanoic acid, decanoic acid, dodecanoic acid, tetradecanoic acid, octadecanoic acid, 4-octyloxybenzoic acid, 4-dodecyl-oxybenzoic acid, adamantoic acid, lipophilic moiety-bearing glutamic acids like 4-tert-butyloxycarbonyl-4-dodecanoyl-amino-butyric acid, 4-tert-butyloxycarbonyl-4-tetradecanoyl-amino-butyric acid, 4-tert-butyloxycarbonyl-4-hexadecanoyl-amino-butyric acid or N-Boc-N'-octyloxycarbonyl-N'''-trifluoromethanesulfonylguanidine.

Procedure B
Attachment of Lipophilic Moieties to Backbone Cyclized Peptides in Solution:

Lipophilic moiety-bearing acids like glycocholic acid, 16-hydroxyhexadecanoic acid, or 3-cyano-4-fluoro-benzoic acid, were coupled by dissolving 2 μmol (4 mM) of the backbone cyclized peptide having a liberated amino group in 0.5 mL PBS-buffer (pH ~8) and adding 4 μmol (2 eq, 8 mM) of one of the above listed acids dissolved in acetonitrile at ° C. The mixture was stirred additionally for 3 h at 0° C. and, if ivDde-protecting groups were still present in the peptide, 200 μL of 5% hydrazine in DMF were added. Finally, the mixture was allowed to be stirred 2 h at room temperature.

Cyclization and Work Up of Backbone Cyclized Peptides
Cleavage of the Fully Protected Peptide Fragment After completion of the synthesis, the resin (0.04 mMol) was suspended in 1 mL (0.13 mMol, 3.4 eq) of 1% TFA in $CH_2Cl_2$ (v/v) for 3 minutes, filtered, and the filtrate was neutralized with 1 mL (0.58 mMol, 14.6 eq) of 10% DIEA in $CH_2Cl_2$ (v/v). This procedure was repeated three times to ensure completion of the cleavage. The filtrate was evaporated to dryness and a sample of the product was fully deprotected by using a cleavage mixture containing 95% trifluoroacetic acid (TFA), 2.5% water and 2.5% triisopropylsilane (TIS) to be analyzed by reverse phase-HPLC($C_{18}$ column) and ESI-MS to monitor the efficiency of the linear peptide synthesis.

Cyclization of the Linear Peptide

The fully protected linear peptide (0.04 mMol) was dissolved in DMF (4 μMol/mL). Then 30.4 mg (0.08 mMol, 2 eq) of HATU, 10.9 mg (0.08 mMol, 2 eq) of HOAt and 28 μl (0.16 mMol, 4 eq) DIEA were added, and the mixture was vortexed at 25° C. for 16 hours and subsequently concentrated under high vacuum. The residue was partitioned between $CH_2Cl_2$ and $H_2O$/$CH_3CN$ (90/10: v/v). The $CH_2Cl_2$ phase was evaporated to yield the fully protected cyclic peptide.

Full Deprotection of the Cyclic Peptide

The cyclic peptide obtained was dissolved in 3 mL of the cleavage mixture containing 82.5% trifluoroacetic acid (TFA), 5% water, 5% thioanisole, 5% phenol and 2.5% ethanedithiole (EDT). The mixture was allowed to stand at 25° C. for 2.5 hours and thereafter concentrated under vacuum. After precipitation of the cyclic fully deprotected peptide in diethylether ($Et_2O$) at 0° C. the solid was washed twice with $Et_2O$ and dried.

Formation of Disulfide β-Strand Linkage and Purification

After full deprotection, the crude peptide was dissolved in 0.1 M ammonium acetate buffer (1 mg/1 mL, pH=7-8). DMSO (up to 5% by volume) was added and the solution was shaken overnight. Following evaporation the residue was purified by preparative reverse phase HPLC.

Analytical Method 1:

Analytical HPLC retention times (RT, in minutes) were determined using an Xbridge C18 2.5 μm column with the following solvents A ($H_2O$+0.1% TFA) and B ($CH_3CN$+0.09% TFA) and the gradient: 0 min: 97% A, 3% B; 2.7 min: 3% A, 97% B; 2.71-3.0 min: 3% A, 97% B; 3.05 min: 97% A, 3% B; 3.06-3.3 min: 97% A, 3% B.

Analytical Method 2:

Analytical HPLC retention times (RT, in minutes) were determined using an Xbridge C18 2.5 μm column with the following solvents A ($H_2O$+0.1% TFA) and B ($CH_3CN$+0.09% TFA) and the gradient: 0 min: 97% A, 3% B; 3.0 min: 3% A, 97% B; 3.01-3.6 min: 3% A, 97% B; 3.7 min: 97% A, 3% B; 3.71-4.3 min: 97% A, 3% B.

Example 1 as shown in Table 1 was synthesized starting with the amino acid Dab(Xaa$^2$), which was grafted to the resin. Starting resin was Fmoc-Dab(Alloc)-O-chlorotrityl resin, which was prepared as described above. The linear peptide was synthesized on solid support according to the procedure described above in the following sequence: Resin-Dab$^2$-Xaa$^1$-Xaa$^{16}$-Xaa$^{15}$-Xaa$^{14}$-Xaa$^{13}$-Xaa$^{12}$-Xaa$^{11}$-Xaa$^{10}$-Xaa$^9$-Xaa$^8$-Xaa$^7$-Xaa$^6$-Xaa$^5$-Xaa$^4$-Xaa$^3$. Thereafter procedure A was applied to attach the dodecanoyl moiety to the side chain of Dab$^2$. Following a final Fmoc deprotection as described above, the peptide was cleaved from the resin, cyclized, deprotected and after formation of the disulfide β-strand linkage purified as indicated above.

The HPLC-retention time (minutes) was determined using the analytical method 1 as described above.

Examples 18 and 21 as shown in Table 1 were synthesized starting with the amino acid Ser(Xaa$^5$), which was grafted to the resin. Starting resin was Fmoc-Ser(tBu)-O-chlorotrityl resin, which was prepared as described above. The linear peptides were synthesized on solid support according to the procedure described above in the following sequence: Resin-Ser$^5$-Xaa$^4$-Xaa$^3$-Xaa$^2$-Xaa$^2$-Xaa$^1$-Xaa$^{16}$-Xaa$^{15}$-Xaa$^{14}$-Xaa$^{13}$-Xaa$^{12}$-Xaa$^{11}$-Xaa$^{10}$-Xaa$^9$-Xaa$^8$-Xaa$^7$-Xaa$^6$. Following a final Fmoc deprotection as described above, the peptides were cleaved from the resin, cyclized and deprotected. Thereafter procedure B was applied for Ex. 18 to attach the tetradecanoyl moiety to the side chain of Lys$^{13}$ and for Ex. 21 to attach the octadecanoyl moiety to the side chain of Lys$^{13}$. After formation of the disulfide β-strand linkage the peptides were purified as indicated above.

HPLC-retention times (minutes) were determined using the analytical method 1 as described above.

Examples 34 and 35 as shown in Table 1 were synthesized starting with the amino acid $^D$Pro (Xaa$^7$), which was grafted to the resin. Starting resin was Fmoc-$^D$Pro-O-chlorotrityl resin, which was prepared as described above. The linear peptides were synthesized on solid support according to the procedure described above in the following sequence: Resin-$^D$Pro$^7$-Xaa$^6$-Xaa$^5$-Xaa$^4$-Xaa$^3$-Xaa$^2$-Xaa$^1$-Xaa$^{16}$-Xaa$^{15}$-Xaa$^{14}$-Xaa$^{13}$-Xaa$^{12}$-Xaa$^{11}$-Xaa$^{10}$-Xaa$^9$-Xaa$^8$. Thereafter procedure A was applied for Ex. 35 to attach the adamantanoyl moiety to the side chain of Lys$^{14}$. Following a final Fmoc deprotection as described above, the peptides were cleaved from the resin, cyclized and deprotected. Thereafter Procedure B was applied for Ex. 34 to attach the glycocholyl moiety to the side chain of Lys$^{14}$. After formation of the disulfide β-strand linkages the peptides were purified as indicated above.

HPLC-retention times (minutes) were determined using the analytical method 1 as described above.

Example 6 as shown in Table 1 was synthesized starting with the amino acid Dab(Xaa$^8$), which was grafted to the resin. Starting resin was Fmoc-Dab(Boc)-O-chlorotrityl resin, which was prepared as described above. The linear peptide was synthesized on solid support according to the procedure described above in the following sequence: Resin-Dab$^8$-Xaa$^7$-Xaa$^6$-Xaa$^5$-Xaa$^4$-Xaa$^3$-Xaa$^2$-Xaa$^1$-Xaa$^{16}$-Xaa$^{15}$-Xaa$^{14}$-Xaa$^{13}$-Xaa$^{12}$-Xaa$^{11}$-Xaa$^{10}$-Xaa$^9$. Thereafter Procedure A was applied to attach the octyloxycarbonylaminoyl moiety to the side chain of Orn$^9$. Following a final Fmoc deprotection as described above, the peptide was cleaved from the resin, cyclized, deprotected and after formation of the disulfide β-strand linkage purified as indicated above.

The HPLC-retention time (minutes) was determined using the gradient method 1 as described above.

Examples 10 and 11 as shown in Table 1 were synthesized starting with the amino acid Dab(Xaa$^{13}$), which was grafted to the resin. Starting resin was Fmoc-Dab(Alloc)-O-chlorotrityl resin, which was prepared as described above. The linear peptides were synthesized on solid support according to the procedure described above in the following sequence: Resin-Dab$^{13}$-Xaa$^{12}$-Xaa$^{11}$-Xaa$^{10}$-Xaa$^9$-Xaa$^8$-Xaa$^7$-Xaa$^6$-Xaa$^5$-Xaa$^4$-Xaa$^3$-Xaa$^2$-Xaa$^1$-Xaa$^{16}$-Xaa$^{15}$-Xaa$^{14}$. Thereafter procedure A was applied for Ex. 10 to attach the decanoyl moiety to the side chain of Dab$^{13}$ whereas for Ex. 11 the attachment of the dodecanoyl moiety to the side chain of Dab$^{13}$ was carried out. Following a final Fmoc deprotection as described above, the peptides were cleaved from the resin, cyclized and deprotected. After formation of the disulfide β-strand linkages the peptides were purified as indicated above.

HPLC-retention times (minutes) were determined using the gradient method 1 as described above.

Examples 13, 14 and 23 as shown in Table 1 were synthesized starting with the amino acid Lys(Xaa$^{13}$), which was grafted to the resin. Starting resin was Fmoc-Lys(Alloc)-O-chlorotrityl resin, which was prepared as described above. The linear peptides were synthesized on solid support according to the procedure described above in the following sequence: Resin-Lys$^{13}$-Xaa$^{12}$-Xaa$^{11}$-Xaa$^{10}$-Xaa$^9$-Xaa$^8$-Xaa$^7$-Xaa$^6$-Xaa$^5$-Xaa$^4$-Xaa$^3$-Xaa$^2$-Xaa$^1$-Xaa$^{16}$-Xaa$^{15}$-Xaa$^{14}$. Thereafter procedure A was applied for Ex. 13 to attach the octanoyl moiety to the side chain of Lys$^{13}$, for Ex. 14 to attach the decanoyl moiety to the side chain of Lys$^{13}$, whereas for Ex. 23 the attachment of the 4'-octyloxybenzoyl moiety to the side chain of Lys$^{13}$ as well was carried out. Following a final Fmoc deprotection as described above, the peptides were cleaved from the resin, cyclized and deprotected. After formation of the disulfide β-strand linkages the peptides were purified as indicated above.

HPLC-retention times (minutes) were determined using the gradient method 1 as described above.

Examples 2-5, 7-9, 12, 15-17, 19-20, 22, 24-33 and 36 as shown in Table 1 were synthesized starting with the amino acid Pro (Xaa$^{16}$), which was grafted to the resin. Starting resin was Fmoc-ProO-chlorotrityl resin, which was prepared as described above. The linear peptides were synthesized on solid support according to the procedure described above in the following sequence: Resin-Pro$^{16}$-Xaa$^{15}$-Xaa$^{14}$-Xaa$^{13}$-Xaa$^{12}$-Xaa$^{11}$-Xaa$^{10}$-Xaa$^9$-Xaa$^8$-Xaa$^7$-Xaa$^6$-Xaa$^5$-Xaa$^4$-Xaa$^3$-Xaa$^2$-Xaa$^1$.

For Ex. 2, 8-9, 20, 30-31 and 36 the lipophilic moiety-containing amino acid building blocks were readily available and incorporated as follows: (2S)-2-aminotetradecanoic acid as Xaa$^3$ for Ex. 2, (2S)-2-aminododecanoic acid as Xaa$^{13}$ for Ex. 8, (2R)-2-aminododecanoic acid as Xaa$^{13}$ for Ex. 9, Lys (N$^ε$-hexadecanoyl) as Xaa$^{13}$ for Ex. 20, Ser(O-decyl) as Xaa$^{13}$ for Ex. 30 and Gln(N$^ω$-adamantyl) as Xaa$^{13}$ for Ex. 31 and Xaa$^{14}$ for Ex. 36. Tyr(O-dedecyl) as Xaa$^{10}$ for Ex. 7 was synthesized afore as described above. For Ex. 3-5, 12, 15-17, 19, 22, 24, 25-29 and 32 Procedure A was applied: The octanoyl moiety was attached to the side chain of Lys$^3$ (Ex. 3), the hexadecanoyl moiety was attached to the side chain of $^D$4AmPyrr1$^7$ (Ex. 4), the dodecanoyl moiety was attached to the side chain of Dab$^8$ (Ex. 5), the octanoyl moiety was attached to the side chain of Lys$^{13}$ (Ex. 12), the decanoyl moiety was attached to the side chain of Lys$^{13}$ of Ex. 15 and Ex. 16, the dodecanoyl moiety was attached to the side chain of Lys$^{13}$ (Ex. 17), the tetradecanoyl moiety was attached to the side chain of Lys$^{13}$ (Ex. 19), the octadecanoyl moiety was attached to the side chain of Lys$^{13}$ (Ex. 22), the 4'-dodecyloxybenzoyl moiety was attached to the side chain of Lys$^{13}$ (Ex. 24), the (4S)-4-carboxy-4-dodecanoylamino-butanoyl moiety was attached to the side chain of Lys$^{13}$ of Ex. 25-27, the (4S)-4-carboxy-4-tetradecanoylamino-butanoyl moiety was attached to the side chain of Lys$^{13}$ (Ex. 28), the (4S) 4-carboxy-4-hexadecanoyl-amino-butanoyl moiety was attached to the side chain of Lys$^{13}$ (Ex. 29) and the octanoyl moiety was attached to the side chain of Lys$^{14}$ (Ex. 32). Following a final Fmoc deprotection as described above, the peptides were cleaved from the resin, cyclized and deprotected. Thereafter Procedure B was applied for Ex. 33 to attach the glycocholyl moiety to the side chain of Lys$^{14}$. After formation of the disulfide β-strand linkages the peptides were purified as indicated above.

HPLC-retention times (minutes) were determined using the analytical method 1 as described above except for Ex. 20. For the latter analytical method 2 was applied.

TABLE 1

| | | | | | | | | |
|---|---|---|---|---|---|---|---|---|
| Ex. Seq ID | | Xaa$^1$ | Xaa$^2$ | Xaa$^3$ | Xaa$^4$ | Xaa$^5$ | Xaa$^6$ | Xaa$^7$ | Xaa$^8$ |
| 1. Seq ID No: 1 | Tyr | Dab (N$^\gamma$dd) | Ala | Cys | Arg | Ala | $^D$Pro | Dab |
| 2. Seq ID No: 2 | Tyr | His | 2Amtd-OH | Cys | Arg | Ala | $^D$Pro | Dab |
| 3. Seq ID No: 3 | Tyr | His | Lys (N$^\epsilon$o) | Cys | Ser | Ala | $^D$Pro | Dab |
| 4. Seq ID No: 4 | Tyr | His | Thr | Cys | Arg | Gly | $^D$p4AmPyrr1Dab(hd) | |
| 5. Seq ID No: 5 | Tyr | His | Ala | Cys | Arg | Ala | $^D$Pro | Dab (N$^\gamma$dd) |
| 6. Seq ID No: 6 | Tyr | His | Tyr | Cys | Ser | Ala | $^D$Pro | Dab |
| 7. Seq ID No: 7 | Tyr | His | Ala | Cys | Arg | Ala | $^D$Pro | Dab |
| 8. Seq ID No: 8 | Tyr | His | Ala | Cys | Arg | Ala | $^D$Pro | Dab |
| 9. Seq ID No: 9 | Tyr | His | Ala | Cys | Arg | Ala | $^D$Pro | Dab |
| 10. Seq ID No: 10 | Tyr | His | Ala | Cys | Arg | Ala | $^D$Pro | Dab |
| 11. Seq ID No: 11 | Tyr | His | Ala | Cys | Arg | Ala | $^D$Pro | Dab |
| 12. Seq ID No: 12 | Tyr | His | Tyr | Cys | Ser | Ala | $^D$Pro | Dab |
| 13. Seq ID No: 13 | Tyr | His | Tyr | Cys | Ser | Ala | $^D$Pro | Dab |
| 14. Seq ID No: 14 | Tyr | His | Thr | Cys | Arg | Ala | $^D$Tyr | Dab |
| 15. Seq ID No: 15 | Tyr | His | Thr | Cys | Arg | Gly | $^D$Pro | Dab |
| 16. Seq ID No: 16 | Tyr | His | Thr | Cys | Arg | Ala | $^D$Pro | Dab |
| 17. Seq ID No: 17 | Tyr | His | Ala | Cys | Arg | Ala | $^D$Pro | Dab |
| 18. Seq ID No: 18 | Tyr | His | Tyr | Cys | Ser | Ala | $^D$Pro | Dab |
| 19. Seq ID No: 19 | Tyr | His | Ala | Cys | Arg | Ala | $^D$Pro | Dab |
| 20. Seq ID No: 20 | Tyr | His | Tyr | Cys | Ser | Ala | $^D$Pro | Dab |
| 21. Seq ID No: 21 | Tyr | His | Tyr | Cys | Ser | Ala | $^D$Pro | Dab |
| 22. Seq ID No: 22 | Tyr | His | Tyr | Cys | Ser | Ala | $^D$Pro | Dab |
| 23. Seq ID No: 23 | Tyr | His | Ala | Cys | Arg | Ala | $^D$Pro | Dab |
| 24. Seq ID No: 24 | Tyr | His | Tyr | Cys | Ser | Ala | $^D$Pro | Dab |
| 25. Seq ID No: 25 | Tyr | His | Tyr | Cys | Ser | Ala | $^D$Pro | Dab |
| 26. Seq ID No: 26 | Tyr | His | Ala | Cys | Arg | Ala | $^D$Pro | Dab |
| 27. Seq ID No: 27 | Tyr | His | Ala | Cys | Arg | Gly | $^D$Pro | Dab |
| 28. Seq ID No: 28 | Tyr | His | Tyr | Cys | Ser | Ala | $^D$Pro | Dab |
| 29. Seq ID No: 29 | Tyr | His | Tyr | Cys | Ser | Ala | $^D$Pro | Dab |
| 30. Seq ID No: 30 | Tyr | His | Thr | Cys | Arg | Gly | $^D$Pro | Dab |
| 31. Seq ID No: 31 | Tyr | His | Thr | Cys | Arg | Gly | $^D$Pro | Dab |
| 32. Seq ID No: 32 | Tyr | His | Tyr | Cys | Ser | Ala | $^D$Pro | Dab |
| 33. Seq ID No: 33 | Tyr | His | Tyr | Cys | Ser | Ala | $^D$Pro | Dab |
| 34. Seq ID No: 34 | Tyr | His | Thr | Cys | Arg | Gly | $^D$Pro | Dab |
| 35. Seq ID No: 35 | Tyr | His | Thr | Cys | Arg | Gly | $^D$Pro | Dab |
| 36. Seq ID No: 36 | Tyr | His | Thr | Cys | Arg | Gly | $^D$Pro | Dab |

TABLE 1-continued

Examples (Ex.)

| Ex. Seq ID | Xaa⁹ | Xaa¹⁰ | Xaa¹¹ | Xaa¹² | Xaa¹³ | Xaa¹⁴ | Xaa¹⁵ | Xaa¹⁶ |
|---|---|---|---|---|---|---|---|---|
| 1. Seq ID No: 1 | Arg | Tyr | Cys | Tyr | Gln | Lys | $^D$Pro | Pro |
| 2. Seq ID No: 2 | Arg | Tyr | Cys | Tyr | Gln | Lys | $^D$Pro | Pro |
| 3. Seq ID No: 3 | Arg | Tyr | Cys | Tyr | Gln | Lys | $^D$Pro | Pro |
| 4. Seq ID No: 4 | Arg | Tyr | Cys | Tyr | Gln | Lys | $^D$Pro | Pro |
| 5. Seq ID No: 5 | Arg | Tyr | Cys | Tyr | Gln | Lys | $^D$Pro | Pro |
| 6. Seq ID No: 6 | Arg (N^ωooxca) | Tyr | Cys | Tyr | Gln | Lys | $^D$Pro | Pro |
| 7. Seq ID No: 7 | Arg | Tyr (Odd) | Cys | Tyr | Gln | Lys | $^D$Pro | Pro |
| 8. Seq ID No: 8 | Arg | Tyr | Cys | Tyr | 2Amdd-OH | Lys | $^D$Pro | Pro |
| 9. Seq ID No: 9 | Arg | Tyr | Cys | Tyr | $^D$2Amdd-OH | Lys | $^D$Pro | Pro |
| 10. Seq ID No: 10 | Arg | Tyr | Cys | Tyr | Dab(N^γd) | Lys | $^D$Pro | Pro |
| 11. Seq ID No: 11 | Arg | Tyr | Cys | Tyr | Dab(N^γdd) | Lys | $^D$Pro | Pro |
| 12. Seq ID No: 12 | Arg | Tyr | Cys | Tyr | Lys(N^εo) | Lys | $^D$Pro | Pro |
| 13. Seq ID No: 13 | Arg | Tyr | Cys | Tyr | Lys(N^εo) | Lys | $^D$Tyr | Pro |
| 14. Seq ID No: 14 | Arg | Tyr | Cys | Tyr | Lys(N^εd) | Lys | $^D$Pro | Pro |
| 15. Seq ID No: 15 | Arg | Tyr | Cys | Tyr | Lys(N^εd) | Lys | $^D$Pro | Pro |
| 16. Seq ID No: 16 | Arg | Tyr | Cys | Tyr | Lys(N^εd) | Lys | $^D$Tyr | Pro |
| 17. Seq ID No: 17 | Arg | Tyr | Cys | Tyr | Lys(N^εdd) | Lys | $^D$Pro | Pro |
| 18. Seq ID No: 18 | Arg | Tyr | Cys | Tyr | Lys(N^εtd) | Lys | $^D$Pro | Pro |
| 19. Seq ID No: 19 | Arg | Tyr | Cys | Tyr | Lys(N^εtd) | Lys | $^D$Pro | Pro |
| 20. Seq ID No: 20 | Arg | Tyr | Cys | Tyr | Lys(N^εhd) | Lys | $^D$Pro | Pro |
| 21. Seq ID No: 21 | Arg | Tyr | Cys | Tyr | Lys (N^ε16OHhd) | Lys | $^D$Pro | Pro |
| 22. Seq ID No: 22 | Arg | Tyr | Cys | Tyr | Lys(N^εod) | Lys | $^D$Pro | Pro |
| 23. Seq ID No: 23 | Arg | Tyr | Cys | Tyr | Lys (N^ε4ooxbe) | Lys | $^D$Pro | Pro |
| 24. Seq ID No: 24 | Arg | Tyr | Cys | Tyr | Lys (N^ε4ddoxbe) | Lys | $^D$Pro | Pro |
| 25. Seq ID No: 25 | Arg | Tyr | Cys | Tyr | Lys (N^εγgluN^αdd) | Lys | $^D$Pro | Pro |
| 26. Seq ID No: 26 | Arg | Tyr | Cys | Tyr | Lys (N^εγgluN^αdd) | Lys | $^D$Pro | Pro |
| 27. Seq ID No: 27 | Arg | Tyr | Cys | Tyr | Lys (N^εγgluN^αdd) | Lys | $^D$Pro | Pro |
| 28. Seq ID No: 28 | Arg | Tyr | Cys | Tyr | Lys (N^εγgluN^αtd) | Lys | $^D$Pro | Pro |
| 29. Seq ID No: 29 | Arg | Tyr | Cys | Tyr | Lys (N^εγluN^αhd) | Lys | $^D$Pro | Pro |
| 30. Seq ID No: 30 | Arg | Tyr | Cys | Tyr | Ser(Od) | Gln | $^D$Pro | Pro |
| 31. Seq ID No: 31 | Arg | Tyr | Cys | Tyr | Gln(N^ωada) | Gln | $^D$Pro | Pro |
| 32. Seq ID No: 32 | Arg | Tyr | Cys | Tyr | Gln | Lys (N^εo) | $^D$Pro | Pro |

TABLE 1-continued

Examples (Ex.)

| | | | | | | | | |
|---|---|---|---|---|---|---|---|---|
| 33. Seq ID No: 33 | Arg | Tyr | Cys | Tyr | Gln | Lys ($N^\epsilon$glcho) | $^D$Pro | Pro |
| 34. Seq ID No: 34 | Arg | Tyr | Cys | Tyr | Gln | Lys ($N^\epsilon$glcho) | $^D$Pro | Pro |
| 35. Seq ID No: 35 | Arg | Tyr | Cys | Tyr | Gln | Lys ($N^\epsilon$ado) | $^D$Pro | Pro |
| 36. Seq ID No: 36 | Arg | Tyr | Cys | Tyr | Gln | Gln ($N^\omega$ad) | $^D$Pro | Pro |

Cys in Xaa$^4$ and Xaa$^{11}$ in Ex. 1-36 form a disulfide bridge.

TABLE 2

| Ex. | Purity [%]$^{a)}$ | (M + 2H)/2 | RT |
|---|---|---|---|
| 1 | 93 | 1040.1 | 1.68 |
| 2 | 93 | 1044.4 | 1.58 |
| 3 | 95 | 1024.2 | 1.48 |
| 4 | 95 | 1087.9 | 1.76 |
| 5 | 95 | 1058.7 | 1.69 |
| 6 | 95 | 1056.9 | 1.62 |
| 7 | 95 | 1051.6 | 1.80 |
| 8 | 95 | 1048.1 | 1.53 |
| 9 | 88 | 1001.9 | 1.61 |
| 10 | 95 | 1030.8 | 1.57 |
| 11 | 95 | 1044.7 | 1.66 |
| 12 | 95 | 1041.9 | 1.53 |
| 13 | 95 | 1075.1 | 1.54 |
| 14 | 95 | 1092.6 | 1.60 |
| 15 | 71 | 1052.4 | 1.64 |
| 16 | 95 | 1092.3 | 1.63 |
| 17 | 95 | 1058.7 | 1.72 |
| 18 | 95 | 1083.9 | 1.86 |
| 19 | 95 | 1072.8 | 1.81 |
| 20 | 95 | 1097.7 | 2.47 |
| 21 | 95 | 1106.3 | 1.72 |
| 22 | 95 | 1112.1 | 2.06 |
| 23 | 95 | 1083.4 | 1.73 |
| 24 | 95 | 1123.2 | 1.97 |
| 25 | 95 | 1134.7 | 1.74 |
| 26 | 95 | 1123.2 | 1.70 |
| 27 | 95 | 1116.1 | 1.66 |
| 28 | 95 | 1148.7 | 1.85 |
| 29 | 95 | 1162.7 | 1.95 |
| 30 | 95 | 1024.9 | 1.69 |
| 31 | 95 | 1042.7 | 1.54 |
| 32 | 95 | 1051.4 | 1.63 |
| 33 | 95 | 1212.1 | 1.68 |
| 34 | 93 | 1199.0 | 1.63 |
| 35 | 95 | 1056.4 | 1.55 |
| 36 | 95 | 1042.2 | 1.58 |

$^{a)}$%-purity of compounds after prep. HPLC.

2. Biological Methods 2.1. Preparation of the Peptides

Lyophilized peptides were weighed on a Microbalance (Mettler MT5) and dissolved in DMSO to a final concentration of 10 mM. Stock solutions were kept at +4° C., light protected. The biological assays were carried out under assay conditions having less than 1% DMSO unlike indicated otherwise.

2.2. Cell Culture

Mouse pre-B cells were cultured in RPMI1640 plus 5% FBS, antibiotic/antimycotic, non essential amino acid, 50 µM β-mercaptoethanol and 1 mM natrium pyruvate. HELA cells were maintained in RPMI1640 plus 10% FBS, pen/strept and 2 mM L-glutamine. Cos-7 cells were grown in DMEM medium with 4500 mg/mL glucose supplemented with 10% FCS, pen/strept and 2 mM L-glutamine. All cell lines were grown at 37° C. at 5% $CO_2$. Cell media, media supplements, PBS-buffer, HEPES, antibiotic/antimycotic, pen/strept, non essential amino acid, L-glutamine, β-mercaptoethanol and sera were purchased from Gibco (Pailsey, UK). All fine chemicals were supplied by Merck (Darmstadt, Germany).

2.3. $Ca^{2+}$-Assay: CXCR4-Antagonizing Activity of the Peptides

Increases in intracellular calcium were monitored using a Flexstation 384 (Molecular Devices, Sunnyvale, Calif.) to assay the peptides for CXCR4 antagonism in a mouse pre-B cell line 300-19 stably transfected with human CXCR4 (E. Oberlin, A. Amara, F. Bachelerie, C. Bessia, J.-L. Virelizier, F. Arenzana-Seisdedos, O, Schwartz, J.-M. Heard, I. Clark-Lewis, D. F. Legler, M. Loetscher, M. Baggiolini, B. Moser, *Nature* 1996, 382, 833-835; M. Loetscher, T. Geiser, T. O'Reilly, R. Zwalen, M. Baggiolini, B. Moser, *J. Biol. Chem.* 1994, 269, 232-237; M. D'Apuuo, A. Rolink, M. Loetscher, J. A. Hoxie, I. Clark-Lewis, F. Melchors, M. Baggiolini, B. Moser, *Eur. J. Immunol.* 1997, 27, 1788-1793). The cells were batch loaded with the Calcium 4 Assay kit (Molecular Devices) in assay buffer (Hanks Balanced salt solution [HBSS], 20 mM HEPES, pH 7.4, 0.1% BSA) for 1 h at room temperature and labeled cells were dispensed into black well assays plates (Costar No. 3603). Calcium mobilization induced by stromal-derived factor-1 (SDF-1) was measured in the Flexstation 384 (excitation: 485 nm; emission: 525 nm) for 90 seconds. Antagonist activity of peptides was determined by spiking the cells with compounds prior to SDF-1 addition. Dose response curves (compound concentration versus % maximum response for SDF-1) were determined for each antagonist and $IC_{50}$ values were calculated by fitting the data to a four parameter logistic equation using SoftmaxPro 4.8 (Molecular Devices).

2.4. Cytotoxicity Assay

The cytotoxicity of the peptides to HELA cells (Acc57) and COS-7 cells (CRL-1651) was determined using the MTT reduction assay (T. Mossman, *J. Immunol. Meth.* 1983, 65, 55-63; M. V. Berridge, A. S. Tan, *Arch. Biochem. Biophys.* 1993, 303, 474-482). Briefly, the method was as follows: 4000 HELA cells/well and 3400 COS-7 cells/well were seeded and grown in 96-well microtiter plates for 24 h at 37° C. at 5% $CO_2$. Thereafter, time zero (Tz) was determined by MTT reduction (see below). The supernatant of the remaining wells was discarded, and fresh medium and compounds in serial dilutions (12.5, 25 and 50 µM, triplicates) were pipetted into the wells. After incubation of the cells for 48 h at 37° C. at 5% $CO_2$ the supernatant was discarded again and 100 µL MTT reagent (0.5 mg/mL in RPMI1640 and DMEM, respectively)/well was added. Following incubation at 37° C. for 2-4 h the media were aspirated and the cells were spiked (100 µL isopropanol/well). The absorbance of the solubilized formazan was measured at 595 nm ($OD_{595}$peptide). For each concentration averages were calculated from triplicates. The percentage of growth was calculated as follows: ($OD_{595}$peptide-$OD_{595}$Tz-$OD_{595}$Empty well)/($OD_{595}$Tz-$OD_{595}$Empty well)×100%. The $GI_{50}$ (Growth Inhibition) concentrations were calculated for each peptide by using a trend line function for the concentrations (50, 25, 12.5 and 0 µM), the corresponding percentages and the value 50, (=TREND ($C_{50}$: $C_0$, %$_{50}$:%$_0$,50).

2.5. Hemolysis

The peptides were tested for their hemolytic activity against human red blood cells (hRBC). Fresh hRBC were washed three times with phosphate buffered saline (PBS) and centrifuged for 10 min at 2000×g. Compounds (100 µM) were incubated with 20% hRBC (v/v) for 1 h at 37° C. and shaking at 300 rpm. The final erythrocyte concentration was approximately $0.9 \times 10^9$ cells/mL. A value of 0% and 100% cell lyses, respectively, was determined by incubation of hRBC in the presence of PBS containing 0.001% acetic acid and 2.5% Triton X-100 in $H_2O$, respectively. The samples were centrifuged, the supernatants were 8-fold diluted in PBS buffer and the optical densities (OD) were measured at 540 nm. The 100% lyses value ($OD_{540}H_2O$) gave an $OD_{540}$ of approximately 0.5-1.0.

Percent hemolysis was calculated as follows:

($OD_{540}$peptide/$OD_{540}H_2O$)×100%.

2.6. Plasma Stability

The stability of the peptides in human and mouse plasma was determined by applying the following method: 346.5 µL/deep well of freshly thawed human plasma (Basler Blutspendedienst) and mouse plasma (Harlan Sera-Lab, UK), respectively, were spiked with 3.5 µL/well of compound dissolved in DMSO/$H_2O$ (90/1 [v/v], 1 mM, triplicate) and incubated at 37° C. At t=0, 15, 30, 60, 120, 240 and 1440 min aliquots of 50 µL were transferred to filtration plate wells containing 150 µL/well of 2% formic acid in acetonitrile. Following shaking for 2 min the occurred suspensions were filtrated by vacuum and 50 µL of each filtrate was mixed with 100 µL of 1% formic acid in $H_2O$. After transfer to a propylene microtiter plate, the filtrates were analyzed by LC/MS as follows: Column: Waters, XBridge C18, mobile phases: (A) water+0.1% formic acid and (B) acetonitrile/water, 95/5 (v/v)+0.1% formic acid, gradient: 5%-100% (B) in 2 minutes, electrospray ionization, MRM detection (triple quadrupole). The peak areas were determined and triplicate values are averaged. The stability is expressed in percent of the initial value at t=0. (tx/t0×100). By using the TREND function of EXCEL (Microsoft Office 2003) T1/2 were determined.

The results of the experiments described under 2.3-2.6 are indicated in the Tables 3, 4 and 5 below.

2.7. Pharmacokinetic Study (PK)

Pharmacokinetic study after intravenous (i.v.) and subcutaneous (s.c.) administration was performed for the compounds of Ex. 17, Ex. 20, Ex. 25, Ex. 26, Ex. 28, and Ex. 29. 30 grams (±20%) The compounds of Ex. 17, Ex. 25, Ex. 26, Ex. 28, and Ex. 29 were administered i.v. and s.c. as a cassette whereas for the compound of Ex. 20 a single i.v. and s.c. administration was accomplished.

30 grams (±20%) male CD-1 mice obtained from Janvier, France, were used in the study testing the cassette compounds. The vehicle, phosphate buffered saline containing 5% DMSO, was added to give a final concentration of 0.5 mg/mL of the compounds (i.v. route and s.c. route). The volume was 2 mL/kg i.v. and 10 mL/kg s.c. and the cassette compounds were injected to give a final intravenous dose of 1 mg/kg and an subcutaneous dose of 5 mg/kg. Approximately 500 µL of blood were removed from the opened heart at predetermined time intervals (5, 15, 30 min and 1, 2, 4, 8 and 12 hours for the i.v. study and 5, 15, 30 min and 1, 2, 4, 8, 12 and 24 hours for the s.c. study) and added to heparinized tubes. Plasma was removed from pelleted cells upon centrifugation and frozen at −80° C. prior to HPLC-MS analysis. For the compound of Ex. 20 30 grams (±20%) male CD-1 mice obtained from Charles River Laboratories Deutschland GmbH were used. The vehicle, phosphate buffered saline, was added to give a final concentration of 0.2 mg/mL of the compound (i.v. route) and 1 mg/mL (s.c. route). The volume was 5 mL/kg i.v. and s.c. and the compound was injected to give a final intravenous dose of 1 mg/kg and an subcutaneous dose of 5 mg/kg. Approximately 300-400 µL of blood was removed under light isoflurane anesthesia by cardiac puncture at predetermined time intervals (5, 15, 30 min and 1, 2, 3, 4, 6, 12 hours for the i.v. study and 15, min and 1, 2, 4, 6, 8, 12 and 24 hours for the s.c. study) and added to heparinized tubes. Plasma was removed from pelleted cells upon centrifugation and frozen at −80° C. prior to HPLC-MS analysis.

Preparation of the Plasma Calibration Samples

"Blank" mouse plasma from untreated animals was used. Aliquots of plasma of 0.2 mL each were spiked with 50 ng of propranolol (Internal Standard, IS), (sample preparation by solid phase extraction on OASIS® HLB cartridges [Waters]) and with known amounts of Ex. 20 in order to obtain 9 plasma calibration samples in the range 10-5000 nM. The OASIS® HLB cartridges were conditioned with 1 mL of methanol and then with 1 mL of 1% $NH_3$ in water. Samples were then diluted with 700 µL of 1% $NH_3$ in water and loaded. The plate was washed with 1 mL of methanol/1% $NH_3$ in water 5/95 (v/v). Elution was performed using 1 mL of 0.1% TFA in methanol.

The plate containing eluates was introduced into the concentrator system and taken to dryness. The residues were dissolved in 100 µL of formic acid 0.1%/acetonitrile, 95/5 (v/v) and analysed in the HPLC/MS on a reverse phase analytical column (Jupiter C18, 50×2.0 mm, 5 µm, Phenomenex), using gradient elution (mobile phases A: 0.1% formic acid in water, B: acetonitrile; from 5% B to 100% B in 2 min.).

Preparation of Plasma Samples

Samples coming from animal treatments were pooled in order to obtain an appropriate volume for the extraction. If the total volume obtained was less than 0.2 mL the appropriate amount of "blank" mouse plasma was added in order to keep the matrix identical to the calibration curve. Samples were than spiked with IS and processed as described for the calibration curve.

Pharmacokinetic Evaluation

In order to perform PK analysis pooled plasma data (n=3 mice) was used. PK parameters were calculated by WinNonLin™ software version 5.2.1 (Pharsight—A Certara™ Company, Mountain View, Calif. 94041 USA) using non-compartmental analysis with a linear up/log down trapezoidal calculation method. For the terminal elimination phase at least 3 time points and a correlation coefficient greater than 0.85 was used. For plasma concentration curves with strong deviation from a linear correlation in a semi-logarithmic plot the last two time points were selected.

Bioavailability was calculated by the ratio of the dose-corrected AUCs ($AUC_{0-\infty\ dcor.}$) of the s.c. route over the corresponding AUC from the i.v. route and is expressed in percent.

The results of the experiments described in 2.7 are indicated in Tables 6 and 7 herein below.

TABLE 3

| Ex. | IC50% [nM] ± SD, CXCR4 receptor |
|---|---|
| 1 | 94 ± 2.1 |
| 2 | 55.8 ± 6 |
| 3 | 19.4 ± 13 |
| 4 | 7.2 ± 0.7 |
| 5 | 95.5 ± 12 |
| 6 | 28.5 ± 9 |
| 7 | 59.8 ± 27 |
| 8 | 21.9 ± 7.3 |
| 9 | 91.3 ± 19 |
| 10 | 8.1 ± 0.9 |
| 11 | 7.3 ± 4.7 |
| 12 | 1.8 ± 1 |
| 13 | 6.3 ± 2.7 |
| 14 | 40.8 ± 12 |
| 15 | 11.2 ± 4 |
| 16 | 18.2 ± 11 |
| 17 | 2.8 ± 0.4 |
| 18 | 15.7 ± 3.9 |
| 19 | 9.1 ± 4.2 |
| 20 | 4.0 ± 1.8 |
| 21 | 6.4 ± 1.3 |
| 22 | 7.3 ± 3 |
| 23 | 8.3 ± 3.2 |
| 24 | 6.1 ± 4.5 |
| 25 | 3.5 ± 0.1 |
| 26 | 2.4 ± 0.5 |
| 27 | 2.6 ± 0.7 |
| 28 | 2.1 ± 0.1 |
| 29 | 1.9 ± 0.8 |
| 30 | 55.1 ± 19 |
| 31 | 3.0 ± 1 |
| 32 | 109.5 ± 49 |
| 33 | 146.1 ± 51.6 |
| 34 | 7.2 ± 0.3 |
| 35 | 11.7 ± 2 |
| 36 | 28.3 ± 12 |

TABLE 4

| | Cytotoxicity | | |
|---|---|---|---|
| Ex. | Hela Cells $GI_{50}$ [μM] | Cos-7 Cells $GI_{50}$ [μM] | Hemolysis at 100 μM [%] |
| 1 | >28 | >50 | 2.6 |
| 2 | >13 | >32 | 1.7 |
| 3 | >45 | >50 | 0.6 |
| 4 | >50 | >50 | 0.8 |
| 5 | >50 | >43 | 0.3 |
| 6 | >10 | >35 | 0.7 |
| 7 | >35 | >50 | 11.5 |
| 8 | >26 | >44 | 1.6 |
| 9 | >13 | >50 | 2.2 |
| 10 | >50 | >50 | 1.0 |
| 11 | >29 | >50 | 0.7 |
| 12 | >50 | >50 | 0.2 |
| 13 | >50 | >50 | 1.2 |
| 14 | >50 | >50 | 0.6 |
| 15 | >50 | >40 | 0.6 |
| 16 | >50 | >50 | 0.5 |
| 17 | >44 | >50 | 4.3 |
| 18 | >25 | >50 | 9.2 |
| 19 | >32 | >50 | 1.2 |
| 20 | >31 | >50 | 9.1 |
| 21 | >50 | >50 | 9.6 |
| 22 | >35 | >50 | 9.6 |
| 23 | >22 | >50 | 7.8 |
| 24 | >29 | >50 | 10.9 |
| 25 | >43 | >50 | 1.0 |
| 26 | >50 | >50 | 1.2 |
| 27 | >48 | >50 | 1.6 |
| 28 | >39 | >50 | 1.9 |
| 29 | >47 | >50 | 5.4 |
| 30 | >50 | >50 | 5.5 |
| 31 | >37 | >50 | 1.3 |
| 32 | >24 | >50 | 1.7 |
| 33 | >18 | >50 | 0.7 |
| 34 | >45 | >50 | 0.6 |
| 35 | >50 | >30 | 0.2 |
| 36 | >50 | >50 | 0.2 |

TABLE 5

| | Plasma stability | | | |
|---|---|---|---|---|
| Ex. | human pl. $T_{1/2}$ [min] | human pl. cpd left at 1440 min [%] | mouse pl. $T_{1/2}$ [min] | mouse pl. cpd left at 1440 min [%] |
| 1 | 1440 | 87 | 1440 | 77 |
| 2 | 1440 | 96 | 1402 | 62 |
| 3 | 1440 | 86 | 1440 | 86 |
| 4 | 315 | 66 | 1440 | 62 |
| 5 | 1440 | 100 | 1440 | 73 |
| 6 | 1440 | 76 | 1440 | 92 |
| 7 | 1440 | 67 | 1440 | 87 |
| 8 | 1440 | 79 | 1440 | 82 |
| 9 | 1440 | 100 | 1440 | 76 |
| 10 | 1440 | 85 | 1440 | 63 |
| 11 | 1440 | 82 | n.d. | n.d. |
| 12 | 1440 | 88 | 420 | 46 |
| 13 | 1440 | 100 | 1345 | 72 |
| 14 | 1440 | 91 | 565 | 23 |
| 15 | 1440 | 73 | n.d. | n.d. |
| 16 | 1192 | 48 | 619 | 35 |
| 17 | 1440 | 65 | 1170 | 59 |
| 18 | 1440 | 71 | 1440 | 78 |
| 19 | 1440 | 99 | 1440 | 76 |
| 20 | 1440 | 54 | 1440 | 83 |
| 21 | 1115 | 49 | 1440 | 63 |
| 22 | 1440 | 72 | 1440 | 82 |
| 23 | 1440 | 100 | 1440 | 74 |
| 24 | 127 | 24 | 556 | 22 |
| 25 | 1440 | 78 | 1440 | 74 |
| 26 | 1440 | 82 | 1440 | 65 |
| 27 | 1440 | 75 | 1440 | 22 |
| 28 | 1147 | 80 | 1440 | 78 |
| 29 | 1440 | 74 | 1440 | 53 |
| 30 | 1440 | 54 | n.d. | n.d. |
| 31 | 1440 | 68 | n.d. | n.d. |
| 32 | 777 | 39 | n.d. | n.d. |
| 33 | 1223 | 61 | n.d. | n.d. |
| 34 | 1440 | 100 | 1440 | 87 |
| 35 | 1440 | 63 | n.d. | n.d. |
| 36 | 1391 | 53 | n.d. | n.d. | n.d. = not determined

TABLE 6

| | a | | | | | |
|---|---|---|---|---|---|---|
| | Ex. 17 i.v. route Dose: 1 mg/kg | | Ex. 25 i.v. route Dose: 1 mg/kg | | Ex. 26 i.v. route Dose: 1 mg/kg | |
| Time [h] | Calc. Conc. [ng/mL] | Num. of anim. pool. | Calc. Conc. [ng/mL] | Num. of anim. pool. | Calc. Conc. [ng/mL] | Num. of anim. pool. |
| 0.083 | 2640 | 3 | 2970 | 3 | 3467 | 3 |
| 0.25 | 2027 | 3 | 2190 | 3 | 2527 | 3 |
| 0.5 | 1563 | 3 | 1987 | 3 | 1980 | 3 |
| 1 | 1290 | 3 | 1597 | 3 | 1540 | 3 |

TABLE 6-continued

| | | | | | | |
|---|---|---|---|---|---|---|
| 2 | 178 | 3 | 160 | 3 | 219 | 3 |
| 4 | 141 | 3 | 180 | 3 | 98 | 3 |
| 8 | 15 | 3 | 18 | 3 | 10 | 3 |
| 12 | 8 | 3 | 16 | 3 | bql | 3 |

| | Ex. 28 i.v. route Dose: 1 mg/kg | | Ex. 29 i.v. route Dose: 1 mg/kg | | Ex. 20 i.v. route Dose: 1 mg/kg | |
|---|---|---|---|---|---|---|
| Time [h] | Calc. Conc. [ng/mL] | Num. of anim. pool. | Calc. Conc. [ng/mL] | Num. of anim. pool. | Calc. Conc. [ng/mL] | Num. of anim. pool. |
| 0.083 | 2817 | 3 | 2317 | 3 | 777 | 3 |
| 0.25 | 2123 | 3 | 1823 | 3 | 1521 | 3 |
| 0.5 | 2030 | 3 | 1730 | 3 | 2210 | 3 |
| 1 | 1673 | 3 | 1503 | 3 | 1377 | 3 |
| 2 | 114 | 3 | 87 | 3 | 992 | 3 |
| 3 | n.d. | n.d. | n.d. | n.d. | 638 | 3 |
| 4 | 148 | 3 | 114 | 3 | 486 | 3 |
| 6 | n.d. | n.d. | n.d. | n.d. | 234 | 3 |
| 8 | 34 | 3 | 35 | 3 | n.d. | n.d. |
| 12 | 17 | 3 | 16 | 3 | 13 | 3 | b

| | Ex. 17 s.c. route Dose: 5 mg/kg | | Ex. 25 s.c. route Dose: 5 mg/kg | | Ex. 26 s.c. route Dose: 5 mg/kg | |
|---|---|---|---|---|---|---|
| Time [h] | Calc. Conc. [ng/mL] | Num. of anim. pool. | Calc. Conc. [ng/mL] | Num. of anim. pool. | Calc. Conc. [ng/mL] | Num. of anim. pool. |
| 0.25 | 140 | 3 | 44 | 3 | 221 | 3 |
| 0.5 | 450 | 3 | 205 | 3 | 779 | 3 |
| 1 | 874 | 3 | 517 | 3 | 1747 | 3 |
| 2 | 1753 | 3 | 2187 | 3 | 3987 | 3 |
| 4 | 1410 | 3 | 1643 | 3 | 2527 | 3 |
| 8 | 1237 | 3 | 1890 | 3 | 1597 | 3 |
| 12 | 567 | 3 | 1207 | 3 | 524 | 3 |
| 24 | 65 | 3 | 108 | 3 | 23 | 3 |

| | Ex. 28 s.c. route Dose: 5 mg/kg | | Ex. 29 s.c. route Dose: 5 mg/kg | | Ex. 20 s.c. route Dose: 5 mg/kg | |
|---|---|---|---|---|---|---|
| Time [h] | Calc. Conc. [ng/mL] | Num. of anim. pool. | Calc. Conc. [ng/mL] | Num. of anim. pool. | Calc. Conc. [ng/mL] | Num. of anim. pool. |
| 0.25 | 16 | 3 | 9 | 3 | bql | 3 |
| 0.5 | 73 | 3 | 41 | 3 | 70 | 3 |
| 1 | 232 | 3 | 137 | 3 | 342 | 3 |
| 2 | 1520 | 3 | 1052 | 3 | 868 | 3 |
| 4 | 1270 | 3 | 958 | 3 | 1703 | 3 |
| 6 | n.d. | n.d. | n.d. | n.d. | 2803 | 3 |
| 8 | 1900 | 3 | 1603 | 3 | 2860 | 3 |
| 12 | 1607 | 3 | 1427 | 3 | 3043 | 3 |
| 24 | 164 | 3 | 175 | 3 | 179 | 3 | bql below quantifiable limit
n.d. not determined

TABLE 7 a

| i.v. route | Ex. 17 | Ex. 25 | Ex. 26 |
|---|---|---|---|
| Dose [mg/kg] | 1 | 1 | 1 |
| $AUC_{0-\infty}$ [ng*h/mL] | 2950.8 | 3480.0 | 3395.6 |
| $AUC_{0-\infty\,dcor.}$ [kg*ng*h/mg/mL] | 2950.8 | 3480.0 | 3395.6 |
| $C_{max}$ [ng/mL] | 2640.0 | 2970.0 | 3467.0 |
| $C_{max\,dcor.}$ [kg* ng/mg/mL] | 2640.0 | 2970.0 | 3467.0 |
| $T_{max}$ [h] | 0.1 | 0.1 | 0.1 |
| Half-life [h] | 2.0 | 2.5 | 1.3 |

| i.v. route | Ex. 28 | Ex. 29 | Ex. 20 |
|---|---|---|---|
| Dose [mg/kg] | 1 | 1 | 1 |
| $AUC_{0-\infty}$ [ng*h/mL] | 3430.8 | 2945.0 | 5504.8 |
| $AUC_{0-\infty\,dcor.}$ [kg*ng*h/mg/mL] | 3430.8 | 2945.0 | 5504.8 |
| $C_{max}$ [ng/mL] | 2817.0 | 2317.0 | 2210.0 |
| $C_{max\,dcor.}$ [kg* ng/mg/mL] | 2817.0 | 2317.0 | 2210.0 |
| $T_{max}$ [h] | 0.1 | 0.1 | 0.5 |
| Half-life [h] | 3.2 | 3.6 | 2.0 | b

| s.c. route | Ex. 17 | Ex. 25 | Ex. 26 |
|---|---|---|---|
| Dose [mg/kg] | 5 | 5 | 5 |
| $AUC_{0-\infty}$ [ng*h/mL] | 16789.5 | 24723.3 | 24033.0 |
| $AUC_{0-\infty\,dcor.}$ [kg*ng*h/mg/mL] | 3357.9 | 4944.7 | 4806.6 |
| $C_{max}$ [ng/mL] | 1753.6 | 2187.0 | 3987.0 |
| $C_{max\,dcor.}$ [kg* ng/mg/mL] | 350.6 | 437.4 | 797.4 |
| $T_{max}$ [h] | 2.0 | 2.0 | 2.0 |
| Half-life [h] | 4.3 | 4.7 | 2.9 |
| Bioavailability [%] | 113.8 | 142.1 | 141.6 |

| s.c. route | Ex. 28 | Ex. 29 | Ex. 20 |
|---|---|---|---|
| Dose [mg/kg] | 5 | 5 | 5 |
| $AUC_{0-\infty}$ [ng*h/mL] | 25687.2 | 22181.1 | 38154.2 |
| $AUC_{0-\infty\,dcor.}$ [kg*ng*h/mg/mL] | 5137.4 | 4436.2 | 7630.8 |
| $C_{max}$ [ng/mL] | 1900.0 | 1603.0 | 3043.3 |
| $C_{max\,dcor.}$ [kg* ng/mg/mL] | 380.0 | 320.6 | 608.7 |
| $T_{max}$ [h] | 8.0 | 8.0 | 12.0 |
| Half-life [h] | 4.3 | 4.7 | 2.9 |
| Bioavailability [%] | 149.7 | 150.6 | 138.6 | dcor. dose corrected
Note:
values above 100% of bioavailability observed at the s.c. route may partially reflect an impaired reliability caused by the limited number of points or caused by tissue deposition

The invention claimed is:

1. Compounds of the general formula Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$-$Xaa^{16}$-),
   wherein
   $Xaa^1$ is Gly, NMeGly, Leu, Val, Ser, Asp, Glu or an amino acid residue of type D as defined herein below,
   $Xaa^2$ is His, Tyr, Arg, Lys or an amino acid residue of type O as defined herein below,
   $Xaa^3$ is Ala, Cha, Tyr, Thr, Cit, Gln or an amino acid residue of type O as defined herein below,
   $Xaa^4$ and $Xaa^{11}$ are amino acid residues, taken together, forming a group of type H as defined herein below,
   $Xaa^5$ is Ser, Arg, Dab, Dap or the D-isomer of an amino acid residue of type F as defined herein below,
   $Xaa^6$ is Ala or Gly,
   $Xaa^7$ is -A-CO— as defined herein below or the D-isomer of an amino acid residue of type D as defined herein below,
   $Xaa^8$ is Dab, Arg, Tyr, His, Thr or an amino acid residue of type O as defined herein below,
   $Xaa^9$ is Arg or an amino acid residue of type O as defined herein below,
   $Xaa^{10}$ is an amino acid residue of type D as described herein below or an amino acid residue of type O as described herein below,
   $Xaa^{12}$ is Ala, Leu, Lys, Ser, Thr or an amino acid residue of type D as defined herein below,
   $Xaa^{13}$ is Gln, Thr, Cit or an amino acid residue of type O as defined herein below,
   $Xaa^{14}$ is Lys, Orn, Arg, Ala, Gln, Glu or an amino acid residue of type O as defined herein below,
   $Xaa^{15}$ is -A-CO— as defined herein below or the D-isomer of an amino acid residue of type C, or of type D, or of type E, or of type F, as defined herein below or a N-substituted glycine residue of type I as defined herein below, and Xaa$^{16}$ is —B—CO— as defined herein below;

with the proviso that

Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) contains at least one but not more than four amino acid residues of type O as defined herein below, and/or Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-) contains -A-CO— having a residue designated as "lipophilic moiety" as defined herein below;

—B—CO— is Gly, NMeGly or the residue of an L-α-amino acid with B being a residue of formula —NR$^{20}$CH(R$^{71}$)—, or —NR$^{20}$CH(R$^{72}$)—, or —NR$^{20}$CH(R$^{73}$)— or —NR$^{20}$CH(R$^{74}$)— or —NR$^{20}$CH(R$^{84}$)— or the enantiomer of one of the groups A1 to A69 and A105 as defined hereinafter;

A of -A-CO— is a group of one of the formulae

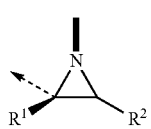
A1

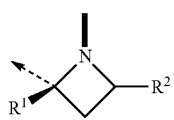
A2

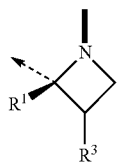
A3

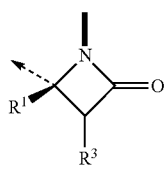
A4

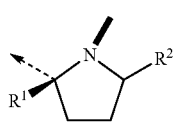
A5

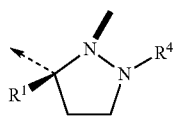
A6

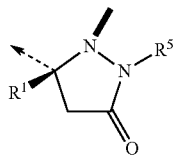
A7

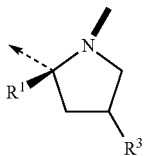
A8

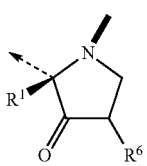
A9

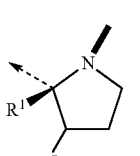
A10

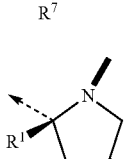
A11

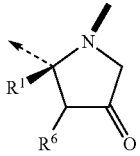
A12

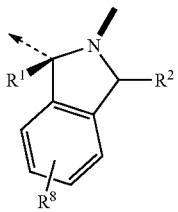
A13

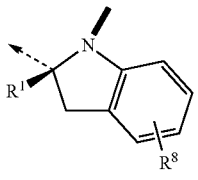
A14

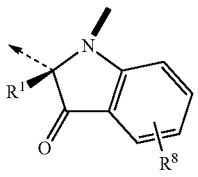
A15

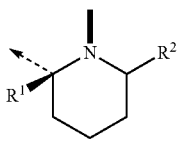
A16

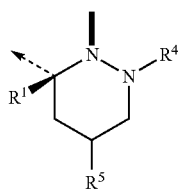 A17
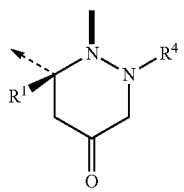 A18
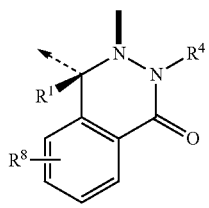 A19
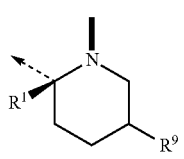 A20
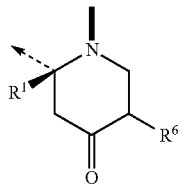 A21
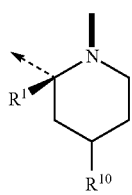 A22
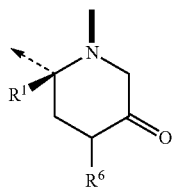 A23
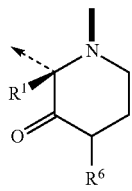 A24
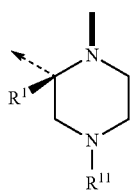 A25
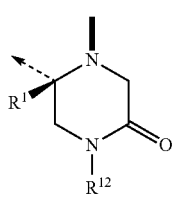 A26
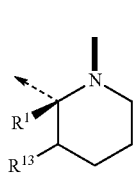 A27
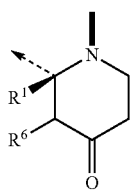 A28
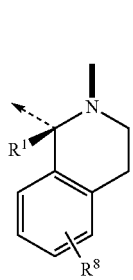 A29
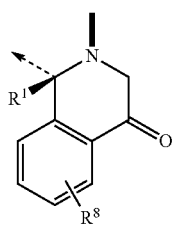 A30
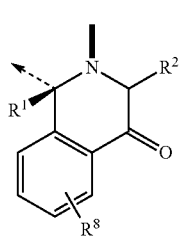 A31

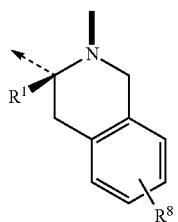 A32
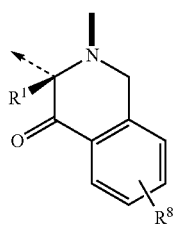 A33
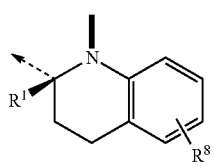 A34
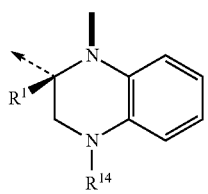 A35
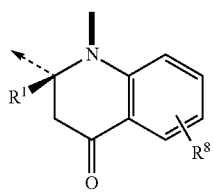 A36
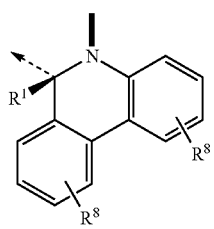 A37
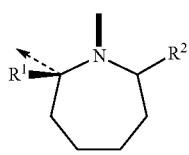 A38
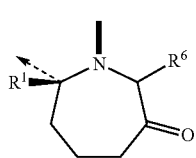 A39
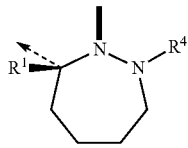 A40
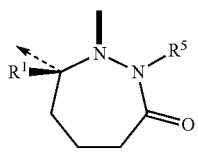 A41
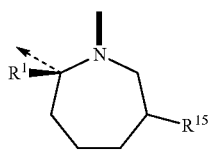 A42
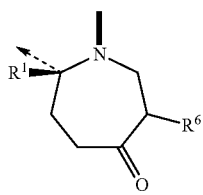 A43
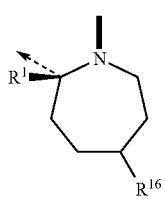 A44
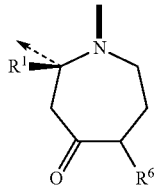 A45
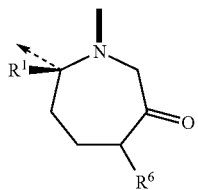 A46
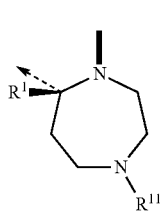 A47

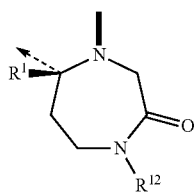 A48
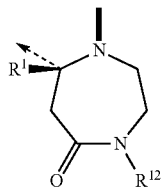 A49
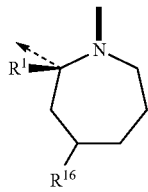 A50
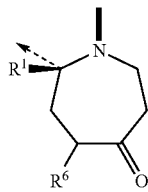 A51
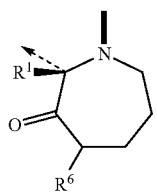 A52
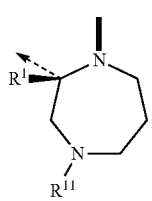 A53
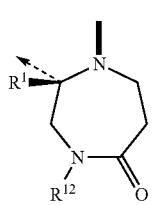 A54
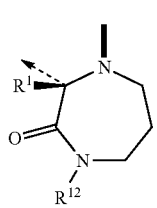 A55
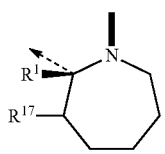 A56
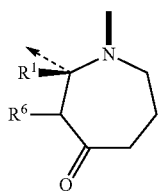 A57
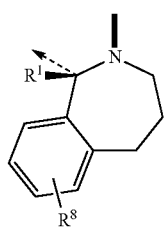 A58
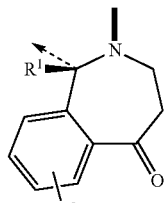 A59
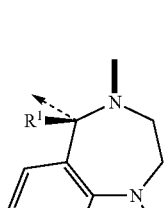 A60
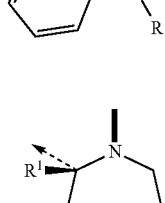 A61
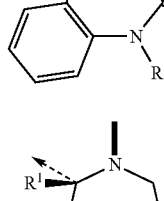 A62

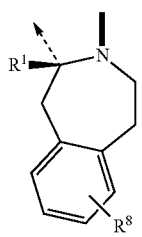
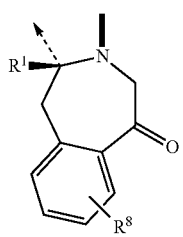
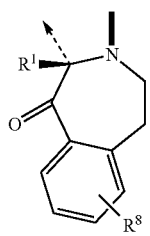
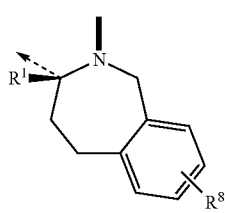
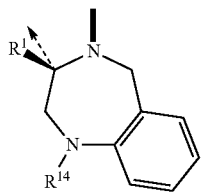
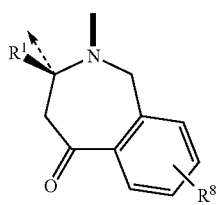
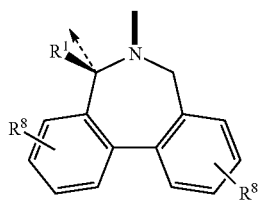
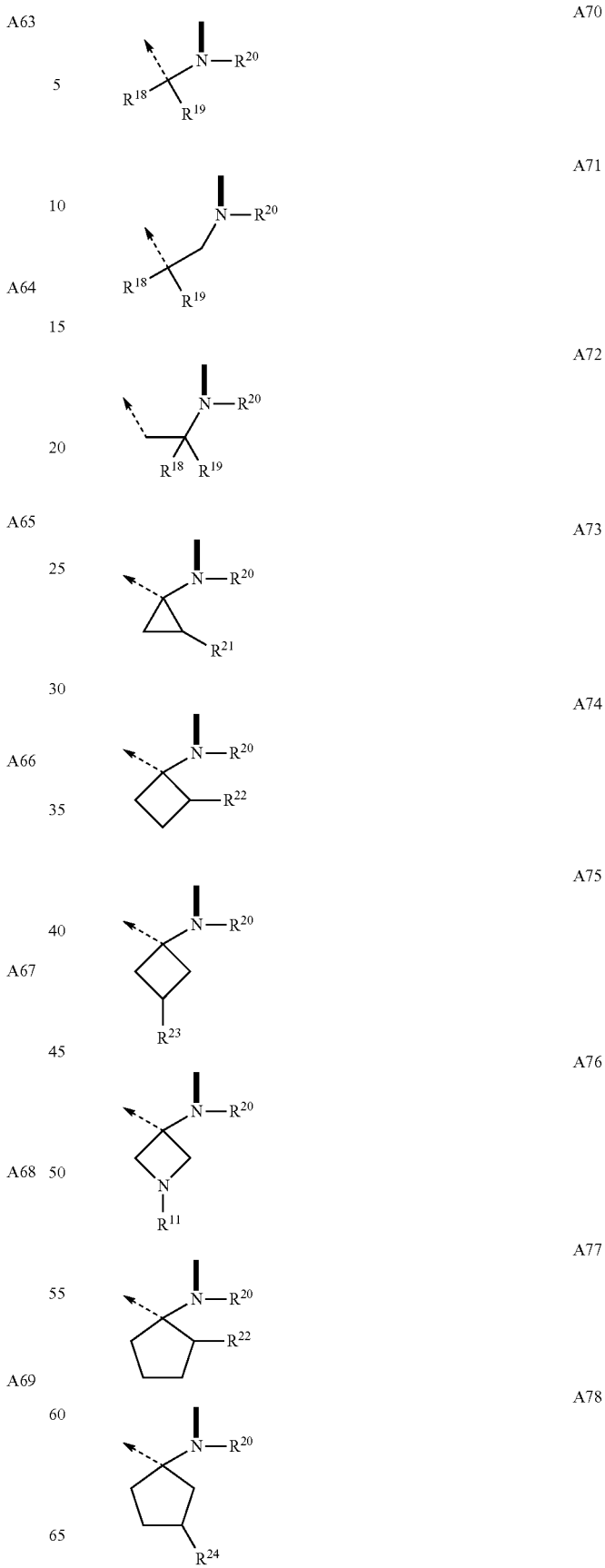

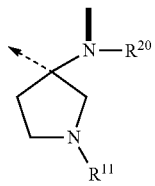 A79
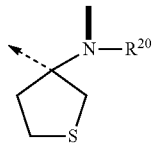 A80
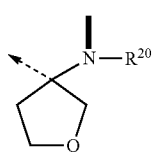 A81
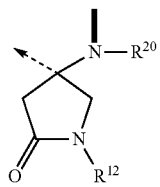 A82
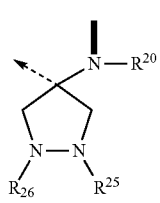 A83
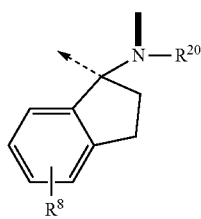 A84
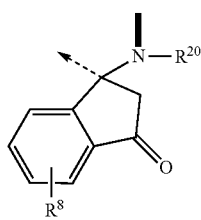 A85
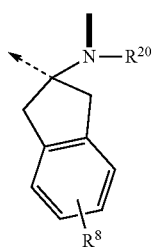 A86
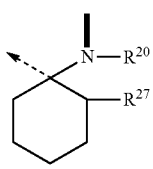 A87
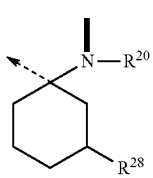 A88
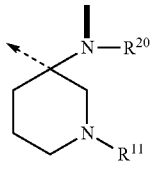 A89
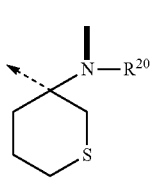 A90
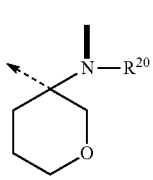 A91
A92
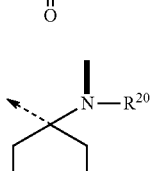 A93
A94

115
-continued

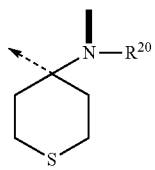
A95

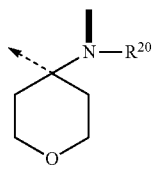
A96

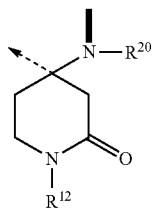
A97

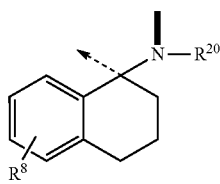
A98

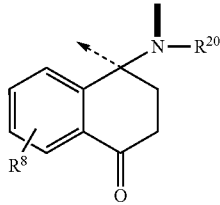
A99

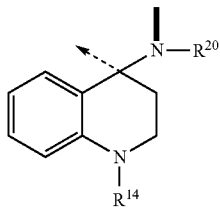
A100

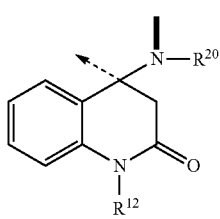
A101

116
-continued

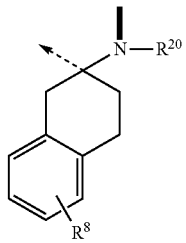
A102

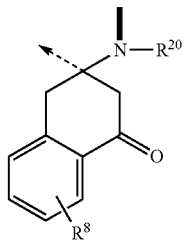
A103

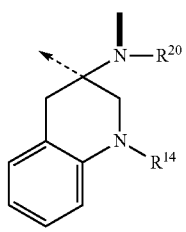
A104

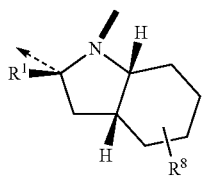
A105

$R^1$ is H; lower alkyl; aryl-lower alkyl; lower alkyl-aryl;
$R^2$ is H; lower alkyl; lower alkenyl; —$(CH_2)_p(CHR^{61})_sOR^{55}$;
—$(CH_2)_p(CHR^{61})_sSR^{56}$;
—$(CH_2)_p(CHR^{61})_sNR^{33}R^{34}$; —$(CH_2)_p(CHR^{61})_sOCONR^{33}R^{75}$;
—$(CH_2)_p(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; —$(CH_2)_o(CHR^{61})_sR^{77}$;
$R^{89}$; —$(CH_2)_p(CHR^{61})_sOR^{89}$;
—$(CH_2)_p(CHR^{61})_sSR^{89}$;
—$(CH_2)_p(CHR^{61})_sNR^{89}R^{34}$; —$(CH_2)_p(CHR^{61})_sOCONR^{89}R^{75}$;
—$(CH_2)_p(CHR^{61})_sNR^{20}CONR^{89}R^{82}$; —$(CH_2)_o(CHR^{61})_sCOOR^{89}$;
—$(CH_2)_o(CHR^{61})_sCONR^{89}R^{59}$; —$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sR^{91}$;
$R^3$ is lower alkyl; lower alkenyl; —$(CH_2)_o(CHR^{61})_sOR^{55}$;
—$(CH_2)_o(CHR^{61})_sR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;

—$(CH_2)_o(CHR^{61})_s SO_2 R^{62}$;
$R^{89}$; —$(CH_2)_o(CHR^{61})_s OR^{89}$;
—$(CH_2)_o(CHR^{61})_s SR^{89}$;
—$(CH_2)_o(CHR^{61})_s NR^{89}R^{34}$;
—$(CH_2)_o(CHR^{61})_s OCONR^{89}R^{75}$;   —$(CH_2)_o(CHR^{61})_s NR^{20}CONR^{89}R^{82}$;
—$(CH_2)_o(CHR^{61})_s COOR^{89}$;   —$(CH_2)_o(CHR^{61})_s CONR^{89}R^{59}$;
—$(CH_2)_o(CHR^{61})_s PO(OR^{60})(OR^{89})$;
—$(CH_2)_o(CHR^{61})_s SO_2 R^{89}$; or   —$(CH_2)_o(CHR^{61})_s C_6H_4R^8$;

$R^4$ is H; lower alkyl; lower alkenyl; —$(CH_2)_m(CHR^{61})_s OR^{55}$;
—$(CH_2)_m(CHR^{61})_s SR^{56}$;
—$(CH_2)_m(CHR^{61})_s NR^{33}R^{34}$;
—$(CH_2)_m(CHR^{61})_s OCONR^{33}R^{75}$;   —$(CH_2)_m(CHR^{61})_s NR^{20}CONR^{33}R^{82}$;
—$(CH_2)_p(CHR^{61})_s COOR^{57}$;   —$(CH_2)_p(CHR^{61})_s CONR^{58}R^{59}$;
—$(CH_2)_p(CHR^{61})_s PO(OR^{60})_2$;
—$(CH_2)_p(CHR^{61})_s SO_2 R^{62}$;
$R^{89}$; —$(CH_2)_m(CHR^{61})_s OR^{89}$;   —$(CH_2)_m(CHR^{61})_s SR^{89}$;
—$(CH_2)_m(CHR^{61})_s NR^{89}R^{34}$;
—$(CH_2)_m(CHR^{61})_s OCONR^{89}R^{75}$;   —$(CH_2)_m(CHR^{61})_s NR^{20}CONR^{89}R^{82}$;
—$(CH_2)_p(CHR^{61})_s COOR^{89}$;   —$(CH_2)_p(CHR^{61})_s CONR^{89}R^{59}$;
—$(CH_2)_p(CHR^{61})_s PO(OR^{60})(OR^{89})$;
—$(CH_2)_p(CHR^{61})_s SO_2 R^{89}$; or   —$(CH_2)_o(CHR^{61})_s C_6H_4R^8$;

$R^5$ is H; lower alkyl; lower alkenyl;
—$(CH_2)_m(CHR^{61})_s OR^{55}$;
—$(CH_2)_m(CHR^{61})_s SR^{56}$;
—$(CH_2)_m(CHR^{61})_s NR^{33}R^{34}$;   —$(CH_2)_m(CHR^{61})_s OCONR^{33}R^{75}$;
—$(CH_2)_m(CHR^{61})_s NR^{20}CONR^{33}R^{82}$;   —$(CH_2)_o(CHR^{61})_s COOR^{57}$;
—$(CH_2)_o(CHR^{61})_s CONR^{58}R^{59}$; —$(CH_2)_o(CHR^{61})_s PO(OR^{60})_2$;
—$(CH_2)_o(CHR^{61})_s SO_2 R^{62}$;
$R^{89}$; —$(CH_2)_m(CHR^{61})_s OR^{89}$;
—$(CH_2)_m(CHR^{61})_s SR^{89}$;
—$(CH_2)_m(CHR^{61})_s NR^{89}R^{34}$;   —$(CH_2)_m(CHR^{61})_s OCONR^{89}R^{75}$;
—$(CH_2)_m(CHR^{61})_s NR^{20}CONR^{89}R^{82}$;   —$(CH_2)_o(CHR^{61})_s COOR^{89}$;
—$(CH_2)_o(CHR^{61})_s CONR^{89}R^{59}$; —$(CH_2)_o(CHR^{61})_s PO(OR^{60})(OR^{89})$;
—$(CH_2)_o(CHR^{61})_s SO_2 R^{89}$; or   —$(CH_2)_o(CHR^{61})_s C_6H_4R^8$;

$R^6$ is H; lower alkyl; lower alkenyl; —$(CH_2)_o(CHR^{61})_s OR^{55}$;
—$(CH_2)_o(CHR^{61})_s SR^{56}$;
—$(CH_2)_o(CHR^{61})_s NR^{33}R^{34}$;
—$(CH_2)_o(CHR^{61})_s OCONR^{33}R^{75}$;   —$(CH_2)_o(CHR^{61})_s NR^{20}CONR^{33}R^{82}$;
—$(CH_2)_o(CHR^{61})_s COOR^{57}$;   —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2 R^{62}$;
$R^{89}$; —$(CH_2)_o(CHR^{61})_s OR^{89}$;
—$(CH_2)_o(CHR^{61})_s SR^{89}$; —$(CH_2)_o(CHR^{61})_s NR^{89}R^{34}$;
—$(CH_2)_o(CHR^{61})_s OCONR^{89}R^{75}$;   —$(CH_2)_o(CHR^{61})_s NR^{20}CONR^{89}R^{82}$;
—$(CH_2)_o(CHR^{61})_s COOR^{89}$;   —$(CH_2)_o(CHR^{61})_s CONR^{89}R^{59}$;
—$(CH_2)_o(CHR^{61})_s PO(OR^{60})(OR^{89})$;
—$(CH_2)_o(CHR^{61})_s SO_2 R^{89}$; or   —$(CH_2)_o(CHR^{61})_s C_6H_4R^8$;

$R^7$ is lower alkyl; lower alkenyl; —$(CH_2)_q(CHR^{61})_s OR^{55}$;
—$(CH_2)_q(CHR^{61})_s NR^{33}R^{34}$;
—$(CH_2)_q(CHR^{61})_s OCONR^{33}R^{75}$;   —$(CH_2)_q(CHR^{61})_s NR^{20}CONR^{33}R^{82}$;
—$(CH_2)_r(CHR^{61})_s COOR^{57}$;   —$(CH_2)_r(CHR^{61})_s CONR^{58}R^{59}$;
—$(CH_2)_r(CHR^{61})_s PO(OR^{60})_2$;
—$(CH_2)_r(CHR^{61})_s SO_2 R^{62}$;
$R^{89}$;   —$(CH_2)_q(CHR^{61})_s OR^{89}$;   —$(CH_2)_q(CHR^{61})_s NR^{89}R^{34}$;
—$(CH_2)_q(CHR^{61})_s OCONR^{89}R^{75}$;   —$(CH_2)_q(CHR^{61})_s NR^{20}CONR^{89}R^{82}$;
—$(CH_2)_r(CHR^{61})_s COOR^{89}$;   —$(CH_2)_r(CHR^{61})_s CONR^{89}R^{59}$;
—$(CH_2)_r(CHR^{61})_s PO(OR^{60})(OR^{89})$;
—$(CH_2)_r(CHR^{61})_s SO_2 R^{89}$; or   —$(CH_2)_r(CHR^{61})_s C_6H_4R^8$;

$R^8$ is H; Cl; F; $CF_3$; $NO_2$; lower alkyl; lower alkenyl; ary lower alkyl-aryl; aryl-lower alkyl; —$(CH_2)_o(CHR^{61})_s R^{77}$
—$(CH_2)_o(CHR^{61})_s OR^{55}$; —$(CH_2)_o(CHR^{61})_s SR^{56}$;
—$(CH_2)_o(CHR^{61}) NR^{33}R^{34}$;
—$(CH_2)_o(CHR^{61})_s OCONR^{33}R^{75}$;   —$(CH_2)_o(CHR^{61})_s NR^{20}CONR^{33}R^{82}$;
—$(CH_2)_o(CHR^{61})_s COOR^{57}$;   —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2 R^{62}$; —$(CH_2)_o(CHR^{61})_s COR^{64}$;
$R^{89}$; —$(CH_2)_o(CHR^{61}) R^{89}$;
—$(CH_2)_o(CHR^{61})_s OR^{89}$; —$(CH_2)_o(CHR^{61})_s SR^{89}$;
—$(CH_2)_o(CHR^{61}) NR^{89}R^{34}$;
—$(CH_2)_o(CHR^{61})_s OCONR^{89}R^{75}$;   —$(CH_2)_o(CHR^{61})_s NR^{20}CONR^{89}R^{82}$;
—$(CH_2)_o(CHR^{61})_s COOR^{89}$;   —$(CH_2)_o(CHR^{61})_s CONR^{89}R^{59}$;
—$(CH_2)_o(CHR^{61})_s PO(OR^{60})(OR^{89})$;
—$(CH_2)_o(CHR^{61})_s SO_2 R^{89}$; or   —$(CH_2)_o(CHR^{61})_s COR^{89}$;

$R^9$ is lower alkyl; lower alkenyl; —$(CH_2)_o(CHR^{61})_s OR^{55}$;
—$(CH_2)_o(CHR^{61})_s SR^{56}$;
—$(CH_2)_o(CHR^{61})_s NR^{33}R^{34}$;
—$(CH_2)_o(CHR^{61})_s OCONR^{33}R^{75}$;   —$(CH_2)_o(CHR^{61})_s NR^{20}CONR^{33}R^{82}$;
—$(CH_2)_o(CHR^{61})_s COOR^{57}$;   —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2 R^{62}$;
$R^{89}$;   —$(CH_2)_o(CHR^{61})_s OR^{89}$;   —$(CH_2)_o(CHR^{61})_s SR^{89}$;
—$(CH_2)_o(CHR^{61})_s NR^{89}R^{34}$;
—$(CH_2)_o(CHR^{61})_s OCONR^{89}R^{75}$;   —$(CH_2)_o(CHR^{61})_s NR^{20}CONR^{89}R^{82}$;
—$(CH_2)_o(CHR^{61})_s COOR^{89}$;   —$(CH_2)_o(CHR^{61})_s CONR^{89}R^{59}$;
—$(CH_2)_o(CHR^{61})_s PO(OR^{60})(OR^{89})_2$;
—$(CH_2)_o(CHR^{61})_s SO_2 R^{89}$; or   —$(CH_2)_o(CHR^{61})_s C_6H_4R^8$;

$R^{10}$ is lower alkyl; lower alkenyl; —$(CH_2)_o(CHR^{61})_s OR^{55}$;
—$(CH_2)_o(CHR^{61})_s SR^{56}$;
—$(CH_2)_o(CHR^{61})_s NR^{33}R^{34}$;
—$(CH_2)_o(CHR^{61})_s OCONR^{33}R^{75}$;   —$(CH_2)_o(CHR^{61})_s NR^{20}CONR^{33}R^{82}$;

—(CH$_2$)$_o$(CHR$^{61}$)$_s$COOR$^{57}$;   —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$;  —(CH$_2$)$_o$(CHR$^{61}$)$_s$OR$^{89}$;  —(CH$_2$)$_o$(CHR$^{61}$)$_s$SR$^{89}$;
—(CH$_2$)$_o$(CHR$^{61}$)$_s$NR$^{89}$R$^{34}$;
—(CH$_2$)$_o$(CHR$^{61}$)$_s$OCONR$^{89}$R$^{75}$;  —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$;  —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or  —(CH$_2$)$_o$(CHR$^{61}$)$_s$C$_6$H$_4$R$^8$;

R$^{11}$ is H; lower alkyl; lower alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$;  —(CH$_2$)$_m$(CHR$^{61}$)$_s$OR$^{89}$;  —(CH$_2$)$_m$(CHR$^{61}$)$_s$NR$^{89}$R$^{34}$;
—(CH$_2$)$_m$(CHR$^{61}$)$_s$OCONR$^{89}$R$^{75}$; —(CH$_2$)$_m$(CHR$^{61}$)$_s$NR$^{20}$CONR$^{89}$R$^{82}$;
—(CH$_2$)$_o$(CHR$^{61}$)$_s$COOR$^{89}$;  —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or —(CH$_2$)$_o$(CHR$^{61}$)$_s$C$_6$H$_4$R$^8$;

R$^{12}$ is H; lower alkyl; lower alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$;  —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$;  —(CH$_2$)$_r$(CHR$^{61}$)$_s$COOR$^{57}$;
—(CH$_2$)$_r$(CHR$^{61}$)$_s$CONR$^{58}$R$^{59}$; —(CH$_2$)$_r$(CHR$^{61}$)$_s$PO(OR$^{60}$)$_2$;
—(CH$_2$)$_r$(CHR$^{61}$)$_s$SO$_2$R$^{62}$;
R$^{89}$; —(CH$_2$)$_m$(CHR$^{61}$)$_s$OR$^{89}$;
—(CH$_2$)$_m$(CHR$^{61}$)$_s$SR$^{89}$;
—(CH$_2$)$_m$(CHR$^{61}$)$_s$NR$^{89}$R$^{34}$;  —(CH$_2$)$_m$(CHR$^{61}$)$_s$OCONR$^{89}$R$^{75}$;
—(CH$_2$)$_m$(CHR$^{61}$)$_s$NR$^{20}$CONR$^{89}$R$^{82}$;  —(CH$_2$)$_r$(CHR$^{61}$)$_s$COOR$^{89}$;
—(CH$_2$)$_r$(CHR$^{61}$)$_s$CONR$^{89}$R$^{59}$; —(CH$_2$)$_r$(CHR$^{61}$)$_s$PO(OR$^{60}$)(OR$^{89}$);
—(CH$_2$)$_r$(CHR$^{61}$)$_s$SO$_2$R$^{89}$; or  —(CH$_2$)$_r$(CHR$^{61}$)$_s$C$_6$H$_4$R$^8$;

R$^{13}$ is lower alkyl; lower alkenyl; —(CH$_2$)$_q$(CHR$^{61}$)$_s$OR$^{55}$;
—(CH$_2$)$_q$(CHR$^{61}$)$_s$SR$^{56}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$;
—(CH$_2$)$_q$(CHR$^{61}$)$_s$COOR$^{57}$;  —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SO$_2$R$^{62}$;
R$^{89}$;  —(CH$_2$)$_q$(CHR$^{61}$)$_s$OR$^{89}$;  —(CH$_2$)$_q$(CHR$^{61}$)$_s$SR$^{89}$;
—(CH$_2$)$_q$(CHR$^{61}$)$_s$NR$^{89}$R$^{34}$;
—(CH$_2$)$_q$(CHR$^{61}$)$_s$OCONR$^{89}$R$^{75}$; —(CH$_2$)$_q$(CHR$^{61}$)$_s$NR$^{20}$CONR$^{89}$R$^{82}$;
—(CH$_2$)$_q$(CHR$^{61}$)$_s$COOR$^{89}$;  —(CH$_2$)$_q$(CHR$^{61}$)$_s$CONR$^{89}$R$^{59}$;
—(CH$_2$)$_q$(CHR$^{61}$)$_s$PO(OR$^{60}$)(OR$^{89}$);
—(CH$_2$)$_q$(CHR$^{61}$)$_s$SO$_2$R$^{89}$; or  —(CH$_2$)$_q$(CHR$^{61}$)$_s$C$_6$H$_4$R$^8$;

R$^{14}$ is H; lower alkyl; lower alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_q$(CHR$^{61}$)$_s$COOR$^{57}$;  —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SOR$^{62}$;
R$^{89}$; —(CH$_2$)$_m$(CHR$^{61}$)$_s$OR$^{89}$;
—(CH$_2$)$_m$(CHR$^{61}$)$_s$NR$^{89}$R$^{34}$;
—(CH$_2$)$_m$(CHR$^{61}$)$_s$OCONR$^{89}$R$^{75}$; —(CH$_2$)$_m$(CHR$^{61}$)$_s$NR$^{20}$CONR$^{89}$R$^{82}$;
—(CH$_2$)$_q$(CHR$^{61}$)$_s$COOR$^{89}$;  —(CH$_2$)$_q$(CHR$^{61}$)$_s$CONR$^{89}$R$^{59}$;
—(CH$_2$)$_q$(CHR$^{61}$)$_s$PO(OR$^{60}$)(OR$^{89}$);
—(CH$_2$)$_q$(CHR$^{61}$)$_s$SOR$^{89}$; or  —(CH$_2$)$_q$(CHR$^{61}$)$_s$C$_6$H$_4$R$^8$;

R$^{15}$ is lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$;  —(CH$_2$)$_o$(CHR$^{61}$)$_s$OR$^{89}$;  —(CH$_2$)$_o$(CHR$^{61}$)$_s$SR$^{89}$;
—(CH$_2$)$_o$(CHR$^{61}$)$_s$NR$^{89}$R$^{34}$;
—(CH$_2$)$_o$(CHR$^{61}$)$_s$OCONR$^{89}$R$^{75}$; —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$;  —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or  —(CH$_2$)$_o$(CHR$^{61}$)$_s$C$_6$H$_4$R$^8$;

R$^{16}$ is lower alkyl; lower alkenyl; —(CH$_2$)$_o$(CHR$^{61}$)$_s$OR$^{55}$;
—(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$;
R$^{89}$;  —(CH$_2$)$_o$(CHR$^{61}$)$_s$OR$^{89}$;  —(CH$_2$)$_o$(CHR$^{61}$)$_s$SR$^{89}$;
—(CH$_2$)$_o$(CHR$^{61}$)$_s$NR$^{89}$R$^{34}$;
—(CH$_2$)$_o$(CHR$^{61}$)$_s$OCONR$^{89}$R$^{75}$; —(CH$_2$)$_o$(CHR$^{61}$)$_s$NR$^{20}$CONR$^{89}$R$^{82}$;
—(CH$_2$)$_o$(CHR$^{61}$)$_s$COOR$^{89}$;  —(CH$_2$)$_o$(CHR$^{61}$)$_s$CONR$^{89}$R$^{59}$;
—(CH$_2$)$_o$(CHR$^{61}$)$_s$PO(OR$^{60}$)(OR$^{89}$);
—(CH$_2$)$_o$(CHR$^{61}$)$_s$SO$_2$R$^{89}$; or  —(CH$_2$)$_o$(CHR$^{61}$)$_s$C$_6$H$_4$R$^8$;

R$^{17}$ is lower alkyl; lower alkenyl; —(CH$_2$)$_q$(CHR$^{61}$)$_s$OR$^{55}$;
—(CH$_2$)$_q$(CHR$^{61}$)$_s$SR$^{56}$;
—(CH$_2$)$_q$(CHR$^{61}$)$_s$NR$^{33}$R$^{34}$;

—$(CH_2)_q(CHR^{61})_sOCONR^{33}R^{75}$; —$(CH_2)_q(CHR^{61})_s NR^{20}CONR^{33}R^{82}$;

—$(CH_2)_q(CHR^{61})_sCOOR^{57}$; —$(CH_2)_q(CHR^{61})_s CONR^{58}R^{59}$;

—$(CH_2)_q(CHR^{61})_sPO(OR^{60})_2$;

—$(CH_2)_q(CHR^{61})_sSO_2R^{62}$;

$R^{89}$; —$(CH_2)_q(CHR^{61})_sOR^{89}$; —$(CH_2)_q(CHR^{61})_s SR^{89}$;

—$(CH_2)_q(CHR^{61})_sNR^{89}R^{34}$;

—$(CH_2)_q(CHR^{61})_sOCONR^{89}R^{75}$; —$(CH_2)_q(CHR^{61})_s NR^{20}CONR^{89}R^{82}$;

—$(CH_2)_q(CHR^{61})_sCOOR^{89}$; —$(CH_2)_q(CHR^{61})_s CONR^{89}R^{59}$;

—$(CH_2)_q(CHR^{61})_sPO(OR^{60})(OR^{89})$;

—$(CH_2)_q(CHR^{61})_sSO_2R^{89}$; or —$(CH_2)_q(CHR^{61})_s C_6H_4R^8$;

$R^{18}$ is lower alkyl; lower alkenyl; —$(CH_2)_p(CHR^{61})_s OR^{55}$;

—$(CH_2)_p(CHR^{61})_sSR^{56}$;

—$(CH_2)_p(CHR^{61})_sNR^{33}R^{34}$;

—$(CH_2)_p(CHR^{61})_sOCONR^{33}R^{75}$; —$(CH_2)_p(CHR^{61})_s NR^{20}CONR^{33}R^{82}$;

—$(CH_2)_p(CHR^{61})_sCOOR^{57}$; —$(CH_2)_p(CHR^{61})_s CONR^{58}R^{59}$;

—$(CH_2)_p(CHR^{61})_sPO(OR^{60})_2$;

—$(CH_2)_p(CHR^{61})_sSO_2R^{62}$;

$R^{89}$; —$(CH_2)_p(CHR^{61})_sOR^{89}$; —$(CH_2)_p(CHR^{61})_s SR^{89}$;

—$(CH_2)_p(CHR^{61})_sNR^{89}R^{34}$;

—$(CH_2)_p(CHR^{61})_sOCONR^{89}R^{75}$; —$(CH_2)_p(CHR^{61})_s NR^{20}CONR^{89}R^{82}$;

—$(CH_2)_p(CHR^{61})_sCOOR^{89}$; —$(CH_2)_p(CHR^{61})_s CONR^{89}R^{59}$;

—$(CH_2)_p(CHR^{61})_sPO(OR^{60})(OR^{89})$;

—$(CH_2)_p(CHR^{61})_sSO_2R^{89}$; or —$(CH_2)_o(CHR^{61})_s C_6H_4R^8$;

$R^{19}$ is lower alkyl; lower alkenyl; —$(CH_2)_p(CHR^{61})_s OR^{55}$;

—$(CH_2)_p(CHR^{61})_sSR^{56}$;

—$(CH_2)_p(CHR^{61})_sNR^{33}R^{34}$;

—$(CH_2)_p(CHR^{61})_sOCONR^{33}R^{75}$; —$(CH_2)_p(CHR^{61})_s NR^{20}CONR^{33}R^{82}$;

—$(CH_2)_p(CHR^{61})_sCOOR^{57}$; —$(CH_2)_p(CHR^{61})_s CONR^{58}R^{59}$;

—$(CH_2)_p(CHR^{61})_sPO(OR^{60})_2$;

—$(CH_2)_p(CHR^{61})_sSO_2R^{62}$;

$R^{89}$; —$(CH_2)_p(CHR^{61})_sOR^{89}$; —$(CH_2)_p(CHR^{61})_s SR^{89}$;

—$(CH_2)_p(CHR^{61})_sNR^{89}R^{34}$;

—$(CH_2)_p(CHR^{61})_sOCONR^{89}R^{75}$; —$(CH_2)_p(CHR^{61})_s NR^{20}CONR^{89}R^{82}$;

—$(CH_2)_p(CHR^{61})_sCOOR^{89}$; —$(CH_2)_p(CHR^{61})_s CONR^{89}R^{59}$;

—$(CH_2)_p(CHR^{61})_sPO(OR^{60})(OR^{89})$;

—$(CH_2)_p(CHR^{61})_sSO_2R^{89}$; or —$(CH_2)_o(CHR^{61})_s C_6H_4R^8$; or $R^{18}$ and $R^{19}$ taken together can form: —$(CH_2)_{2-6}$—;

—$(CH_2)_2O(CH_2)_2$—; —$(CH_2)_2S(CH_2)_2$—; —$(CH_2)_2 NR^{57}(CH_2)_2$—;

—$(CH_2)_2NR^{89}(CH_2)_2$—;

$R^{20}$ is H; alkyl; alkenyl; or $R^{89}$;

$R^{21}$ is H; lower alkyl; lower alkenyl; —$(CH_2)_o(CHR^{61})_s OR^{55}$;

—$(CH_2)_o(CHR^{61})_sSR^{56}$; —$(CH_2)_o(CHR^{61})_sNR^{33}R^{34}$;

—$(CH_2)_o(CHR^{61})_sOCONR^{33}R^{75}$; —$(CH_2)_o(CHR^{61})_s NR^{20}CONR^{33}R^{82}$;

—$(CH_2)_o(CHR^{61})_sCOOR^{57}$; —$(CH_2)_o(CHR^{61})_s CONR^{58}R^{59}$;

—$(CH_2)_o(CHR^{61})_sPO(OR^{60})_2$;

—$(CH_2)_o(CHR^{61})_sSO_2R^{62}$;

$R^{89}$; —$(CH_2)_o(CHR^{61})_sOR^{89}$;

—$(CH_2)_o(CHR^{61})_sSR^{89}$; —$(CH_2)_o(CHR^{61})_sNR^{89}R^{34}$;

—$(CH_2)_o(CHR^{61})_sOCONR^{89}R^{75}$; —$(CH_2)_o(CHR^{61})_s NR^{20}CONR^{89}R^{82}$;

—$(CH_2)_o(CHR^{61})_sCOOR^{89}$; —$(CH_2)_o(CHR^{61})_s CONR^{89}R^{59}$;

—$(CH_2)_o(CHR^{61})_sPO(OR^{60})(OR^{89})$;

—$(CH_2)_o(CHR^{61})_sSO_2R^{89}$; or —$(CH_2)_o(CHR^{61})_s C_6H_4R^8$;

$R^{22}$ is H lower alkyl; lower alkenyl; —$(CH_2)_o(CHR^{61})_s OR^{55}$;

—$(CH_2)_o(CHR^{61})_sSR^{56}$; —$(CH_2)_o(CHR^{61})_sNR^{33}R^{34}$;

—$(CH_2)_o(CHR^{61})_sOCONR^{33}R^{75}$; —$(CH_2)_o(CHR^{61})_s NR^{20}CONR^{33}R^{82}$;

—$(CH_2)_o(CHR^{61})_sCOOR^{57}$; —$(CH_2)_o(CHR^{61})_s CONR^{58}R^{59}$;

—$(CH_2)_o(CHR^{61})_sPO(OR^{60})_2$;

—$(CH_2)_o(CHR^{61})_sSO_2R^{62}$;

$R^{89}$; —$(CH_2)_o(CHR^{61})_sOR^{89}$;

—$(CH_2)_o(CHR^{61})_sSR^{89}$; —$(CH_2)_o(CHR^{61})_sNR^{89}R^{34}$;

—$(CH_2)_o(CHR^{61})_sOCONR^{89}R^{75}$; —$(CH_2)_o(CHR^{61})_s NR^{20}CONR^{89}R^{82}$;

—$(CH_2)_o(CHR^{61})_sCOOR^{89}$; —$(CH_2)_o(CHR^{61})_s CONR^{89}R^{59}$;

—$(CH_2)_o(CHR^{61})_sPO(OR^{60})(OR^{89})$;

—$(CH_2)_o(CHR^{61})_sSO_2R^{89}$; or —$(CH_2)_o(CHR^{61})_s C_6H_4R^8$;

$R^{23}$ is lower alkyl; lower alkenyl; —$(CH_2)_o(CHR^{61})_s OR^{55}$;

—$(CH_2)_o(CHR^{61})_sSR^{56}$;

—$(CH_2)_o(CHR^{61})_sNR^{33}R^{34}$;

—$(CH_2)_o(CHR^{61})_sOCONR^{33}R^{75}$; —$(CH_2)_o(CHR^{61})_s NR^{20}CONR^{33}R^{82}$;

—$(CH_2)_o(CHR^{61})_sCOOR^{57}$; —$(CH_2)_o(CHR^{61})_s CONR^{58}R^{59}$;

—$(CH_2)_o(CHR^{61})_sPO(OR^{60})_2$;

—$(CH_2)_o(CHR^{61})_sSO_2R^{62}$;

$R^{89}$; —$(CH_2)_o(CHR^{61})_sOR^{89}$; —$(CH_2)_o(CHR^{61})_s SR^{89}$;

—$(CH_2)_o(CHR^{61})_sNR^{89}R^{34}$;

—$(CH_2)_o(CHR^{61})_sOCONR^{89}R^{75}$; —$(CH_2)_o(CHR^{61})_s NR^{20}CONR^{89}R^{82}$;

—$(CH_2)_o(CHR^{61})_sCOOR^{89}$; —$(CH_2)_o(CHR^{61})_s CONR^{89}R^{59}$;

—$(CH_2)_o(CHR^{61})_sPO(OR^{60})(OR^{89})$;

—$(CH_2)_o(CHR^{61})_sSO_2R^{89}$; or —$(CH_2)_o(CHR^{61})_s C_6H_4R^8$;

$R^{24}$ is lower alkyl; lower alkenyl; —$(CH_2)_o(CHR^{61})_s OR^{55}$;

—$(CH_2)_o(CHR^{61})_sSR^{56}$;

—$(CH_2)_o(CHR^{61})_sNR^{33}R^{34}$;

—$(CH_2)_o(CHR^{61})_sOCONR^{33}R^{75}$; —$(CH_2)_o(CHR^{61})_s NR^{20}CONR^{33}R^{82}$;

—$(CH_2)_o(CHR^{61})_sCOOR^{57}$; —$(CH_2)_o(CHR^{61})_s CONR^{58}R^{59}$;

—$(CH_2)_o(CHR^{61})_sPO(OR^{60})_2$;

—$(CH_2)_o(CHR^{61})_sSO_2R^{62}$;

$R^{89}$; —$(CH_2)_o(CHR^{61})_sOR^{89}$;

—$(CH_2)_o(CHR^{61})_sSR^{89}$;

—$(CH_2)_o(CHR^{61})_sNR^{89}R^{34}$;

—$(CH_2)_o(CHR^{61})_sOCONR^{89}R^{75}$; —$(CH_2)_o(CHR^{61})_s NR^{20}CONR^{89}R^{82}$;

—$(CH_2)_o(CHR^{61})_sCOOR^{89}$; —$(CH_2)_o(CHR^{61})_s$ CONR$^{89}$R$^{59}$;
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sC_6H_4R^8$;

R$^{25}$ is H; lower alkyl; lower alkenyl; —$(CH_2)_m(CHR^{61})_sOR^{55}$;
—$(CH_2)_m(CHR^{61})_sSR^{56}$;
—$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;
R$^{89}$; —$(CH_2)_m(CHR^{61})_sOR^{89}$;
—$(CH_2)_m(CHR^{61})_sSR^{89}$;
—$(CH_2)_m(CHR^{61})_sNR^{89}R^{34}$; —$(CH_2)_m(CHR^{61})_sOCONR^{89}R^{75}$;
—$(CH_2)_m(CHR^{61})_sNR^{20}CONR^{89}R^{82}$; —$(CH_2)_o(CHR^{61})_sCOOR^{89}$;
—$(CH_2)_o(CHR^{61})_sCONR^{89}R^{59}$; —$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sC_6H_4R^8$;

R$^{26}$ is H; lower alkyl; lower alkenyl; —$(CH_2)_m(CHR^{61})_sOR^{55}$;
—$(CH_2)_m(CHR^{61})_sSR^{56}$;
—$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;
R$^{89}$; —$(CH_2)_m(CHR^{61})_sOR^{89}$;
—$(CH_2)_m(CHR^{61})_sSR^{89}$;
—$(CH_2)_m(CHR^{61})_sNR^{89}R^{34}$; —$(CH_2)_m(CHR^{61})_sOCONR^{89}R^{75}$;
—$(CH_2)_m(CHR^{61})_sNR^{20}CONR^{89}R^{82}$; —$(CH_2)_o(CHR^{61})_sCOOR^{89}$;
—$(CH_2)_o(CHR^{61})_sCONR^{89}R^{59}$; —$(CH_2)_o(CHR^{61})_sPO(OR^{60})(OR^{89})$;
—$(CH_2)_o(CHR^{61})_sSO_2R^{89}$; —$(CH_2)_o(CHR^{61})_sC_6H_4R^8$; or R$^{25}$ and R$^{26}$ taken together can form: —$(CH_2)_{2-6}$—;
—$(CH_2)_r$—O—$(CH_2)_r$—;
—$(CH_2)_rS(CH_2)_r$—; —$(CH_2)_rNR^{57}(CH_2)_r$—; or
—$(CH_2)_rNR^{89}(CH_2)_r$—;

R$^{27}$ is H; lower alkyl; lower alkenyl; —$(CH_2)_o(CHR^{61})_sOR^{55}$;
—$(CH_2)_o(CHR^{61})_sSR^{56}$; —$(CH_2)_o(CHR^{61})_sNR^{33}R^{34}$;
—$(CH_2)_o(CHR^{61})_sCOOR^{57}$; —$(CH_2)_o(CHR^{61})_sCONR^{58}R^{59}$;
—$(CH_2)_o(CHR^{61})_sOCONR^{33}R^{75}$;
—$(CH_2)_o(CHR^{61})_sNR^{20}CONR^{33}R^{82}$; —$(CH_2)_o(CHR^{61})_sPO(OR^{60})_2$;
—$(CH_2)_o(CHR^{61})_sSO_2R^{62}$;
R$^{89}$; —$(CH_2)_o(CHR^{61})_sOR^{89}$;
—$(CH_2)_o(CHR^{61})_sSR^{89}$; —$(CH_2)_o(CHR^{61})_sNR^{89}R^{34}$;
—$(CH_2)_o(CHR^{61})_sCOOR^{89}$; —$(CH_2)_o(CHR^{61})_sCONR^{89}R^{59}$;
—$(CH_2)_o(CHR^{61})_sOCONR^{89}R^{75}$;
—$(CH_2)_o(CHR^{61})_sNR^{20}CONR^{89}R^{82}$; —$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sC_6H_4R^8$;

R$^{28}$ is lower alkyl; lower alkenyl; —$(CH_2)_o(CHR^{61})_s$—OR$^{55}$;
—$(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$;
R$^{89}$; —$(CH_2)_o(CHR^{61})_s$—OR$^{89}$;
—$(CH_2)_o(CHR^{61})_sSR^{89}$;
—$(CH_2)_o(CHR^{61})_sNR^{89}R^{34}$;
—$(CH_2)_o(CHR^{61})_sOCONR^{89}R^{75}$; —$(CH_2)_o(CHR^{61})_sNR^{20}CONR^{89}R^{82}$;
—$(CH_2)_o(CHR^{61})_sCOOR^{89}$; —$(CH_2)_o(CHR^{61})_sCONR^{89}R^{59}$;
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sC_6H_4R^8$;

R$^{29}$ is lower alkyl; lower alkenyl; —$(CH_2)_o(CHR^{61})_sOR^{55}$;
—$(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$;
R$^{89}$; —$(CH_2)_o(CHR^{61})_sOR^{89}$; —$(CH_2)_o(CHR^{61})_sSR^{89b}$;
—$(CH_2)_o(CHR^{61})_sNR^{89}R^{34}$;
—$(CH_2)_o(CHR^{61})_sOCONR^{89}R^{75}$; —$(CH_2)_o(CHR^{61})_sNR^{20}CONR^{89}R^{82}$;
—$(CH_2)_o(CHR^{61})_sCOOR^{89}$; —$(CH_2)_o(CHR^{61})_sCONR^{89}R^{59}$;
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sC_6H_4R^8$;

R$^{33}$ is H; lower alkyl; lower alkenyl; —$(CH_2)_m(CHR^{61})_sOR^{55}$;
—$(CH_2)_m(CHR^{61})_sNR^{34}R^{63}$;
—$(CH_2)_m(CHR^{61})_sOCONR^{75}R^{82}$; —$(CH_2)_m(CHR^{61})_sNR^{20}CONR^{78}R^{82}$;
—$(CH_2)_o(CHR^{61})_sCOR^{64}$; —$(CH_2)_o(CHR^{61})_s$—CONR$^{58}$R$^{59}$;
—$(CH_2)_o(CHR^{61})_sPO(OR^{60})_2$;
—$(CH_2)_o(CHR^{61})_sSO_2R^{62}$;
R$^{89}$; —$(CH_2)_m(CHR^{61})_sOR^{89}$;
—$(CH_2)_m(CHR^{61})_sNR^{34}R^{89}$;
—$(CH_2)_m(CHR^{61})_sOCONR^{89}R^{75}$; —$(CH_2)_m(CHR^{61})_sNR^{20}CONR^{89}R^{82}$;
—$(CH_2)_o(CHR^{61})_sCOR^{89}$; —$(CH_2)_o(CHR^{61})_s$—CONR$^{89}$R$^{59}$,
—$(CH_2)_o(CHR^{61})_sPO(OR^{60})(OR^{89})$;
—$(CH_2)_o(CHR^{61})_sSO_2R^{89}$; or —$(CH_2)_o(CHR^{61})_sC_6H_4R^8$;

R$^{34}$ is H; lower alkyl; aryl, lower alkyl-aryl;
aryl-lower alkyl; or

R$^{33}$ and R$^{34}$ taken together can form: —$(CH_2)_{2-6}$—;
—$(CH_2)_2$—O—$(CH_2)_2$—; —$(CH_2)_2S(CH_2)_2$—;
—$(CH_2)_2NR^{57}(CH_2)_2$—; or —$(CH_2)_2NR^{89}(CH_2)_2$—;

R$^{50}$ is H; lower alkyl; lower alkyl-aryl; or aryl-lower alkyl;
R$^{55}$ is H; lower alkyl; lower alkenyl; lower alkyl-aryl;
aryl-lower alkyl;
—$(CH_2)_m(CHR^{61})_sOR^{57}$;

—(CH$_2$)$_m$(CHR$^{61}$)$_s$NR$^{34}$R$^{63}$;  —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$;  —(CH$_2$)$_o$(CHR$^{61}$)$_s$—COR$^{64}$;
—(CH$_2$)$_o$(CHR$^{61}$)$_s$COOR$^{57}$; or
—(CH$_2$)$_o$(CHR$^{61}$)$_s$CONR$^{58}$R$^{59}$;

R$^{56}$ is H; lower alkyl; lower alkenyl; lower alkyl-aryl; aryl-lower alkyl;
—(CH$_2$)$_m$(CHR$^{61}$)$_s$OR$^{57}$;
—(CH$_2$)$_m$(CHR$^{61}$)$_s$NR$^{34}$R$^{63}$;  —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$;  —(CH$_2$)$_o$(CHR$^{61}$)$_s$—COR$^{64}$; or
—(CH$_2$)$_o$(CHR$^{61}$)$_s$CONR$^{58}$R$^{59}$;

R$^{57}$ is H; lower alkyl; lower alkenyl; lower alkyl-aryl; lower alkyl-heteroaryl; aryl-lower alkyl; or heteroaryl-lower alkyl;

R$^{58}$ is H; lower alkyl; lower alkenyl; lower alkyl-aryl; lower alkyl-heteroaryl; aryl; aryl-lower alkyl; heteroaryl; or heteroaryl-lower alkyl;

R$^{59}$ is H; lower alkyl; lower alkenyl; lower alkyl-aryl; lower alkyl-heteroaryl; aryl; aryl-lower alkyl; heteroaryl; or heteroaryl-lower alkyl; or R$^{58}$ and R$^{59}$ taken together can form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{60}$ is H; H lower alkyl; lower alkenyl; lower alkyl-aryl; aryl-lower alkyl; aryl;

R$^{61}$ is alkyl; alkenyl; lower alkyl-aryl;
lower alkyl-heteroaryl; aryl;
aryl-lower alkyl; heteroaryl; heteroaryl-lower alkyl;
—(CH$_2$)$_p$OR$^{55}$;  —(CH$_2$)$_p$NR$^{33}$R$^{34}$;  —(CH$_2$)$_p$OCONR$^{75}$R$^{82}$;
—(CH$_2$)$_p$NR$^{20}$CONR$^{78}$R$^{82}$;  —(CH$_2$)$_o$COOR$^{57}$; or
—(CH$_2$)$_o$PO(OR$^{60}$)$_2$;

R$^{62}$ is lower alkyl; lower alkenyl; lower alkyl-aryl;
lower alkyl-heteroaryl; aryl,
aryl-lower alkyl; heteroaryl; or
heteroaryl-lower alkyl;

R$^{63}$ is H; lower alkyl; lower alkenyl; lower alkyl-aryl;
lower alkyl-heteroaryl; aryl,
aryl-lower alkyl; heteroaryl;
heteroaryl-lower alkyl;
—COR$^{64}$; —COOR$^{57}$; —CONR$^{58}$R$^{59}$; —SO$_2$R$^{62}$; or
—PO(OR$^{60}$)$_2$; or R$^{34}$ and R$^{63}$ taken together can form: —(CH$_2$)$_{2-6}$—;
—(CH$_2$)$_2$O(CH$_2$)$_2$—;
—(CH$_2$)$_2$S(CH$_2$)$_2$—; or —(CH$_2$)$_2$NR$^{57}$(CH$_2$)$_2$—;

R$^{64}$ is H; lower alkyl; lower alkenyl; lower alkyl-aryl;
lower alkyl-heteroaryl; aryl,
aryl-lower alkyl; heteroaryl;
heteroaryl-lower alkyl;
—(CH$_2$)$_p$(CHR$^{61}$)$_s$OR$^{65}$; —(CH$_2$)$_p$(CHR$^{61}$)$_s$SR$^{66}$;
—(CH$_2$)$_p$(CHR$^{61}$)$_s$NR$^{34}$R$^{63}$;
—(CH$_2$)$_p$(CHR$^{61}$)$_s$OCONR$^{75}$R$^{82}$;  or  —(CH$_2$)$_p$(CHR$^{61}$)$_s$NR$^{20}$CONR$^{78}$R$^{82}$;

R$^{65}$ is H; lower alkyl; lower alkenyl; lower alkyl-aryl;
lower alkyl-heteroaryl; aryl,
aryl-lower alkyl; heteroaryl;
heteroaryl-lower alkyl;
COR$^{57}$; COOR$^{57}$; or —CONR$^{58}$R$^{59}$;

R$^{66}$ is H; lower alkyl; lower alkenyl; lower alkyl-aryl;
lower alkyl-heteroaryl; aryl,
aryl-lower alkyl; heteroaryl;
heteroaryl-lower alkyl; or —CONR$^{58}$R$^{59}$;

R$^{67}$ is H; Cl; Br; F; NO$_2$; —NR$^{34}$COR$^{57}$; —CF$_3$; CN;
—OCF$_3$; —OCHF$_2$;
—OR$^{57}$; —SR$^{62}$; lower alkyl; or lower alkenyl;

R$^{68}$ is H; Cl; Br; F; NO$_2$; —NR$^{34}$COR$^{57}$; —CF$_3$; CN;
—OCF$_3$; —OCHF$_2$;
—OR$^{57}$; —SR$^{62}$; lower alkyl; or lower alkenyl;

R$^{69}$ is H; Cl; Br; F; NO$_2$; —NR$^{34}$COR$^{57}$; —CF$_3$; CN;
—OCF$_3$; —OCHF$_2$;
—OR$^{57}$; —SR$^{62}$; lower alkyl; or lower alkenyl;

R$^{70}$ is H; Cl; Br; F; NO$_2$; —NR$^{34}$COR$^{57}$; —CF$_3$; CN;
—OCF$_3$; —OCHF$_2$;
—OR$^{57}$; —SR$^{62}$; lower alkyl; or lower alkenyl;

R$^{71}$ is lower alkyl; lower alkenyl; —(CH$_2$)$_p$(CHR$^{61}$)$_s$OR$^{75}$;
—(CH$_2$)$_p$(CHR$^{61}$)$_s$SR$^{75}$;
—(CH$_2$)$_p$(CHR$^{61}$)$_s$NR$^{33}$R$^{34}$;  —(CH$_2$)$_p$(CHR$^{61}$)$_s$OCONR$^{33}$R$^{75}$;
—(CH$_2$)$_p$(CHR$^{61}$)$_s$NR$^{20}$CONR$^{33}$R$^{82}$;
—(CH$_2$)$_o$(CHR$^{61}$)$_s$COOR$^{75}$;  —(CH$_2$)$_p$CONR$^{58}$R$^{59}$;
—(CH$_2$)$_p$PO(OR$^{62}$)$_2$;
—(CH$_2$)$_p$SO$_2$R$^{62}$; or
—(CH$_2$)$_o$—C$_6$R$^{67}$R$^{68}$R$^{69}$R$^{70}$R$^{76}$;

R$^{72}$ is alkyl; alkenyl; —(CH$_2$)$_p$(CHR$^{61}$)$_s$OR$^{85}$; or
—(CH$_2$)$_p$(CHR$^{61}$)$_s$SR$^{85}$;

R$^{73}$ is —(CH$_2$)$_o$R$^{77}$; —(CH$_2$)$_r$—O—(CH$_2$)$_o$R$^{77}$; —(CH$_2$)$_s$S(CH$_2$)$_o$R$^{77}$; or
—(CH$_2$)$_r$NR$^{20}$(CH$_2$)$_o$R$^{77}$;

R$^{74}$ is —(CH$_2$)$_p$NR$^{78}$R$^{79}$; —(CH$_2$)$_p$NR$^{77}$R$^{80}$; —(CH$_2$)$_p$C(=NR$^{80}$)NR$^{78}$R$^{79}$;
—(CH$_2$)$_p$C(=NOR$^{50}$)NR$^{78}$R$^{79}$;
—(CH$_2$)$_p$C(=NNR$^{78}$R$^{79}$)NR$^{78}$R$^{79}$;  —(CH$_2$)$_p$NR$^{80}$C(=NR$^{80}$)NR$^{78}$R$^{79}$;
—(CH$_2$)$_p$N=C(NR$^{78}$R$^{80}$)NR$^{79}$R$^{80}$;  —(CH$_2$)$_p$C$_6$H$_4$NR$^{78}$R$^{79}$;
—(CH$_2$)$_p$C$_6$H$_4$NR$^{77}$R$^{80}$;
—(CH$_2$)$_p$C$_6$H$_4$C(=NR$^{80}$)NR$^{78}$R$^{79}$;  —(CH$_2$)$_p$C$_6$H$_4$C(=NOR$^{50}$)NR$^{78}$R$^{79}$;
—(CH$_2$)$_p$C$_6$H$_4$C(=NNR$^{78}$R$^{79}$)NR$^{78}$R$^{79}$;  —(CH$_2$)$_p$C$_6$H$_4$NR$^{80}$C(=NR$^{80}$)NR$^{78}$R$^{79}$;
—(CH$_2$)$_p$C$_6$H$_4$N=C(NR$^{78}$R$^{80}$)NR$^{79}$R$^{80}$;  —(CH$_2$)$_r$O(CH$_2$)$_m$NR$^{78}$R$^{79}$;
—(CH$_2$)$_r$O(CH$_2$)$_m$NR$^{77}$R$^{80}$;
—(CH$_2$)$_r$O(CH$_2$)$_p$C(=NR$^{80}$)NR$^{78}$R$^{79}$;  —(CH$_2$)$_r$O(CH$_2$)$_p$C(=NOR$^{50}$)NR$^{78}$R$^{79}$;
—(CH$_2$)$_r$O(CH$_2$)$_p$C(=NNR$^{78}$R$^{79}$)NR$^{78}$R$^{79}$;
—(CH$_2$)$_r$O(CH$_2$)$_m$NR$^{80}$C(=NR$^{80}$)NR$^{78}$R$^{79}$;
—(CH$_2$)$_r$O(CH$_2$)$_m$N=C(NR$^{78}$R$^{80}$)NR$^{79}$R$^{80}$;
—(CH$_2$)$_r$O(CH$_2$)$_p$C$_6$H$_4$CNR$^{78}$R$^{79}$;
—(CH$_2$)$_r$O(CH$_2$)$_p$C$_6$H$_4$C(=NR$^{80}$)NR$^{78}$R$^{79}$;
—(CH$_2$)$_r$O(CH$_2$)$_p$C$_6$H$_4$C(=NOR$^{50}$)NR$^{78}$R$^{79}$;
—(CH$_2$)$_r$O(CH$_2$)$_p$C$_6$H$_4$C(=NNR$^{78}$R$^{79}$)NR$^{78}$R$^{79}$;
—(CH$_2$)$_r$O(CH$_2$)$_p$C$_6$H$_4$NR$^{80}$C(=NR$^{80}$)NR$^{78}$R$^{79}$;
—(CH$_2$)$_r$S(CH$_2$)$_m$NR$^{78}$R$^{79}$;
—(CH$_2$)$_r$S(CH$_2$)$_m$NR$^{77}$R$^{80}$;  —(CH$_2$)$_r$S(CH$_2$)$_p$C(=NR$^{80}$)NR$^{78}$R$^{79}$;
—(CH$_2$)$_r$S(CH$_2$)$_p$C(=NOR$^{50}$)NR$^{78}$R$^{79}$;
—(CH$_2$)$_r$S(CH$_2$)$_p$C(=NNR$^{78}$R$^{79}$)NR$^{78}$R$^{79}$;
—(CH$_2$)$_r$S(CH$_2$)$_m$NR$^{80}$C(=NR$^{80}$)NR$^{78}$R$^{79}$;
—(CH$_2$)$_r$S(CH$_2$)$_m$N=C(NR$^{78}$R$^{80}$)NR$^{79}$R$^{80}$;
—(CH$_2$)$_r$S(CH$_2$)$_p$C$_6$H$_4$CNR$^{78}$R$^{79}$;  —(CH$_2$)$_r$S(CH$_2$)$_p$C$_6$H$_4$C(=NR$^{80}$)NR$^{78}$R$^{79}$;
—(CH$_2$)$_r$S(CH$_2$)$_p$C$_6$H$_4$C(=NOR$^{50}$)NR$^{78}$R$^{79}$;
—(CH$_2$)$_r$S(CH$_2$)$_p$C$_6$H$_4$C(=NNR$^{78}$R$^{79}$)NR$^{78}$R$^{79}$;
—(CH$_2$)$_r$S(CH$_2$)$_p$C$_6$H$_4$NR$^{80}$C(=NR$^{80}$)NR$^{78}$R$^{79}$;
—(CH$_2$)$_p$NR$^{80}$COR$^{64}$;
—(CH$_2$)$_p$NR$^{80}$COR$^{77}$;
—(CH$_2$)$_p$NR$^{80}$CONR$^{78}$R$^{79}$;  or  —(CH$_2$)$_p$C$_6$H$_4$NR$^{80}$CONR$^{78}$R$^{79}$;

R$^{75}$ is lower alkyl; lower alkenyl; or aryl-lower alkyl; or

R³³ and R⁷⁵ taken together can form: —(CH₂)₂₋₆—; —(CH₂)₂O(CH₂)₂—; —(CH₂)₂S(CH₂)₂—; or —(CH₂)₂NR⁵⁷(CH₂)₂—; or R⁷⁵ and R⁸² taken together can form: —(CH₂)₂₋₆—; —(CH₂)₂O(CH₂)₂—; —(CH₂)₂S(CH₂)₂—; or —(CH₂)₂R⁵⁷(CH₂)₂—;

R⁷⁶ is H; lower alkyl; lower alkenyl; lower alkyl-aryl; aryl-lower alkyl; —(CH₂)ₒOR⁷²; —(CH₂)ₒSR⁷²; —(CH₂)ₒNR³³R³⁴; —(CH₂)ₒOCONR³³R⁷⁵; —(CH₂)ₒNR²⁰CONR³³R⁸¹; —(CH₂)ₒCOOR⁷⁵; —(CH₂)ₒCONR⁵⁸R⁵⁹; —(CH₂)ₒPO(OR⁶⁰)₂; —(CH₂)ₚSO₂R⁶²; or —(CH₂)ₒCOR⁶⁴;

R⁷⁷ is —C₆R⁶⁷R⁶⁸R⁶⁹R⁷⁰R⁷⁶ with the proviso that at least two of R⁶⁷, R⁶⁸, R⁶⁹ and R⁷⁰ are H; or a heteroaryl group of one of the formulae

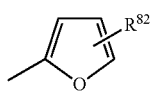
H1

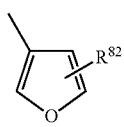
H2

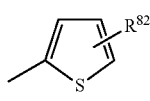
H3

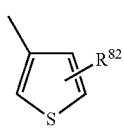
H4

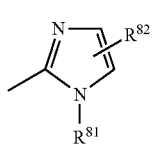
H5

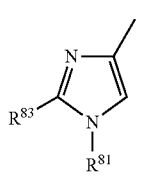
H6

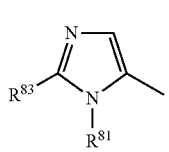
H7

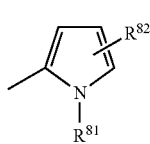
H8

-continued

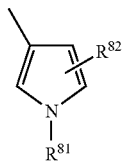
H9

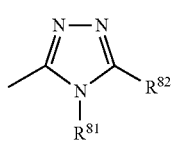
H10

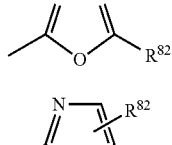
H11

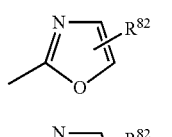
H12

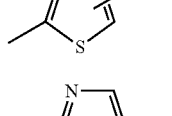
H13

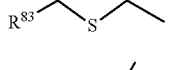
H14

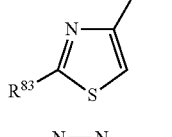
H15

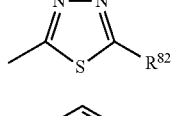
H16

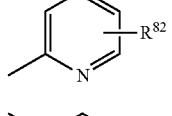
H17

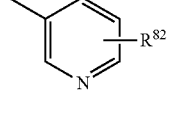
H18

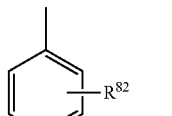
H19

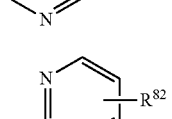
H20

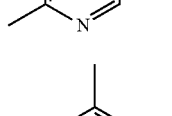
H21

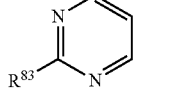

-continued
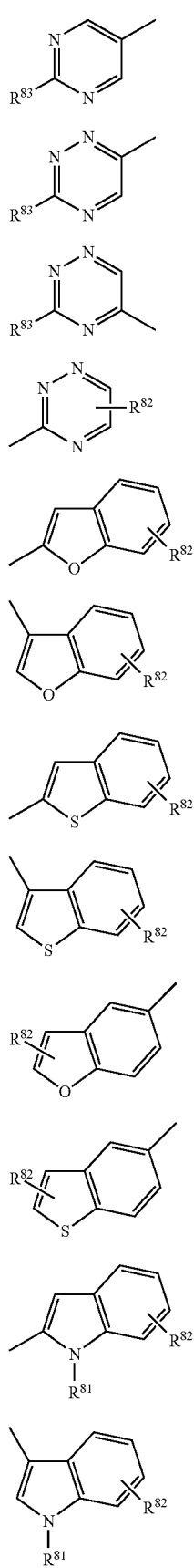
-continued
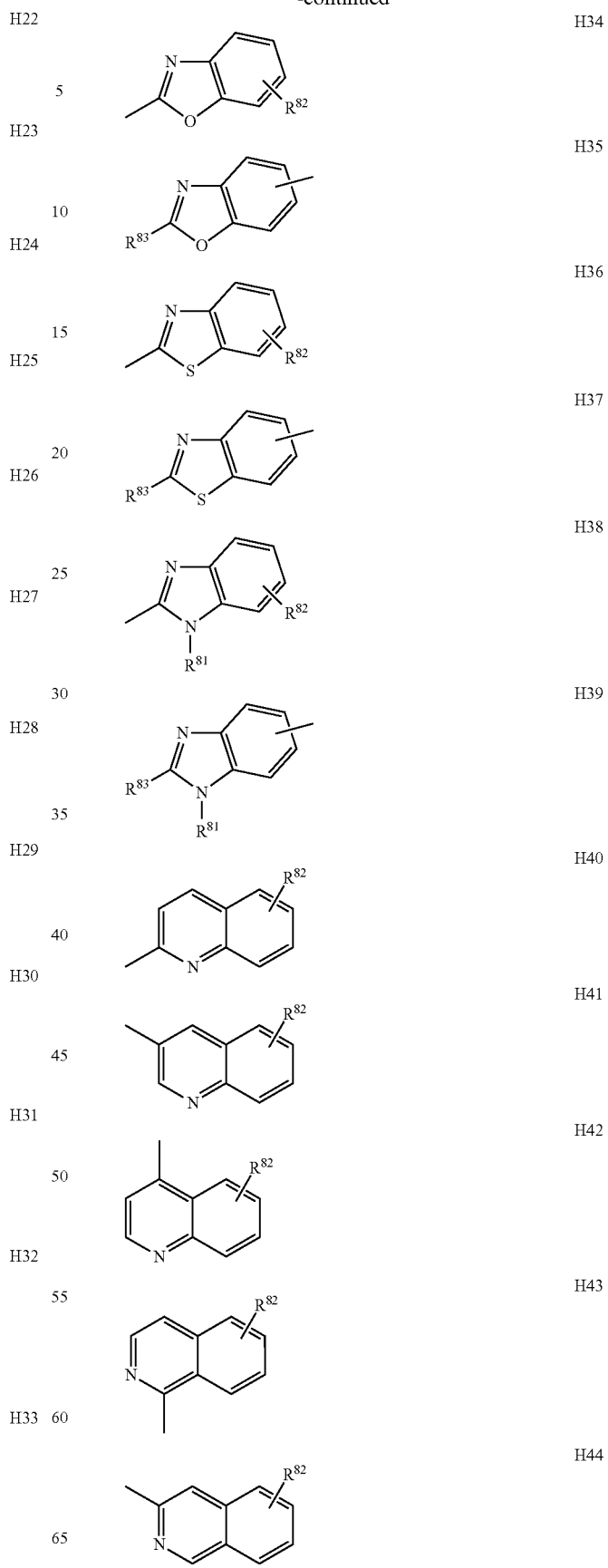

-continued

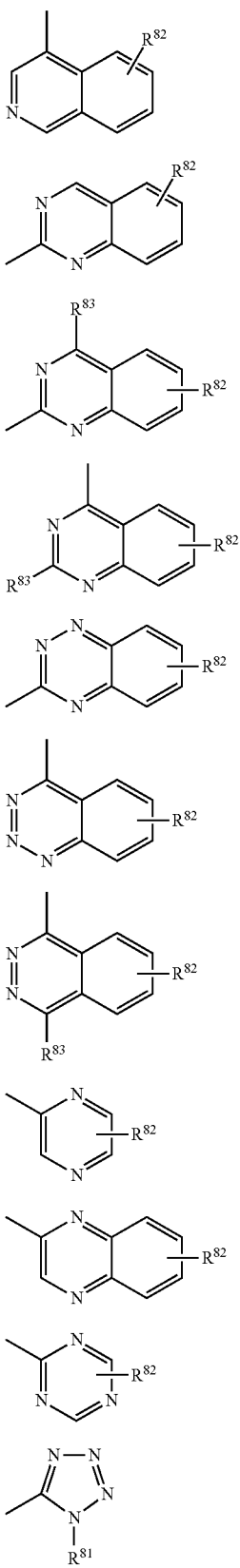

R⁷⁸ is H; lower alkyl; lower alkyl-aryl; aryl; or aryl-lower alkyl; or

R⁷⁸ and R⁸² taken together can form: —(CH₂)₂₋₆—; —(CH₂)₂O(CH₂)₂—; —(CH₂)₂S(CH₂)₂—; or —(CH₂)₂NR⁵⁷(CH₂)₂—;

R⁷⁹ is H; lower alkyl; lower alkyl-aryl; aryl; or aryl-lower alkyl; or

R⁷⁸ and R⁷⁹, taken together, can be —(CH₂)₂₋₇—; —(CH₂)₂ O(CH₂)₂—; or —(CH₂)₂NR⁵⁷(CH₂)₂—;

R⁸⁰ is H; n or lower alkyl;

R⁸¹ is H; lower alkyl; lower alkyl-aryl; aryl-lower alkyl; or

R³³ and R⁸¹ taken together can form: —(CH₂)₂₋₆—; —(CH₂)₂O(CH₂)₂—; —(CH₂)₂S(CH₂)₂—; or —(CH₂)₂NR⁵⁷(CH₂)₂—;

R⁸² is H; —CF₃; —OCF₃; —OCHF₂; lower alkyl; lower alkyl-aryl; lower alkyl-heteroaryl; aryl; aryl-lower alkyl; heteroaryl; heteroaryl-lower alkyl;

R⁸³ is H; lower alkyl; aryl; or —NR⁷⁸R⁷⁹;

R⁸⁴ is —(CH₂)ₚ(CHR⁶¹)ₛOH; —(CH₂)pCOOR⁸⁰; —(CH₂)ₚ(CHR⁶¹)ₛSH; —(CH₂)ₚCONR⁷⁸R⁷⁹; —(CH₂)ₚNR⁸⁰CONR⁷⁸R⁷⁹; —(CH₂)ₚ C₆H₄CONR⁷⁸R⁷⁹; or —(CH₂)ₚ C₆H₄NR⁸⁰CONR⁷⁸R⁷⁹;

R⁸⁵ is lower alkyl; or lower alkenyl;

R⁸⁶ is R⁷⁴; —(CH₂)ₒR⁷⁷; —(CH₂)ₙ—CHR³³R⁷⁵; R⁸⁴; —[(CH₂)ᵤ—X']ₜ—(CH₂)ᵥNR⁷⁸R⁷⁹; —[(CH₂)ᵤ—X']ₜ—(CH₂)ᵥ—C(=NR⁸⁰)NR⁷⁸R⁷⁹; —[(CH₂)ᵤ—X']ₜ—(CH₂)ᵥOR⁷⁸; —[(CH₂)ᵤ—X']ₜ—(CH₂)ᵥ—CONR⁷⁸R⁷⁹; —[(CH₂)ᵤ—X']ₜ—(CH₂)ᵥ—NR⁸⁰CONR⁷⁸R⁷⁹; —[(CH₂)ᵤ—X']ₜ—(CH₂)ᵥSR⁷⁸ where X' is —O—, —NR²⁰—, —S—; or —OCOO—, u is 1-3, t is 1-6, and v is 1-3;

R⁸⁷ is fatty alkyl; fatty alkyl-OR⁶⁵; fatty alkyl-SR⁶⁶; fatty alkyl-NR⁷⁸R⁸²; fatty alkyl-OCONR⁷⁵R⁸²; fatty alkyl-NR³⁴CONR⁷⁸R⁸²;
fatty alkyl-COOR⁸⁰; fatty alkyl-CONR⁷⁵R⁸²;
fatty alkenyl; fatty alkenyl-OR⁶⁵; fatty alkenyl-SR⁶⁶; fatty alkenyl-NR⁷⁸R⁸²; fatty alkenyl-OCONR⁷⁵R⁸²; fatty alkenyl-NR³⁴CONR⁷⁸R⁸²;
fatty alkenyl-COOR⁸⁰; fatty alkenyl-CONR⁷⁵R⁸²;
fatty alkyl-aryl; fatty alkyl-aryl-OR⁶⁵; fatty alkyl-aryl-SR⁶⁶;
fatty alkyl-aryl-NR⁷⁸R⁸²; fatty alkyl-aryl-OCONR⁷⁵R⁸²;
fatty alkyl-aryl-NR³⁴CONR⁷⁸R⁸²;
fatty alkyl-aryl-COOR⁸⁰; fatty alkyl-aryl-CONR⁷⁵R⁸²;
fatty alkyl-heteroaryl; fatty alkyl-heteroaryl-OR⁶⁵;
fatty alkyl-heteroaryl-SR⁶⁶;
fatty alkyl-heteroaryl-NR⁷⁸R⁸²;
fatty alkyl-heteroaryl-OCONR⁷⁵R⁸²;
fatty alkyl-heteroaryl-NR³⁴CONR⁷⁸R⁸²;
fatty alkyl-heteroaryl-COOR⁸⁰;
fatty alkyl-heteroaryl-CONR⁷⁵R⁸²;
fatty alkenyl-aryl; fatty alkenyl-aryl-OR⁶⁵;
fatty alkenyl-aryl-SR⁶⁶;
fatty alkenyl-aryl-NR⁷⁸R⁸²;
fatty alkenyl-aryl-OCONR⁷⁵R⁸²;
fatty alkenyl-aryl-NR³⁴CONR⁷⁸R⁸²;
fatty alkenyl-aryl-COOR⁸⁰;
fatty alkenyl-aryl-CONR⁷⁵R⁸²;
fatty alkenyl-heteroaryl;
fatty alkenyl-heteroaryl-OR⁶⁵;
fatty alkenyl-heteroaryl-SR⁶⁶;
fatty alkenyl-heteroaryl-NR⁷⁸R⁸²;
fatty alkenyl-heteroaryl-OCONR⁷⁵R⁸²;
fatty alkenyl-heteroaryl-NR³⁴CONR⁷⁸R⁸²;
fatty alkenyl-heteroaryl-COOR⁸⁰;
fatty alkenyl-heteroaryl-CONR⁷⁵R⁸²;

aryl-fatty alkyl; aryl-fatty alkyl-OR$^{65}$;
aryl-fatty alkyl-SR$^{66}$;
aryl-fatty alkyl-NR$^{78}$R$^{82}$; aryl-fatty alkyl-OCONR$^{75}$R$^{82}$;
aryl-fatty alkyl-NR$^{34}$CONR$^{78}$R$^{82}$;
aryl-fatty alkyl-COOR$^{80}$;
aryl-fatty alkyl-CONR$^{75}$R$^{82}$;
aryl-fatty alkenyl; aryl-fatty alkenyl-OR$^{65}$;
aryl-fatty alkyenl-SR$^{66}$;
aryl-fatty alkenyl-NR$^{78}$R$^{82}$;
aryl-fatty alkenyl-OCONR$^{75}$R$^{82}$;
aryl-fatty alkenyl-NR$^{34}$CONR$^{78}$R$^{82}$;
aryl-fatty alkenyl-COOR$^{80}$;
aryl-fatty alkenyl-CONR$^{75}$R$^{82}$;
heteroaryl-fatty alkyl; heteroaryl-fatty alkyl-OR$^{65}$;
heteroaryl-fatty alkyl-SR$^{66}$;
heteroaryl-fatty alkyl-NR$^{78}$R$^{82}$;
heteroaryl-fatty alkyl-OCONR$^{75}$R$^{82}$;
heteroaryl-fatty alkyl-NR$^{34}$CONR$^{78}$R$^{82}$;
heteroaryl-fatty alkyl-COOR$^{80}$;
heteroaryl-fatty alkyl-CONR$^{75}$R$^{82}$;
heteroaryl-fatty alkenyl;
heteroaryl-fatty alkenyl-OR$^{65}$;
heteroaryl-fatty alkenyl-SR$^{66}$;
heteroaryl-fatty alkenyl-NR$^{78}$R$^{82}$;
heteroaryl-fatty alkenyl-OCONR$^{75}$R$^{82}$;
heteroaryl-fatty alkenyl-NR$^{34}$CONR$^{78}$R$^{82}$;
heteroaryl-fatty alkenyl-COOR$^{80}$;
heteroaryl-fatty alkenyl-CONR$^{75}$R$^{82}$;
adamantyl;
—(CH$_2$)$_p$(CHR$^{61}$)$_s$OR$^{89}$; —(CH$_2$)$_p$(CHR$^{61}$)$_s$SR$^{89}$;
—(CH$_2$)$_o$R$^{91}$;    —(CH$_2$)$_r$O(CH$_2$)$_o$R$^{91}$;    —(CH$_2$)$_r$S(CH$_2$)$_o$R$^{91}$
—(CH$_2$)$_r$NR$^{20}$(CH$_2$)$_o$R$^{91}$;
—(CH$_2$)$_p$NR$^{88}$R$^{79}$;   —(CH$_2$)$_p$NR$^{77}$R$^{88}$;   —(CH$_2$)$_p$C(=NR$^{80}$)NR$^{88}$R$^{79}$;
—(CH$_2$)$_p$C(=NOR$^{50}$)NR$^{88}$R$^{79}$;
—(CH$_2$)$_p$C(=NNR$^{78}$R$^{79}$)NR$^{78}$R$^{79}$;   —(CH$_2$)$_p$NR$^{80}$C(=NR$^{80}$)NR$^{88}$R$^{79}$;
—(CH$_2$)$_p$N=C(NR$^{88}$R$^{80}$)NR$^{79}$R$^{80}$;   —(CH$_2$)$_p$N=C(NR$^{78}$R$^{80}$NR$^{79}$R$^{88}$;
—(CH$_2$)$_p$C$_6$H$_4$NR$^{88}$R$^{79}$; —(CH$_2$)$_p$C$_6$H$_4$NR$^{77}$R$^{88}$;
—(CH$_2$)$_p$C$_6$H$_4$C(=NR$^{80}$)NR$^{88}$R$^{79}$;   —(CH$_2$)$_p$C$_6$H$_4$C(=NOR$^{50}$)NR$^{88}$R$^{79}$;
—(CH$_2$)$_p$C$_6$H$_4$C(=NNR$^{78}$R$^{79}$)NR$^{78}$R$^{79}$;   —(CH$_2$)$_p$C$_6$H$_4$NR$^{80}$C(=NR$^{80}$)NR$^{78}$R$^{79}$;
—(CH$_2$)$_p$C$_6$H$_4$N=C(NR$^{88}$R$^{80}$)NR$^{79}$R$^{80}$;   —(CH$_2$)$_p$C$_6$H$_4$N=C(NR$^{78}$R$^{80}$)NR$^{79}$R$^{88}$;
—(CH$_2$)$_r$O(CH$_2$)$_m$NR$^{88}$R$^{79}$;   —(CH$_2$)$_r$O(CH$_2$)$_m$NR$^{77}$R$^{88}$;
—(CH$_2$)$_r$O(CH$_2$)$_p$C(=NR$^{88}$)NR$^{78}$R$^{79}$;   —(CH$_2$)$_r$O(CH$_2$)$_p$C(=NR$^{80}$)NR$^{88}$R$^{79}$;
—(CH$_2$)$_r$O(CH$_2$)$_p$C(=NOR$^{50}$)NR$^{88}$R$^{79}$;
—(CH$_2$)$_r$O(CH$_2$)$_p$C(=NNR$^{88}$R$^{79}$)NR$^{78}$R$^{79}$;
—(CH$_2$)$_r$O(CH$_2$)$_p$C(=NNR$^{78}$R$^{79}$)NR$^{88}$R$^{79}$;
—(CH$_2$)$_r$O(CH$_2$)$_m$NR$^{88}$C(=NR$^{80}$)NR$^{78}$R$^{79}$;
—(CH$_2$)$_r$O(CH$_2$)$_m$NR$^{80}$C(=NR$^{80}$)NR$^{88}$R$^{79}$;
—(CH$_2$)$_r$O(CH$_2$)$_m$N=C(NR$^{88}$R$^{80}$)NR$^{79}$R$^{80}$;
—(CH$_2$)$_r$O(CH$_2$)$_m$N=C(NR$^{78}$R$^{80}$)NR$^{79}$R$^{88}$; —(CH$_2$)$_r$O(CH$_2$)$_p$C$_6$H$_4$CNR$^{88}$R$^{79}$;
—(CH$_2$)$_r$O(CH$_2$)$_p$C$_6$H$_4$C(=NR$^{80}$)NR$^{88}$R$^{79}$;
—(CH$_2$)$_r$O(CH$_2$)$_p$C$_6$H$_4$C(=NOR$^{50}$)NR$^{88}$R$^{79}$;
—(CH$_2$)$_r$O(CH$_2$)$_p$C$_6$H$_4$C(=NNR$^{88}$R$^{79}$)NR$^{78}$R$^{79}$;
—(CH$_2$)$_r$O(CH$_2$)$_p$C$_6$H$_4$C(=NNR$^{78}$R$^{79}$)NR$^{88}$R$^{79}$;
—(CH$_2$)$_r$O(CH$_2$)$_p$C$_6$H$_4$NR$^{88}$C(=NR$^{80}$)NR$^{78}$R$^{79}$;
—(CH$_2$)$_r$O(CH$_2$)$_p$C$_6$H$_4$NR$^{80}$C(=NR$^{80}$)NR$^{88}$R$^{79}$;
—(CH$_2$)$_r$S(CH$_2$)$_m$NR$^{88}$R$^{79}$;
—(CH$_2$)$_r$S(CH$_2$)$_m$NR$^{77}$R$^{88}$;   —(CH$_2$)$_r$S(CH$_2$)$_p$C(=NR$^{80}$) NR$^{88}$R$^{79}$;
—(CH$_2$)$_r$S(CH$_2$)$_p$C(=NOR$^{50}$)NR$^{88}$R$^{79}$;
—(CH$_2$)$_r$S(CH$_2$)$_p$C(=NNR$^{88}$R$^{79}$)NR$^{78}$R$^{79}$;
—(CH$_2$)$_r$S(CH$_2$)$_p$C(=NNR$^{78}$R$^{79}$)NR$^{88}$R$^{79}$;
—(CH$_2$)$_r$S(CH$_2$)$_m$NR$^{88}$C(=NR$^{80}$)NR$^{78}$R$^{79}$;
—(CH$_2$)$_r$S(CH$_2$)$_m$NR$^{80}$C(=NR$^{80}$)NR$^{88}$R$^{79}$;
—(CH$_2$)$_r$S(CH$_2$)$_m$N=C(NR$^{88}$R$^{80}$)NR$^{79}$R$^{80}$;
—(CH$_2$)$_r$S(CH$_2$)$_m$N=C(NR$^{78}$R$^{80}$)NR$^{79}$R$^{88}$;
—(CH$_2$)$_r$S(CH$_2$)$_p$C$_6$H$_4$CNR$^{88}$R$^{79}$;   —(CH$_2$)$_r$S(CH$_2$)$_p$C$_6$H$_4$C(=NR$^{80}$)NR$^{88}$R$^{79}$;
—(CH$_2$)$_r$S(CH$_2$)$_p$C$_6$H$_4$C(=NOR$^{50}$)NR$^{88}$R$^{79}$;
—(CH$_2$)$_r$S(CH$_2$)$_p$C$_6$H$_4$C(=NNR$^{88}$R$^{79}$)NR$^{78}$R$^{79}$;
—(CH$_2$)$_r$S(CH$_2$)$_p$C$_6$H$_4$C(=NNR$^{78}$R$^{79}$)NR$^{88}$R$^{79}$;
—(CH$_2$)$_r$S(CH$_2$)$_p$C$_6$H$_4$NR$^{88}$C(=NR$^{80}$)NR$^{78}$R$^{79}$;
—(CH$_2$)$_r$S(CH$_2$)$_p$C$_6$H$_4$NR$^{80}$C(=NR$^{80}$)NR$^{88}$R$^{79}$;
—(CH$_2$)$_p$COOR$^{89}$;   —(CH$_2$)$_p$CONR$^{89}$R$^{79}$;   —(CH$_2$)$_p$NR$^{80}$CONR$^{89}$R$^{79}$;
—(CH$_2$)$_p$C$_6$H$_4$CONR$^{89}$R$^{79}$;   or   —(CH$_2$)$_p$C$_6$H$_4$NR$^{80}$CONR$^{89}$R$^{79}$ R$^{88}$ is —COR$^{89}$; —COOR$^{89}$; —CONR$^{34}$R$^{89}$;
—CO(CH$_2$)$_p$(CHCOOR$^{34}$)$_s$NR$^{34}$COR$^{89}$;
—CO(CH$_2$)$_p$(CHCOOR$^{34}$)$_s$NR$^{34}$COOR$^{89}$;
—CO(CH$_2$)$_p$(CHCONR$^{34}$)$_s$NR$^{34}$CONR$^{34}$R$^{89}$;
—COCHR$^{90}$NR$^{34}$COR$^{89}$;
—COCHR$^{90}$NR$^{34}$COOR$^{89}$;
—COCHR$^{90}$NR$^{34}$CONR$^{34}$R$^{89}$
—CO(CH$_2$)$_p$(CHCONR$^{34}$)$_s$NR$^{34}$-choloyl;
—CO(CH$_2$)$_p$(CHCONR$^{34}$)$_s$NR$^{34}$-chenodeoxycholoyl
—CO(CH$_2$)$_p$(CHCONR$^{34}$)$_s$NR$^{34}$-deoxycholoyl
—SO$_2$(CH$_2$)$_p$(CHCONR$^{34}$)$_s$NR$^{34}$-choloyl;
—[CO(CH$_2$)$_v$—[X'—(CH$_2$)$_u$]$_t$—NR$^{34}$]$_{t'}$—R$^{88}$ where X' is —O—, —NR$^{20}$—, —S—; or —OCOO—, t is 1-6, t' is 1-6, u is 1-3, and v is 1-3 with the proviso that R$^{88}$ is not —[CO(CH$_2$)$_v$—[X'—(CH$_2$)$_u$]$_t$—NR$^{34}$]$_{t'}$—R$^{88}$;

R$^{89}$ is fatty alkyl; fatty alkyl-OR$^{65}$; fatty alkyl-SR$^{66}$;
fatty alkyl-NR$^{78}$R$^{82}$; fatty alkyl-OCONR$^{75}$R$^{82}$;
fatty alkyl-NR$^{34}$CONR$^{78}$R$^{82}$;
fatty alkyl-COOR$^{80}$; fatty alkyl-CONR$^{75}$R$^{82}$;
fatty alkenyl; fatty alkenyl-OR$^{65}$; fatty alkenyl-SR$^{66}$;
fatty alkenyl-NR$^{78}$R$^{82}$; fatty alkenyl-OCONR$^{75}$R$^{82}$;
fatty alkenyl-NR$^{34}$CONR$^{78}$R$^{82}$;
fatty alkenyl-COOR$^{80}$; fatty alkenyl-CONR$^{75}$R$^{82}$;
fatty alkyl-aryl; fatty alkyl-aryl-OR$^{65}$;
fatty alkyl-aryl-SR$^{66}$;
fatty alkyl-aryl-NR$^{78}$R$^{82}$; fatty alkyl-aryl-OCONR$^{75}$R$^{82}$;
fatty alkyl-aryl-NR$^{34}$CONR$^{78}$R$^{82}$;
fatty alkyl-aryl-COOR$^{80}$, fatty alkyl-aryl-CONR$^{75}$R$^{82}$;
fatty alkyl-heteroaryl; fatty alkyl-heteroaryl-OR$^{65}$;
fatty alkyl-heteroaryl-SR$^{66}$;
fatty alkyl-heteroaryl-NR$^{78}$R$^{82}$;
fatty alkyl-heteroaryl-OCONR$^{75}$R$^{82}$;
fatty alkyl-heteroaryl-NR$^{34}$CONR$^{78}$R$^{82}$;
fatty alkyl-heteroaryl-COOR$^{80}$;
fatty alkyl-heteroaryl-CONR$^{75}$R$^{82}$;
fatty alkenyl-aryl; fatty alkenyl-aryl-OR$^{65}$;
fatty alkenyl-aryl-SR$^{66}$;
fatty alkenyl-aryl-NR$^{78}$R$^{82}$;
fatty alkenyl-aryl-OCONR$^{75}$R$^{82}$;
fatty alkenyl-aryl-NR$^{34}$CONR$^{78}$R$^{82}$;
fatty alkenyl-aryl-COOR$^{80}$;
fatty alkenyl-aryl-CONR$^{75}$R$^{82}$;
fatty alkenyl-heteroaryl;
fatty alkenyl-heteroaryl-OR$^{65}$;
fatty alkenyl-heteroaryl-SR$^{66}$;

fatty alkenyl-heteroaryl-NR$^{78}$R$^{82}$;
fatty alkenyl-heteroaryl-OCONR$^{75}$R$^{82}$;
fatty alkenyl-heteroaryl-NR$^{34}$CONR$^{78}$R$^{82}$;
fatty alkenyl-heteroaryl-COOR$^{80}$;
fatty alkenyl-heteroaryl-CONR$^{75}$R$^{82}$;
aryl-fatty alkyl; aryl-fatty alkyl-OR$^{65}$;
aryl-fatty alkyl-SR$^{66}$;
aryl-fatty alkyl-NR$^{78}$R$^{82}$; aryl-fatty alkyl-OCONR$^{75}$R$^{82}$;
aryl-fatty alkyl-NR$^{34}$CONR$^{78}$R$^{82}$;
aryl-fatty alkyl-COOR$^{80}$;
aryl-fatty alkyl-CONR$^{75}$R$^{82}$;
aryl-fatty alkenyl; aryl-fatty alkenyl-OR$^{65}$;
aryl-fatty alkyenl-SR$^{66}$;
aryl-fatty alkenyl-NR$^{78}$R$^{82}$;
aryl-fatty alkenyl-OCONR$^{75}$R$^{82}$;
aryl-fatty alkenyl-NR$^{34}$CONR$^{78}$R$^{82}$;
aryl-fatty alkenyl-COOR$^{80}$;
aryl-fatty alkenyl-CONR$^{75}$R$^{82}$;
heteroaryl-fatty alkyl; heteroaryl-fatty alkyl-OR$^{65}$;
heteroaryl-fatty alkyl-SR$^{66}$;
heteroaryl-fatty alkyl-NR$^{78}$R$^{82}$;
heteroaryl-fatty alkyl-OCONR$^{75}$R$^{82}$;
heteroaryl-fatty alkyl-NR$^{34}$CONR$^{78}$R$^{82}$;
heteroaryl-fatty alkyl-COOR$^{80}$;
heteroaryl-fatty alkyl-CONR$^{75}$R$^{82}$;
heteroaryl-fatty alkenyl;
heteroaryl-fatty alkenyl-OR$^{65}$;
heteroaryl-fatty alkenyl-SR$^{66}$;
heteroaryl-fatty alkenyl-NR$^{78}$R$^{82}$;
heteroaryl-fatty alkenyl-OCONR$^{75}$R$^{82}$;
heteroaryl-fatty alkenyl-NR$^{34}$CONR$^{78}$R$^{82}$;
heteroaryl-fatty alkenyl-COOR$^{80}$;
heteroaryl-fatty alkenyl-CONR$^{75}$R$^{82}$;
adamantyl;
—C$_6$R$^{67}$R$^{68}$R$^{69}$R$^{70}$R$^{89}$; with the proviso that at least two of R$^{67}$, R$^{68}$, R$^{69}$ and R$^{70}$ are H, and with the further proviso that R$^{89}$ in —C$_6$R$^{67}$R$^{68}$R$^{69}$R$^{70}$R$^{89}$ is not —C$_6$R$^{67}$R$^{68}$R$^{69}$R$^{70}$R$^{89}$;
R$^{90}$ is —(CH$_2$)$_p$COOR$^{34}$; —(CH$_2$)$_p$CONR$^{34}$;
R$^{91}$ is —C$_6$R$^{67}$R$^{68}$R$^{69}$R$^{70}$R$^{89}$; —C$_6$R$^{67}$R$^{68}$R$^{69}$R$^{70}$OR$^{89}$; or —C$_6$R$^{67}$R$^{68}$R$^{69}$R$^{70}$NR$^{34}$R$^{89}$; with the proviso that at least two of R$^{67}$, R$^{68}$, R$^{69}$ and R$^{70}$ are H, and with the further that R$^{89}$ in —C$_6$R$^{67}$R$^{68}$R$^{69}$R$^{70}$R$^{89}$, —C$_6$R$^{67}$R$^{68}$R$^{69}$R$^{70}$OR$^{89}$ or —C$_6$R$^{67}$R$^{68}$R$^{69}$R$^{70}$NR$^{34}$R$^{89}$ is not C$_6$R$^{67}$R$^{68}$R$^{69}$R$^{70}$R$^{89}$, —C$_6$R$^{67}$R$^{68}$R$^{69}$R$^{70}$OR$^{89}$ or —C$_6$R$^{67}$R$^{68}$R$^{69}$R$^{70}$NR$^{34}$R$^{89}$;
m is 2-4; o is 0-4; p is 1-4; q is 0-2; r is 1 or 2; s is 0 or 1;
the amino acid residue of type C is a residue of formula —NR$^{20}$CH(R$^{72}$)CO— but not octylglycine;
the amino acid residue of type D is a residue of formula —NR$^{20}$CH(R$^{73}$)CO—;
the amino acid residue of type E is a residue of the formula —NR$^{20}$CH(R$^{74}$)CO—;
the amino acid residue of type F is a residue of the formula —NR$^{20}$CH(R$^{84}$)CO—;
the amino acid residue of type H is a residue of the one of the formulae —NR$^{20}$—CH(CO—)-alkylene-CH(CO—)—NR$^{20}$—; —NR$^{20}$—CH(CO—)-alkenylene-CH(CO—)—NR$^{20}$—;
—NR$^{20}$—CH(CO—)-alkynylene-CH(CO—)—NR$^{20}$—;
—NR$^{20}$—CH(CO—)—(CH$_2$)$_p$SS(CH$_2$)$_p$—CH(CO—)—NR$^{20}$—;
—NR$^{20}$—CH(CO—)—(—(CH$_2$)$_p$NR$^{20}$CO(CH$_2$)$_p$—CH(CO—)—NR$^{20}$—; and
—NR$^{20}$—CH(CO—)—(—(CH$_2$)$_p$NR$^{20}$CONR$^{20}$(CH$_2$)$_p$—CH(CO—)—NR$^{20}$—;
the N-substituted glycine residue of type I is a residue of formula —NR$^{86}$CH$_2$CO—;
the amino acid residue of type O is a residue of formula —NR$^{20}$CH(R$^{87}$)CO— but not octylglycine;
the term "lipophilic moiety" designates a substituent or a part of a substituent comprising a hydrocarbon radical designated as "fatty alkyl" or a hydrocarbon radical designated as "fatty alkenyl" or a radical comprising a cyclopentanophenanthrene skeleton or an adamantyl radical, and the term "fatty" designates a radical having 7 up to 40 carbon atoms;
and pharmaceutically acceptable salts thereof.

2. Compounds according to claim 1 wherein A is a group of one of the formulae A1-A69 and A105;

R$^1$ is hydrogen or lower alkyl;

R$^2$ is H; lower alkyl; lower alkenyl;
—(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—;
—(CH$_2$)$_2$O(CH$_2$)$_2$—;
—(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_p$OCONR$^{33}$R$^{75}$ (where R$^{33}$: H; lower alkyl; or lower alkenyl; R$^{75}$: lower alkyl; or
R$^{33}$ and R$^{75}$ taken together form: —(CH$_2$)$_{2-6}$—);
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_p$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$N(R$^{20}$)COR$^{64}$ (where R$^{20}$: H; or lower alkyl; R$^{64}$: lower alkyl; or lower alkenyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: H; lower alkyl; or lower alkenyl);
—(CH$_2$)$_o$SO$_2$R$^{62}$ (where R$^{62}$: lower alkyl; or lower alkenyl);
—(CH$_2$)$_q$C$_6$H$_4$R$^8$ (where R$^8$: H; F; Cl; CF$_3$; lower alkyl; lower alkenyl; or lower alkoxy);

R$^3$ is H; lower alkyl; lower alkenyl;
—(CH$_2$)$_o$OR$^{55}$ (where R$^{55}$: lower alkyl; or lower alkenyl);
—(CH$_2$)$_o$SR$^{56}$ (where R$^{56}$: lower alkyl; or lower alkenyl);
—(CH$_2$)$_o$NR$^{33}$R$^{34}$ (where R$^{33}$: lower alkyl; or lower alkenyl; R$^{34}$: H; or lower alkyl; or
R$^{33}$ and R$^{34}$ taken together form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$OCONR$^{33}$R$^{75}$ (where R$^{33}$: H; lower alkyl; or lower alkenyl; R$^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy);

$R^4$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy);

$R^5$ is lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl;

or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: alkyl; alkenyl; aryl; aryl-lower alkyl; or heteroaryl-lower alkyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy);

$R^6$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy);

$R^7$ is lower alkyl; lower alkenyl;
- —$(CH_2)_qOR^{55}$ (where $R^{55}$: lower alkyl; or lower alkenyl);
- —$(CH_2)_qSR^{56}$ (where $R^{56}$: lower alkyl; or lower alkenyl);
- —$(CH_2)_qNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_qOCONR^{33}R^{75}$ (where $R^{33}$: H; lower alkyl; or lower alkenyl; $R^{75}$: lower alkyl; or
$R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_qN(R^{20})COR^{64}$ (where $R^{20}$: H; or lower alkyl; $R^{64}$: lower alkyl; or lower alkenyl);
- —$(CH_2)_rCOOR^{57}$ (where $R^{57}$: lower alkyl; or lower alkenyl);
- —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_rPO(OR^{60})_2$ (where $R^{60}$: lower alkyl; or lower alkenyl);
- —$(CH_2)_rSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy);

$R^8$ is H; F; Cl; $CF_3$; lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or
$R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy);

$R^9$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or
$R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy);

$R^{10}$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy);

$R^{11}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl;

or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy);

$R^{12}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl;

or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_rCOOR^{57}$ (where $R^{57}$: lower alkyl; or lower alkenyl);

—$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_rPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy);

$R^{13}$ is lower alkyl; lower alkenyl;

—$(CH_2)_qOR^{55}$ (where $R^{55}$: lower alkyl; or lower alkenyl);

—$(CH_2)_qSR^{56}$ (where $R^{56}$: lower alkyl; or lower alkenyl);

—$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_qN(R^{20})COR^{64}$ (where $R^{20}$: H; or lower alkyl; $R^{64}$: lower alkyl; or lower alkenyl);

—$(CH_2)_rCOO^{57}$ (where $R^{57}$: lower alkyl; or lower alkenyl);

—$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_rPO(OR^{60})_2$ (where $R^{60}$: lower alkyl; or lower alkenyl);
—$(CH_2)_rSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy);

$R^{14}$ is H; lower alkyl; lower alkenyl;
—$(CH_2)_mOR^{55}$ (where $R^{55}$: lower alkyl; or lower alkenyl);
—$(CH_2)_mSR^{56}$ (where $R^{56}$: lower alkyl; or lower alkenyl);
—$(CH_2)_mNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mOCONR^{33}R^{75}$ (where $R^{33}$: H; lower alkyl; or lower alkenyl; $R^{75}$: lower alkyl;
or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mN(R^{20})COR^{64}$ (where $R^{20}$: H; lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl);
—$(CH_2)_qC_6H_4R^8$ (where $R^8$: H; F; Cl; $CF_3$; lower alkyl; lower alkenyl; or lower alkoxy);

$R^{15}$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or
$R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl); particularly favoured being —$NR^{20}CO$-lower alkyl (where $R^{20}$: H; or lower alkyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy);

$R^{16}$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or
$R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy);

$R^{17}$ is lower alkyl; lower alkenyl;
—$(CH_2)_qOR^{55}$ (where $R^{55}$: lower alkyl; or lower alkenyl);
—$(CH_2)_qSR^{56}$ (where $R^{56}$: lower alkyl; or lower alkenyl);
—$(CH_2)_qNR^{33}R^{34}$ (where $R^{33}$: lower alkyl; or lower alkenyl; $R^{34}$: H; or lower alkyl; or
$R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—(CH$_2$)$_q$OCONR$^{33}$R$^{75}$ (where R$^{33}$: H; lower alkyl; or lower alkenyl; R$^{75}$: lower alkyl; or
R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_q$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$— (where R$^{57}$: H; or lower alkyl);
—(CH$_2$)$_r$N(R$^{20}$)COR$^{64}$ (where R$^{20}$: H; or lower alkyl; R$^{64}$: lower alkyl; or lower alkenyl);
—(CH$_2$)$_r$COOR$^{57}$ (where R$^{57}$: lower alkyl; or lower alkenyl);
—(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$— (where R$^{57}$: H; or lower alkyl);
—(CH$_2$)$_r$PO(OR$^{60}$)$_2$ (where R$^{60}$: lower alkyl; or lower alkenyl);
—(CH$_2$)$_r$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy).

3. Compounds according to claim 1 wherein A is a group of formula

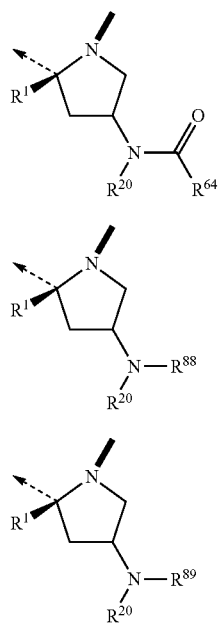

A8'

A8''

A8''' wherein R$^1$, R$^{20}$, R$^{64}$, R$^{88}$ and R$^{89}$ are as defined in claim 1.

4. Compounds according to claim 1 wherein A is a group of one of the formulae A70 to A104;
R$^{18}$ is lower alkyl;
R$^{19}$ is lower alkyl; lower alkenyl;
—(CH$_2$)$_p$OR$^{55}$ (where R$^{55}$ is lower alkyl; or lower alkenyl);
—(CH$_2$)$_p$SR$^{56}$ (where R$^{56}$ is lower alkyl; or lower alkenyl);

—(CH$_2$)$_p$NR$^{33}$R$^{34}$ (where R$^{33}$ is lower alkyl; or lower alkenyl; R$^{34}$ is H; or lower alkyl;
or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);
—(CH$_2$)$_p$OCONR$^{33}$R$^{75}$ (where R$^{33}$ is H; lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);
—(CH$_2$)$_p$NR$^{20}$CONR$^{33}$R$^{81}$ (where R$^{20}$ is H; or lower alkyl; R$^{33}$ is H; lower alkyl; or lower alkenyl; R$^{81}$ is H; or lower alkyl; or R$^{33}$ and R$^{81}$ taken together are —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$— (where R$^{57}$ is H; or lower alkyl);
—(CH$_2$)$_p$N(R$^{20}$)COR$^{64}$ (where R$^{20}$ is H; or lower alkyl; R$^{64}$ is lower alkyl; or lower alkenyl);
—(CH$_2$)$_p$COOR$^{57}$ (where R$^{57}$ is lower alkyl; or lower alkenyl);
—(CH$_2$)$_p$CONR$^{58}$R$^{59}$ (where R$^{58}$ is lower alkyl; or lower alkenyl; and R$^{59}$ is H; or lower alkyl; or R$^{58}$ and R$^{59}$ taken together are —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$— (where R$^{57}$ is H; or lower alkyl);
—(CH$_2$)$_o$PO(OR$^{60}$)$_2$ (where R$^{60}$ is lower alkyl; or lower alkenyl);
—(CH$_2$)$_p$SO$_2$R$^{62}$ (where R$^{62}$ is lower alkyl; or lower alkenyl); or
—(CH$_2$)$_o$C$_6$H$_4$R$^8$ (where R$^8$ is H; F; Cl; CF$_3$; lower alkyl; lower alkenyl; or lower alkoxy);
R$^{20}$ is H; or lower alkyl;
R$^{21}$ is H; lower alkyl; lower alkenyl;
—(CH$_2$)$_o$OR$^{55}$ (where R$^{55}$ is lower alkyl; or lower alkenyl);
—(CH$_2$)$_o$SR$^{56}$ (where R$^{56}$ is lower alkyl; or lower alkenyl);
—(CH$_2$)$_o$NR$^{33}$R$^{34}$ (where R$^{33}$ is lower alkyl; or lower alkenyl; R$^{34}$ is H; or lower alkyl;
or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);
—(CH$_2$)$_o$OCONR$^{33}$R$^{75}$ (where R$^{33}$ is H; lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);
—(CH$_2$)$_o$NR$^{20}$CONR$^{33}$R$^{81}$ (where R$^{20}$ is H; or lower alkyl; R$^{33}$ is H; lower alkyl; or lower alkenyl; R$^{81}$ is H; or lower alkyl; or R$^{33}$ and R$^{81}$ taken together are —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$— (where R$^{57}$ is H; or lower alkyl);
—(CH$_2$)$_o$N(R$^{20}$)COR$^{64}$ (where R$^{20}$ is H; or lower alkyl; R$^{64}$ is lower alkyl; or lower alkenyl);
—(CH$_2$)$_o$COOR$^{57}$ (where R$^{57}$ is lower alkyl; or lower alkenyl);
—(CH$_2$)$_o$CONR$^{58}$R$^{59}$ (where R$^{58}$ is lower alkyl, or lower alkenyl; and R$^{59}$ is H; or lower alkyl; or R$^{58}$ and R$^{59}$ taken together are —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$— (where R$^{57}$ is H; or lower alkyl);
—(CH$_2$)$_o$PO(OR$^{60}$)$_2$ (where R$^{60}$ is lower alkyl; or lower alkenyl);

—$(CH_2)_oSO_2R^{62}$ (where $R^{62}$ is lower alkyl; or lower alkenyl); or

—$(CH_2)_qC_6H_4R^8$ (where $R^8$ is H; F; Cl; $CF_3$; lower alkyl; lower alkenyl; or lower alkoxy);

$R^{22}$ is lower alkyl; lower alkenyl;

—$(CH_2)_oOR^{55}$ (where $R^{55}$ is lower alkyl; or lower alkenyl);

—$(CH_2)_oSR^{56}$ (where $R^{56}$ is lower alkyl; or lower alkenyl);

—$(CH_2)_oNR^{33}R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oOCONR^{33}R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oNR^{20}CONR^{33}R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oN(R^{20})COR^{64}$ (where $R^{20}$ is H; or lower alkyl; $R^{64}$ is lower alkyl; or lower alkenyl);

—$(CH_2)_oCOOR^{57}$ (where $R^{57}$ is lower alkyl; or lower alkenyl);

—$(CH_2)_oCONR^{58}R^{59}$ (where $R^{58}$ is lower alkyl, or lower alkenyl; and $R^{59}$ is H; or lower alkyl; or $R^{58}$ and $R^{59}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oPO(OR^{60})_2$ (where $R^{60}$ is lower alkyl; or lower alkenyl);

—$(CH_2)_oSO_2R^{62}$ (where $R^{62}$ is lower alkyl; or lower alkenyl); or

—$(CH_2)_qC_6H_4R^8$ (where $R^8$ is H; F; Cl; CF; lower alkyl; lower alkenyl; or lower alkoxy);

$R^{23}$ is H; lower alkyl; lower alkenyl;

—$(CH_2)_oOR^{55}$ (where $R^{55}$ is lower alkyl; or lower alkenyl);

—$(CH_2)_oSR^{56}$ (where $R^{56}$ is lower alkyl; or lower alkenyl);

—$(CH_2)_oNR^{33}R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oOCONR^{33}R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oNR^{20}CONR^{33}R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oN(R^{20})COR^{64}$ (where $R^{20}$ is H; or lower alkyl; $R^{64}$ is lower alkyl; or lower alkenyl); —$NR^{20}CO$-lower alkyl (where $R^{20}$ is H; or lower alkyl) being particularly favoured;

—$(CH_2)_oCOOR^{57}$ (where $R^{57}$ is lower alkyl; or lower alkenyl);

—$(CH_2)_oCONR^{58}R^{59}$ (where $R^{58}$ is lower alkyl, or lower alkenyl; and $R^{59}$ is H; or lower alkyl; or $R^{58}$ and $R^{59}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oPO(OR^{60})_2$ (where $R^{60}$ is lower alkyl; or lower alkenyl);

—$(CH_2)_oSO_2R^{62}$ (where $R^{62}$ is lower alkyl; or lower alkenyl); or

—$(CH_2)_qC_6H_4R^8$ (where $R^8$ is H; F; Cl; $CF_3$; lower alkyl; lower alkenyl; or lower alkoxy);

$R^{24}$ is lower alkyl; lower alkenyl;

—$(CH_2)_oOR^{55}$ (where $R^{55}$ is lower alkyl; or lower alkenyl);

—$(CH_2)_oSR^{56}$ (where $R^{56}$ is lower alkyl; or lower alkenyl);

—$(CH_2)_oNR^{33}R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oOCONR^{33}R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oNR^{20}CONR^{33}R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oN(R^{20})COR^{64}$ (where $R^{20}$ is H; or lower alkyl; $R^{64}$ is lower alkyl; or lower alkenyl); —$NR^{20}CO$-lower alkyl (where $R^{20}$ is H; or lower alkyl) being particularly favoured;

—$(CH_2)_oCOOR^{57}$ (where $R^{57}$ is lower alkyl; or lower alkenyl);

—$(CH_2)_oCONR^{58}R^{59}$ (where $R^{58}$ is lower alkyl, or lower alkenyl; and $R^{59}$ is H; or lower alkyl; or $R^{58}$ and $R^{59}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_oPO(OR^{60})_2$ (where $R^{60}$ is lower alkyl; or lower alkenyl);

—$(CH_2)_oSO_2R^{62}$ (where $R^{62}$ is lower alkyl; or lower alkenyl); or

—$(CH_2)_qC_6H_4R^8$ (where $R^8$ is H; F; Cl; $CF_3$; lower alkyl; lower alkenyl; or lower alkoxy);

$R^{25}$ is H; lower alkyl; lower alkenyl;

—$(CH_2)_mOR^{55}$ (where $R^{55}$ is lower alkyl; or lower alkenyl);

—$(CH_2)_mNR^{33}R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_mOCONR^{33}R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$ is H; or lower alkyl);

—$(CH_2)_m NR^{20} CONR^{33} R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_m N(R^{20})COR^{64}$ (where $R^{20}$ is H; or lower alkyl; $R^{64}$ is lower alkyl; or lower alkenyl);

—$(CH_2)_o COOR^{57}$ (where $R^{57}$ is lower alkyl; or lower alkenyl);

—$(CH_2)_o CONR^{58} R^{59}$ (where $R^{58}$ is lower alkyl; or lower alkenyl; and $R^{59}$ is H; or lower alkyl; or $R^{58}$ and $R^{59}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_p PO(OR^{60})_2$ (where $R^{60}$ is lower alkyl; or lower alkenyl);

—$(CH_2)_r SO_2 R^{62}$ (where $R^{62}$ is lower alkyl; or lower alkenyl); or

—$(CH_2)_q C_6 H_4 R^8$ (where $R^8$ is H; F; Cl; $CF_3$; lower alkyl; lower alkenyl; or lower alkoxy);

$R^{26}$ is H; lower alkyl; lower alkenyl;

—$(CH_2)_m OR^{55}$ (where $R^{55}$ is lower alkyl; or lower alkenyl);

—$(CH_2)_m NR^{33} R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_m OCONR^{33} R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_m NR^{20} CONR^{33} R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_m N(R^{20})COR^{64}$ (where $R^{20}$ is H; or lower alkyl; $R^{64}$ is lower alkyl; or lower alkenyl);

—$(CH_2)_o COOR^{57}$ (where $R^{57}$ is lower alkyl; or lower alkenyl);

—$(CH_2)_o CONR^{58} R^{59}$ (where $R^{58}$ is lower alkyl; or lower alkenyl; and $R^{59}$ is H; or lower alkyl; or $R^{58}$ and $R^{59}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_p PO(OR^{60})_2$ (where $R^{60}$ is lower alkyl; or lower alkenyl);

—$(CH_2)_r SO_2 R^{62}$ (where $R^{62}$ is lower alkyl; or lower alkenyl); or

—$(CH_2)_q C_6 H_4 R^8$ (where $R^8$ is H; F; Cl; $CF_3$; lower alkyl; lower alkenyl; or lower alkoxy); or, alternatively, $R^{25}$ and $R^{26}$ taken together are —$(CH_2)_{2-6}$—; —$(CH_2)_2 O(CH_2)_2$—; or —$(CH_2)_2 S(CH_2)_2$—;

$R^{27}$ is H; lower alkyl; lower alkenyl;

—$(CH_2)_o OR^{55}$ (where $R^{55}$ is lower alkyl; or lower alkenyl);

—$(CH_2)_o SR^{56}$ (where $R^{56}$ is lower alkyl; or lower alkenyl);

—$(CH_2)_o NR^{33} R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o OCONR^{33} R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o NR^{20} CONR^{33} R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o N(R^{20})COR^{64}$ (where $R^{20}$ is H; or lower alkyl; $R^{64}$ is lower alkyl; or lower alkenyl);

—$(CH_2)_o COOR^{57}$ (where $R^{57}$ is lower alkyl; or lower alkenyl);

—$(CH_2)_o CONR^{58} R^{59}$ (where $R^{58}$ is lower alkyl, or lower alkenyl; and $R^{59}$ is H; or lower alkyl; or $R^{58}$ and $R^{59}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o PO(OR^{60})_2$ (where $R^{60}$ is lower alkyl; or lower alkenyl);

—$(CH_2)_o SO_2 R^{62}$ (where $R^{62}$ is lower alkyl; or lower alkenyl); or

—$(CH_2)_q C_6 H_4 R^8$ (where $R^8$ is H; F; Cl; $CF_3$; lower alkyl; lower alkenyl; or lower alkoxy);

$R^{28}$ is lower alkyl; lower alkenyl;

—$(CH_2)_o OR^{55}$ (where $R^{55}$ is lower alkyl; or lower alkenyl);

—$(CH_2)_o SR^{56}$ (where $R^{56}$ is lower alkyl; or lower alkenyl);

—$(CH_2)_o NR^{33} R^{34}$ (where $R^{33}$ is lower alkyl; or lower alkenyl; $R^{34}$ is H; or lower alkyl;

or $R^{33}$ and $R^{34}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o OCONR^{33} R^{75}$ (where $R^{33}$ is H; lower alkyl; or lower alkenyl; $R^{75}$ is lower alkyl; or $R^{33}$ and $R^{75}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o NR^{20} CONR^{33} R^{81}$ (where $R^{20}$ is H; or lower alkyl; $R^{33}$ is H; lower alkyl; or lower alkenyl; $R^{81}$ is H; or lower alkyl; or $R^{33}$ and $R^{81}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o N(R^{20})COR^{64}$ (where $R^{20}$ is H; or lower alkyl; $R^{64}$ is lower alkyl; or lower alkenyl);

—$(CH_2)_o COOR^{57}$ (where $R^{57}$ is lower alkyl; or lower alkenyl);

—$(CH_2)_o CONR^{58} R^{59}$ (where $R^{58}$ is lower alkyl, or lower alkenyl; and $R^{59}$ is H; or lower alkyl; or $R^{58}$ and $R^{59}$ taken together are —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$ is H; or lower alkyl);

—$(CH_2)_o PO(OR^{60})_2$ (where $R^{60}$ is lower alkyl; or lower alkenyl);

—$(CH_2)_o SO_2 R^{62}$ (where $R^{62}$ is lower alkyl; or lower alkenyl); or

—(CH$_2$)$_q$C$_6$H$_4$R$^8$ (where R$^8$ is H; F; Cl; CF$_3$; lower alkyl; lower alkenyl; or lower alkoxy); and R$^{29}$ is lower alkyl; lower alkenyl;

—(CH$_2$)$_o$OR$^{55}$ (where R$^{55}$ is lower alkyl; or lower alkenyl);

—(CH$_2$)$_o$SR$^{56}$ (where R$^{56}$ is lower alkyl; or lower alkenyl);

—(CH$_2$)$_o$NR$^{33}$R$^{34}$ (where R$^{33}$ is lower alkyl; or lower alkenyl; R$^{34}$ is H; or lower alkyl;

or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);

—(CH$_2$)$_o$OCONR$^{33}$R$^{75}$ (where R$^{33}$ is H; lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);

—(CH$_2$)$_o$NR$^{20}$CONR$^{33}$R$^{81}$ (where R$^{20}$ is H; or lower alkyl; R$^{33}$ is H; lower alkyl; or lower alkenyl; R$^{81}$ is H; or lower alkyl; or R$^{33}$ and R$^{81}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$ is H; or lower alkyl);

—(CH$_2$)$_o$N(R$^{20}$)COR$^{64}$ (where R$^{20}$ is H; or lower alkyl; R$^{64}$ is lower alkyl; or lower alkenyl); —NR$^{20}$CO-lower-alkyl (where R$^{20}$ is H; or lower alkyl) being particularly favoured;

—(CH$_2$)$_o$COOR$^{57}$ (where R$^{57}$ is lower alkyl; or lower alkenyl);

—(CH$_2$)$_o$CONR$^{58}$R$^{59}$ (where R$^{58}$ is lower alkyl, or lower alkenyl; and R$^{59}$ is H; or lower alkyl; or R$^{58}$ and R$^{59}$ taken together are —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$— (where R$^{57}$ is H; or lower alkyl);

—(CH$_2$)$_o$PO(OR$^{60}$)$_2$ (where R$^{60}$ is lower alkyl; or lower alkenyl);

—(CH$_2$)$_o$SO$_2$R$^{62}$ (where R$^{62}$ is lower alkyl; or lower alkenyl); or —(CH$_2$)$_q$C$_6$H$_4$R$^8$ (where R$^8$ is H; F; Cl; CF$_3$; lower alkyl; lower alkenyl; or lower alkoxy).

5. Compounds according to claim 1 wherein B is a group of formula —NR$^{20}$CH(R$^{71}$)—, or —NR$^{20}$CH(R$^{72}$)— or —NR$^{20}$CH(R$^{73}$)— or —NR$^{20}$CH(R$^{74}$)— or —NR$^{20}$CH (R$^{84}$)—, or an enantiomer of one of the groups A5 (with R$^2$ being H); A8; A22; A25; A38 (with R$^2$ being H); A42; A47 A50 and A105.

6. Compounds according to claim 5 wherein B—CO is Ala; Arg; Asn; Asp; Cys; Gln; Glu; Gly; His; Ile; Leu; Lys; Met; Phe; Pro; Ser; Thr; Trp; Tyr; Val; Cit; Orn; tBuA; Sar; t-BuG; 4AmPhe; 3AmPhe; 2AmPhe; Phe(mC(NH$_2$)=NH); Phe(pC (NH$_2$)=NH); Phe(mNHC (NH$_2$)=NH); Phe(pNHC(NH$_2$) =NH); Phg; Cha; C$_4$al; C$_5$al; Nle; 2-Nal; 1-Nal; 4Cl-Phe; 3Cl-Phe; 2Cl-Phe; 3,4Cl$_2$Phe; 4F-Phe; 3F-Phe; 2F-Phe; Tic; Thi; Tza; Mso; AcLys; Dpr; A$_2$Bu; Dbu; Abu; Aha; Aib; Y(Bzl); Bip; S(Bzl); T(Bzl); hCha; hCys; hSer, hArg; hPhe; Bpa; Pip; OctG; MePhe; MeNle; MeAla; MeIle; MeVal; MeLeu; 4Hyp1; 4Hyp2; 4 Mp1; 4 Mp2; Oic.

7. Compounds according to claim 1 wherein B is a group, having (L)-configuration, of formula

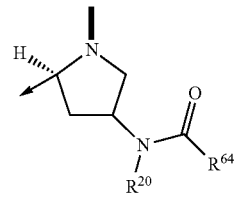

A8'''' wherein

R$^{20}$ is H; or lower alkyl; and R$^{64}$ is alkyl; alkenyl;

—[(CH$_2$)$_u$—X]$_t$—CH$_3$, wherein X is —O—, —NR$^{20}$—, or —S—; and u=1-3 and t=1-6; aryl; aryl-lower alkyl; or heteroaryl-lower alkyl, particularly wherein R$^{64}$ is n-hexyl; n-heptyl; 4-(phenyl)benzyl; diphenylmethyl, 3-amino-propyl; 5-amino-pentyl; methyl; ethyl; isopropyl; isobutyl; n-propyl; cyclohexyl; cyclohexylmethyl; n-butyl; phenyl; benzyl; (3-indolyl)methyl; 2-(3-indolyl)ethyl; (4-phenyl)-phenyl; n-nonyl; CH$_3$—OCH$_2$CH$_2$—OCH$_2$— or CH$_3$—(OCH$_2$CH$_2$)$_2$—OCH$_2$—.

8. Compounds according to claim 1 wherein Xaa$^{15}$ is $^D$Pro, $^D$Cha, NMe$^D$Ile, $^D$Tyr, $^D$His, $^D$His(Bzl), $^D$4Pal, NMe$^D$Tyr, NMe$^D$Lys, (ABu)G, $^D$Ile, NMe$^D$Ala, $^D$Lys, or $^D$Dab; Xaa$^{16}$ is $^L$Pro or Oic; the aforesaid $^D$Pro moiety and/or the aforesaid $^L$Pro moiety being optionally substituted as shown in formulae A8', A8'', A8''' and, respectively, A8'''', as defined in claim 3 and, respectively, in claim 7.

9. Compounds according to claim 1 wherein the amino acid residues are:

Xaa$^1$: Gly, NMeGly, Leu, Val, Ser, Asp, Glu, His, Tyr or Trp;

Xaa$^2$: His, Tyr, Arg, Lys or of type O;

Xaa$^3$: Ala, Cha, Tyr, Thr, Cit, Gln or of type O;

Xaa$^5$: Ser, Arg, Dab, Dap or the D-Isomer of type F;

Xaa$^6$: Ala, Gly;

Xaa$^7$: of formula -A-CO— or D-isomer of type D;

Xaa$^8$: Tyr, Dab, Arg, Thr or of type O;

Xaa$^9$: Arg or of type O;

Xaa$^{10}$: Tyr, Tip, 2Nal or of type O;

Xaa$^{12}$: Ala, Leu, Lys, Ser, Thr, Tyr or Trp;

Xaa$^{13}$: Gln, Thr, Cit or of type O;

Xaa$^{14}$: Ala, Lys, Orn, Arg, Gln, Glu or of type O;

Xaa$^{15}$: of formula -A-CO—, D-isomer of type C, D, E or F, or N-substituted glycine of type I;

Xaa$^{16}$: of formula B—CO—;

Xaa$^4$ and Xaa$^{11}$, taken together, of type H;

with the proviso that the molecule contains at least one but not more than four amino acid residues of type O and/or -A-CO— having a residue designated as "lipophilic moiety".

10. Compounds according to claim 9 wherein the amino acid residues of type O and/or the amino acid residues of -A-CO— are having a substituent R88 which is —CO(CH$_2$)$_p$(CHCOOR$^{34}$)$_s$NR$^{34}$COR$^{89}$, —CO(CH$_2$)$_p$(CHCOOR$^{34}$)$_s$NR$^{34}$COOR$^{89}$ or —CO(CH$_2$)$_p$(CHCONR$^{34}$)$_s$NR$^{34}$CONR$^{34}$R$^{89}$ (R$^{34}$, R$^{89}$, p, and s according to the general definitions of R$^{34}$, R$^{89}$, p, and s).

11. Compounds according to claim 1 wherein the amino acid residues are:

Xaa$^1$: Tyr;

Xaa$^2$: His, Arg or Dab(N$^\gamma$dd);

Xaa$^3$: Ala, Tyr, Thr, Lys(N$^\epsilon$o) or 2Amtd-OH;

Xaa$^4$: Cys;

Xaa⁵: Arg or Ser;
Xaa⁶: Ala or Gly;
Xaa⁷: $^D$Pro, $^D$Tyr, or $^D$4AmPyrr1(td);
Xaa⁸: Dab, Arg or Dab(N$^\gamma$dd);
Xaa⁹: Arg or Arg(N$^\omega$ooxca);
Xaa¹⁰: Tyr or Tyr(Odd);
Xaa¹¹: Cys;
Xaa¹²: Tyr
Xaa¹³: Gln, Dab(N$^\gamma$d), Dab(N$^\gamma$dd), Lys(N$^\epsilon$o), Lys(N$^\epsilon$d), Lys(N$^\epsilon$dd), Lys(N$^\epsilon$td), Lys(N$^\epsilon$hd), Lys((N$^\epsilon$od), Lys (N$^\epsilon$16OHhd), Lys(N$^\epsilon$4ooxbe), Lys(N$^\epsilon$4ddoxbe), Lys (N$^\epsilon$3CN4Fbe), 2Amdd-OH, $^D$2Amdd-OH, Lys(N$^\epsilon$εglu-N$^\alpha$dd), Lys(N$^\epsilon$γgluN$^\alpha$td), Lys(N$^\epsilon$γgluN$^\alpha$hd), Gln (N$^\omega$ad) or Ser(Od);
Xaa¹⁴: Lys, Gln, Lys(N$^\epsilon$o), Lys(N$^\epsilon$glcho), Lys(N$^\epsilon$ado) or Gln(N$^\omega$ad);
Xaa¹⁵: $^D$Tyr or $^D$Pro;
Xaa¹⁶: Pro;
Xaa⁴ and Xaa¹¹, taken together, form a disulfide bridge.

12. A compound according to claim 1 wherein the amino acid residues are:
Xaa¹: Tyr;
Xaa²: His;
Xaa³: Ala;
Xaa⁴: Cys;
Xaa⁵: Arg;
Xaa⁶: Ala;
Xaa⁷: $^D$Pro;
Xaa⁸: Dab;
Xaa⁹: Arg;
Xaa¹⁰: Tyr;
Xaa¹¹: Cys;
Xaa¹²: Tyr;
Xaa¹³: Lys(N$^\epsilon$dd);
Xaa¹⁴: Lys;
Xaa¹⁵: $^D$Pro;
Xaa¹⁶: Pro;
Xaa⁴ and Xaa¹¹, taken together, form a disulfide bridge; or wherein the amino acid residues are:
Xaa¹: Tyr;
Xaa²: His;
Xaa³: Tyr;
Xaa⁴: Cys;
Xaa⁵: Ser;
Xaa⁶: Ala;
Xaa⁷: $^D$Pro;
Xaa⁸: Dab;
Xaa⁹: Arg;
Xaa¹⁰: Tyr;
Xaa¹¹: Cys;
Xaa¹²: Tyr;
Xaa¹³: Lys(N$^\epsilon$hd);
Xaa¹⁴: Lys;
Xaa¹⁵: $^D$Pro;
Xaa¹⁶: Pro;
Xaa⁴ and Xaa¹¹, taken together, form a disulfide bridge; or wherein the amino acid residues are:
Xaa¹: Tyr;
Xaa²: His;
Xaa³: Tyr;
Xaa⁴: Cys;
Xaa⁵: Ser;
Xaa⁶: Ala;
Xaa⁷: $^D$Pro;
Xaa⁸: Dab;
Xaa⁹: Arg;
Xaa¹⁰: Tyr;

Xaa¹¹: Cys;
Xaa¹²: Tyr;
Xaa¹³: Lys(N$^\epsilon$γgluN$^\alpha$dd);
Xaa¹⁴: Lys;
Xaa¹⁵: $^D$Pro;
Xaa¹⁶: Pro;
Xaa⁴ and Xaa¹¹, taken together, form a disulfide bridge; or wherein the amino acid residues are:
Xaa¹: Tyr;
Xaa²: His;
Xaa³: Ala;
Xaa⁴: Cys;
Xaa⁵: Arg;
Xaa⁶: Ala;
Xaa⁷: $^D$Pro;
Xaa⁸: Dab;
Xaa⁹: Arg;
Xaa¹⁰: Tyr;
Xaa¹¹: Cys;
Xaa¹²: Tyr;
Xaa¹³: Lys(N$^\epsilon$γgluN$^\alpha$dd);
Xaa¹⁴: Lys;
Xaa¹⁵: $^D$Pro;
Xaa¹⁶: Pro;
Xaa⁴ and Xaa¹¹, taken together, form a disulfide bridge.

13. Enantiomers of the compounds as defined in claim 1.

14. A method of decreasing inflammation, treating cancer, treating viral infection, or treating an immunological disease, which comprises contacting an effective amount of a compound according to claim 1 with a CXCR4 receptor in a subject in need thereof, wherein the inflammation, cancer, viral infection, or immunological disease is mediated or resulting from CXCR4 receptor activity.

15. A pharmaceutical composition comprising a compound according to claim 1 and a pharmaceutically inert carrier.

16. A method of treating immuno suppression or inducing mobilization of stem cells to regulate tissue repair, which comprises contacting an effective amount of a compound according to claim 1 with a CXCR4 receptor in a subject in need thereof, wherein the immune suppression and mobilization of stem cells is mediated or resulting from CXCR4 receptor activity.

17. A process for the manufacture of compounds according to claim 1, which process comprises:
(a) coupling an appropriately functionalized solid support with an appropriately N-protected derivative of that amino acid which in the desired end-product corresponds to Xaa$^n$, wherein n is 16, 13, 8, 7, 5 or 2, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product corresponds to Xaa$^{n-1}$, any functional group which may be present in said N-protected amino acid derivative being likewise appropriately protected;
(d) removing the N-protecting group from the product obtained in step (c);
(e) effecting steps substantially corresponding to steps (c) and (d) using appropriately N-protected derivatives of amino acids which in the desired end-product are in positions n−2 to 1, any functional group(s) which may be present in said N-protected amino acid derivatives being likewise appropriately protected;

(f) if n is not 16, further effecting steps substantially corresponding to steps (c) and (d) using appropriately N-protected derivatives of amino acids which in the desired end-product are in positions 16 to n+1, any functional group(s) which may be present in said N-protected amino acid derivatives being likewise appropriately protected;

(g) optionally, selectively deprotecting one or several protected functional group(s) present in the molecule and appropriately substituting the reactive group(s) thus liberated by attaching one or several lipophilic moieties;

(h) optionally, forming an interstrand linkage between side-chains of appropriate amino acid residues at P4 and P11, or alternatively, forming the aforesaid linkage subsequent to step (m), as described herein below;

(i) detaching the product thus obtained from the solid support;

(j) cyclizing the product cleaved from the solid support;

(k) removing any protecting groups present on functional groups of any members of the chain of amino acid residues and, optionally, any protecting group(s) which may in addition be present in the molecule;

(l) optionally, attaching one or several lipophilic moieties;

(m) optionally, removing any protecting groups present on functional groups of any members of the chain of amino acid residues and/or any protecting group(s) which may in addition be present in the molecule; and (n) optionally, converting the product thus obtained into a pharmaceutically acceptable salt or converting a pharmaceutically acceptable, or unacceptable, salt thus obtained into the corresponding free compound or into a different, pharmaceutically acceptable, salt.

18. The process according to claim 17, wherein enantiomers of all chiral starting materials are provided and utilized in each step.

19. The composition of claim 15, wherein the composition is in a form selected from one or more of: tablets, dragees, capsules, solutions, liquids, gels, plaster, creams, ointments, syrup, slurries, suspensions, spray, nebuliser and suppositories.

20. The composition of claim 15, wherein the composition is in a form suitable for oral, topical, transdermal, injection, buccal, transmucosal, pulmonary or inhalation administration.

* * * * *